(12) United States Patent
Venn-Watson et al.

(10) Patent No.: US 11,951,088 B2
(45) Date of Patent: Apr. 9, 2024

(54) FATTY ACID ANALOGS AND THEIR USE IN THE TREATMENT OF CONDITIONS RELATED TO METABOLIC SYNDROME

(71) Applicant: Epitracker, Inc., San Diego, CA (US)

(72) Inventors: Stephanie Venn-Watson, San Diego, CA (US); John Reiner, Carlsbad, CA (US); Richard Lumpkin, San Diego, CA (US)

(73) Assignee: EPITRACKER, INC., San Diego, CA (US)

( * ) Notice: Subject to any disclaimer, the term of this patent is extended or adjusted under 35 U.S.C. 154(b) by 384 days.

(21) Appl. No.: 16/932,508

(22) Filed: Jul. 17, 2020

(65) Prior Publication Data

US 2020/0345676 A1 Nov. 5, 2020

Related U.S. Application Data

(62) Division of application No. 16/164,573, filed on Oct. 18, 2018, now Pat. No. 10,792,266.

(60) Provisional application No. 62/575,973, filed on Oct. 23, 2017.

(51) Int. Cl.
| | |
|---|---|
| *A61K 31/20* | (2006.01) |
| *A61K 31/16* | (2006.01) |
| *A61K 31/41* | (2006.01) |
| *A61K 31/421* | (2006.01) |
| *A61K 31/4245* | (2006.01) |

(52) U.S. Cl.
CPC .............. *A61K 31/20* (2013.01); *A61K 31/16* (2013.01); *A61K 31/41* (2013.01); *A61K 31/421* (2013.01); *A61K 31/4245* (2013.01)

(58) Field of Classification Search
CPC ........ A61K 31/20; A61K 31/16; A61K 31/41; A61K 31/421; A61K 31/4245
See application file for complete search history.

(56) References Cited

U.S. PATENT DOCUMENTS

| | | | |
|---|---|---|---|
| 4,252,159 A | 2/1981 | Maki | |
| 4,718,430 A | 1/1988 | Holzer | |
| 4,985,015 A | 1/1991 | Obermann et al. | |
| 5,318,521 A | 6/1994 | Slettenmark | |
| 5,449,688 A | 9/1995 | Wahl et al. | |
| 5,465,728 A | 11/1995 | Phillips | |
| 5,741,816 A | 4/1998 | Tsujihara et al. | |
| 6,214,875 B1 | 4/2001 | Yang | |
| 6,384,252 B1 | 5/2002 | Pageat | |
| 6,441,036 B1 | 8/2002 | Berge | |
| 6,544,541 B1 | 4/2003 | Zahradka | |
| 7,012,053 B1 | 3/2006 | Barnabas et al. | |
| 7,375,135 B2 | 5/2008 | Najib-Fruchart et al. | |
| 7,651,845 B2 | 1/2010 | Doyle et al. | |
| 8,030,348 B2 | 10/2011 | Sampalis | |
| 8,088,825 B2 | 1/2012 | Berge et al. | |
| 8,106,093 B2 | 1/2012 | Roe | |
| 8,251,904 B2 | 8/2012 | Zivitz et al. | |
| 8,759,558 B2 | 6/2014 | Holmeide et al. | |
| 8,827,957 B2 | 9/2014 | Searle et al. | |
| 9,282,760 B2 | 3/2016 | Bryhn et al. | |
| 9,295,637 B2 | 3/2016 | Perricone | |
| 9,561,206 B2 | 2/2017 | Venn-Watson | |
| 9,662,306 B2 | 5/2017 | Venn-Watson | |
| 9,687,461 B2 | 6/2017 | Venn-Watson | |
| 9,707,199 B2 | 7/2017 | Venn-Watson | |
| 9,713,600 B2 | 7/2017 | Venn-Watson | |
| 10,022,347 B2 | 7/2018 | Venn-Watson | |
| 10,111,849 B2 | 10/2018 | Henderson | |
| 10,238,618 B2 | 3/2019 | Venn-Watson | |
| 10,307,388 B2 | 6/2019 | Venn-Watson | |
| 10,449,170 B2 | 10/2019 | Venn-Watson | |
| 10,792,266 B2 | 10/2020 | Venn-Watson et al. | |
| 11,116,740 B2 | 9/2021 | Venn-Watson | |
| 2002/0156351 A1 | 10/2002 | Sagel | |
| 2003/0086869 A1 | 5/2003 | Stallings | |
| 2003/0203004 A1 | 10/2003 | Kelm et al. | |
| 2003/0203042 A1 | 10/2003 | Cook | |
| 2006/0154833 A1 | 7/2006 | Katou et al. | |
| 2006/0269495 A1 | 11/2006 | Popp et al. | |
| 2006/0275294 A1 | 12/2006 | Omoigui | |
| 2007/0088170 A1 | 4/2007 | Bryhn et al. | |

(Continued)

FOREIGN PATENT DOCUMENTS

| | | |
|---|---|---|
| CN | 1939332 A | 4/2007 |
| CN | 102327368 A | 1/2012 |

(Continued)

OTHER PUBLICATIONS

Crossno et al. Am J Physiol Lung Cell Mol Physiol. Apr. 2007;292(4):L885-97 (Year: 2007).*
Stenmark et al. Am J Physiol Lung Cell Mol Physiol297: L1013-L1032, 2009 (Year: 2009).*
Abdullah et al., "Recommended dairy product intake modulates circulating fatty acid orofile in health adults: a multi-centre crossover study", Br J Nutr. 113(3):435-444.
Adams et al., "Hemochronatosis and iron-overload screening in a racially diverse population." New Engl J Med. 2005, 352(17):1769-1778.
Adams et al., "A diagnostic approach to hyperferritinemia with a non-elevated transferrin saturation", J Hepatol. 2011, 55(2):453-458.

(Continued)

*Primary Examiner* — Jeffrey S Lundgren
*Assistant Examiner* — William Y Lee
(74) *Attorney, Agent, or Firm* — Knobbe, Martens, Olson & Bear LLP

(57) ABSTRACT

Compositions comprising fatty acid analogs are provided for treating metabolic syndrome, anemia, cancer, cardiovascular disease, diabetes, dyslipidemia, hypertension, inflammation, insulin resistance, prediabetes, fatty liver disease, steatohepatitis, iron overload, neurodegenerative diseases, including Alzheimer's disease and other forms of dementia, and other related conditions. Methods for the diagnosis and monitoring of metabolic syndrome and other conditions are also provided.

7 Claims, 5 Drawing Sheets

(56) References Cited

U.S. PATENT DOCUMENTS

| | | |
|---|---|---|
| 2009/0069331 A1 | 3/2009 | Vallance et al. |
| 2009/0318369 A1 | 12/2009 | Paige et al. |
| 2011/0077301 A1 | 3/2011 | Deminiere et al. |
| 2011/0098358 A1 | 4/2011 | Fujimoto et al. |
| 2011/0182943 A1 | 7/2011 | Kanwar et al. |
| 2011/0190395 A1 | 8/2011 | Holmeide et al. |
| 2011/0190702 A1 | 8/2011 | Stumber |
| 2011/0201558 A1 | 8/2011 | Roe et al. |
| 2012/0071418 A1 | 3/2012 | Copeland et al. |
| 2012/0072236 A1 | 3/2012 | Atkin |
| 2012/0122940 A1 | 5/2012 | Hovland et al. |
| 2014/0303228 A1 | 10/2014 | Lawton et al. |
| 2015/0291523 A1 | 10/2015 | Ishikawa et al. |
| 2016/0045533 A1 | 2/2016 | Power et al. |
| 2016/0193170 A1 | 7/2016 | Venn-Watson et al. |
| 2016/0193171 A1 | 7/2016 | Venn-Watson |
| 2016/0193172 A1 | 7/2016 | Venn-Watson |
| 2016/0195558 A1 | 7/2016 | Venn-Watson et al. |
| 2016/0195559 A1 | 7/2016 | Venn-Watson |
| 2016/0324814 A1 | 11/2016 | Venn-Watson |
| 2017/0266144 A1 | 9/2017 | Venn-Watson |
| 2017/0319149 A1 | 11/2017 | Koehler et al. |
| 2018/0148682 A1 | 5/2018 | Ross |
| 2018/0185316 A1 | 7/2018 | Venn-Watson |
| 2018/0296518 A1 | 10/2018 | Venn-Watson et al. |
| 2018/0311195 A1 | 11/2018 | Venn-Watson |
| 2018/0311303 A1 | 11/2018 | Maione et al. |
| 2019/0054052 A1 | 2/2019 | Shchepinov |
| 2019/0240181 A1 | 8/2019 | Venn-Watson |
| 2019/0358183 A1 | 11/2019 | Venn-Watson |
| 2020/0222351 A1 | 7/2020 | Dhamane et al. |
| 2021/0046034 A1 | 2/2021 | Venn-Watson |
| 2021/0052535 A1 | 2/2021 | Venn-Watson |
| 2021/0330734 A1 | 10/2021 | Venn-Watson |
| 2021/0346419 A1 | 11/2021 | Venn-Watson |
| 2021/0386710 A1 | 12/2021 | Venn-Watson |
| 2023/0132955 A1 | 5/2023 | Venn-Watson |
| 2023/0201153 A1 | 6/2023 | Venn-Watson |
| 2023/0293491 A1 | 9/2023 | Venn-Watson |

FOREIGN PATENT DOCUMENTS

| | | |
|---|---|---|
| DE | 2615061 | 10/1977 |
| EP | 1000071 A1 | 5/2000 |
| EP | 1020179 A2 | 7/2000 |
| EP | 3301090 A1 | 4/2018 |
| JP | S60172925 | 9/1985 |
| JP | S61015809 A | 1/1986 |
| JP | S62012716 | 1/1987 |
| JP | S63099063 | 4/1988 |
| JP | H06172168 A | 6/1994 |
| JP | 2003160486 A | 6/2003 |
| JP | 2004115438 A | 4/2004 |
| JP | 2005523331 A | 8/2005 |
| JP | 2008255022 A | 10/2008 |
| JP | 2008540393 | 11/2008 |
| JP | 2010260833 A | 11/2010 |
| JP | 2011528350 A | 11/2011 |
| JP | 2014080432 A | 5/2014 |
| JP | 2015010067 A | 1/2015 |
| JP | 2016504403 | 2/2016 |
| JP | 2017200910 A | 11/2017 |
| JP | 2017536879 A | 12/2017 |
| KR | 20170087813 A | 7/2017 |
| KR | 201701009096 A | 9/2017 |
| KR | 102087634 B1 | 3/2020 |
| WO | WO 1996/26647 | 9/1996 |
| WO | WO 1996/32850 | 10/1996 |
| WO | WO 1999/001103 | 1/1999 |
| WO | WO 1999/002485 | 1/1999 |
| WO | WO 2000/040217 | 7/2000 |
| WO | WO 2004/057982 | 7/2004 |
| WO | WO 2004/069240 | 8/2004 |
| WO | WO 2005/099483 | 10/2005 |
| WO | WO 2005/120485 | 12/2005 |
| WO | WO 2006/038063 | 4/2006 |
| WO | WO 2006/117668 | 11/2006 |
| WO | WO 2007/002365 | 1/2007 |
| WO | WO 2007/100435 | 9/2007 |
| WO | WO 2008/114732 | 9/2008 |
| WO | WO 2010/123930 | 10/2010 |
| WO | WO 2012/001336 | 1/2012 |
| WO | WO 2012/069790 | 5/2012 |
| WO | WO 2013/007700 | 1/2013 |
| WO | WO 2014/108573 | 7/2014 |
| WO | WO 2014/179341 | 11/2014 |
| WO | WO 2015/110977 | 7/2015 |
| WO | WO 2015/140545 | 9/2015 |
| WO | WO 2015/157514 | 10/2015 |
| WO | WO 2016/111843 | 7/2016 |
| WO | WO 2017/186928 | 11/2017 |
| WO | WO 2018/157013 | 8/2018 |
| WO | WO 2019/212196 A1 | 11/2019 |
| WO | WO 2019/222254 | 11/2019 |
| WO | WO 2019/226572 | 11/2019 |
| WO | WO 2020/146263 | 7/2020 |
| WO | WO 2020/154173 | 7/2020 |

OTHER PUBLICATIONS

Ahmad et al., "Interaction of Osteopontin with IL-18 in Obese Individuals: Implications for Insulin Resistance". PLoS ONE 2013, 8(5):e63944 in 9 pages.

Akbar et al., Alterations in Hepatic FGF21, Co-Regulated Genes, and Upstream Metabolic Genes in Response to Nutrition, Ketosis and Inflammation in Peripartal Holstein Cows, PLoS One 2015, 10(10):e0139963 in 16 pages.

Akhter, J. MD; Asthma-cure, 2017, https://www.scientificamerican.com/article/can-asthma-be-cured-what/ in 7 pages.

Aksenov et al., "Metabolite Content Profiling of Bottlenose Dolphin Exhaled Breath", Anal Chem 2014, 86(21):10616-10624.

Altamura et al., "Iron toxicity in diseases of aging: Alzheimer's disease, Parkinson's disease and atherosclerosis." J Alzheimer's Dis. 2009, 16(4):879-895.

Angulo et al., "Liver Fibrosis, but no Other Histologic Features, Associates with Long-term Outcomes of Patients With Nonalcoholic Fatty Liver Disease". Gastroenterology. 2015, 149(2):389-397.

Barish et al., "PPARδ: a dagger in the heart of the metabolic syndrome", J Clin Invest. 2006, 116(3):590-597.

Barros et al., "Prey and feeding patterns of resident bottlenose dolphins (Tursiops truncatus) in Sarasota Bay, Florida", J Mammal. 1998, 79:1045-1059.

Batista et al., "Structural Insights into Human Peroxisome Proliferator Activated Receptor Delta (PPAR-Delta) Selective Ligand Binding", PLoS ONE. 2012, 7(5):e33643 in 7 pages.

Beaton et al., "Treatment of Hyperferritinemia", Ann Hepatol. 2012, 11(3):294-300.

Benatar et al., "The effects of changing dairy intake on trans and saturated fatty acid levels—results from a randomized controlled study". Nutr J. 2014, 13:32 in 10 pages.

Berens-McCabe et al., "Prey selection in a resident common bottlenose dolphin (Tursiops truncatus) community in Sarasota Bay, Florida", Marine Biol. 2010, 157:931-942.

Bettcher et al., "MCP-1 and eotaxin-1 selectively and negatively associate with memory in MCI and Alzheimer's disease dementia phenotypes", Alzheimers Dement (Amst). 2016, 3:91-97.

Bossùet al., "Interleukin-18 produced by peripheral blood cells is increased in Alzheimer's disease and correlates with cognitive impairment". Brain Behav Immun. 2008, 22(4):487-492.

Calder et al., "n-3 polyunsaturated fatty acids, inflammation, and inflammatory diseases." Am J Clin Nutr. 2006, 83(6 suppl):1505S-1519S.

Calder P.C., "Long-chain polyunsaturated fatty acids and inflammation", Scandinavian J food nutrition 2006, 50(S2):54-61.

Cater et al., "Behenic acid is a cholesterol-raising saturated fatty acid in humans." Am J Clin Nutr. 2001, 73(1):41-44.

Cheng et al., "Distinct Metabolomic Signatures Are Associated with Longevity in Humans.", Nat Commun. 2015, 6:6791 in 22 pages.

(56) References Cited

OTHER PUBLICATIONS

Choi et al., "Dairy consumption and risk of type 2 diabetes mellitus in men: a prospective study". Arch Intern Med. 2005, 165(9):997-1003.
Colegrove K., Histomorphology of the bottlenose dolphin (*Tursiops truncatus*) pancreas and association of increasing islet ß-cell size with chronic hypercholesterolemia. Gen Comp Endocrinol. 2015, 214:17-23.
Collino et al., "Metabolic Signatures of Extreme Longevity in Northern Italian Centenarians Reveal a Complex Remodeling of Lipids, Amino Acids, and Gut Microbiota Metabolism". PLoS ONE. 2013, 8(3):e56564 in.
Corso et al., Corso et al., "Serum Amino Acid Profiles in Normal Subjects and in Patients with or at Risk of Alzheimer Dementia", Dement Geriatr Cogn Disord Extra. 2017, 7(1):143-159.
Craik J., GLUT-1 mediation of rapid glucose transport in dolphin (*Tursiops truncatus*) red blood cells. Am J Physiol. 1998, 274(1 Pt 2):R112-R119.
Croes et al., Formation of a 2-methyl-branched fatty aldehyde during peroxisomal alpha-oxidation. FEBS Lett. 1997, 412(3):643. 645.
Cronet et al., "Structure of the PPARα and -γ Ligand Binding Domain in Complex with AZ 242; Ligand Selectivity and Agonist Activation in the PPAR Family", Structure. 2001, 9(8):699-706.
Cusi et al., "Long-Term Pioglitazone Treatment for Patients With Nonalcoholic Steatohepatitis and Prediabetes or Type 2 Diabetes Mellitus: A Randomized Trial". Ann Intern Med. 2016, 165(5):305-315.
Daak et al., "Effect of omega-3 (n-3) fatty acid supplementation in patients with sickle cell anemia: randomized, double-blind, placebo-controlled trial". Am J Clin Nutr. 2013, 97(1):37-44.
Das Undurti N., "Arachidonic acid in health and disease with focus on hypertension and diabetes mellitus: A review", J Adv Res. 2018, 11:43-55.
Diehl et al., "Cause, Pathogenesis, and Treatment of Nonalcoholic Steatohepatitis". N Engl J Med. 2017, 377(21):2063-2072.
Di Paolo et al., "Linking Lipids to Alzheimer's Disease: Cholesterol and Beyond", Nat Rev Neurosci. 2011, 12(5):284-296.
Dongiovanni et al., "Iron in fatty liver and in the metabolic syndrome: a promising therapeutic target". J Hepatol. 2011, 55:920-932.
Dursun et al., 2015, The interleukin 1 alpha, interleukin 1 beta, interleukin 6 and alpha-2-macroglobulin serum levels in patients with early or late onset Alzheimer's disease, mild cognitive impairment or Parkinson's disease. J Neuroinflammunol. 2015, 283: 50-57.
Ekstedt et al., "Fibrosis stage is the strongest predictor for disease-specific mortality in NAFLD after up to 33 years of follow-up." Hepatology. 2015; 61(5): 1547-1554.
Ellervik et al., "Prevalence of hereditary haemochromatosis in late-onset type 1 diabetes mellitus: a retrospective study", Lancet 2001, 358(9291):1405-1409.
Evans et al., "NAD+ metabolite levels as a function of vitamins and calorie restriction: evidence for different mechanisms of longevity." BMC Chem Biol. 2010, 10:2 in 10 pages.
Fargion et al., "Hyperferritinemia, iron overload, and multiple metabolic alterations identify patients at risk for nonalcoholic steatohepatitis". Am J Gastroenterol. 2001, 96(8):2448-2455.
Favé et al., "Physicochemical properties of lipids: new strategies to manage fatty acid bioavailability". Cell Mol Biol. 2004, 50(7):815-831.
FDA Guidance for Industry. "Estimating the maximum safe starting dose in initial clinical trials for therapeutics in adult healthy volunteers." US. Food and Drug Administration, Jul. 2005 in 30 pages.
FDA (2017) FDA drug safety communication: FDA warns about serious liver injury with Ocaliva (obeticholic acid) for rare chronic liver disease. Accessed Dec. 5, 2017 https://www.fda.gov/Drugs/DrugSafety/ucm576656.htm in 4 pages.
Fernandes et al., "Relationship between Acute Phase Proteins and Serum Fatty Acid Composition in Morbidly Obese Patients", Dis Markers 2013, 35(2):104-112.
Forman et al., "Hypolipidemic drugs, polyunsaturated fatty acids, and eicosanoids are ligands for peroxisome proliferator-activated receptors α and δ", Proc Natl Acad Sci U.S.A., 1997, 94(9):4312-4317.
Forouhi et al., "Differences in the Prospective Association Between Individual Plasma Phospholipid Saturated Fatty Acids and Incident Type 2 Diabetes: The EPIC-InterAct Case-Cohort Study", Lancet Diabetes Endocrinal, 2014, 2:810-818.
Gabrielsen et al., "Adipocyte iron regulates adiponectin and insulin sensitivity". J Clin Invest. 2012, 122(10):3529-3540.
Gibson RA., "Australian fish—An excellent source of both arachidonic acid and ω-3 golyunsaturated fatty acids", Ligids 1983, 18(11):743-752.
Giunta et al., "Inflammaging as a prodrome to Alzheimer's disease", J Neuroinflammation 2008, 5:51; 15 pages.
Glauber et al., "Adverse metabolic effect of omega-3 fatty acids in non-insulin-dependent diabetes mellitus", Ann Intern Med. 1988, 108(5):663-668.
Gonzalez-Covarrubias et al., "Lipidomics of familial longevity". Aging Cell. 2013, 12(3):426-434.
Gonzalez-Covarrubias V., "Lipidomics in longevity and healthy aging". Biogerontology. 2013, 14(6):663-672.
Grundy et al., "Definition of metabolic syndrome: Report of the National Heart, Lung, and Blood Institute/American Heart Association conference on scientific issues related to definition", Circulation. 2004, 109(3):433-438.
Gunstone et al. [Eds.], "A review of even-chain fatty acid metabolism and the role of arachidic acid (C20:0) and lignoceric acid (C24:0) in health and disease", The Lipid Handbook, Gunstone et al. [Eds.] 3rd Edition, 2008, 604-635.
Hall et al., "Annual, seasonal and individual variation in hematology and clinical blood chemistry profiles in bottlenose dolphins (*Tursiops truncatus*) from Sarasota Bay, Florida", Comp Biochem Physiol A Mol Integr Physiol. 2007, 148(2):266-277.
HANNUN et al., "Principles of bioactive lipid signalling: lessons from sphingolipids", Nat Rev Mol Cell Biol. 2008, 9(2):139-150.
Hassanali et al., "Dietary supplementation of n-3 PUFA reduces weight gain and improves postprandial lipaemia and the associated inflammatory response in the obese JCR:LA-cp rat", Diabetes Obes Metab. 2010, 12(2):139-147.
Heneka et al., "Neuroinflammation in Alzheimer's Disease", Lancet Neurol. 2015, 14(4):388-405.
Hodson et al., "Fatty acid composition of adipose tissue and blood in humans and its use as a biomarker of dietary intake", Prog Lipid Res. 2008, 47:348-380.
Holmes et al., "Systemic inflammation and disease progression in Alzheimer disease". Neurology 2009, 73(10):768-774.
International Diabetes Federation (2006) The IDF consensus worldwide definition of the Metabolic Syndrome. Brussels, Belgium., in 24 pages.
Jaruvongvanich et al., "Outcome of phlebotomy for treating non-alcoholic fatty liver disease: a systematic review and meta-analysis". Sauid J Gastroenterol. 2016, 22(6):407-414.
Jenkins et al., "A Review of Odd-Chain Fatty Acid Metabolism and the Role of Pentadecanoic Acid (C15:0) and Heptadecanoic Acid (C17:0) in Health and Disease", Molecules (2015) 20(2):2425-2444.
Johnson et al., "Use of phlebotomy treatment in Atlantic bottlenose dolphins with iron overload". J Am Vet Med Assoc. 2009, 235(2):194-200.
Kanda et al., "MCP-1 contributes to macrophage infiltration into adipose tissue, insulin resistance, and hepatic steatosis in obeity", J Clin Invest. 2006, 116(6):1494-1505.
Kersten et al., "Roles of PPARs in health and disease", Nature. 2000, 405(6785):421-424.
Kiyota et al., "CCL2 Accelerates Microglia-Mediated Aβ Oligomer Formation and Progression of Neurocognitive Dysfunction". PLoS ONE. 2009, 4:e6197 in 12 pages.

(56) References Cited

OTHER PUBLICATIONS

Klock et al.,"Sodium ascorbyl phosphate shows in vitro and in vivo efficacy in the prevention and treatment of acne vulgaris", International Journal of Cosmetic Science, 2005, 27(3):171-176.
Krachler et al., "Fatty Acid Profile of the Erythrocyte Membrane Preceding Development of Type 2 Diabetes Mellitus", Nutri Metabol Cardiovasc Diseases, (2008) 18(7):503-510.
Kratz et al., "Dairy fat intake is associated with glucose tolerance, hepatic and systemic insulin sensitivity, and liver fat but not β-cell function in humans", Am J Clin Nutr. 2014, 99(6):1385-1396.
Kristal et al., "Metabolomics: Opening Another Window into Aging". Sci Aging Knowledge Environ. 2005, 26:pe19 in 2 Pages.
Kühn et al., 2012, "Effect of Multipeak Spectral Modeling of Fat for Liver Iron and Fat Quantification: Correlation of Biopsy with MR Imaging Results". Radiology. 2012, 265(1):133-142.
LaBrecque et al., "World Gastroenterology Organisation global guidelines: Nonalcoholic fatty liver disease and nonalcoholic steatohepatitis". J Clin Gastroenterol. 2014, 48(6):467-473.
Lagerstedt et al., "Quantitative determination of plasma c8-c26 total fatty acids for the biochemical diagnosis of nutritional and metabolic disorders", Mol Genet Metab. 2001, 73(1):38-45.
Lai et al., "The protective effects and genetic pathways of thorn grape seeds oil against high glucose-induced apoptosis in pancreatic beta-cells", BMC Complement Altern Med. 2014, 14:10 (7 pages).
Lee et al., "PPARα and glucocorticoid receptor synergize to promote erythroid progenitor self-renewal", Nature 2005, 522:474-477.
Lefebvre et al., "Antifibrotic Effects of the Dual CCR2/CCR5 Antagonist Cenicriviroc in Animal Models of Liver and Kidney Fibrosis". PLoS ONE. 2016. 11(6):e0158156 in 19 pages.
Leyton et al., "Differential oxidation of saturated and unsaturated fatty acids in vivo in the rat". Br J Nutr. 1987, 57(3):383-393.
Liao et al., "Pioglitazone and cardiovascular outcomes in patients with insulin resistance, pre-diabetes and type 2 diabetes: a systematic review and meta-analysis". BMJ Open. 2017, 7(1):e013927 in 13 pages.
Liu et al., "Serum biomarkers for nonalcoholic fatty liver disease: Are we there yet?", Hepatology. 2017, 65(1):8-11.
Livrea et al., "Oxidative stress and antioxidant status in B-thalassemia major: iron overload and depletion of lipid-soluble antioxidants." Blood. 1996, 88(9):3608-3614.
Loomba et al., "The ASK1 inhibitor selonsertib in patients with nonalcoholic steatohepatitis: A randomized, phase 2 trial". Hepatology. 2018, 67(2):549-559; avail online Dec. 2017; in 11 pages.
Luquet et al., "Roles of PPAR δ in lipid absorption and metabolism: a new target for the treatment of type 2 diabetes", Biochim Biophys Acta. 2005, 1740:313-317.
Luzia et al., "The influence of season on the lipid profiles of five commercially important species of Brazilian fish", Food Chem. 2003, 83(1):93-97.
Ma et al., "Organization of the mammalian metabolome according to organ function, lineage specialization, and longevity". Cell Metab. 2015, 22(2):332-343.
Madsen et al., "Tetradecylthioacetic acid prevents high fat diet induced adposity and insulin resistance", J Lipid Res. 2002, 43:742-750.
Magnusdottir et al., "Plasma alkylresorcinols C17:0/C21:0 ratio, a biomarker of relative whole-grain rye intake, is associated to insulin sensitivity: a randomized study", Eur J Clin Nutr. 2014, 68(4):453-458.
Månsson H.L., "Fatty acids in bovine milk fat". Food Nutr Res. 2008, 52:4 in 3 pages.
Martin-Jiménez et al., Relationship between obesity, Alzheimer's disease, and Parkinson's disease: an astrocentric View. Publ. online Oct. 28, 2016; Mol Neurobiol. 2017, 54(9):7096-7115.
Maruyama et al., "Differences in Serum Phospholipid Fatty Acid Compositions and Estimated Desaturase Activities Between Japanese Men With and Without Metabolic Syndrome", J Atheroscler Thromb. 2008, 15(6):306-313.
Mayneris-Perxachs et al., "Plasma fatty acid composition, estimated desaturase activities, and their relation with the metabolic syndrome in a population at high risk of cardiovascular disease". Clinical Nutrition. 2013, HTTP://dx.doi.org/10.1016/j.clnu.2013.03.001.
Mayo Clinic, Asthma, 2017, https://www.mayoclinic.org/diseases-conditions/asthma/basics/treatment/con-20026992 in 6 pages.
Mayo Clinic, Cholesterolgallstones, 2017, https://www.mayoclinic.org/diseases-conditions/gallstones/diagnosis-treatment/drc-20354220 in 3 pages.
Mazzaro et al., "Iron indices among bottlenose dolphins (*Tursiops truncatus*)". Comp Med. 2012, 62(6):508-515.
McGeer et al., "Inflammation, Antiinflammatory Agents, and Alzheimer's Disease: The Last 22 Years". J Alzheimers Dis. 2016, 54(3):853-857.
McGowen M., "Dolphin genome provides evidence for adaptive evolution of nervous system genes and a molecular rate slowdown", Proc Biol Sci. 2012, 279(1743):3643-3651.
McMurchie E.J., "Dietary lipids and the regulation of membrane fluidity and function". Publisher: Alan R. Liss, Inc.; Physiol Req Memb Fuid. 1988, 189-237.
Mennen et al., "Possible protective effect of bread and dairy products on the risk of the metabolic syndrome", Nutrition Res. 2000, 20(3):335-347.
Mi, "Myocardial Infarction", 2017, MedlinePlus Medical Encyclopedia; URL: <https://medlineplus.gov/ency/article/000195.htm> in 7 pages.
Montoliu et al., Serum profiling of healthy aging identifies phosphor- and sphingolipid sgecies as markers of human longevity. Aging (Albany NY). 2014, 6(1):9-25.
Morsy et al., "Can eicosapentaenoic acid maintain the original ribavirin dose or affect the response during the treatment course of chronic hepatitis C virus (HCV) patients?", Turk J Gastroenterol. 2016, 27:55-61.
Nanji et al., "Dietary saturated fatty acids reverse inflammatory and fibrotic changes in rat liver despite continued ethanol administration." J Pharmacol Exp Ther. 2001, 299(2):638-644.
Nelson et al., "Relationship between the pattern of hepatic iron deposition and histologic severity in nonalcoholic fatty liver disease". Hepatology. 2011, 53(2):448-457.
Nestel et al., Specific plasma lipid classes and phospholipid fatty acids indicative of dairy food consumption associate with insulin sensitivity. Am J Clin Nutr., 2014, 99(1):46-53.
Nestel P., "Trans fatty acids: are its cardiovascular risks fully appreciated?". Clin Ther. 2014, 36(3):315-321.
Neuschwander-Tetri et al., "Farnesoid X nuclear receptor ligand obeticholic acid for non-cirrhotic, non-alcoholic steatohepatitis (FLINT): a multicentre, randomised, placebo-controlled trial". Lancet. 2015, 385(9972):956-965. 956-965.
Novgorodtseva et al., "Composition of fatty acids in plasma and erythrocytes and eicosanoids level in patients with metabolic syndrome". Lipids Health Dis. 2011, 10:82 in 5 pages.
Novgorodtseva et al., "Modification of fatty acids composition in erythrocytes lipids in arterial hypertension associated with dyslipidemia". Lipids Health Dis. 2011, 10:18 in 5 pages.
Ojala et al., "Expression of interleukin-18 is increased in the brains of Alzheimer's disease patients". Neurobiol Aging. 2009, 30(2):198-209.
Otogawa et al., "Erythrophagocytosis by Liver Macrophages (Kupffer Cells) Promotes Oxidative Stress, Inflammation, and Fibrosis in a Rabbit Model of Steatohepatitis: Implications for the Pathogenesis of Human Nonalcoholic Steatohepatitis". Am J Pathol. 2007, 170(3):967-980.
Özogul et al., Fatty acid profiles and fat contents of commercially important seawater and freshwater fish species of Turkey: A comparative study. Food Chem. 2007, 103:217-223.
Panee J., "Monocyte Chemoattractant Protein 1 (MCP-1) in Obesity and Diabetes", Cytokine. (2012) 60(1):1-12.
Patel et al., "Fatty acids measured in plasma and erythrocyte-membrane phospholipids and derived by food-frequency questionnaire and the risk of new-onset type 2 diabetes: a pilot study in the European Prospective Investigation into Cancer and Nutrition (EPIC)-Norfolk cohort". Am J Clin Nutri. 2010, 92(5):1214-1222.
Penckofer et al., "Oxidative stress and cardiovascular disease in type 2 diabetes: the role of antioxidants and prooxidants". J Cardiovasc Nurs. 2002, 16(2):68-85.

(56) References Cited

OTHER PUBLICATIONS

Pereira et al., "Dairy consumption, obesity, and the insulin resistance syndrome in young adults: the CARDIA study", JAMA. 2002, 287(16):2081-2089.
Perry VH., "Contribution of systemic inflammation to chronic neurodegeneration". Acta Neuropathol. 2010, 120(3):277-286.
Pfeuffer et al., "Milk and the metabolic syndrome", Obes Rev. 2007, 8(2):109-118.
Pfeuffer et al., "Pentadecanoic and Heptadecanoic Acids: Multifaceted Odd-Chain Fatty Acids", Adv Nutr. 2016, 7:730-734.
Pietrangelo A. "Iron in Nash, chronic liver diseases and HCC: how much iron is too much?", J Hepatol. 2009, 50(2):249-251.
Popp-Snijders et al., "Dietary supplementation of omega-3 polyunsaturated fatty acids improves insulin sensitivity in non-insulin-dependent diabetes", Diabetes Res 1987, 4(3):141-147.
Profenno et al., "Meta-analysis of Alzheimer's disease risk with obesity, diabetes, and related disorders", Biol Psychiatry. 2010, 67(6):505-512.
Qin et al., "Peroxisome proliferator-activated receptor-6 induces insulin-induced gene-1 and suppresses hepatic lipogenesis in obese diabetic mice", Hepatology, 2008, 48(2):432-441.
Ramírez et al., "Absorption and distribution of dietary fatty acids from different sources". Early Hum Develop. 2001, 65(Suppl):S95-S101.
Ratziu V., "Novel pharmacotherapy options for Nash". Dig Dis Sci. 2016, 61(5):1398-1405.
Ratziu et al., "Elafibranor, an agonist of the peroxisome proliferator-activated receptor-α and -δ, induces resolution of nonalcoholic steatohepatitis without fibrosis worsening". Gastroenterology. 2016, 150(5):1147-1159.
Robinson et al., "N-3 polyunsaturated fatty acids: relationship to inflammation in healthy adults and adults exhibiting features of metabolic syndrome." Lipids. 2013, 48(4):319-332.
Ross et al., "CHF5074 reduces biomarkers of neuroinflammation in patients with mild cognitive impairment: a 12-week, double-blind, placebo-controlled study". Curr Alzheimer Res. 2013, 10(7):742-753.
Ruidavets et al., "High consumptions of grain, fish, dairy products and combinations of these are associated with a low prevalence of metabolic syndrome", J Epidemiol Community Health, 2007, 61(9):810-817.
Safadi et al., "The fatty acid-bile acid conjugate Aramchol reduces liver fat content in patients with nonalcoholic fatty liver disease". Clin Gastroenterol Hepatol. 2014, 12(12):2085-2091.
Salameh et al., "Insulin resistance, dyslipidemia, and apolipoprotein E interactions as mechanisms in cognitive impairment and Alzheimer's disease", Exp Biol Med (Maywood). 2016, 241(15):1676-1683.
Sanches et al., "Nonalcoholic Steatohepatitis: a Search for Factual Animal Models". Biomed Res Int. 2015, doi: [10.1155/2015/574832] in 13 pages.
Sandrou et al., "Low-fat/calorie foods: current state and perspectives", Crit Rev Food Sci Nutr. 2000, 40(5):427-447.
Sarikurkcu et al., "Screening of Possible In Vitro Neuroprotective, Skin Care, Antihyperglycemic, and Antioxidative Effects of *Anchusa undulata* L. subsp. *hybrida* (Ten.) Coutinho from Turkey and Its Fatty Acid Profile", International J Food Proper. 2015, 18(7):1491-1504.
Sarikurkcu et al., Publication date, 2019, email dated Jun. 18, 2019 in 19 pages.
Schmeda-Hirschmann et al., Anti-inflammatory activity of animal oils from the Peruvian Amazon. J Ethnopharmacol. 2014, 156:9-15.
Seki et al., "Eicosapentaenoic Acid (EPA) Attenuates the Anemia Due to Ribavirin/Interferon a Treatment in Patients with Chronic Hapatitis C", 2004, 3199 in 4 pages.
Sindhu et al., "Obesity Is a Positive Modulator of IL-6R and IL-6 Expression in the Subcutaneous Adipose Tissue: Significance for Metabolic Inflammation". PLoS ONE. 2015, 10(7):e0133494 in 17 pages.

Slifka KA. KA., Comparative diet analysis of fish species commonly consumed by managed and free-ranging bottlenose dolphins (*Tursiops truncatus*). Int J Vet Med. (2013) 10:1.
Sobolesky et al., "Feeding a Modified Fish Diet to Bottlenose Dolphins Leads to an Increase in Serum Adiponectin and Sphingolipids", Front Endocrinol. 2016, 7:33 in 11 pages.
Sorrentino et al., "Liver iron excess in patients with hepatocellular carcinoma developed on non-alcoholic steato-hepatitis". J Hepatol. 2009, 50(2):351-357.
Spyridaki et al., (2016) Obesity, inflammation and cognition. Curr Opin Behav Sci. 2016, 9: 169-175.
Stephenson et al., "Building a Roadmap for Developing Combination Therapies for Alzheimer's Disease", Expert Rev Neurother. 2015, 15(3):327-333.
Suresh et al., "Protective action of arachidonic acid against alloxan-induced cytotoxicity and diabetes mellitus". Prostaglandins Leukot Essent Fatty Acids, 2001, 64(1):37-52.
Swaminathan et al., "The role of iron in diabetes and its complications", Diabetes Care. 2007, 30(7):1926-1933.
Targher et al., "Risk of Cardiovascular Disease in Patients with Nonalcoholic Fatty Liver Disease", N Engl J Med., 2010, 363:1341-1350.
Tucsek et al., "Obesity in Aging Exacerbates Blood-Brain Barrier Disruption, Neuroinflammation, and Oxidative Stress in the Mouse Hippocampus: Effects on Expression of Genes Involved in Beta-Amyloid Generation and Alzheimer's Disease", J Gerontol A Biol Sci Med Sci. 2014, 69(10):1212-1226; publ. online Nov. 11, 2013.
Unnikrishnan et al., "Antiinflammatory activity of methionine, methionine sulfoxide and methionine sulfone". Agents Actions. 1990, 31(1-2):110-112.
Valenti et al., "Iron depletion by phlebotomy improves insulin resistance in patients with nonalcoholic fatty liver disease and hyperferritinemia: evidence from a case-control study". Am J Gastroenterol. 2007, 102(6):1251-1258.
Valenti et al., "[769] Iron Depletion by phlebotomy improves insulin resistance in patients with nonalcoholic fatty liver disease and hyperferritinemia: evidence from a case-control study", J Hepatol. (Apr. 2007) 46:S288-S289.
Valenti et al., "A randomized trial of iron depletion in patients with nonalcoholic fatty liver disease and hyperferritinemia". World J Gastroenterol. 2014, 20(11):3002-3010.
Van Eldik et al., The roles of inflammation and immune mechanisms in Alzheimer's disease. Alzheimers Dement (N.Y.), 2016, 2(2):99-109.
Venn-Watson et al., "Big brains and blood glucose: common ground for diabetes mellitus in humans and healthy dolphins", Comp Med., 2007, 57(4):390-395.
Venn-Watson et al., "Assessment of increased serum aminotransferases in a managed Atlantic bottlenose dolphin (*Tursiops truncatus*) population", J Wildlf Dis. 2008, 44(2):318-330.
Venn-Watson et al., "Dolphins as animal models for type 2 diabetes: sustained, post-prandial hyperglycemia and hyperinsulinemia", Gen Comp Endocrinol. 2011, 170(1):193-199.
Venn-Watson et al., Physiology of aging among healthy, older bottlenose dolphins (*Tursiops truncatus*): comparisons with aging humans. J Comp Phys B. 2011, 181(15):667-680.
Venn-Watson et al., "Hemochromatosis and fatty liver disease: building evidence for insulin resistance in bottlenose dolphins (*Tursiops truncatus*)." J Zoo Wildl Med. 2012, 43(3 Suppl):S35-S47.
Venn-Watson et al., "Blood-Based Indicators of Insulin Resistance and Metabolic Syndrome in Bottlenose Dolphins (*Tursiops truncatus*)", Front Endocrinol (Lausanne) 2013, 4:136 in 8 pages.
Venn-Watson et al., Associations of ceruloplasmin and haptoglobin with inflammation and glucose in bottlenose dolphins (*Tursiops truncatus*) J Comp Clin Path. 2014, 23(4):1031-1036.
Venn-Watson S., "Dolphins and Diabetes: Applying One Health for breakthrough discoveries". Front Endocrinol (Lausanne); 2014, 5:227 in 2 pages.
Venn-Watson et al., "Investigation of Fish-Based Nutrients to Protect Against Metabolic Syndrome In Bottlenose Dolphins (*Tursiops Truncatus*)", presentation at International Association for Aguatic Animal Medicine (IAAAM), Gold Coast, Australia, May 2014.

(56) References Cited

OTHER PUBLICATIONS

Venn-Watson et al., "Adrenal Gland and Lung Lesions in Gulf of Mexico Common Bottlenose Dolphins (*Tursiops truncatus*) Found Dead following the Deepwater Horizon Oil Spill". PLoS ONE 2015 10(5):e0126538 in 23 pages.
Venn-Watson et al., "Evaluation of annual survival and mortality rates and longevity of bottlenose dolphins (*Tursiops truncatus*) at the United States Navy Marine Mammal Program from 2004 through 2013", J Am Vet Med. 2015, 246(8):893-898.
Venn-Watson et al., "Increased Dietary Intake of Saturated Fatty Acid Heptadecanoic Acid (C17:0) Associated with Decreasing Ferritin and Alleviated Metabolic Syndrome in Dolphins", PLoS ONE, 2016, 10(7):e0132117 in 17 pages.
Wang et al., "Obesity modifies the relations between serum markers of dairy fats and inflammation and oxidative stress among adolescents." Obesity (Silver Spring), 2011, 19(12):2404-2410.
Warensjö et al., "Biomarkers of milk fat and the risk of myocardial infarction in men and women: a prospective, matched case-control study." Am J Clin Nutr. (2010) 92(1):194-202.
Weiss et al., "Anemia of chronic disease." New Engl J Med. 2005, 352:1011-1023.
Wells et al., "Bottlenose dolphins as marine ecosystem sentinels: developing a health monitoring system", EcoHealth 2004, 1:246-254.
Wells et al., "Evaluation of Potential Protective Factors Against Metabolic Syndrome in Bottlenose Dolphins: Feeding and Activity Patterns of Dolphins in Sarasota Bay, Florida", Front Endocrinol (Lausanne), 2013, 4:139 in 16 pages.
Wlazlo et al., Iron metabolism is associated with adipocyte insulin resistance and plasma adiponectin. Diabetes Care, 2012, 36(2):309-315.
Wu et al., "Alterations of the Neuroinflammatory Markers IL-6 and TRAIL in Alzheimer's Disease", Dement Geriatr Cogn Dis Extra. 2015, 5(3):424-434.
Xu et al., "Molecular Recognition of Fatty Acids by Peroxisome Proliferator-Activated Receptors", Mol Cell. 1999, 3:397-403.
Zandman-Goddard et al., "Hyperferritinemia in autoimmunity". IMAJ, 2008, 10: 83-84.
Zandman-Goddard et al., "Ferritin in autoimmune diseases". Autoimmunity Rev. 2007, 6:457-463.
Zhao et al., Body iron stores and heme-iron intake in relation to type 2 diabetes: a systematic review and meta-analysis. PLoS ONE 2012, 7:e41641.
Partial International Search Report dated Nov. 26, 2018 for PCT/US2018/056545.
International Search Report and Written Opinion dated Feb. 7, 2019 for PCT/US2018/056545.
International Search Report and Written Opinion dated Jul. 24, 2019 for PCT/US2019/032274.
International Search Report and Written Opinion dated Sep. 27, 2019 for PCT/US2019/033175.
Yamano et al., "A long-term high-fat diet changes iron distribution in the body, increasing iron accumulation specifically in the mouse spleen.". J Nutr Sci Vitaminol. (Tokyo) 2015, 61(1):20-27.
Aleshin et al. Peroxisome proliferator-activated receptor (PPAR)β/δ, a possible nexus of PPARα- and PPARγ-dependent molecular pathways in neurodegenerative diseases: review and novel hypotheses. Neurochem Int. (2013) 63:322-330.
Barba et al., Alzheimer's disease beyond the genomic era: nuclear magnetic resonance (NMR) spectroscopy-based metabolomics. J Cell Mol Med. 2008. 12(5a): 1477-1485.
Bhargava et al., "Metabolic alterations in multiple sclerosis and the impact of vitamin D supplementation", JCI Insight. 2017, 2(19): 1-13.
Bogdanov et al., "Metabolomic profiling to develop blood biomarkers for Parkinson's disease", Brain 2008. 131(2): 389-396.
Bonomo et al., "Iron overload potentiates diet-induced hypercholesterolemia and reduces liver PPAR- αexpression in hamsters". J Biochem Mol Toxicol. (2012) 26(6): 224-229.
Borodina et al., "The biology of ergothioneine, an antioxidant nutraceutical". Nutri Res Reviews (2020) 33: 190-217.
Chiba et al., Topical application of PPARα (but not β/δ or γ) suppresses atopic dermatitis in NC/Nga mice. Allergy (2012) 67: 936-942.
Choi et al., The nuclear receptor PPARs as important regulators of T-cell functions and autoimmune diseases. Mol Cell. (2012) 33(3): 217-222.
Database WPI, "Pentadecanoic acid compound", Clarivate Analytics, AN: 2017-637713. Clarivate Analytics, dated: Jul. 2017; 2 pages.
Database WPI, "Immunosuppressive agent . . . ", AN: 1994-238645. Clarivate Analytics, dated: 1994; 2 pages.
Database WPI, "An effective Saururus chinensisrhizome part . . . ", AN: 2012-890946, Clarivate Analytics, dated: 2012; 2 pages.
Database WPI, "An anti-aging composition . . . ", AN: 2004-310751, Clarivate Analytics, dated: 2004; 2 pages.
Durzan D.J., "Arginine, scurvy and Cartier's tree of life". J Ethnobio Ethnomed. 2009. 5(1): 1-16.
Ghannadi et al., "An Investigation of the Analgesic and Anti-Inflammatory Effects of Nigella sativa Seed Polyphenols", J Med Food. 2005, 8(4): 488-493.
Hosokawa et al., "Fucoxanthin induces apoptosis and enhances the antiproliferative effect of the PPARγ ligand, troglitazone, on colon cancer cells. BBA Gen Subj. (2004) 675: 113-119.
Hwang et al., "Inhibitory Effects of 4-Guanidinobutyric Acid against Gastric Lesions", Biomol Ther. 2012, 20(2): 239-244.
Janani et al., PPAR gamma gene—a review. Diab Metab Synd Clin Res Rev. (2015) 9: 46-50.
Jeon et al., "S-adenosylhomocysteine treatment of adult female fibroblasts alters X-chromosome inactivation and improves in vitro embryo development after somatic cell nuclear transfer", Reproduction, (2008) 135: 815-828.
Jové et al. Metabolomics of human brain aging and age-related neurodegenerative diseases. J Neuropathol Exp Neurol. 2014, 73(7): 640-657.
Kaddurah-Daouk, et al., Metabolomics: A global biochemical approach to the study of central nervous system diseases. Neuropsychopharmacol 2009. 34(1): 173-186.
Leibovitz et al., PPAR activation: a new target for the treatment of hypertension. J Cardio Pharmacol. (2007) 50: 120-125.
Madrazo et al., The PPAR trio: Regulators of myocardial energy metabolism in health and disease. J Mol Cell Cariol. (2008) 44: 968-975.
Milam et al., PPAR-γ agonists inhibit profibrotic phenotypes in human lung fibroblasts and bleomycin-induced pulmonary fibrosis. Am J Physiol Lung Cell Mol Physiol. (2008) 94: L891-L901.
Nilsson S., "Long-term treatment with methenamine hippurate in recurrent urinary tract infection", Acta Med Scand. (1975) 198(1-2): 81-85.
Pubchem. CID 325395, Mar. 26, 2005; pp. 1-13; retrieved from the Internet <URL: https://pubchem.ncbi.nlm.nih.gov//compound/325395>.
Salek et al., A metabolomic study of the CRND8 transgenic mouse model of Alzheimer's disease. Neurochem Int. 2010. 56(8): 937-947
Sertznig et al., Peroxisome proliferator-activated receptors (PPARs) and the human skin. Am J Clin Dermatol. (2008) 9: 15-31.
Shaw C., "Possible Modulation by Glutathione of Glutamatergic", in Glutathione in the Nervous System, CRC Press, 1998. Chapter 7, pp. 140-142.
Sokolowska et al., Peroxisome proliferator-activated receptor gamma (PPAR-gamma) and their role in immunoregulation and inflammation control. Postepy Higieny (2005) 59: 472-484; Abstract in 2 pages.
Sotgia et al., "Hercynine content in widely consumed commercial beverages". LWT Food Science Tech. Dec. 1, 2018;98: 465-469.
Trifilieff et al., PPAR-α and -γ but not -δ agonists inhibit airway inflammation in a murine model of asthma: in vitro evidence for an NF-kβ-independent effect. Br J Pharmacol. (2003) 139: 163-171.

(56) References Cited

OTHER PUBLICATIONS

Trushina et al., Identification of altered metabolic pathways in plasma and CSF in mild cognitive impairment and Alzheimer's disease using metabolomics. PLoS ONE 2013. 8(5): e63644 in 13 pages.
Trushina et al., Recent advances in the application of metabolomics to Alzheimer's disease. Bioch Biophy Acta. 2014.1842(8): 1232-1239.
Wei et al., Peroxisome proliferator-activated receptor γ: innate protection from excessive fibrinogenesis and potential therapeutic target in systemic sclerosis. Curr Opin Rheumatol. (2010) 22(6): 671-676.
Anderson et al., "Cholesterol and mortality: 30 years of follow-up from the Framingham Study." JAMA (1987) 257(16): 2176-2180.
Barcellini et al., "Clinical Applications of Hemolytic Markers in the Differential Diagnosis and Management of Hemolytic Anemia". Disease Markers (2015) Article ID 635670 in 7 pages.
Bartke et al., "Bioactive sphingolipids: metabolism and function". J Lipid Res. (2009) 50(Suppl):S91-S96.
Camaschella C., "Iron-Deficiency Anemia", New Engl J Med. (2015) 372(19):1832-1843.
Fujiwara et al., "Biology of Heme in mammalian Erythroid Cells and Related Disorders". BioMed Res Int'l. (2015) Article ID 278536 in 9 pages.
Ghosh et al., "PAI-1 in tissue fibrosis." J Cell Physiol. (2011) 227(2):493-507.
Hallgren et al., "Lymphocyte phytohemagglutinin responsiveness, immunoglobulins and autoantibodies in aging humans." J Immunol. (1973) 111:1101-1107.
Hebbel et al., A Systems Biology Consideration of the Vasculopathy of Sickle Cell Anemia: The Need for Multi-Modality Chemo-Prophylaxis, Cardiovsc Hematol Disord Drug Targets (200() 9(4):271-291.
Hodge et al., "Plasma phospholipid and dietary fatty acids as predictors of type 2 diabetes: Interpreting the role of linoleic acid."Am J Clin Nutrition (2007) 86(1): 189-197.
Kratz et al., The relationship between high-fat dairy consumption and obesity, cardiovascular, and metabolic disease. Eur J Nutr. (2013) 52: 1-24.
Kriesberg et al., Cholesterol metabolism and aging, Am J Med. (1987) 82: 54-60.
Meikle et al., "Plasma Lipid Profiling Shows Similar Associations with Prediabetes and Type 2 Diabetes". PloS one, 2013, 8(9), e74341; 43 pages.
Miyake et al., "Maternal consumption of dairy products, calcium, and vitamin D during pregnancy and infantile allergic disorders." Ann Allergy Asthma Immunol. (2014) 113(1): 82-87. (Abstract p. S224).
Oberley et al., "Laboratory testing for cobalamin deficiency in megaloblastic anemia". Am J Hematol. (2013) 88(6):522-524.
Perry et al., "Microglia and macrophages of the central nervous system: the contribution of microglia priming and systemic inflammation to chronic neurodegeneration". Semin Immunopathol. (2013) 35:601-612.
Targher et al., "Elevated levels of interleukin-6 in young adults with type 1 diabetes without clinical evidence of microvascular and macrovascular complications". Diabetes Care (2001) 24(5):956-957.
Yin et al., "Concurrent Epstein-Barr virus associated NK/T cell lymphoma after immunosuppressive therapy for aplastic anemia: report of a case and review of literature". Int'l J Clin Exper Pathol. (2015) 8(6):7588 in 6 pages.
Ballatore et al., "Carboxylic Acid (Bio)Isosteres in Drug Design". ChemMedChem. 2013, 8(3):385-395.
Partial European Search Report dated Apr. 13, 2021 for Application No. 18870336.7.
Aglago et al., Association between serum phospholipid fatty acid levels and adiposity in Mexican women. J Lipid Res. Jul. 1, 2017;58(7): 1462-1470.
Ananthakrishnan et al., Inflammatory bowel disease in the elderly is associated with worse outcomes: a national study of hospitalizations. Inflamm Bowel Dis. Feb. 1, 2009;15(2): 182-189.
Bartzokis et al., Brain ferritin iron may influence age- and gender-related risks of neurodegeneration. Neurobiol Aging. Mar. 1, 2007;28(3): 414-423.
Baum et al., Drug utilization in the U.S .—1985: Seventh annual review. Rockville, MD: Food and Drug Administration, Center for Drugs and Biologies. Dec. 1986 .; TOC in 4 pages.
Beanes et al., Down-regulation of decorin, a transforming growth factor-beta modulator, is associated with scarless fetal wound healing. J Pediatr Surg. Nov. 1, 2001;36(11): 1666-1671.
Bielec et al., Homologies between human and dolphin chromosomes detected by heterologous chromosome painting. Cytogen Genome Res. 1998;81(1): 18-25.
Bialek et al., "Fatty acid composition and oxidative characteristics of novel edible oils in Poland". CyTA-Journal of Food. Jan. 2, 2017;15(1): 1-8; (published online Jul. 13, 2016).
CAS Database Accession No. 1989:205056; "Relationship between structure and anticonvulsant activities of 2-substituted 3-pyrazolidinones". DU et al., Jun. 10, 1989; 2 pages.
Chaudhari et al., Increased mitochondrial fusion allows the survival of older animals in diverse C. elegans longevity pathways. Nat Commun. Aug. 3, 2017;8(1): 182 in 16 pages.
Chebib et al., "Guanidino acids act as p1 GABAC receptor antagonists". Neurochem Res. Apr. 23, 2009; 34(10): 1704-1711.
Coccia et al., IL-1β mediates chronic intestinal inflammation by promoting the accumulation of IL-17A secreting innate lymphoid cells and CD4+ Th17 cells. J Exp Med. Aug. 2, 20127;209(9): 1595-1609.
Cordaro et al., "2-Pentadecyl-2-Oxazoline reduces neuroinflammatory environment in the MPTP Model of Parkinson Disease". Mol Neurobiol. Dec. 2018;55(12): 9251-9266.
De Martinis et al., Allergy and aging: an old/new emerging health issue. Aging and Dis. Apr. 2017;8(2): 162-175.
Deng et al., Cross-talk between mitochondrial fusion and the hippo pathway in controlling cell proliferation during drosophila development. Genetics Aug. 1, 2016; 203(4): 1777-1788.
Farage et al., Characteristics of the aging skin. Adv Wound Care. Feb. 1, 2013;2(1): 5-10.
Franceschi et al., Chronic Inflammation (Inflammaging) and Its Potential Contribution to Age-Associated Diseases. J Gerontol. Jun. 2014; 69(suppl 1): S4-S9.
Fu et al., Oleylethanolamide regulates feeding and body weight through activation of the nuclear receptor PPAR-α. Nature. Sep. 4, 2003;425(6953): 90-93.
Gao et al., "In vitro evaluation of dual agonists for PPARγ/β from the flower of Edgeworthia gardneri (wall.) Meisn". J Ethnopharma.. Mar. 13, 2015;162: 14-19.
Goncalves et al., "Fenofibrate prevents skeletal muscle loss in mice with lung cancer". PNAS. Jan. 23, 2018;115(4): E743-E752.
Greenberg et al., "Omega-3 fatty acid supplementation during pregnancy". Rev Obstet Gynecol. 2008;1(4): 162-169.
Gregg et al., Trends in lifetime risk and years of life lost due to diabetes in the USA, 1985-2011: A modelling study. Lancet Diab Endocrinol. Nov. 1, 2014;2(22): 867-874.
Gunn-Moore et al., Alzheimer's disease in humans and other animals: a consequence of postreproductive life span and longevity rather than aging. Alzheimer's & Dementia. Feb. 1, 2018;14(2): 195-204.
Hayaishi O., Molecular mechanisms of sleep-wake regulation: roles of prostaglandins D2 and E2. Faseb J. Aug. 1991;5(11): 2575-2581.
Hirose et al., Age-associated increases in heme oxygenase-1 and ferritin immunoreactivity in the autopsied brain. Legal Med. Mar. 1, 2003;5: S360-366.
Iwakura et al., The roles of IL-17A in inflammatory immune responses and host defense against pathogens. Immun Rev. Dec. 2008;226(1): 57-79.
Jubie et al., "Design, synthesis and antidepressant activities of some novel fatty acid analogues". Med Chem Res. Apr. 2015;24(4): 1605-1616.
Kirkham T.C., Endocannabinoids in the regulation of appetite and body weight. Behav Pharmacol. Sep. 1, 2005;16(5-6): 297-313.

(56) References Cited

OTHER PUBLICATIONS

Kohnken et al., "Overview of the use of murine models in leukemia and lymphoma research", Front Oncol. Feb. 20, 2017;7:22 in 11 pages.
Larsen et al., "Sulfur-substituted and a-methylated fatty acids as peroxisome proliferator-activated receptor activators". Lipids. Jan. 2005;40(1): 49-57.
Lee et al., A current review of molecular mechanisms regarding osteoarthritis and pain. Gene Sep. 25, 2013;527(2): 440-447.
Liechty K.W., Diminished interleukin-8 (IL-8) production in the fetal wound healing response. J Surg Res. Jun. 1, 1998;77(1): 80-84.
Lim et al., The global impact of hepatic fibrosis and end-stage liver disease. Clinics in Liver Dis. Nov. 1, 2008;12(4): 733-746.
López-Ótin et al., "The Hallmarks of Aging", Cell Jun. 6, 2013;153(6):1194-1217.
Lyu et al., Association between anemia and 3-year all-cause mortality among oldest old people in longevity areas in China. Zhonghua Liuxingbingxue Zazhi. Jul. 1, 2015;36(7): 682-686.
Maeda T., Current topics on basic research for methamphetamine dependence and psychosis. J Wakayama Med. Soc., 2010, vol. 61, pp. 36-41.
Meglasson et al., Antihyperglycemic action of guanidinoalkanoic acids: 3-Guanidinopropionic Acid Ameliorates Hyperglycemia in Diabetic KKA/\ y and C57BL6J ob/ob Mice and Increases Glucose Disappearance in Rhesus Monkeys. J Pharm Exp Thera. Sep. 1, 1993;266(3): 1454-1462.
Mihalik et al., "Increased levels of plasma acylcarnitines in obesity and type 2 diabetes and identification of a marker of glucolipotoxicity". Obesity Sep. 2010; 18(9): 1695-1700.
Monjan et al., Incidence of chronic insomnia associated with medical and psychosocial factors: an epidemiologic study among older persons. Sleep Res. Jun. 1996;25: 108.
Murphy et al., The origin of human chromosome 1 and its homologs in placental mammals. Genome Res. Aug. 1, 2003;13(8): 1880-1888.
Novelle et al., Metformin: A hopeful promise in aging research. CSH Persp Med. Mar. 1, 2016;6(3): a025932 in 13 pages.
Pamplona et al., Increased oxidation, glycoxidation, and lipoxidation of brain proteins in prion disease. Free Radical Biol Med. Oct. 15, 2008;45(8): 1159-1166.
Paolisso et al., Low insulin resistance and preserved B-cell function contribute to human longevity but are not associated with TH-INS genes. Exp Gerontol. Dec. 1, 2001; 37(1):147-156.
Patel et al., Prevalence and impact of pain among older adults in the United States: Findings from the 2011 National Health and Aging Trends Study. Pain Dec. 1, 2013;154(12): 2649-2657.
Perreault et al., PPARδ agonism for the treatment of obesity and associated disorders: Challenges and opportunities. PPAR Res. 2008;2008: Article ID125387; in 9 pages.
Perrone et al., Selective COX01 inhibition: A therapeutic target to be reconsidered. Curr Med Chem. Nov. 1, 2010;17(32): 3769-3805.
Quintanilla et al., "Role of PPARγ in the Differentiation and Function of Neurons", Hindawi Publ. Corp. 2014; Article ID 768594 in 10 pages.
Sgnoc et al., Age-related aspects of cutaneous wound healing: a mini review. Gerontol. 2013;59(2): 159-164.
Shamburek et al., Disorders of the digestive system in the elderly. New Engl J Med. Feb. 1, 19905;322(7): 438-443.
Song et al., Hippocampal PPARα is a novel therapeutic target for depression and mediates the antidepressant actions of fluoxetine in mice, Br J Pharmacol. Jul. 2018; 175(14): 2968-2987.
Vaarhorst et al., Lipid metabolism in long-lived families: the Leiden Longevity Study. Age. Jun. 2011;33(2): 219-227.
Venn-Watson et al., Efficacy of dietary odd-chain saturated fatty acid pentadecanoic acid parallelsbroad associated health benefits in humans: could it be essential ?. Scientific Rep. May 18, 2020;10(1): 1-4.
Venn-Watson et al., A 25-y longitudinal dolphin cohort supports that long-lived individuals in same environment exhibit variation in aging rates. PNAS Aug. 25, 2020;117(34): 20950-20958.
Vitiello M.V., Sleep disorders and aging: understanding the causes. J Gerontol. Jul. 1, 1997;52(4): M189-M191.
Wang et al., Peroxisome-proliferator-activated receptor δ activates fat metabolism to prevent obesity. Cell. Apr. 1, 20038;113(2): 159-170.
Vasto et al., Inflammatory networks in ageing, age-related diseases, and longevity. Mech Ageing and Dev. Jan. 1, 2007;128(1): 83-91.
Zhai et al., Anemia status and its relevant factors among elderly people aged above 80 years old in longevity areas in China. Chinese J of Prev Med. Feb. 1, 2010;44(2):115-118.
European Partial Supplementary Search Report dated Apr. 13, 2021 for Application No. 118870336.7 in 15 pages.
European Extended Search Report dated Jul. 14, 2021 for Application No. 118870336.7 in 14 pages.
European Office Action dated Jul. 13, 2023 for Application No. 118870336.7 in 7 pages.
Adachi et al., "Effect of the glyceride of pentadecanoic acid on energy metabolism in hair follicles". Int J Cosmetic Sci. Jun. 1993; 15(3): 125-131.
Agius et al., "The metformin mechanism on gluconeogenesis and AMPK activation: the metabolite perspective". Int J Mol Sci. May 3, 2020;21(9): 3240 in 19 pages.
Ali et al., "Recent advances and limitations of mTOR inhibitors in the treatment of cancer". Cancer Cell Int. Dec. 2022;22(1): 284 in 16 pages.
Anisimov et al., "Metformin slows down aging and extends life span of female SHR mice". Cell Cycle Sep. 1, 2008;7(17): 2769-2773.
Barzilai et al., "Metformin as a tool to target aging". Cell Metab. Jun. 14, 2016;23(6): 1060-1065.
Berg E.L. Phenotypic chemical biology for predicting safety and efficacy. Drug Disc Today Technol. Mar. 1, 2017;23: 53-60.
Bettcher et al., Increases in pro-inflammatory chemokine, MCP-1, are related to decreases in memory over time. Frontiers in aging neuroscience. Feb. 13, 2019; 11:25.
Biong et al., Intake of milk fat, reflected in adipose tissue fatty acids and risk of myocardial infarction: a case-control study. Eur J Clin Nutr. Feb. 2006;60(2): 236-244.
Bishop et al., Heptadecanoic acid is not a key mediator in the prevention of diet-induced hepatic steatosis and insulin resistance in mice. Nutrients Apr. 24, 2023;15(9): 2052 in 14 pages.
Blagosklonny M.V., Aging and immortality: Quasi-programmed senescence and its pharmacologic inhibition. Cell cycle. Sep. 15, 2006;5(18): 2087-2102.
Blagosklonny M.V., Rapamycin for longevity: opinion article. Aging Oct. 15, 2019;11(19): 8048- 8067.
Blagosklonny M.V., "Cell senescence, rapamycin and hyperfunction theory of aging". Cell Cycle Jul. 18, 2022;21(14): 1456-1467.
Bridle et al., "Rapamycin inhibits hepatic fibrosis in rats by attenuating multiple profibrogenic pathways". Transplantation Oct. 2009; 15(10): 1315-1324.
Browner et al., "The genetics of human longevity". Am J Med. Dec. 1, 2004;117(11): 851-860.
Brydges et al., Metabolomic and inflammatory signatures of symptom dimensions in major depression. Brain, Behavior, and Immunity. May 1, 2022;102: 42-52 (available Aug. 5, 2021).
Budczies et al., "Remodeling of central metabolism in invasive breast cancer compared to normal breast tissue—a GC-TOFMS based metabolomics study". BMC Genomics Dec. 2012;13(1): 334 in 11 pages.
Chaib et al., "Cellular senescence and senolytics: the path to the clinic". Nat Med. Aug. 2022;28(8): 1556-1568.
Cheng et al., "Metformin's mechanisms in attenuating hallmarks of aging and age-related disease". Aging Dis. Jul. 7, 2022;13(4): 970-986.
Crimmins E.M., "Lifespan and healthspan: past, present, and promise". The Gerontologist Dec. 1, 2015;55(6): 901-911.
De Mello et al., "Serum levels of plasmalogens and fatty acid metabolites associate with retinalmicroangiopathy in participants from the Finnish Diabetes Prevention Study". Nutrients Dec. 14, 2021;13(12): 4452 in.

(56) References Cited

OTHER PUBLICATIONS

DeVito et al., "Extending human lifespan and longevity: a symposium report". Ann N Y Acad Sci. Jan. 2022;1507(1): 70-83 [publ. online Sep. 8, 2021}.

Djousse et al., Serum individual nonesterified fatty acids and risk of heart failure in older adults. Cardiology Feb. 25, 2021;146(3): 351-358.

Dornan et al., Odd chain fatty acids and odd chain phenolic lipids (alkylresorcinols) are essential for diet. J Am Chem Soc. Aug. 2021;98(8): 813-824.

Dugan et al., Inflammaging as a target for healthy ageing. Age and Ageing. Feb. 1, 2023;52(2): afac328 in 15 Pages.

Ediriweera et al., "Odd-chain fatty acids as novel histone deacetylase 6 HDAC6) inhibitors". Biochimie Jul. 1, 2021;186: 147-156.

Ehninger et al., "Longevity, aging and rapamycin". Cell Mol Life Sci. Nov. 2014;71(22): 4325-4346.

Fonteh et al., Human cerebrospinal fluid fatty acid levels differ between supernatant fluid brain-derived nanoparticle fractions, and are altered in Alzheimer's disease. PloS One. Jun. 23, 2014;9(6): e100519 in 14 pages.

Fu et al., "Pentadecanoic acid promotes basal and insulin-stimulated glucose uptake in C2C12 myotubes". Food Nutr Res. 2021;65: 4527 in 9 pages.

Galdiero et al., Pentadecanoic acid against Candida albicans-Klebsiella pneumoniae biofilm:Towards the development of an anti-biofilm coating to prevent polymicrobial infections. Res Microbiology. Nov. 1, 2021;172(7-8): 103880 in 11 pages.

Garay R.P., "Investigational drugs and nutrients for human longevity. Recent clinical trials registered in ClinicalTrials.gov and clinicaltrialsregister.eu". Expert Opin Investig Drugs Jul. 3, 2021;30(7): 749-758.

Gibson et al., Cooperative care. The time has come. JONA: J Nurs Admin. Mar. 1, 1987;17(3): 19-21.

Giulani A., The application of principal component analysis to drug discovery and biomedical data. Drug Disc Today. Jul. 1, 2017;22(7): 1069-1076.

Gonzalez-Freire et al., "The road ahead for health and lifespan interventions". Ageing Res Rev. May 1, 2020;59:101037 in 46 pages.

Gosmanova et al., "Effect of metformin containing antidiabetic regimens on all-cause mortality in veterans with type 2 diabetes mellitus". Am J Med Sci. Sep. 1, 2008;336(3): 241-247.

Groarke et al., "Aging and hematopoiesis". Clin Geriatr Med. Aug. 1, 2019;35(3): 285-293.

Harrison et al., "Acarbose, 17- a-estradiol, and nordihydroguaiaretic acid extend mouse lifespan preferentially in males". Aging Cell Apr. 2014; 13(2): 273-282.

Hori et al., "Serum sphingomyelin species profile is altered in hematologic malignancies". Clin Chim Acta Mar. 1, 2021;514: 29-33.

Huang et al., "Circulating saturated fatty acids and incident type 2 diabetes: A systematic review and meta-analysis". Nutrients May 1, 2019;11(5): 998 in 20 pages.

Hulbert A.J. "On the importance of fatty acid composition of membranes for aging". J Theor Biol. May 21, 2005;234(2): 277-288.

Imamura et al., "Fatty acid biomarkers of dairy fat consumption and incidence of type 2 diabetes: A pooled analysis of prospective cohort studies". PLoS Med. Oct. 10, 2018;15(10): e1002670 in 18 pages.

Jee et al., "Clinical relevance of glycerophospholipid, sphingomyelin and glutathione metabolism in the pathogenesis of pharyngolaryngeal cancer in smokers: the Korean Cancer Prevention Study-II". Metabolomics Nov. 2016; 12: 164 in 12 Pages.

Jiao et al., Circulating fatty acids associated with advanced liver fibrosis and hepatocellular carcinoma in South Texas Hispanics. Cancer Epide., Biomark & Prev. Sep. 1, 2021;30(9): 1643-1651.

Jimenez-Cepeda et al., Dietary intake of fatty acids and its relationship with FEV1/FVC in patients with chronic obstructive pulmonary disease. Clin Nutr. ESPEN. Feb. 1, 2019;29: 92-96.

Jing et al., Metformin improves obesity-associated inflammation by altering macrophages polarization. Mol Cell Endocrin. Feb. 5, 2018;461: 256-264.

Justice et al., "Frameworks for proof-of-concept clinical trials of interventions that target fundamental aging processes". J Gerontol A Biol Sci Med Sci. Nov. 1, 2016;71(11): 1415-1423.

Justice et al., "Development of clinical trials to extend healthy lifespan". Cardiovasc Endocrinol Metab. Dec. 2018;7(4): 80-83.

Kaestner et al., "The potential of erythrocytes as cellular aging models". Cell Death Differ. Sep. 2017;24(9): 1475-1477.

Kaikkonen et al., "Associations of serum fatty acid proportions with obesity, insulin resistance, blood pressure and fatty liver: the cardiovascular risk in young Finns study". J Nutr Apr. 2021;151(4): 970-978.

Kaur et al., "Essential fatty acids as functional components of foods-a review". J Food Sci Technol. Oct. 2014;51: 2289-2303.

Khaw et al., Plasma phospholipid fatty acid concentration and incident coronary heart disease in men and women: the EPIC-Norfolk prospective study. PLoS Med. Jul. 3, 2012;9(7): e1001255 in 12 pages.

Khwaja et al., "Efficacy and Cardiovascular Safety of Alpha Glucosidase Inhibitors". Drug Safety Jul. 1, 2021;16(2): 122-128.

Kobayashi et al., New directions in cancer and aging: State of the science and recommendations to improve the quality of evidence on the intersection of aging with cancer control. Cancer. May 1, 2022;128(9): 1730-1737.

Kritchevsky et al., "Testing the geroscience hypothesis: early days". J Gerontol A Biol Sci Med Sci. Jan. 1, 2020;75(1): 99-101 [publ. online Dec. 13, 2019].

Kruchinina et al., "Erythrocyte membrane fatty acids as the potential biomarkers for detection of early-stage and progression of colorectal cancer". Ann Oncol. Jun. 1, 2018;29(Suppl 5): v52.

Kurotani et al., "Even- and odd-chain saturated fatty acids in serum phospholipids are differentially associated with adipokines". PLoS One May 26, 2017;12(5): e0178192 in 14 pages.

Lankinen et al., "Plasma fatty acids as predictors of glycaemia and type 2 diabetes". Diabetologia Nov. 2015;58: 2533-2544.

Li et al., Design, synthesis and antitumor activity study of a gemcitabine prodrug conjugated with a HDAC6 inhibitor. Bioorg Med Chem Lttrs. Sep. 15, 2022;72: 128881 in ?? pages.

Li et al., "Extraction, purification, and elucidation of six ginkgo homologs from Ginkgo biloba sarcotesta and evaluation of their anticancer activities". Molecules Nov. 11, 2022;27(22): 7777 in 15 pages.

Liang et al., "Biomarkers of dairy fat intake and risk of cardiovascular disease: a systematic review and meta analysis of prospective studies". Crit Rev Food Sci Nutr. May 3, 2018;58(7): 1122-1130.

Lin et al., Effects of the mTOR inhibitor Rapamycin on monocyte-secreted chemokines. BMC Immunol. Dec. 2014;15(1): 1-9.

Lin et al., Efficacy and safety of topical mechanistic target of rapamycin inhibitors for facial angiofibromas in patients with tuberous sclerosis complex: a systematic review and network meta-analysis. Biomedicines Mar. 31, 2022; 10(4): 826 in 13 pages.

Lipschitz et al., The anemia of senescence. Am J Hematol. Aug. 1981;11(1): 47-54.

Longo et al., "Interventions to slow aging in humans: are we ready?" Aging Cell Aug. 2015;14(4): 497-510.

Manca et al., Circulating fatty acids and endocannabinoide-related mediator profiles associated to human longevity. GeroScience. Aug. 2021;43(4): 1783-1798.

Martin-Montalvo et al., "Metformin improves healthspan and lifespan in mice". Nat Commun. Jul. 30, 2013;4(1): 2192 in 23 pages.

Matthan et al., Spillover effects of a family-based childhood weight-management intervention on parent nutrient biomarkers and cardiometabolic risk factors. Curr Dev Nutrition Feb. 2022;6(2): 152 in 41 pages.

McArtor et al., Extending multivariate distance matrix regression with an effect size measure and the asymptotic null distribution of the test statistic. Psychometrika. Dec. 2017;82: 1052-1077.

Millner et al., "Lipid players of cellular senescence". Metabolites Aug. 21, 2020;10(9): 399 in 17 pages.

Moskalev et al., "Targeting aging mechanisms: pharmacological perspectives". Trends Endocrinol Metab. Apr. 1, 2022;33:266-280.

(56) References Cited

OTHER PUBLICATIONS

Nadon et al., "NIA interventions testing program: investigating putative aging intervention agents in a genetically heterogeneous mouse model". EBioMedicine Jul. 1, 2017;21: 3-4.
Niedernhofer et al., Molecular pathology endpoints useful for aging studies. Age Res Rev. May 1, 2017;35: 241-249.
Qi et al., "High-resolution metabolomic biomarkers for lung cancer diagnosis and prognosis". Sci Rep. Jun. 3, 2021;11(1): 11805 in 10 pages.
Ricciardelli et al., Pentadecanal and pentadecanoic acid coatings reduce biofilm formation of Staphylococcus epidermidis on PDMS. Patho Dis. Apr. 2020;78(3): ftaa012 in 8 pages.
Roh et al., A clinical study of pentadecanoic glyceride (LHOP) on male pattern alopecia. J Korean Soc Clin Pharma Thera. Dec. 1, 1998;6(2): 199-206.
Salvatore et al., "Metformin: an old drug against old age and associated morbidities". Diab Res Clin Prac. Feb. 1, 2020;160: 108025 in 11 pages.
Santaren et al., "Serum pentadecanoic acid (15:0), a short-term marker of dairy food intake, is inversely associated with incident type 2 diabetes and its underlying disorders". Am J Clin Nutr. Dec. 1, 2014;100(6): 1532-1540.
Sawh et al., Dairy fat iintake, plasma pentadecanoic acid, and plasma iso-heptadecanoic acid are inversely associated with liver fat in children. J Ped Gastroent Nutr. Apr. 4, 2021;72(4): e90 in 18 pages.
Schork et al., "Does modulation of an epigenetic clock define a geroprotector?" Adv Geriatr Med Res. Mar. 29, 2022;4(1): e220002 in 11 pages.
Singh et al., MCP-1: Function, regulation and involvement in disease. Int Immunopharm. Dec. 1, 2021;101: 107598 in 9 pages.
Smedman et al., "Pentadecanoic acid in serum as a marker of intake of milk fat: relations between intake of milk fat and metabolic risk factors". Am J Clin Nutr. Jan. 1, 1999;69(1): 22-29.
Smith et al., "Changes in the gut microbiome and fermentation products concurrent with enhanced longevity in acarbose-treated mice". BMC Microbiol. Dec. 2019;19(1): 1-6.
Soboleva et al., "Fatty acids of the lipid fraction of erythrocyte membranes and intensity of lipid peroxidation in iron deficiency". Bull Exp Biol Med. Jun. 1994; 117: 600-603. (1994).
Sorrenti et al., "Immunomodulatory and antiaging mechanisms of resveratrol, rapamycin, and metformin: focus on mTOR and AMPK signaling networks". Pharmaceuticals Jul. 23, 2022;15(8): 912 in 20 pages.
Soukas et al., "Metformin as anti-aging therapy: is it for everyone?" Trends Endocrinol Metab. Oct. 1, 2019;30(10): 745-755.
To et al., "Pentadecanoic acid, an odd-chain fatty acid, suppresses the stemness of MCF-7/SC human breast cancer stem-like cells through JAK2/STAT3 signaling". Nutrients Jun. 3, 2020;12(6): 1663 in 20 pages.
To et al., "Effects of combined pentadecanoic acid and tamoxifen treatment on tamoxifen resistance in MCF-7/SC breast cancer cell". Int J Mol Sci. Sep. 26, 2022;23(19): 11340 in 20 pages.
Tsoukalas et al., Application of metabolomics Part II: Focus on fatty acids and their metabolites in healthy adults. Int J Mol Med. Jan. 1, 2019;43(1): 233-242.
Venn-Watson et al., "Modified fish diet shifted serum metabolome and alleviated chronic anemia in bottlenose dolphins (*Tursiops truncatus*): Potential role of odd-chain saturated fatty acids". PLoS One Apr. 7, 2020;15(4): e0230769 (2020).
Venn-Watson et al., "Broader and safer clinically-relevant activities of pentadecanoic acid comparedto omega-3: evaluation of an emerging essential fatty acid across twelve primary human cell-based disease systems". PLoS One May 2, 20226;17(5): e0268778 in 17 pages.
Venn-Watson et al., Pentadecanoylcarnitine is a newly discovered endocannabinoid with pleiotropiclactivities relevant to supporting physical and mental health. Sci Rep. Aug. 23, 2022;12(1): 13717 in 11 pages.
Vézina et al., "Rapamycin (AY-22, 989), a new antifungal antibiotic"—Part I. J Antibio. 1975;28(10): 721-726.
Wagner et al., Combined treatment with exercise training and acarbose improves metabolic control and cardiovascular risk factor profile in subjects with mild type 2 diabetes. Diabetes Care Jul. 1, 2006;29(7): 1471-1477.
Warensjö et al., "Estimated intake of milk fat is negatively associated with cardiovascular risk factorsand does not increase the risk of a first myocardial infarction. A prospective case-control study". Br J Nutr. Apr. 2004;91(4): 635-642.
Webster et al., "Target of rapamycin inhibitors (sirolimus and everolimus) for primaryimmunosuppression of kidney transplant recipients: a systemic review and meta-analysis of randomized trials". Transplantation May 15, 2006;81(9): 1234-1248.
Wolf et al., "The MalR type regulator AcrC is a transcriptional repressor of acarbose biosynthetic genes in Actinoplanes sp. SE50/110". BMC Genomics Dec. 2017; 18(1): 1-4.
Wu et al., "Extension of life span by acarbose: is it mediated by the gut microbiota"? Aging Dis. Jul. 7, 2022;13(4): 1005-1014.
Xu et al., "Rapamycin for lymphangioleiomyomatosis: optimal timing and optimal dosage". Thorax Apr. 1, 2018;73(4): 308-310.
Xu et al., Cross-sectional associations of adipokines and abdominal fat distribution with aging in men. The Aging Male. Dec. 4, 2020;23(5): 1576-1582.
Ye et al., A pharmacological network for lifespan extension in Caenorhabditis elegans. Aging cell. Apr. 2014; 13(2): 206-215.
Yoo et al., "An overview of rapamycin: from discovery to future perspectives". J Indus Microbiol Biotech. May 1, 2017;44(4-5): 537-553.
Yoo et al., Fatty acids in non-alcoholic steatohepatitis: : Focus on pentadecanoic acid. PLoS One. Dec. 15, 2017;12(12): e0189965 in 15 pages.
Yousefzadeh et al., Circulating levels of monocyte chemoattractant protein-1 as a potential measure of biological age in mice and frailty in humans. Aging cell. Apr. 2018; 17(2): e12706 in 7 pages.
Zapala et al., Multivariate regression analysis of distance matrices for testing associations between gene expression patterns and related variables. Proc Nat Acad Scie. Dec. 19, 2006;103(51): 19430-19435.
Zapala et al., Statistical properties of multivariate distance matrix regression for high-dimensional data analysis. Front Genetics. Sep. 27, 2012;3: 190 in 10 pages.
Zheng et al., Association between plasma phospholipid saturated fatty acids and metabolic markers oflipid, hepatic, inflammation and glycaemic pathways in eight European countries: a cross-sectional analysis in the EPIC-Interact study. BMC Med. Dec. 2017; 15(1): 203 in 13 pages.
Zheng et al., Changes in plasma phospholipid fatty acid profiles over 13 years and correlates of change: European Prospective Investigation into Cancer and Nutrition-Norfolk Study. Am J Clin Nutr. Jun. 1, 2019;109(6): 1527-1534.
Zhu et al., Synthesis and inhibitory activities against colon cancer cell growth and proteasome of alkylresorcinols. J Agric Food Chem. Sep. 5, 2012;60(35): 8624-8631.
Zhu et al., A prospective study and longitudinal study of plasma phospholipid saturated fatty acid profile in relation to cardiometabolic markers and the risk of gestational diabetes. Am J Clin Nutr. Jun. 1, 2018;107(6): 1017-1026.
Zhuang et al., Saturated fatty acid intake is associated with total mortality in a nationwide cohort study. J Nutr. Jan. 1, 2019;149(1): 68-77.
Cusi et al., Metformin: A review of its metabolic effects. Diab Rev. Jan. 1, 1998;6(2): 89-131.

\* cited by examiner

| Human Cell System | Recapitulated Disease State | Protein-Based Biomarker | Free fatty acid C15:0 | | 2-methyl-C15:0 | | 2,2-dimethyl-C15:0 | | 1-tetrazole-C15:0 | |
|---|---|---|---|---|---|---|---|---|---|---|
| | | | 6.7 μM | 20 μM | 6.7 μM | 20 μM | 6.7 μM | 20 μM | 6.7 μM | 20 μM |
| Venular endothelial cells + TNFα, IL-1β, IFNγ | Cardiovascular Disease, Chronic Inflammation | CD142/Tissue factor | 0.042 | 0.003 | 0.060 | 0.091 | -0.025* | -0.058* | -0.019* | -0.103* |
| Venular endothelial cells + IL-4, histamine | Autoimmunity, Allergy, Asthma | 4H: MCP-1 | -0.033 | -0.026 | -0.012 | 0.001 | -0.077 | -0.182* | -0.049 | -0.088* |
| | | CCL26/Eotaxin-3 | 0.012 | 0.012 | -0.020 | -0.063* | -0.034 | -0.001 | 0.001 | -0.030 |
| Venular endothelial cells + PBMCs + TLR4 ligand | Cardiovascular Disease, Chronic Inflammation | CD40 | -0.008 | -0.086* | -0.050 | -0.200* | -0.025 | -0.083 | -0.050 | -0.116* |
| Venular endothelial cells + PBMCs + TCR ligands | Chronic Inflammation, Autoimmune Disease | CD38 | -0.024 | -0.017 | -0.007 | -0.023 | -0.010 | -0.067* | -0.016 | -0.057* |
| | | CD40 | 0.002 | -0.020 | -0.008 | -0.026 | -0.010 | -0.018 | -0.036 | -0.071* |
| | | CD69 | 0.008 | -0.037 | -0.011 | -0.039 | -0.004 | -0.086* | 0.022 | -0.114* |
| | | T cell proliferation | 0.043 | 0.051 | -0.130* | -0.206* | -0.059 | -0.109* | 0.021 | -0.034 |
| PBMCs + B cells + α-IgM, TCR ligands | Asthma, Oncology, Autoimmunity, Allergy | B cell proliferation | 0.001 | -0.023 | -0.123* | -0.225* | -0.022 | -0.021 | 0.002 | 0.019 |
| | | Secreted IgG | -0.169* | -0.554* | -0.123 | -0.753* | -0.127 | -0.322* | 0.073 | -0.086 |
| Bronchial epithelial cells + dermal fibroblasts + IL-4, TNFα | Fibrosis, Lung Inflammation, Asthma, Allergy | MCP-1 | -0.011 | -0.040 | -0.021 | -0.512* | -0.048 | -0.628* | -0.029 | -0.390* |
| | | Eotaxin-3 | 0.038 | 0.004 | 0.079 | -0.805* | -0.321* | -0.584* | -0.475* | -0.584* |
| | | VCAM-1 | 0.006 | 0.069 | -0.001 | -0.243* | -0.048 | -0.174* | -0.088* | -0.103* |
| | | ICAM-1 | 0.020 | 0.042 | 0.012 | -0.292* | 0.012 | -0.295* | -0.035* | -0.180* |
| | | IL-8 | 0.005 | 0.015 | 0.026 | -0.139* | 0.068 | -0.174* | 0.234 | -0.017 |
| | | IL-1 alpha | -0.002 | 0.008 | -0.010 | -0.488* | -0.019 | -0.443* | -0.159* | -0.373* |
| | | Keratin 8/18 | -0.010 | 0.026 | -0.025 | -0.366* | -0.018 | -0.207* | -0.026 | -0.094* |
| | | MMP-1 | -0.020 | -0.019 | 0.021 | -0.264* | -0.023 | -0.166* | 0.013 | -0.107* |
| | | MMP-3 | -0.024 | -0.005 | -0.034 | -0.287* | 0.038 | -0.185* | 0.076 | -0.143* |
| | | MMP-9 | -0.042 | 0.001 | 0.023 | -0.356* | -0.022 | -0.296* | -0.078* | -0.189* |
| | | PAI-1 | -0.011 | -0.022 | 0.007 | -0.234* | 0.014 | -0.177* | -0.081* | -0.123* |
| Bronchial epithelial cells + TNFα, IL-1β, IFNγ | COPD, Lung Inflammation | BE3C: MMP-9 | 0.013 | 0.031 | - | - | - | - | -0.206* | -0.309* |
| | | BE3C: PAI-1 | 0.014 | 0.012 | - | - | - | - | -0.208* | -0.304* |

FIG. 2A

| Human Cell System | Recapitulated Disease State | Cell-Based Activity | Log-Transformed Ratio of Biomarker Readout for Drug-Treated Sample over Vehicle Controls | | | | | | | | |
|---|---|---|---|---|---|---|---|---|---|---|---|
| | | | Free fatty acid | | 2-methyl | | 2,2-dimethyl | | 1-tetrazole | |
| | | | 6.7 µM | 20 µM | 6.7 µM | 20 µM | 6.7 µM | 20 µM | 6.7 µM | 20 µM |
| Keratinocytes + dermal fibroblasts + TNFα, IL-1β, IFNγ, TGF-β | Dermatitis, psoriasis | MCP-1 | 0.006 | 0.035 | 0.015 | -0.656* | 0.031 | -0.643* | - | - |
| | | ICAM-1 | 0.029 | 0.010 | -0.026 | -0.680* | 0.014 | -0.370* | - | - |
| | | CXCL10/IP-10 | 0.006 | 0.003 | 0.001 | -1.274* | -0.001 | -1.064* | - | - |
| | | CXCL8/IL-18 | -0.001 | -0.002 | 0.037 | -0.503* | 0.012 | -0.183* | - | - |
| | | CXCL9/MIG | 0.004 | -0.011 | 0.004 | -1.272* | 0.010 | -0.667* | - | - |
| | | IL-1alpha | -0.014 | 0.014 | 0.003 | -0.601* | -0.004 | -0.562* | - | - |
| | | MMP-9 | -0.010 | -0.054 | -0.045 | -0.775* | -0.053* | -0.621* | - | - |
| | | PAI-1 | -0.001 | -0.046 | -0.057* | -1.00 | -0.006 | -0.842* | - | - |

FIG. 2B

FATTY ACID ANALOGS AND THEIR USE IN THE TREATMENT OF CONDITIONS RELATED TO METABOLIC SYNDROME

INCORPORATION BY REFERENCE TO RELATED APPLICATION

Any and all priority claims identified in the Application Data Sheet, or any correction thereto, are hereby incorporated by reference under 37 CFR 1.57. This application is a divisional of U.S. application Ser. No. 16/164,573, filed Oct. 18, 2018, which claims the benefit of U.S. Provisional Application No. 62/575,973 filed Oct. 23, 2017. Each of the aforementioned applications is incorporated by reference herein in its entirety, and each is hereby expressly made a part of this specification.

FIELD OF THE INVENTION

Compositions comprising fatty acid analogs are provided for treating metabolic syndrome, anemia, cancer, cardiovascular disease, diabetes, dyslipidemia, hypertension, inflammation, insulin resistance, prediabetes, fatty liver disease, steatohepatitis, iron overload, neurodegenerative diseases, including Alzheimer's disease and other forms of dementia, and other related conditions. Methods for the diagnosis and monitoring of metabolic syndrome and other conditions are also provided.

BACKGROUND OF THE INVENTION

Metabolic syndrome is an underlying disorder of energy utilization and storage. Metabolic syndrome affects a substantial proportion of the population of developed countries, including the United States. It is associated with the risk of developing cardiovascular disease, diabetes (especially type 2 diabetes), and other conditions such as polycystic ovary syndrome, fatty liver disease, cholesterol gallstones, asthma, sleep disturbances, and some forms of cancer. Metabolic syndrome is characterized by abdominal (central) obesity, elevated blood pressure, elevated insulin, elevated fasting plasma glucose, elevated serum triglycerides, decreased high-density lipoprotein (HDL) levels, proinflammatory state (recognized clinically by elevations of C-reactive protein (CRP)), and a prothrombotic state.

Metabolic syndrome is alternatively known as Syndrome X, prediabetes, cardiometabolic syndrome, insulin resistance syndrome, Reaven's syndrome, and CHAOS. A number of risk factors for metabolic syndrome have been identified, which include but are not limited to obesity, advancing age, high stress, and poor diet. Metabolic syndrome can also arise due to genetic disorders or other in-born errors of metabolism.

Treatment of metabolic syndrome generally targets the indices named above. Often treatment focuses on conditions associated with more advanced stages of metabolic syndrome, such as cardiovascular disease and diabetes. For diabetes, administration of metformin, insulin, or an insulin analog is sometimes indicated, as is administration of other medicaments such as statins, fibrates, and niacin. However, these medicaments may lead to undesirable side effects. Early stage treatment and prevention of metabolic syndrome is generally limited to recommendation of a low saturated fat diet with increased daily exercise. Some subjects are unable to effectively comply with, or unresponsive to, these regimens.

SUMMARY OF THE INVENTION

Compositions and methods for treatment and prevention of metabolic syndrome, and treating associated conditions are provided. These compositions comprise fatty acid compounds, and salts thereof, which may be administered alone or in combination with other medicaments or as part of various treatment regimens. The provided compositions are effective for modulating markers associated with metabolic syndrome, anemia, cancer, cardiovascular disease, diabetes, dyslipidemia, hypertension, inflammation, insulin resistance, prediabetes, fatty liver disease, steatohepatitis, iron overload, neurodegenerative diseases, including Alzheimer's disease and other forms of dementia, and other related conditions. Methods are provided for administering the compositions.

Accordingly, in a generally applicable first aspect (i.e., independently combinable with any of the aspects or embodiments identified herein), a method of treatment or prophylaxis of metabolic syndrome, cardiovascular disease, diabetes, type 2 diabetes, anemia, cancer, cardiovascular disease, dyslipidemia, hypertension, inflammation, insulin resistance, prediabetes, fatty liver disease, steatohepatitis, iron overload, neurodegenerative diseases, or Alzheimer's disease, is provided, comprising administering to a patient in need thereof a compound of Formula (I), or a pharmaceutically acceptable salt thereof. In various embodiments, the compound of Formula (I) may be a compound of Formula (Ia), Formula (Ib), Formula (Ic), Formula (Id), Formula (Ie), Formula (If), Formula (Ig), or Formula (Ih).

Accordingly, in a generally applicable second aspect (i.e., independently combinable with any of the aspects or embodiments identified herein), a pharmaceutical composition comprising a compound, or pharmaceutically acceptable salt thereof is provided, wherein the compound is a saturated fatty acid substituted with one or more substituents selected from the group consisting of a 2-methyl, 2,2-dimethyl, 2-ethyl, 2,2-diethyl, 3-oxa, 2,2-dimethyl-3-oxa, 1-tetrazole, 1-oxazolone, 1-oxadiazolone, N-hydroxyamide, 2-methyl-1-tetrazole, and 2-methyl-2-ethyl; wherein the fatty acid is selected from tridecanoic acid (C13:0), myristic acid (C14:0), pentadecanoic acid (C15:0), palmitic acid (C16:0), heptadecanoic acid (C17:0) and stearic acid (C18:0), and a pharmaceutically acceptable carrier. Structures for compounds of the embodiments include, but are not limited to the following.

Stearic Acid Analogs

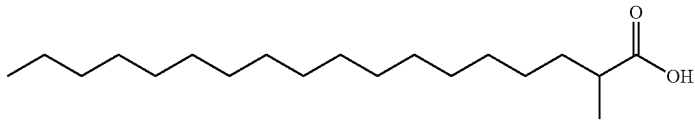 [SMILES: CCCCCCCCCCCCCCCCC(C)C(=O)O]

2-methyl-stearic acid

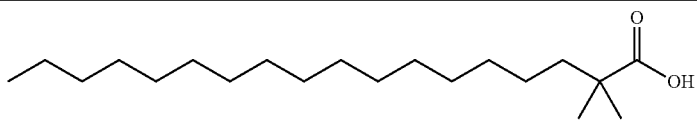
2,2-dimethyl-stearic acid
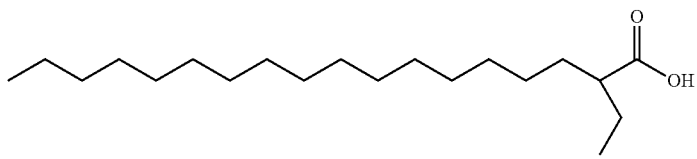 [SMILES: CCCCCCCCCCCCCCCCC(CC)C(=O)O]
2-ethyloctadecanoic acid
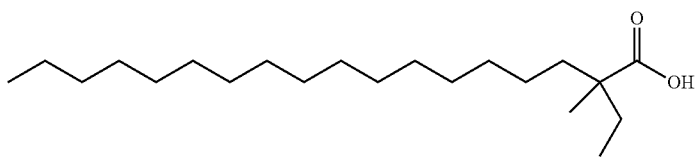 [SMILES: CCCCCCCCCCCCCCCCC(C)(CC)C(=O)O]
2-ethyl-2-methyloctadecanoic acid
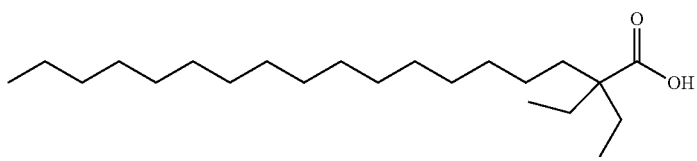 [SMILES: CCCCCCCCCCCCCCCCC(CC)(CC)C(=O)O]
2,2-diethyloctadecanoic acid
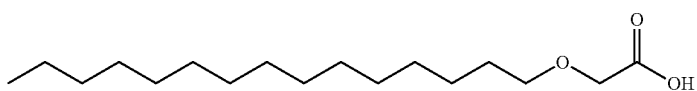 [SMILES: CCCCCCCCCCCCCCCOCC(=O)O]
3-oxa-stearic acid
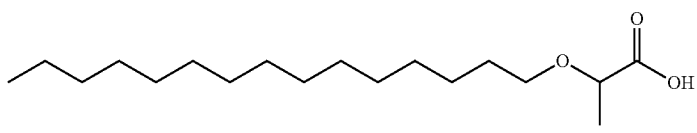 [SMILES: CCCCCCCCCCCCCCCOC(C)C(=O)O]
2-(pentadecyloxy)propanoic acid
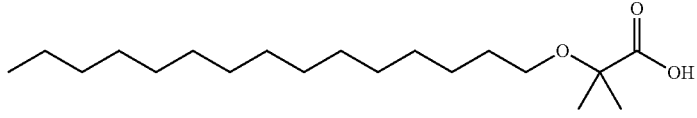 [SMILES: CCCCCCCCCCCCCCCOC(C)(C)C(=O)O]
2,2-dimethyl-3-oxa-stearic acid
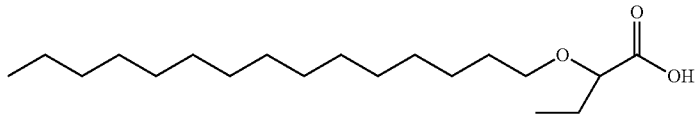 [SMILES: CCCCCCCCCCCCCCCOC(CC)C(=O)O]
2-(pentadecyloxy)butanoic acid
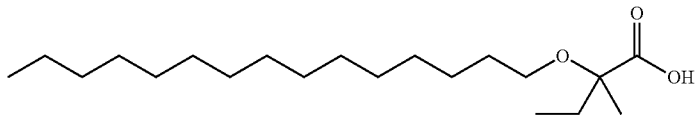 [SMILES: CCCCCCCCCCCCCCCOC(C)(CC)C(=O)O]
2-methyl-2-(pentadecyloxy)butanoic acid

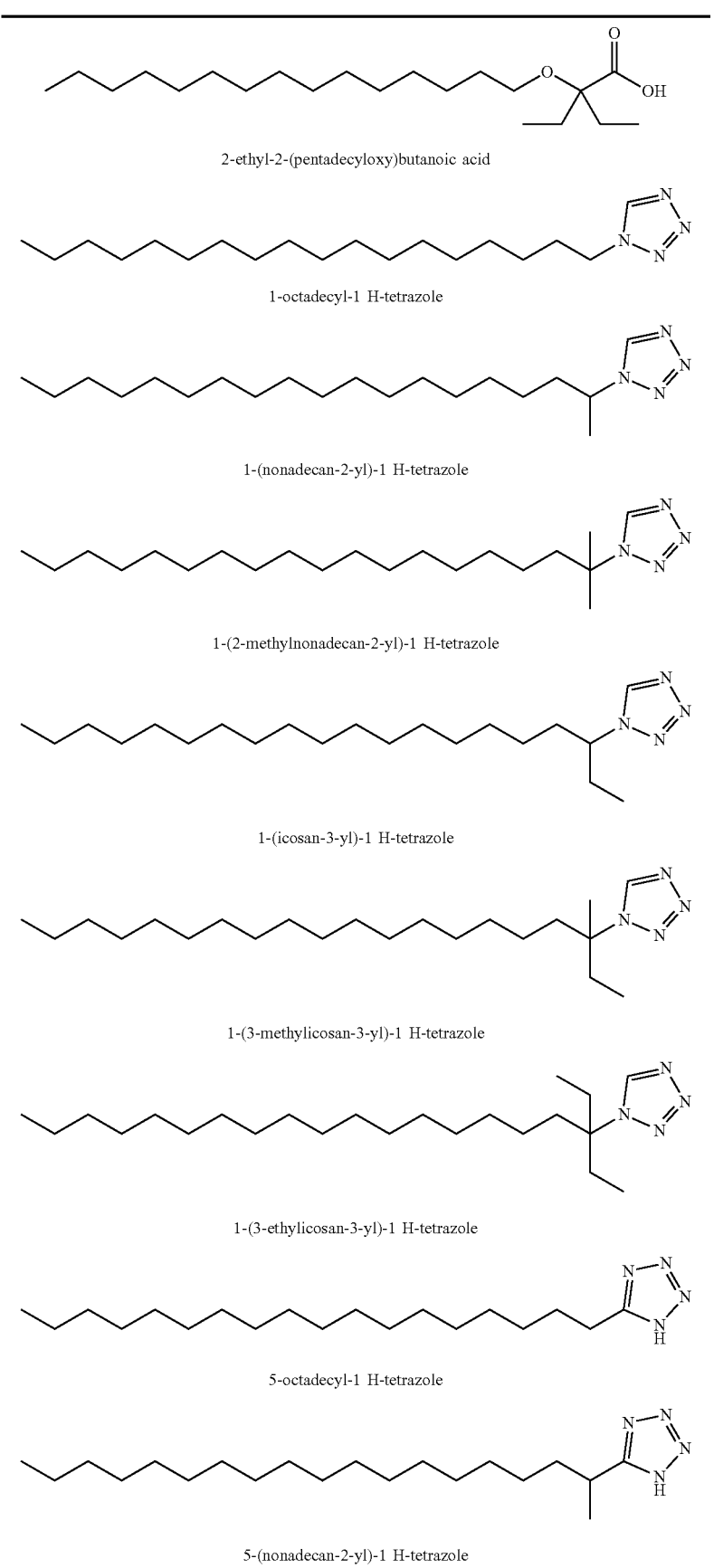
2-ethyl-2-(pentadecyloxy)butanoic acid
1-octadecyl-1 H-tetrazole
1-(nonadecan-2-yl)-1 H-tetrazole
1-(2-methylnonadecan-2-yl)-1 H-tetrazole
1-(icosan-3-yl)-1 H-tetrazole
1-(3-methylicosan-3-yl)-1 H-tetrazole
1-(3-ethylicosan-3-yl)-1 H-tetrazole
5-octadecyl-1 H-tetrazole
5-(nonadecan-2-yl)-1 H-tetrazole -continued
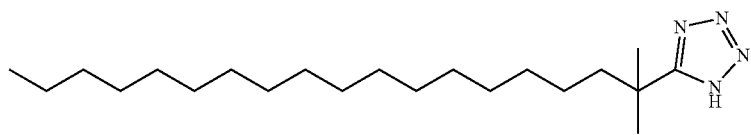 [SMILES: CCCCCCCCCCCCCCCCCC(C)(C)c1nnn[nH]1]
5-(2-methylnonadecan-2-yl)-1 H-tetrazole
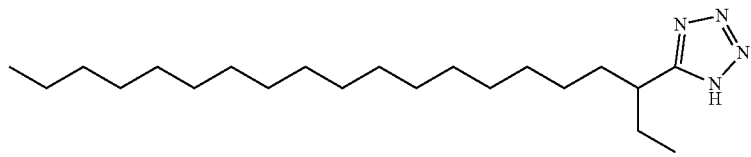 [SMILES: CCCCCCCCCCCCCCCCCC(CC)c1nnn[nH]1]
5-(icosan-3-yl)-1 H-tetrazole
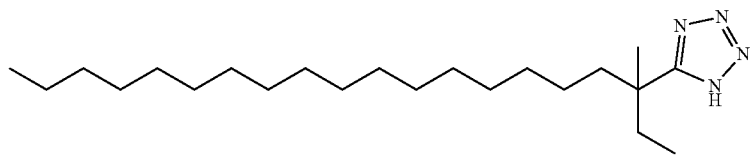 [SMILES: CCCCCCCCCCCCCCCCCC(C)(CC)c1nnn[nH]1]
5-(3-methylicosan-3-yl)-1 H-tetrazole
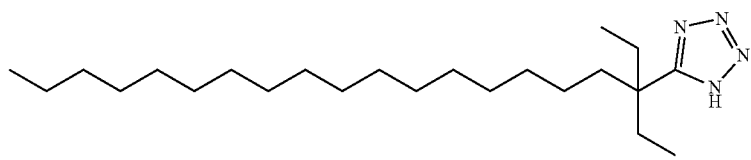 [SMILES: CCCCCCCCCCCCCCCCCC(CC)(CC)c1nnn[nH]1]
5-(3-ethylicosan-3-yl)-1 H-tetrazole
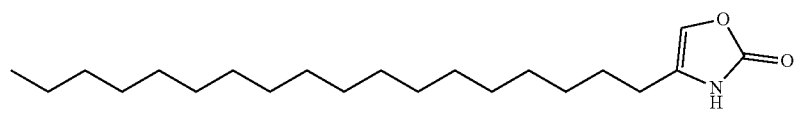 [SMILES: CCCCCCCCCCCCCCCCCCc1coc(=O)[nH]1]
4-octadecyloxazol-2(3 H)-one
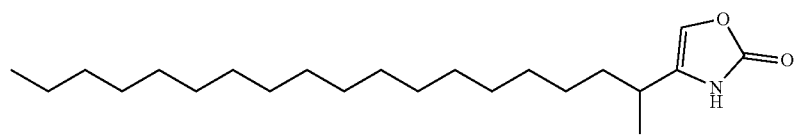 [SMILES: CCCCCCCCCCCCCCCCCC(C)c1coc(=O)[nH]1]
4-(nonadecan-2-yl)oxazol-2(3 H)-one
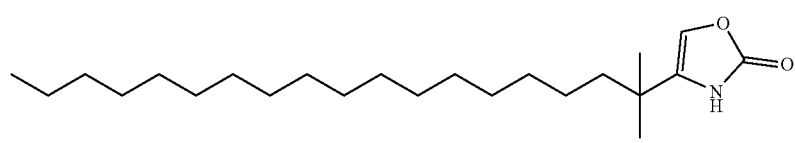 [SMILES: CCCCCCCCCCCCCCCCCC(C)(C)c1coc(=O)[nH]1]
4-(2-methylnonadecan-2-yl)oxazol-2(3 H)-one
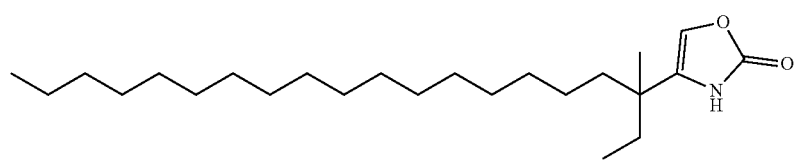 [SMILES: CCCCCCCCCCCCCCCCCC(C)(CC)c1coc(=O)[nH]1]
4-(3-methylicosan-3-yl)oxazol-2(3 H)-one

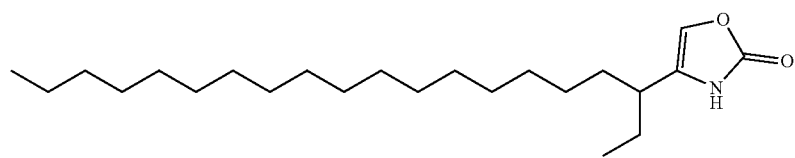 [SMILES: CCCCCCCCCCCCCCCCCC(CC)c1coc(=O)[nH]1]
4-(icosan-3-yl)oxazol-2(3H)-one
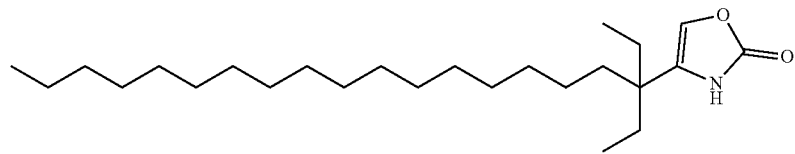 [SMILES: CCCCCCCCCCCCCCCCCC(CC)(CC)c1coc(=O)[nH]1]
4-(3-ethylicosan-3-yl)oxazol-2(3H)-one
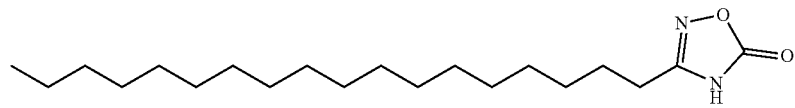 [SMILES: CCCCCCCCCCCCCCCCCCc1noc(=O)[nH]1]
3-octadecyl-1,2,4-oxadiazol-5(4H)-one
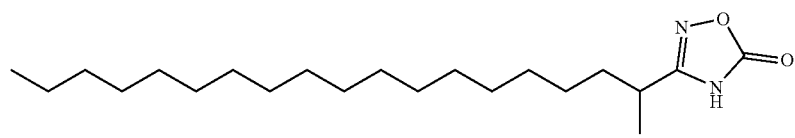 [SMILES: CCCCCCCCCCCCCCCCCC(C)c1noc(=O)[nH]1]
3-(nonadecan-2-yl)-1,2,4-oxadiazol-5(4H)-one
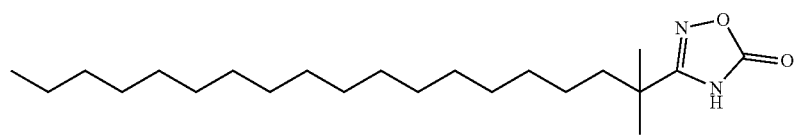 [SMILES: CCCCCCCCCCCCCCCCCC(C)(C)c1noc(=O)[nH]1]
3-(2-methylnonadecan-2-yl)-1,2,4-oxadiazol-5(4H)-one
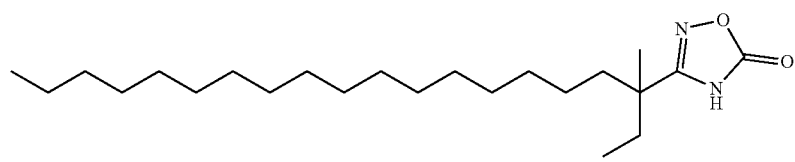 [SMILES: CCCCCCCCCCCCCCCCCC(C)(CC)c1noc(=O)[nH]1]
3-(3-methylicosan-3-yl)-1,2,4-oxadiazol-5(4H)-one
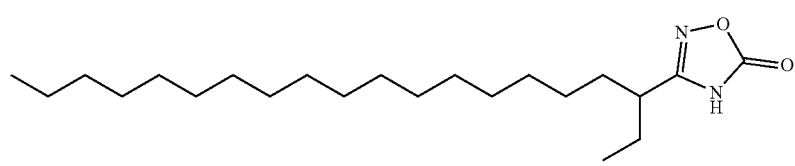 [SMILES: CCCCCCCCCCCCCCCCCC(CC)c1noc(=O)[nH]1]
3-(icosan-3-yl)-1,2,4-oxadiazol-5(4H)-one
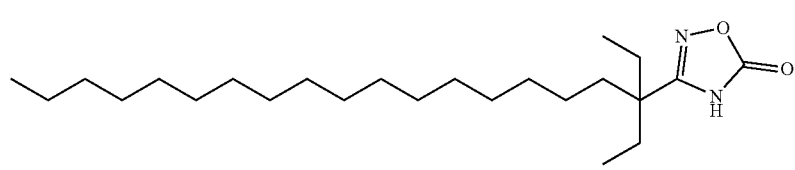 [SMILES: CCCCCCCCCCCCCCCCCC(CC)(CC)c1noc(=O)[nH]1]
3-(3-ethylicosan-3-yl)-1,2,4-oxadiazol-5(4H)-one

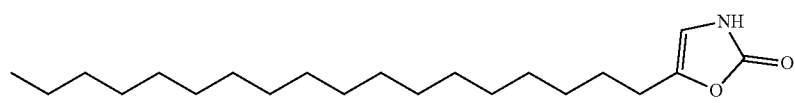 [SMILES: CCCCCCCCCCCCCCCCCCc1c[nH]c(=O)o1]
5-octadecyloxazol-2(3H)-one
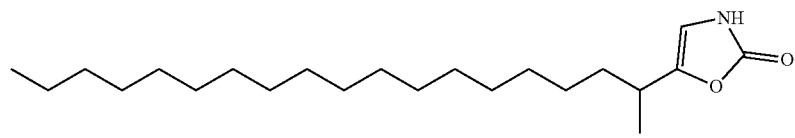 [SMILES: CCCCCCCCCCCCCCCCCC(C)c1c[nH]c(=O)o1]
5-(nonadecan-2-yl)oxazol-2(3H)-one
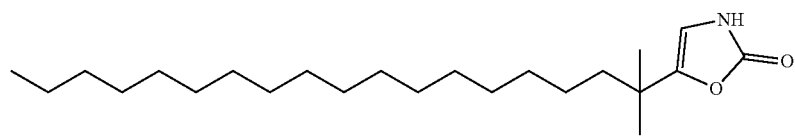 [SMILES: CCCCCCCCCCCCCCCCCC(C)(C)c1c[nH]c(=O)o1]
5-(2-methylnonadecan-2-yl)oxazol-2(3H)-one
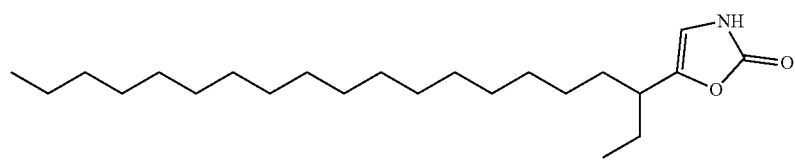 [SMILES: CCCCCCCCCCCCCCCCCC(CC)c1c[nH]c(=O)o1]
5-(icosan-3-yl)oxazol-2(3H)-one
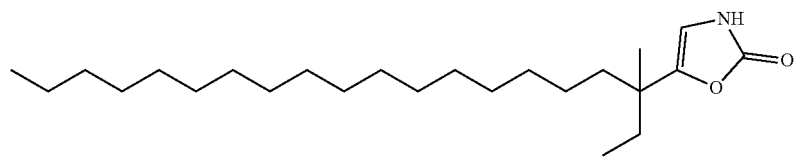 [SMILES: CCCCCCCCCCCCCCCCCC(C)(CC)c1c[nH]c(=O)o1]
5-(3-methylicosan-3-yl)oxazol-2(3H)-one
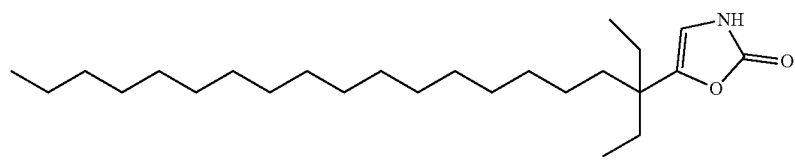 [SMILES: CCCCCCCCCCCCCCCCCC(CC)(CC)c1c[nH]c(=O)o1]
5-(3-ethylicosan-3-yl)oxazol-2(3H)-one
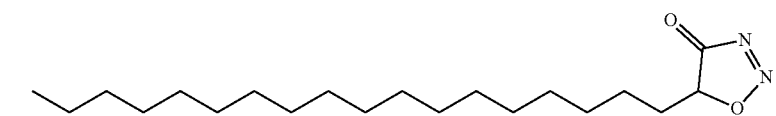 [SMILES: CCCCCCCCCCCCCCCCCCC1ON=NC1=O]
5-octadecyl-1,2,3-oxadiazol-4(5H)-one
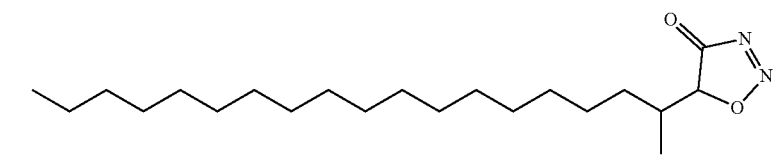 [SMILES: CCCCCCCCCCCCCCCCCC(C)C1ON=NC1=O]
5-(nonadecan-2-yl)-1,2,3-oxadiazol-4(5H)-one

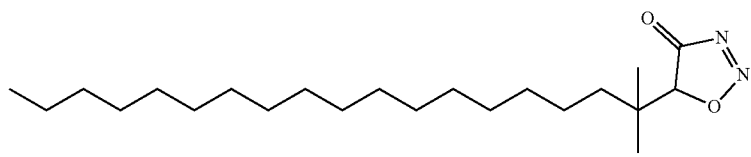 [SMILES: CCCCCCCCCCCCCCCCCC(C)(C)C1ON=NC1=O]
5-(2-methylnonadecan-2-yl)-1,2,3-oxadiazol-4(5 H)-one
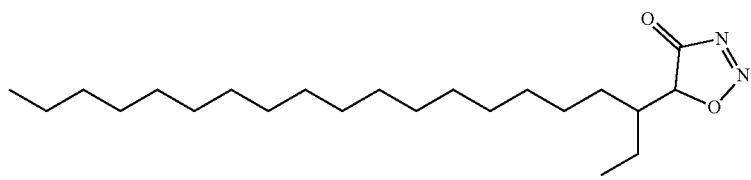 [SMILES: CCCCCCCCCCCCCCCCCC(CC)C1ON=NC1=O]
5-(icosan-3-yl)-1,2,3-oxadiazol-4(5 H)-one
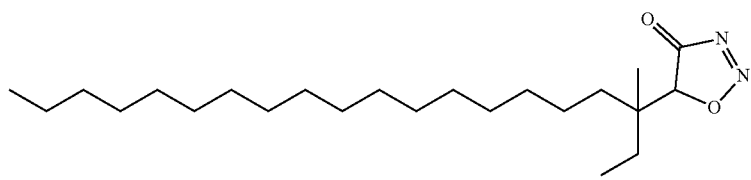 [SMILES: CCCCCCCCCCCCCCCCCC(C)(CC)C1ON=NC1=O]
5-(3-methylicosan-3-yl)-1,2,3-oxadiazol-4(5 H)-one
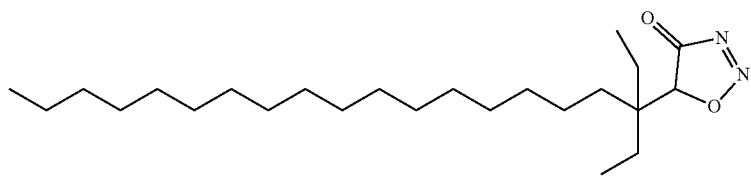 [SMILES: CCCCCCCCCCCCCCCCCC(CC)(CC)C1ON=NC1=O]
5-(3-ethylicosan-3-yl)-1,2,3-oxadiazol-4(5 H)-one
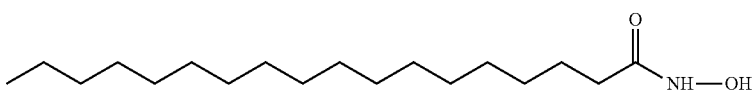 [SMILES: CCCCCCCCCCCCCCCCCC(=O)NO]
N-hydroxystearamide
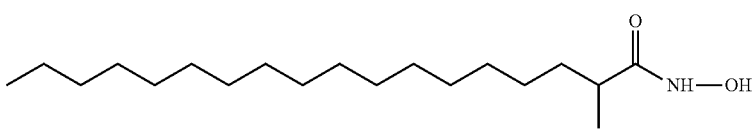 [SMILES: CCCCCCCCCCCCCCCCC(C)C(=O)NO]
N-hydroxy-2-methyloctadecanamide
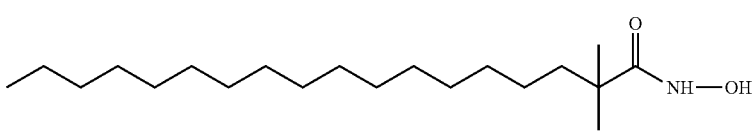 [SMILES: CCCCCCCCCCCCCCCCC(C)(C)C(=O)NO]
N-hydroxy-2,2-dimethyloctadecanamide
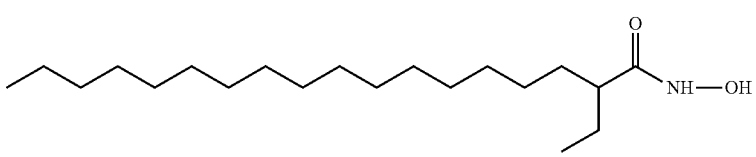 [SMILES: CCCCCCCCCCCCCCCCC(CC)C(=O)NO]
2-ethyl-N-hydroxyoctadecanamide -continued
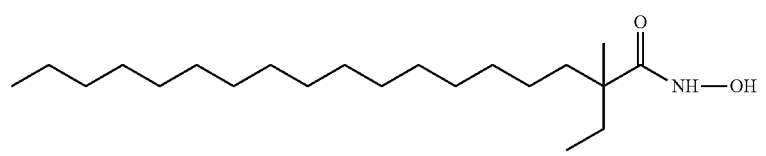 [SMILES: CCCCCCCCCCCCCCCCC(C)(CC)C(=O)NO]
2-ethyl-N-hydroxy-2-methyloctadecanamide
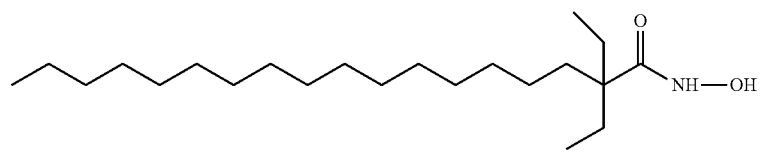 [SMILES: CCCCCCCCCCCCCCCCC(CC)(CC)C(=O)NO]
2,2-diethyl-N-hydroxyoctadecanamide
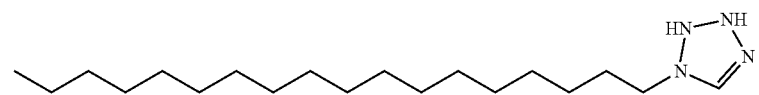 [SMILES: CCCCCCCCCCCCCCCCCCN1C=NNN1]
1-octadecyl-2,3-dihydro-1H-tetrazole
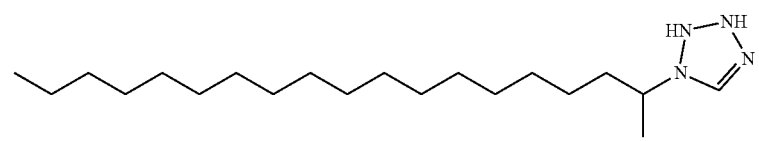 [SMILES: CCCCCCCCCCCCCCCCCC(C)N1C=NNN1]
1-(nonadecan-2-yl)-2,3-dihydro-1H-tetrazole
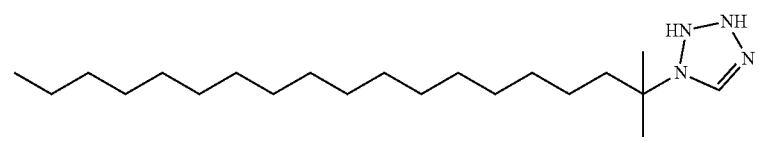 [SMILES: CCCCCCCCCCCCCCCCCC(C)(C)N1C=NNN1]
1-(2-methylnonadecan-2-yl)-2,3-dihydro-1H-tetrazole
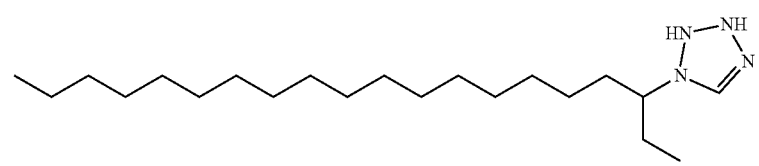 [SMILES: CCCCCCCCCCCCCCCCCC(CC)N1C=NNN1]
1-(icosan-3-yl)-2,3-dihydro-1H-tetrazole
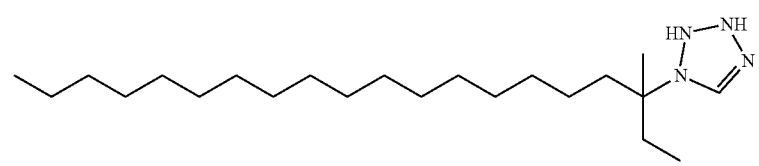 [SMILES: CCCCCCCCCCCCCCCCCC(C)(CC)N1C=NNN1]
1-(3-methylicosan-3-yl)-2,3-dihydro-1H-tetrazole
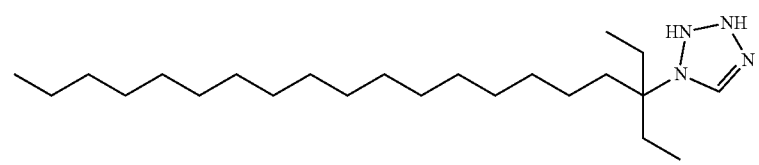 [SMILES: CCCCCCCCCCCCCCCCCC(CC)(CC)N1C=NNN1]
1-(3-ethylicosan-3-yl)-2,3-dihydro-1H-tetrazole

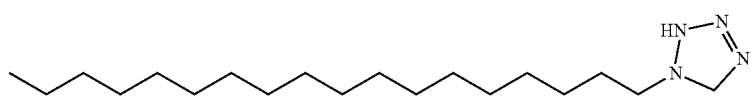 [SMILES: CCCCCCCCCCCCCCCCCCN1CN=NN1]
1-octadecyl-2,5-dihydro-1 H-tetrazole
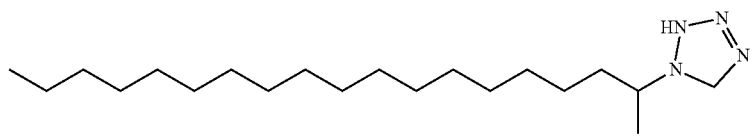 [SMILES: CCCCCCCCCCCCCCCCCC(C)N1CN=NN1]
1-(nonadecan-2-yl)-2,5-dihydro-1 H-tetrazole
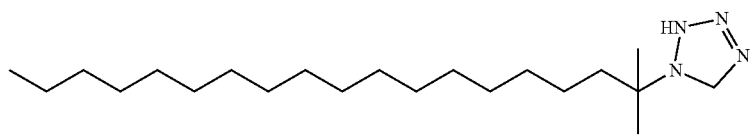 [SMILES: CCCCCCCCCCCCCCCCCC(C)(C)N1CN=NN1]
1-(2-methylnonadecan-2-yl)-2,5-dihydro-1 H-tetrazole
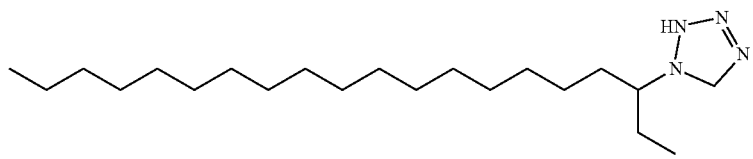 [SMILES: CCCCCCCCCCCCCCCCCC(CC)N1CN=NN1]
1-(icosan-3-yl)-2,5-dihydro-1 H-tetrazole
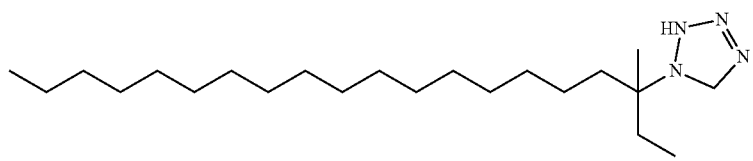 [SMILES: CCCCCCCCCCCCCCCCCC(C)(CC)N1CN=NN1]
1-(3-methylicosan-3-yl)-2,5-dihydro-1 H-tetrazole
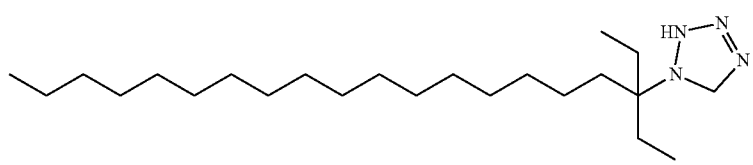 [SMILES: CCCCCCCCCCCCCCCCCC(CC)(CC)N1CN=NN1]
1-(3-ethylicosan-3-yl)-2,5-dihydro-1 H-tetrazole
Heptadecanoic Acid Analogs
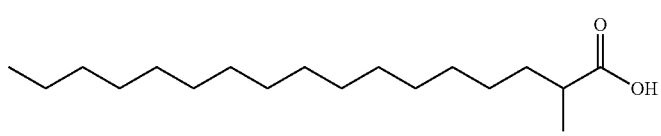 [SMILES: CCCCCCCCCCCCCCCC(C)C(=O)O]
2-methylheptadecanoic acid
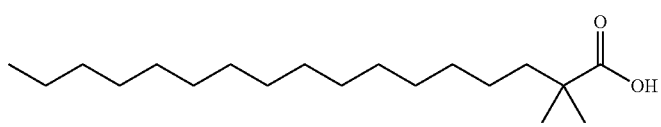 [SMILES: CCCCCCCCCCCCCCCC(C)(C)C(=O)O]
2,2-dimethylheptadecanoic acid -continued
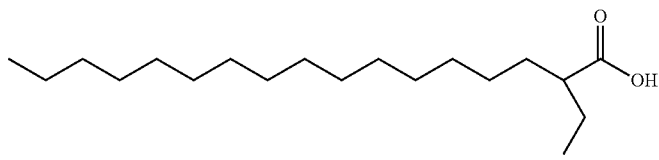 [SMILES: CCCCCCCCCCCCCCCC(CC)C(=O)O]
2-ethylheptadecanoic acid
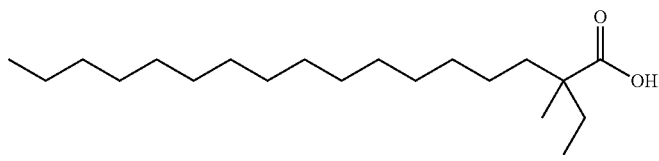 [SMILES: CCCCCCCCCCCCCCCC(C)(CC)C(=O)O]
2-ethyl-2-methylheptadecanoic acid
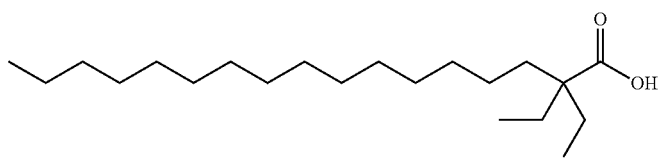 [SMILES: CCCCCCCCCCCCCCCC(CC)(CC)C(=O)O]
2,2-diethylheptadecanoic acid
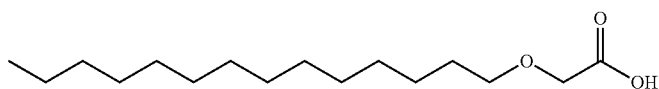 [SMILES: CCCCCCCCCCCCCCOCC(=O)O]
2-(tetradecyloxy)acetic acid
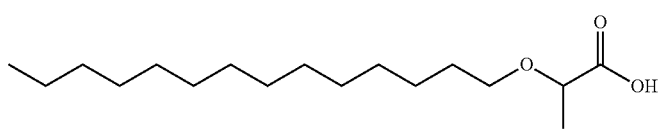 [SMILES: CCCCCCCCCCCCCCOC(C)C(=O)O]
2-(tetradecyloxy)propanoic acid
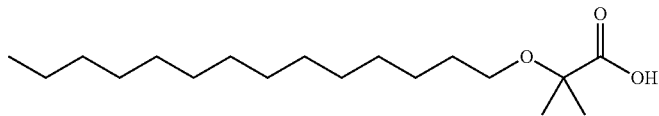 [SMILES: CCCCCCCCCCCCCCOC(C)(C)C(=O)O]
2-methyl-2-(tetradecyloxy)propanoic acid
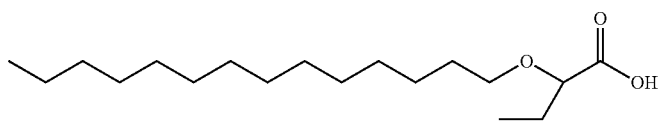 [SMILES: CCCCCCCCCCCCCCOC(CC)C(=O)O]
2-(tetradecyloxy)butanoic acid
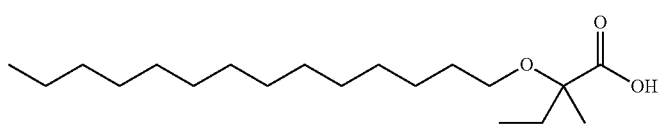 [SMILES: CCCCCCCCCCCCCCOC(C)(CC)C(=O)O]
2-methyl-2-(tetradecyloxy)butanoic acid
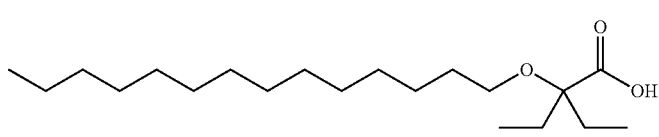 [SMILES: CCCCCCCCCCCCCCOC(CC)(CC)C(=O)O]
2-ethyl-2-(tetradecyloxy)butanoic acid

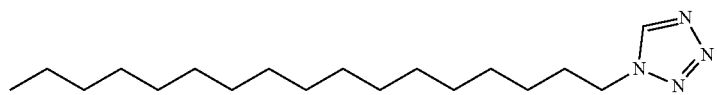 [SMILES: CCCCCCCCCCCCCCCCCn1cnnn1]
1-heptadecyl-1H-tetrazole
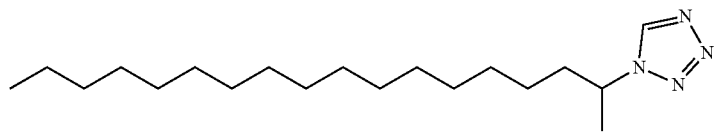
1-(octadecan-2-yl)-1H-tetrazole
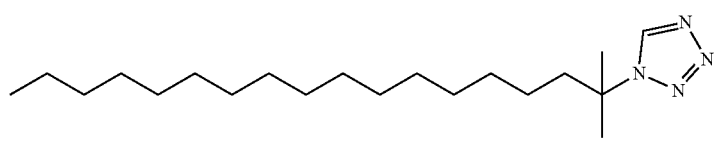 [SMILES: CCCCCCCCCCCCCCCCC(C)(C)n1cnnn1]
1-(2-methyloctadecan-2-yl)-1H-tetrazole
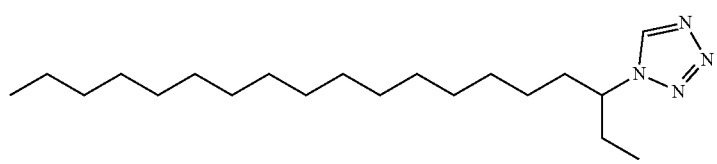 [SMILES: CCCCCCCCCCCCCCCCC(CC)n1cnnn1]
1-(nonadecan-3-yl)-1H-tetrazole
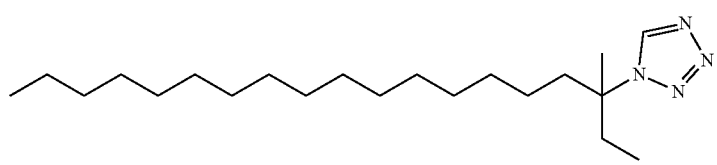 [SMILES: CCCCCCCCCCCCCCCCC(C)(CC)n1cnnn1]
1-(3-methylnonadecan-3-yl)-1H-tetrazole
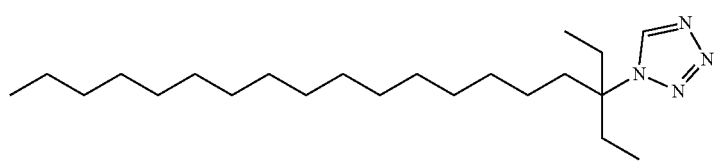 [SMILES: CCCCCCCCCCCCCCCCC(CC)(CC)n1cnnn1]
1-(3-ethylnonadecan-3-yl)-1H-tetrazole
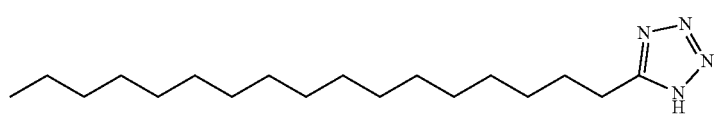 [SMILES: CCCCCCCCCCCCCCCCCc1nnn[nH]1]
5-heptadecyl-1H-tetrazole
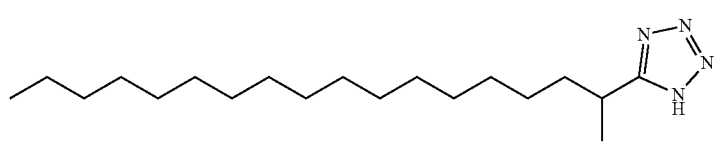 [SMILES: CCCCCCCCCCCCCCCCC(C)c1nnn[nH]1]
5-(octadecan-2-yl)-1H-tetrazole -continued
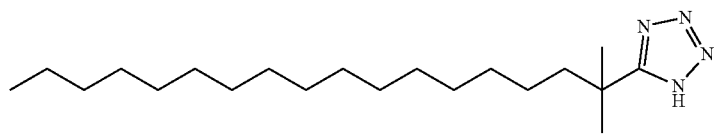 [SMILES: CCCCCCCCCCCCCCCCC(C)(C)c1nnn[nH]1]
5-(2-methyloctadecan-2-yl)-1 H-tetrazole
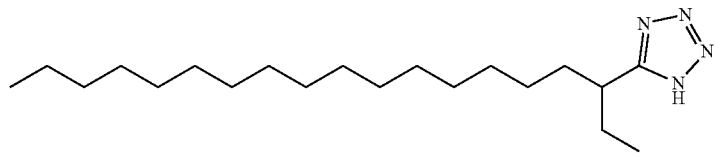 [SMILES: CCCCCCCCCCCCCCCCC(CC)c1nnn[nH]1]
5-(nonadecan-3-yl)-1 H-tetrazole
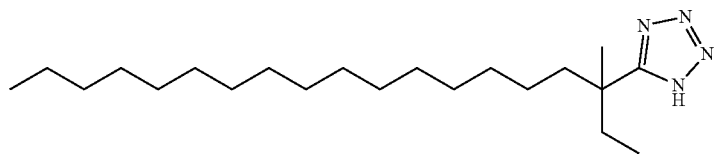 [SMILES: CCCCCCCCCCCCCCCCC(C)(CC)c1nnn[nH]1]
5-(3-methylnonadecan-3-yl)-1 H-tetrazole
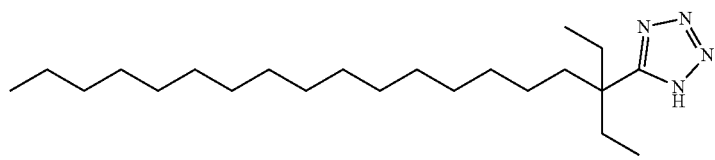 [SMILES: CCCCCCCCCCCCCCCCC(CC)(CC)c1nnn[nH]1]
5-(3-ethylnonadecan-3-yl)-1 H-tetrazole
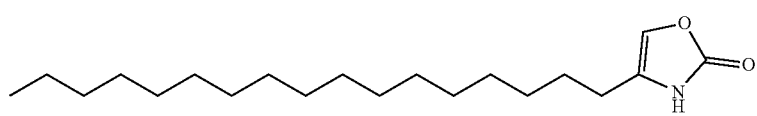 [SMILES: CCCCCCCCCCCCCCCCCc1coc(=O)[nH]1]
4-heptadecyloxazol-2(3 H)-one
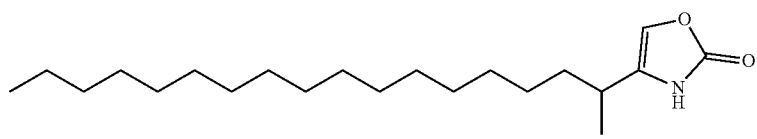 [SMILES: CCCCCCCCCCCCCCCCC(C)c1coc(=O)[nH]1]
4-(octadecan-2-yl)oxazol-2(3 H)-one
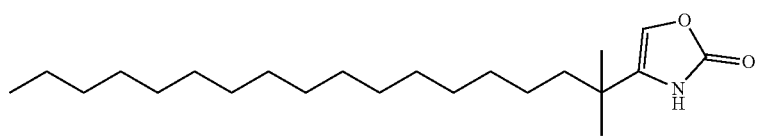 [SMILES: CCCCCCCCCCCCCCCCC(C)(C)c1coc(=O)[nH]1]
4-(2-methyloctadecan-2-yl)oxazol-2(3 H)-one
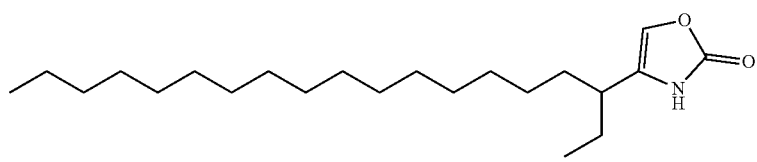 [SMILES: CCCCCCCCCCCCCCCCC(CC)c1coc(=O)[nH]1]
4-(nonadecan-3-yl)oxazol-2(3 H)-one

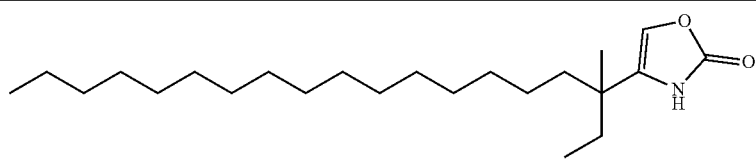
4-(3-methylnonadecan-3-yl)oxazol-2(3H)-one
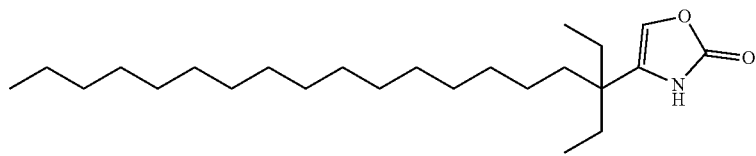 [SMILES: CCCCCCCCCCCCCCCCC(CC)(CC)c1coc(=O)[nH]1]
4-(3-ethylnonadecan-3-yl)oxazol-2(3H)-one
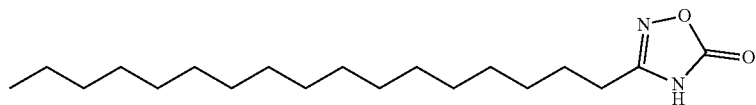 [SMILES: CCCCCCCCCCCCCCCCCc1noc(=O)[nH]1]
3-heptadecyl-1,2,4-oxadiazol-5(4H)-one
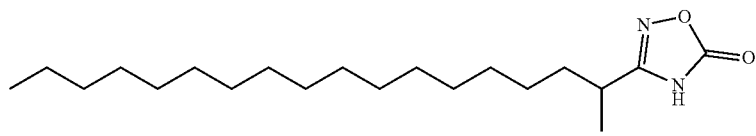 [SMILES: CCCCCCCCCCCCCCCCC(C)c1noc(=O)[nH]1]
3-(octadecan-2-yl)-1,2,4-oxadiazol-5(4H)-one
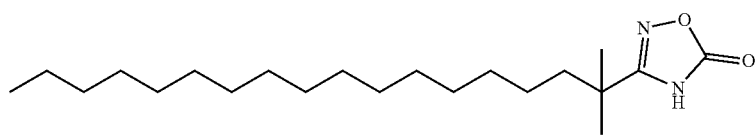 [SMILES: CCCCCCCCCCCCCCCCC(C)(C)c1noc(=O)[nH]1]
3-(2-methyloctadecan-2-yl)-1,2,4-oxadiazol-5(4H)-one
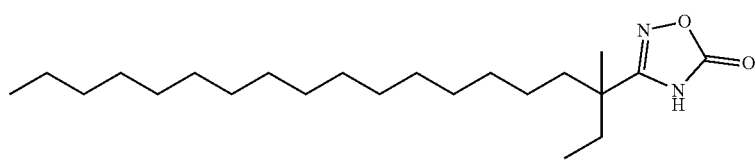 [SMILES: CCCCCCCCCCCCCCCCC(C)(CC)c1noc(=O)[nH]1]
3-(3-methylnonadecan-3-yl)-1,2,4-oxadiazol-5(4H)-one
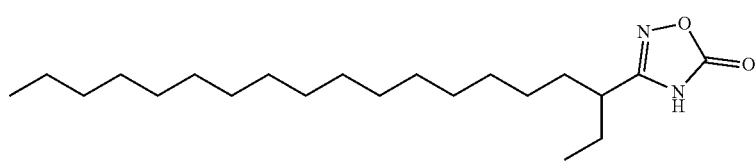 [SMILES: CCCCCCCCCCCCCCCCC(CC)c1noc(=O)[nH]1]
3-(nonadecan-3-yl)-1,2,4-oxadiazol-5(4H)-one
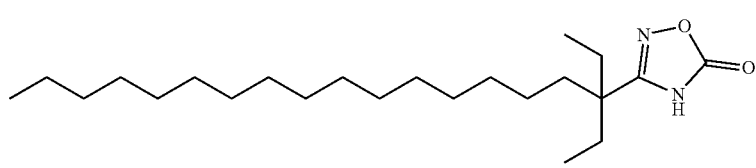 [SMILES: CCCCCCCCCCCCCCCCC(CC)(CC)c1noc(=O)[nH]1]
3-(3-ethylnonadecan-3-yl)-1,2,4-oxadiazol-5(4H)-one

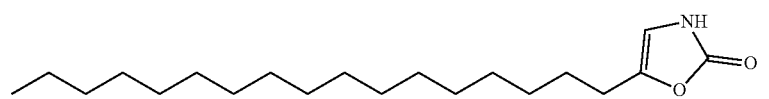 [SMILES: CCCCCCCCCCCCCCCCCc1c[nH]c(=O)o1]
5-heptadecyloxazol-2(3H)-one
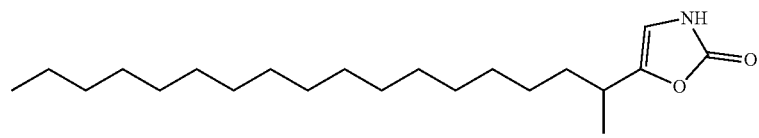 [SMILES: CCCCCCCCCCCCCCCCC(C)c1c[nH]c(=O)o1]
5-(octadecan-2-yl)oxazol-2(3H)-one
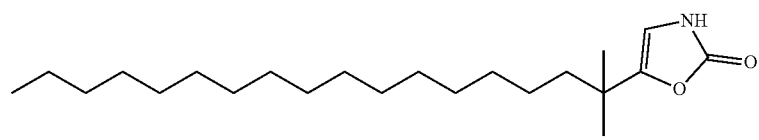 [SMILES: CCCCCCCCCCCCCCCCC(C)(C)c1c[nH]c(=O)o1]
5-(2-methyloctadecan-2-yl)oxazol-2(3H)-one
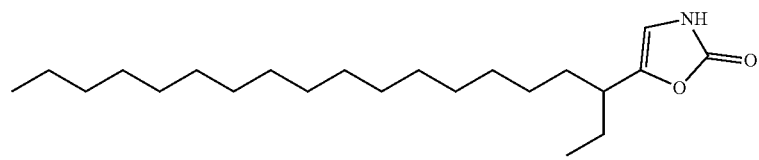 [SMILES: CCCCCCCCCCCCCCCCC(CC)c1c[nH]c(=O)o1]
5-(nonadecan-3-yl)oxazol-2(3H)-one
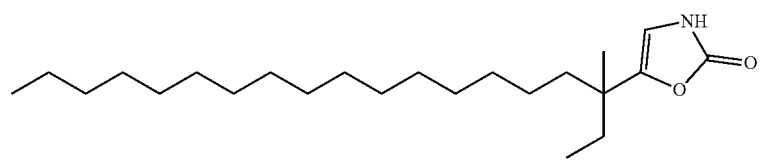
5-(3-methylnonadecan-3-yl)oxazol-2(3H)-one
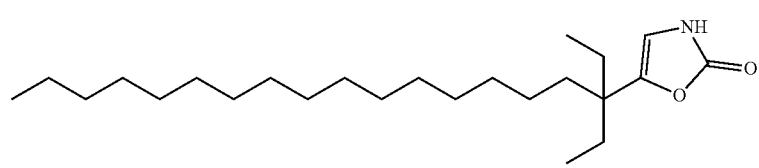 [SMILES: CCCCCCCCCCCCCCCCC(CC)(CC)c1c[nH]c(=O)o1]
5-(3-ethylnonadecan-3-yl)oxazol-2(3H)-one
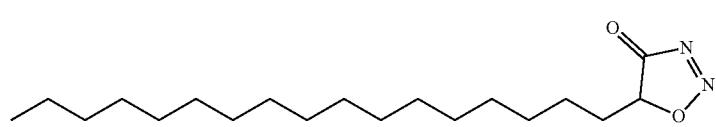 [SMILES: CCCCCCCCCCCCCCCCCC1ON=NC1=O]
5-heptadecyl-1,2,3-oxadiazol-4(5H)-one
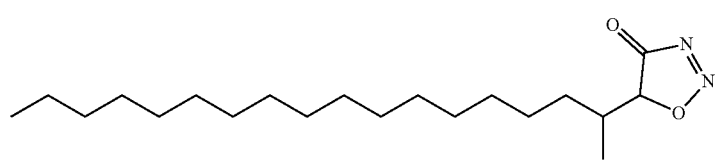 [SMILES: CCCCCCCCCCCCCCCCC(C)C1ON=NC1=O]
5-(octadecan-2-yl)-1,2,3-oxadiazol-4(5H)-one

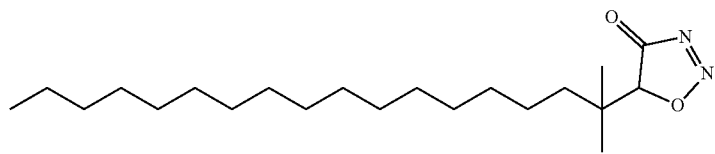 [SMILES: CCCCCCCCCCCCCCCCC(C)(C)C1ON=NC1=O]
5-(2-methyloctadecan-2-yl)-1,2,3-oxadiazol-4(5 H)-one
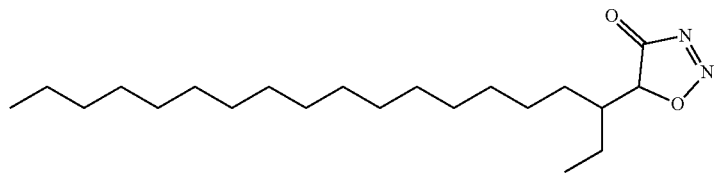 [SMILES: CCCCCCCCCCCCCCCCC(CC)C1ON=NC1=O]
5-(nonadecan-3-yl)-1,2,3-oxadiazol-4(5 H)-one
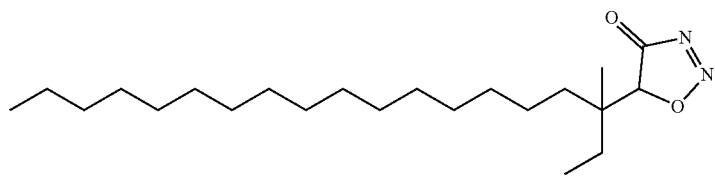 [SMILES: CCCCCCCCCCCCCCCCC(C)(CC)C1ON=NC1=O]
5-(3-methylnonadecan-3-yl)-1,2,3-oxadiazol-4(5 H)-one
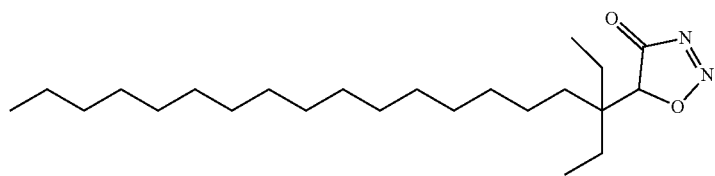 [SMILES: CCCCCCCCCCCCCCCCC(CC)(CC)C1ON=NC1=O]
5-(3-ethylnonadecan-3-yl)-1,2,3-oxadiazol-4(5 H)-one
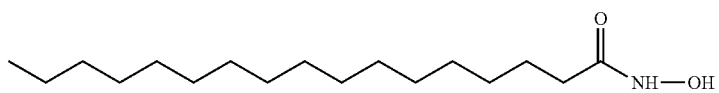 [SMILES: CCCCCCCCCCCCCCCCC(=O)NO]
N-hydroxyheptadecanamide
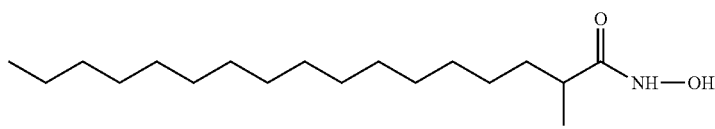 [SMILES: CCCCCCCCCCCCCCCC(C)C(=O)NO]
N-hydroxy-2-methylheptadecanamide
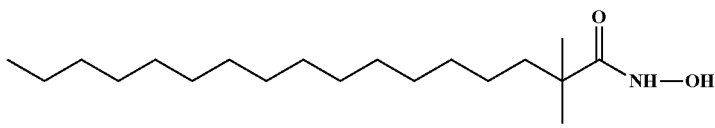 [SMILES: CCCCCCCCCCCCCCCC(C)(C)C(=O)NO]
N-hydroxy-2,2-dimethylheptadecanamide
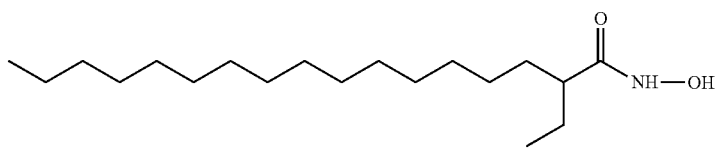 [SMILES: CCCCCCCCCCCCCCCC(CC)C(=O)NO]
2-ethyl-N-hydroxyheptadecanamide

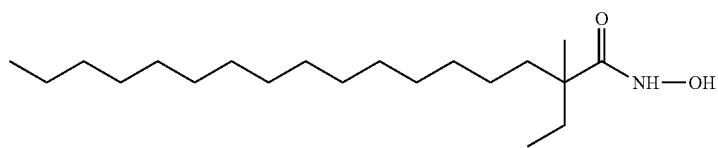 [SMILES: CCCCCCCCCCCCCCCC(C)(CC)C(=O)NO]
2-ethyl-N-hydroxy-2-methylheptadecanamide
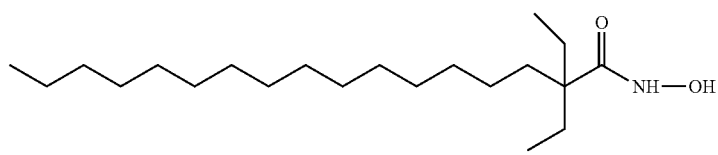 [SMILES: CCCCCCCCCCCCCCCC(CC)(CC)C(=O)NO]
2,2-diethyl-N-hydroxyheptadecanamide
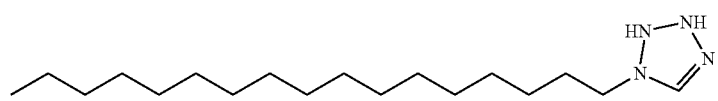 [SMILES: CCCCCCCCCCCCCCCCCN1C=NNN1]
1-heptadecyl-2,3-dihydro-1 H-tetrazole
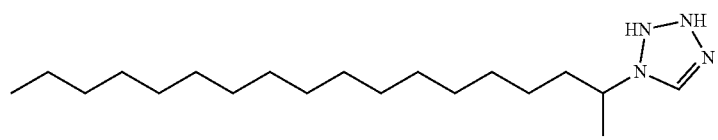 [SMILES: CCCCCCCCCCCCCCCCC(C)N1C=NNN1]
1-(octadecan-2-yl)-2,3-dihydro-1 H-tetrazole
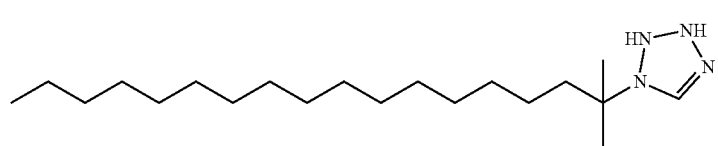 [SMILES: CCCCCCCCCCCCCCCCC(C)(C)N1C=NNN1]
1-(2-methyloctadecan-2-yl)-2,3-dihydro-1 H-tetrazole
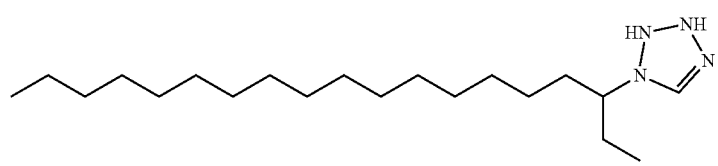 [SMILES: CCCCCCCCCCCCCCCCC(CC)N1C=NNN1]
1-(nonadecan-3-yl)-2,3-dihydro-1 H-tetrazole
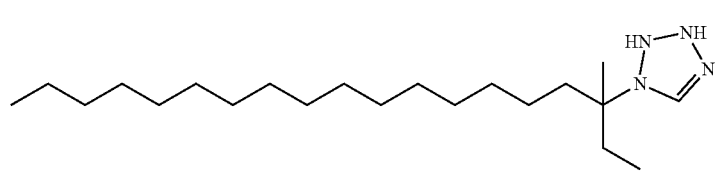 [SMILES: CCCCCCCCCCCCCCCCC(C)(CC)N1C=NNN1]
1-(3-methylnonadecan-3-yl)-2,3-dihydro-1 H-tetrazole
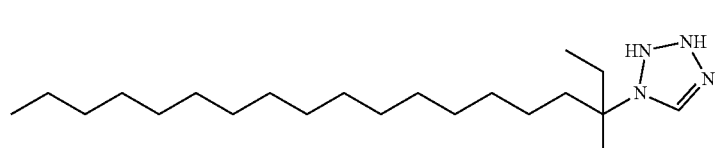
1-(3-ethylnonadecan-3-yl)-2,3-dihydro-1 H-tetrazole -continued
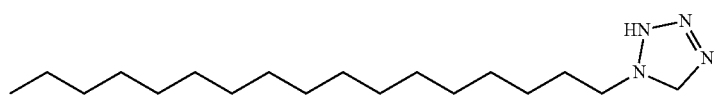 [SMILES: CCCCCCCCCCCCCCCCCN1CN=NN1]
1-heptadecyl-2,5-dihydro-1 H-tetrazole
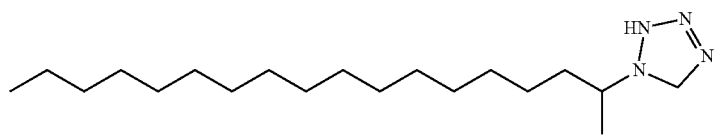 [SMILES: CCCCCCCCCCCCCCCCC(C)N1CN=NN1]
1-(octadecan-2-yl)-2,5-dihydro-1 H-tetrazole
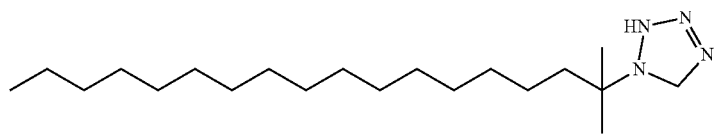 [SMILES: CCCCCCCCCCCCCCCCC(C)(C)N1CN=NN1]
1-(2-methyloctadecan-2-yl)-2,5-dihydro-1 H-tetrazole
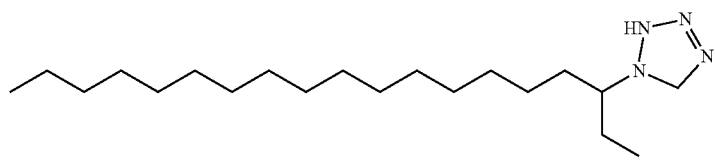 [SMILES: CCCCCCCCCCCCCCCCC(CC)N1CN=NN1]
1-(nonadecan-3-yl)-2,5-dihydro-1 H-tetrazole
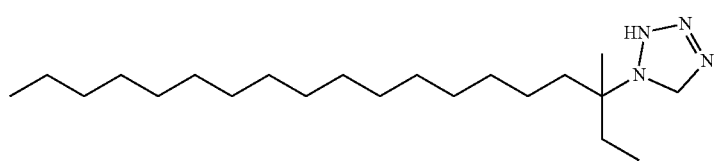 [SMILES: CCCCCCCCCCCCCCCCC(C)(CC)N1CN=NN1]
1-(3-methylnonadecan-3-yl)-2,5-dihydro-1 H-tetrazole
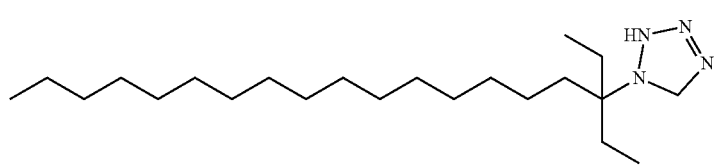 [SMILES: CCCCCCCCCCCCCCCCC(CC)(CC)N1CN=NN1]
1-(3-ethylnonadecan-3-yl)-2,5-dihydro-1 H-tetrazole
| Palmitic Acid Analogs |
| --- |
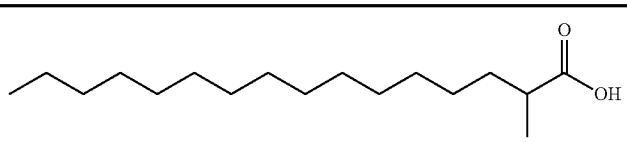
2-methylhexadecanoic acid
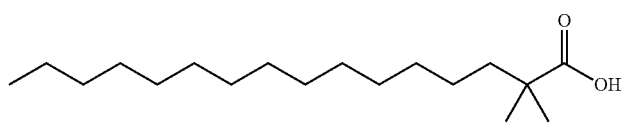 [SMILES: CCCCCCCCCCCCCCC(C)(C)C(=O)O]
2,2-dimethylhexadecanoic acid -continued
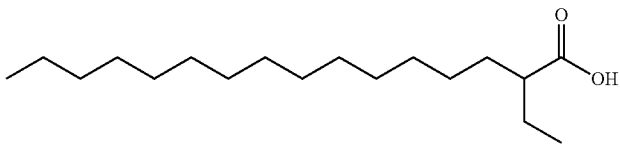 [SMILES: CCCCCCCCCCCCCCC(CC)C(=O)O]
2-ethylhexadecanoic acid
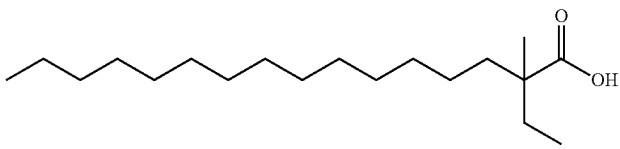 [SMILES: CCCCCCCCCCCCCCC(C)(CC)C(=O)O]
2-ethyl-2-methylhexadecanoic acid
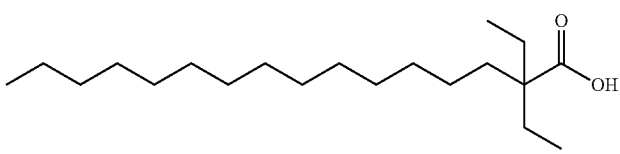 [SMILES: CCCCCCCCCCCCCCC(CC)(CC)C(=O)O]
2,2-diethylhexadecanoic acid
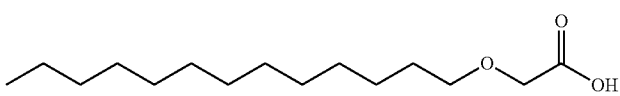 [SMILES: CCCCCCCCCCCCCOCC(=O)O]
2-(tridecyloxy)acetic acid
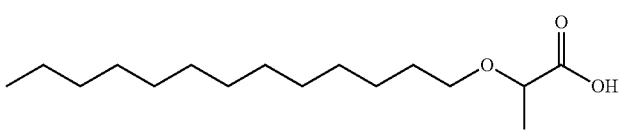 [SMILES: CCCCCCCCCCCCCOC(C)C(=O)O]
2-(tridecyloxy)propanoic acid
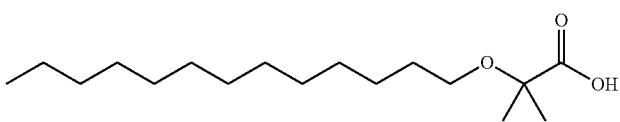 [SMILES: CCCCCCCCCCCCCOC(C)(C)C(=O)O]
2-methyl-2-(tridecyloxy)propanoic acid
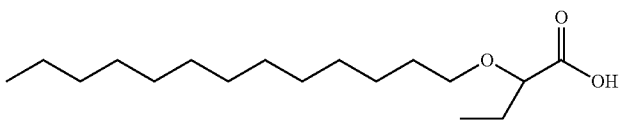 [SMILES: CCCCCCCCCCCCCOC(CC)C(=O)O]
2-(tridecyloxy)butanoic acid
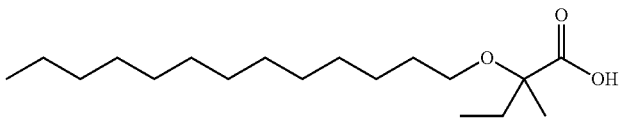 [SMILES: CCCCCCCCCCCCCOC(C)(CC)C(=O)O]
2-methyl-2-(tridecyloxy)butanoic acid
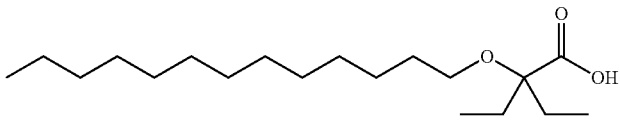 [SMILES: CCCCCCCCCCCCCOC(CC)(CC)C(=O)O]
2-ethyl-2-(tridecyloxy)butanoic acid -continued
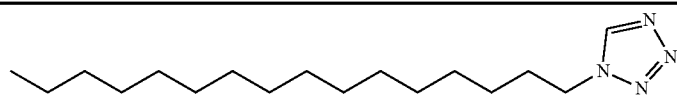
1-hexadecyl-1 H-tetrazole
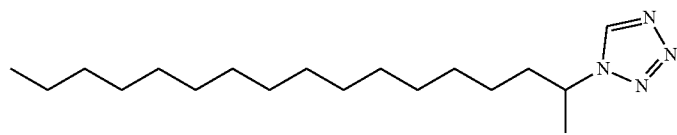 [SMILES: CCCCCCCCCCCCCCCC(C)n1cnnn1]
1-(heptadecan-2-yl)-1 H-tetrazole
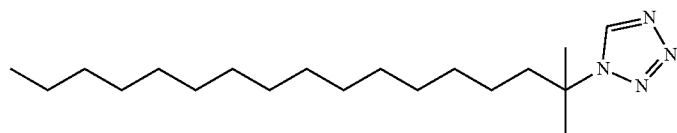 [SMILES: CCCCCCCCCCCCCCCC(C)(C)n1cnnn1]
1-(2-methylheptadecan-2-yl)-1 H-tetrazole
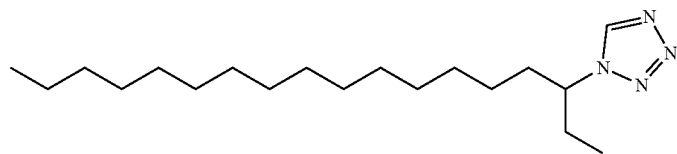 [SMILES: CCCCCCCCCCCCCCCC(CC)n1cnnn1]
1-(octadecan-3-yl)-1 H-tetrazole
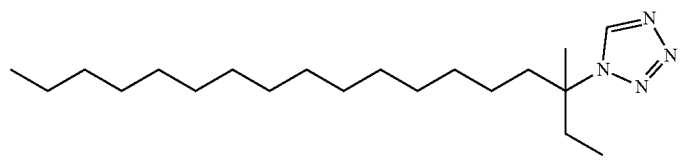 [SMILES: CCCCCCCCCCCCCCCC(C)(CC)n1cnnn1]
1-(3-methyloctadecan-3-yl)-1 H-tetrazole
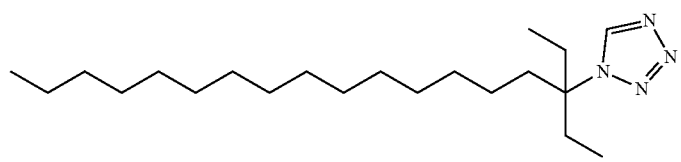 [SMILES: CCCCCCCCCCCCCCCC(CC)(CC)n1cnnn1]
1-(3-ethyloctadecan-3-yl)-1 H-tetrazole
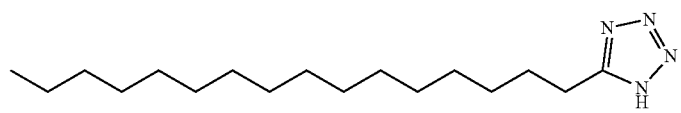 [SMILES: CCCCCCCCCCCCCCCCc1nnn[nH]1]
5-hexadecyl-1 H-tetrazole
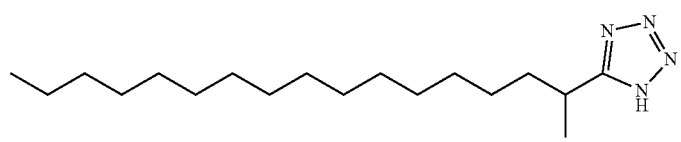 [SMILES: CCCCCCCCCCCCCCCC(C)c1nnn[nH]1]
5-(heptadecan-2-yl)-1 H-tetrazole
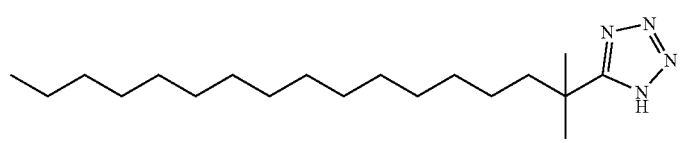 [SMILES: CCCCCCCCCCCCCCCC(C)(C)c1nnn[nH]1]
5-(2-methylheptadecan-2-yl)-1 H-tetrazole

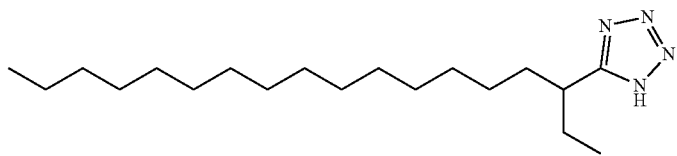 [SMILES: CCCCCCCCCCCCCCCC(CC)c1nnn[nH]1]
5-(octadecan-3-yl)-1 H-tetrazole
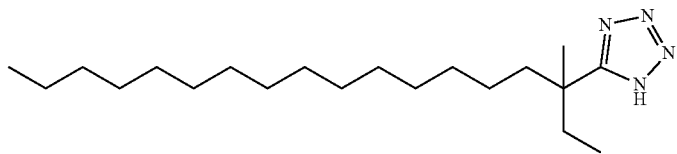 [SMILES: CCCCCCCCCCCCCCCC(C)(CC)c1nnn[nH]1]
5-(3-methyloctadecan-3-yl)-1 H-tetrazole
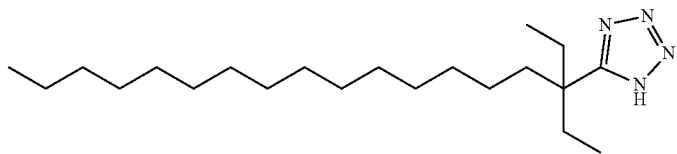 [SMILES: CCCCCCCCCCCCCCCC(CC)(CC)c1nnn[nH]1]
5-(3-ethyloctadecan-3-yl)-1 H-tetrazole
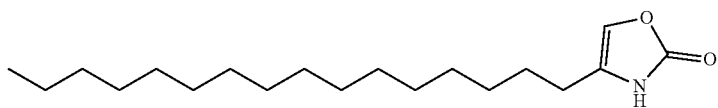 [SMILES: CCCCCCCCCCCCCCCCc1coc(=O)[nH]1]
4-hexadecyloxazol-2(3 H)-one
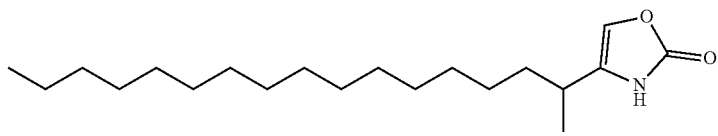 [SMILES: CCCCCCCCCCCCCCCC(C)c1coc(=O)[nH]1]
4-(heptadecan-2-yl)oxazol-2(3 H)-one
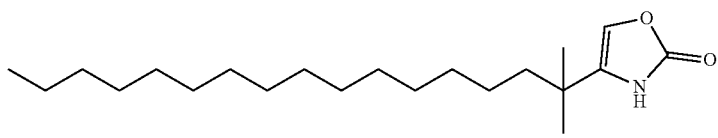 [SMILES: CCCCCCCCCCCCCCCC(C)(C)c1coc(=O)[nH]1]
4-(2-methylheptadecan-2-yl)oxazol-2(3 H)-one
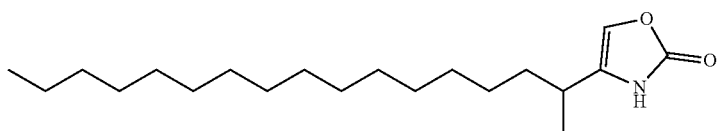
4-(octadecan-3-yl)oxazol-2(3 H)-one
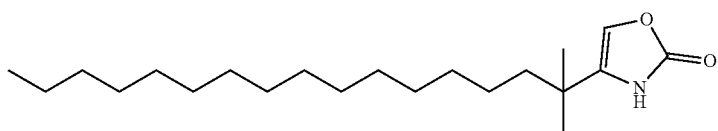
4-(3-methyloctadecan-3-yl)oxazol-2(3 H)-one -continued
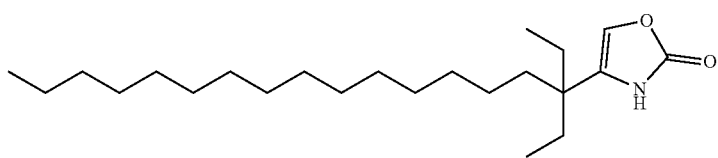
4-(3-ethyloctadecan-3-yl)oxazol-2(3H)-one
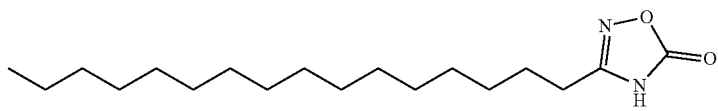
3-hexadecyl-1,2,4-oxadiazol-5(4H)-one
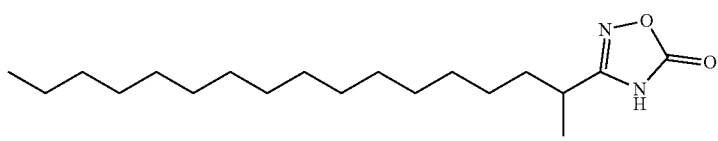 [SMILES: CCCCCCCCCCCCCCCC(C)c1noc(=O)[nH]1]
3-(heptadecan-2-yl)-1,2,4-oxadiazol-5(4H)-one
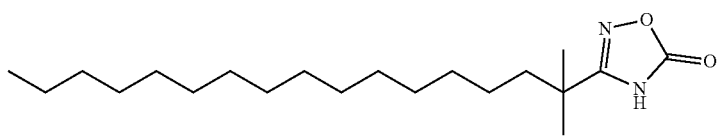
3-(2-methylheptadecan-2-yl)-1,2,4-oxadiazol-5(4H)-one
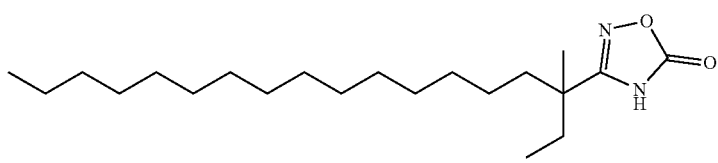 [SMILES: CCCCCCCCCCCCCCCC(C)(CC)c1noc(=O)[nH]1]
3-(3-methyloctadecan-3-yl)-1,2,4-oxadiazol-5(4H)-one
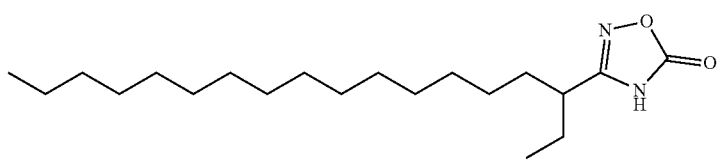 [SMILES: CCCCCCCCCCCCCCCC(CC)c1noc(=O)[nH]1]
3-(octadecan-3-yl)-1,2,4-oxadiazol-5(4H)-one
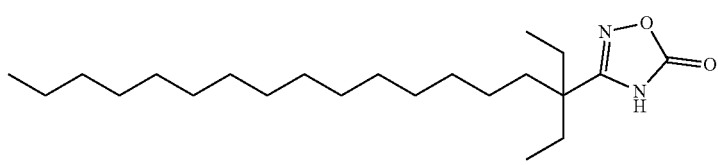
3-(3-ethyloctadecan-3-yl)-1,2,4-oxadiazol-5(4H)-one
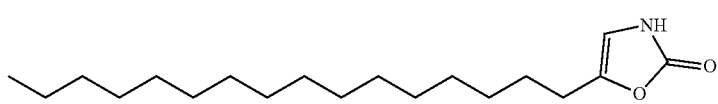 [SMILES: CCCCCCCCCCCCCCCCc1c[nH]c(=O)o1]
5-hexadecyloxazol-2(3H)-one -continued
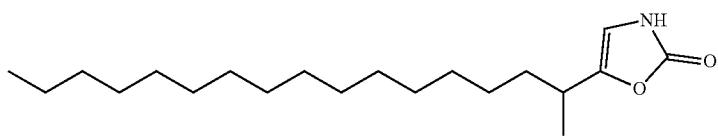 [SMILES: CCCCCCCCCCCCCCCC(C)c1c[nH]c(=O)o1]
5-(heptadecan-2-yl)oxazol-2(3H)-one
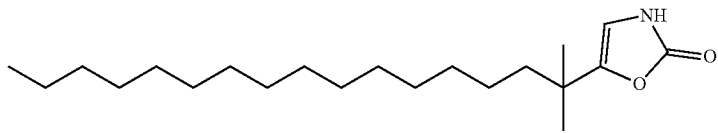 [SMILES: CCCCCCCCCCCCCCCC(C)(C)c1c[nH]c(=O)o1]
5-(2-methylheptadecan-2-yl)oxazol-2(3H)-one
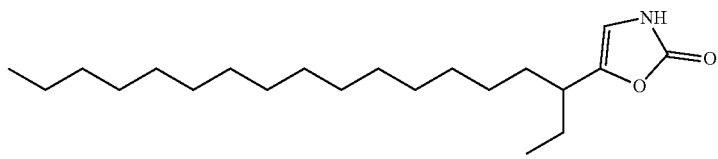 [SMILES: CCCCCCCCCCCCCCCC(CC)c1c[nH]c(=O)o1]
5-(octadecan-3-yl)oxazol-2(3H)-one
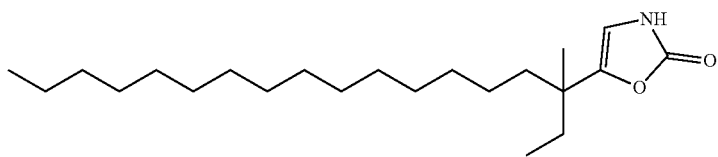 [SMILES: CCCCCCCCCCCCCCCC(C)(CC)c1c[nH]c(=O)o1]
5-(3-methyloctadecan-3-yl)oxazol-2(3H)-one
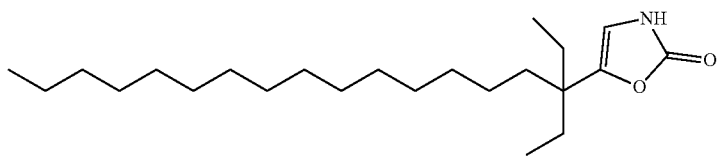 [SMILES: CCCCCCCCCCCCCCCC(CC)(CC)c1c[nH]c(=O)o1]
5-(3-ethyloctadecan-3-yl)oxazol-2(3H)-one
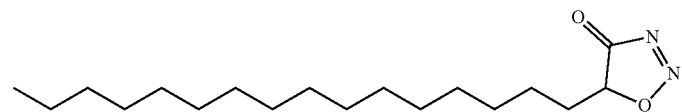 [SMILES: CCCCCCCCCCCCCCCCC1ON=NC1=O]
5-hexadecyl-1,2,3-oxadiazol-4(5H)-one
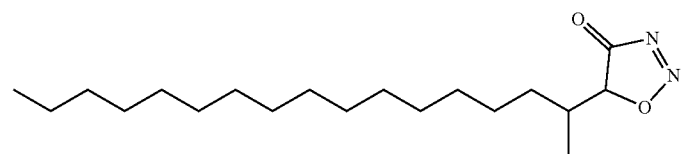 [SMILES: CCCCCCCCCCCCCCCC(C)C1ON=NC1=O]
5-(heptadecan-2-yl)-1,2,3-oxadiazol-4(5H)-one
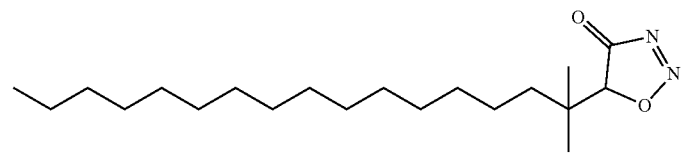 [SMILES: CCCCCCCCCCCCCCCC(C)(C)C1ON=NC1=O]
5-(2-methylheptadecan-2-yl)-1,2,3-oxadiazol-4(5H)-one

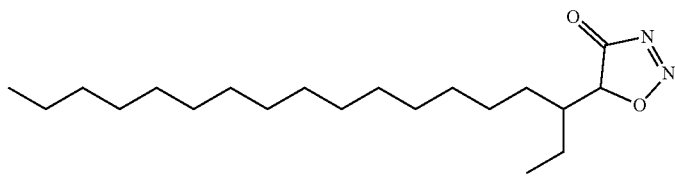 [SMILES: CCCCCCCCCCCCCCCC(CC)C1ON=NC1=O]
5-(octadecan-3-yl)-1,2,3-oxadiazol-4(5H)-one
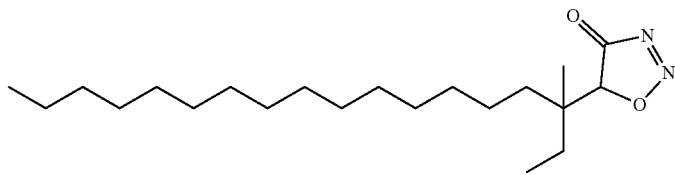 [SMILES: CCCCCCCCCCCCCCCC(C)(CC)C1ON=NC1=O]
5-(3-methyloctadecan-3-yl)-1,2,3-oxadiazol-4(5H)-one
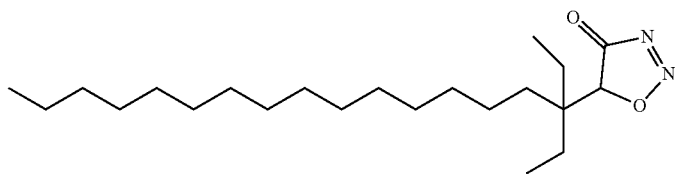 [SMILES: CCCCCCCCCCCCCCCC(CC)(CC)C1ON=NC1=O]
5-(3-ethyloctadecan-3-yl)-1,2,3-oxadiazol-4(5H)-one
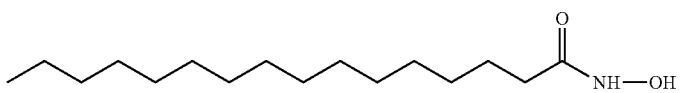 [SMILES: CCCCCCCCCCCCCCCC(=O)NO]
N-hydroxypalmitamide
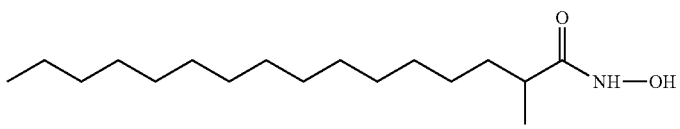 [SMILES: CCCCCCCCCCCCCCC(C)C(=O)NO]
N-hydroxy-2-methylhexadecanamide
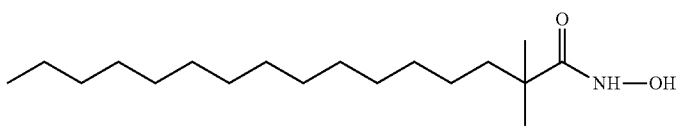 [SMILES: CCCCCCCCCCCCCCC(C)(C)C(=O)NO]
N-hydroxy-2,2-dimethylhexadecanamide
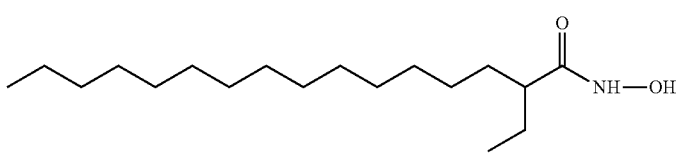 [SMILES: CCCCCCCCCCCCCCC(CC)C(=O)NO]
2-ethyl-N-hydroxyhexadecanamide
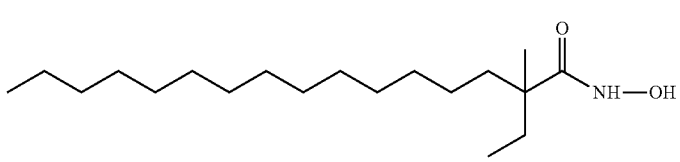 [SMILES: CCCCCCCCCCCCCCC(C)(CC)C(=O)NO]
2-ethyl-N-hydroxy-2-methylhexadecanamide

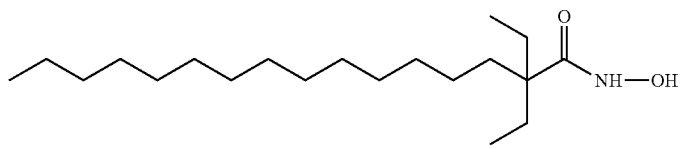 [SMILES: CCCCCCCCCCCCCCC(CC)(CC)C(=O)NO]
2,2-diethyl-N-hydroxyhexadecanamide
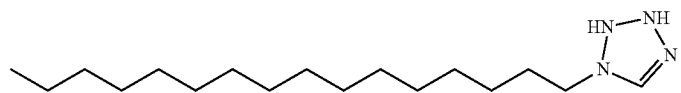 [SMILES: CCCCCCCCCCCCCCCCN1C=NNN1]
1-hexadecyl-2,3-dihydro-1 H-tetrazole
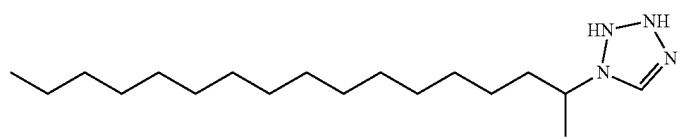 [SMILES: CCCCCCCCCCCCCCCC(C)N1C=NNN1]
1-(heptadecan-2-yl)-2,3-dihydro-1 H-tetrazole
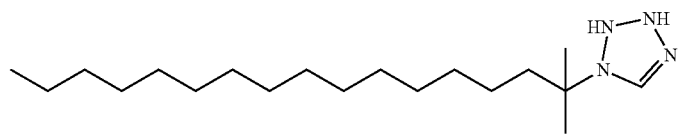 [SMILES: CCCCCCCCCCCCCCCC(C)(C)N1C=NNN1]
1-(2-methylheptadecan-2-yl)-2,3-dihydro-1 H-tetrazole
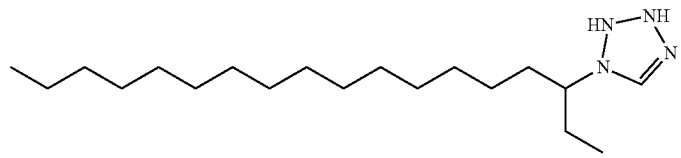 [SMILES: CCCCCCCCCCCCCCCC(CC)N1C=NNN1]
1-(octadecan-3-yl)-2,3-dihydro-1 H-tetrazole
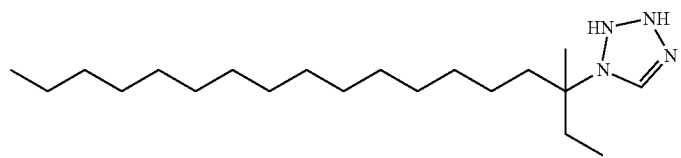 [SMILES: CCCCCCCCCCCCCCCC(C)(CC)N1C=NNN1]
1-(3-methyloctadecan-3-yl)-2,3-dihydro-1 H-tetrazole
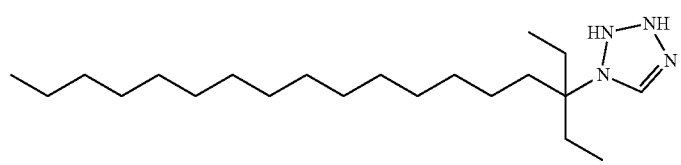 [SMILES: CCCCCCCCCCCCCCCC(CC)(CC)N1C=NNN1]
1-(3-ethyloctadecan-3-yl)-2,3-dihydro-1 H-tetrazole
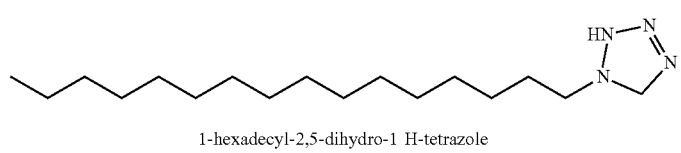
1-hexadecyl-2,5-dihydro-1 H-tetrazole

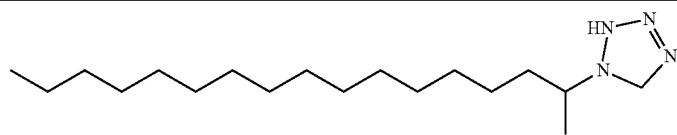
1-(heptadecan-2-yl)-2,5-dihydro-1 H-tetrazole
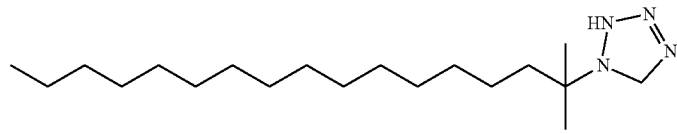 [SMILES: CCCCCCCCCCCCCCCC(C)(C)N1CN=NN1]
1-(2-methylheptadecan-2-yl)-2,5-dihydro-1 H-tetrazole
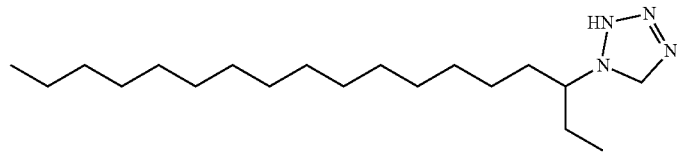 [SMILES: CCCCCCCCCCCCCCCC(CC)N1CN=NN1]
1-(octadecan-3-yl)-2,5-dihydro-1 H-tetrazole
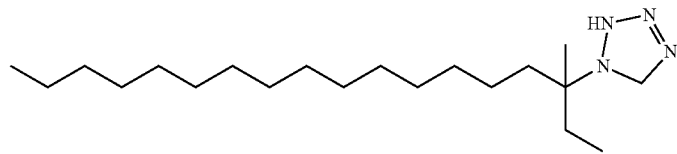 [SMILES: CCCCCCCCCCCCCCCC(C)(CC)N1CN=NN1]
1-(3-methyloctadecan-3-yl)-2,5-dihydro-1 H-tetrazole
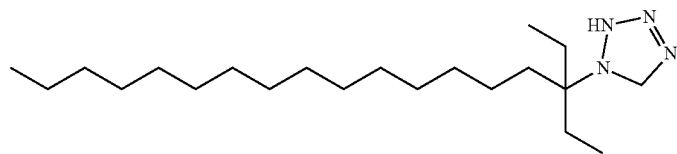 [SMILES: CCCCCCCCCCCCCCCC(CC)(CC)N1CN=NN1]
1-(3-ethyloctadecan-3-yl)-2,5-dihydro-1 H-tetrazole
| Pentadecanoic Acid Analogs |
|---|
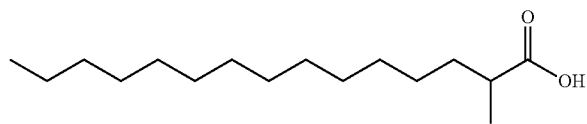 [SMILES: CCCCCCCCCCCCCC(C)C(=O)O]
2-methylpentadecanoic acid
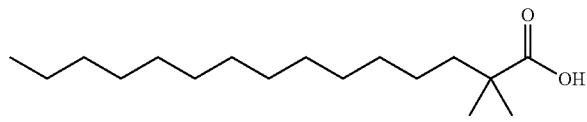 [SMILES: CCCCCCCCCCCCCC(C)(C)C(=O)O]
2,2-dimethylpentadecanoic acid
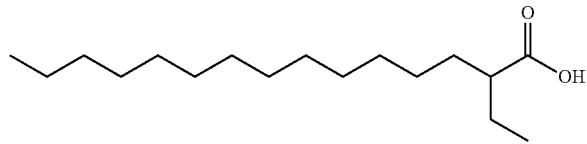 [SMILES: CCCCCCCCCCCCCC(CC)C(=O)O]
2-ethylpentadecanoic acid

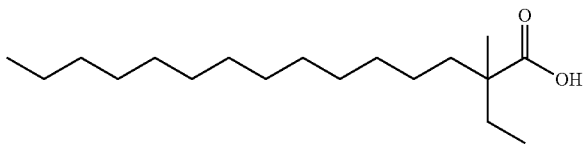 [SMILES: CCCCCCCCCCCCCC(C)(CC)C(=O)O]
2-ethyl-2-methylpentadecanoic acid
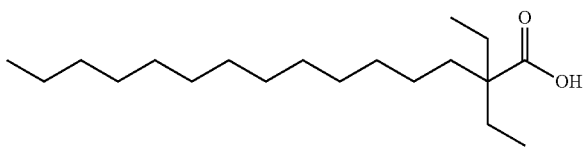 [SMILES: CCCCCCCCCCCCCC(CC)(CC)C(=O)O]
2,2-diethylpentadecanoic acid
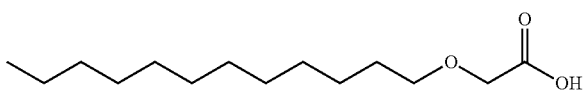 [SMILES: CCCCCCCCCCCCOCC(=O)O]
2-(dodecyloxy)acetic acid
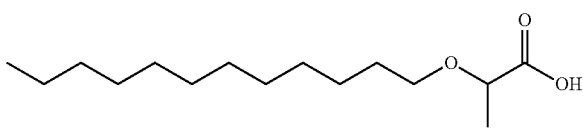 [SMILES: CCCCCCCCCCCCOC(C)C(=O)O]
2-(dodecyloxy)propanoic acid
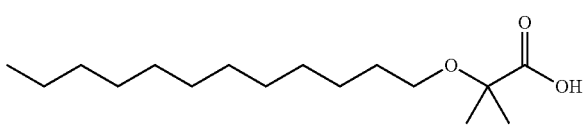 [SMILES: CCCCCCCCCCCCOC(C)(C)C(=O)O]
2-(dodecyloxy)-2-methylpropanoic acid
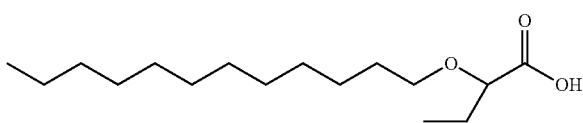 [SMILES: CCCCCCCCCCCCOC(CC)C(=O)O]
2-(dodecyloxy)butanoic acid
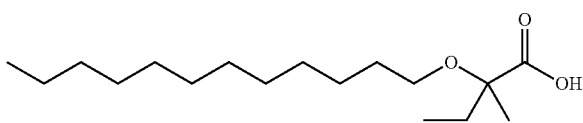 [SMILES: CCCCCCCCCCCCOC(C)(CC)C(=O)O]
2-(dodecyloxy)-2-methylbutanoic acid
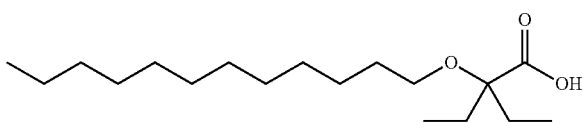 [SMILES: CCCCCCCCCCCCOC(CC)(CC)C(=O)O]
2-(dodecyloxy)-2-ethylbutanoic acid
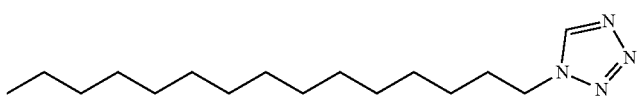 [SMILES: CCCCCCCCCCCCCCCn1cnnn1]
1-pentadecyl-1H-tetrazole -continued
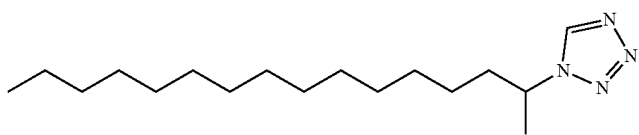 [SMILES: CCCCCCCCCCCCCCC(C)n1cnnn1]
1-(hexadecan-2-yl)-1 H-tetrazole
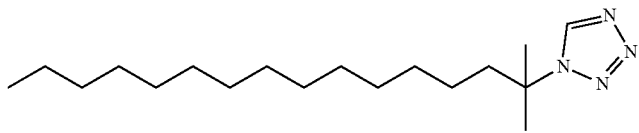 [SMILES: CCCCCCCCCCCCCCC(C)(C)n1cnnn1]
1-(2-methylhexadecan-2-yl)-1 H-tetrazole
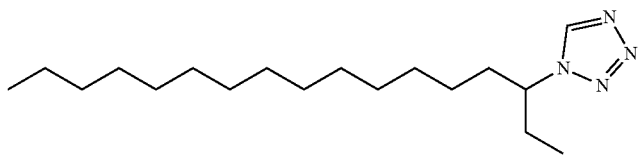 [SMILES: CCCCCCCCCCCCCCC(CC)n1cnnn1]
1-(heptadecan-3-yl)-1 H-tetrazole
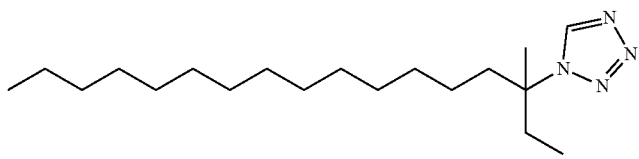 [SMILES: CCCCCCCCCCCCCCC(C)(CC)n1cnnn1]
1-(3-methylheptadecan-3-yl)-1 H-tetrazole
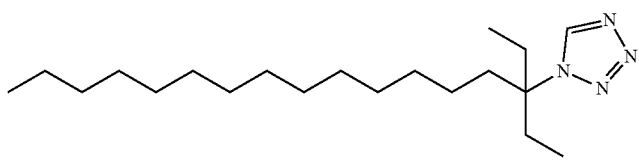 [SMILES: CCCCCCCCCCCCCCC(CC)(CC)n1cnnn1]
1-(3-ethylheptadecan-3-yl)-1 H-tetrazole
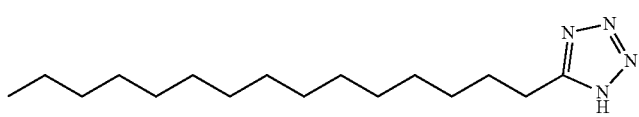 [SMILES: CCCCCCCCCCCCCCCc1nnn[nH]1]
5-pentadecyl-1 H-tetrazole
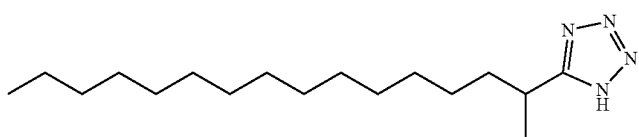 [SMILES: CCCCCCCCCCCCCCC(C)c1nnn[nH]1]
5-(hexadecan-2-yl)-1 H-tetrazole
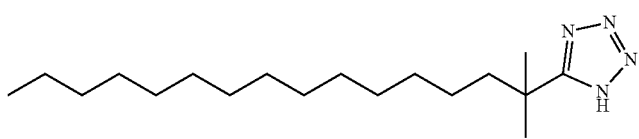 [SMILES: CCCCCCCCCCCCCCC(C)(C)c1nnn[nH]1]
5-(2-methylhexadecan-2-yl)-1 H-tetrazole

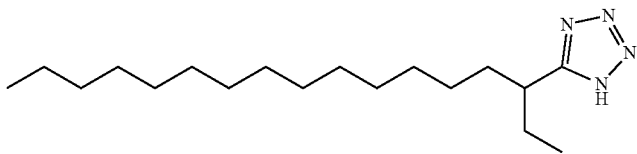 [SMILES: CCCCCCCCCCCCCCC(CC)c1nnn[nH]1]
5-(heptadecan-3-yl)-1 H-tetrazole
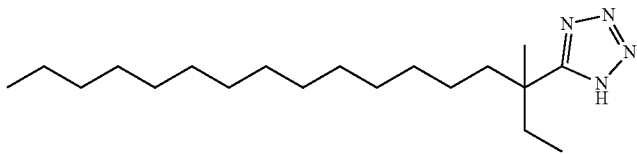 [SMILES: CCCCCCCCCCCCCCC(C)(CC)c1nnn[nH]1]
5-(3-methylheptadecan-3-yl)-1 H-tetrazole
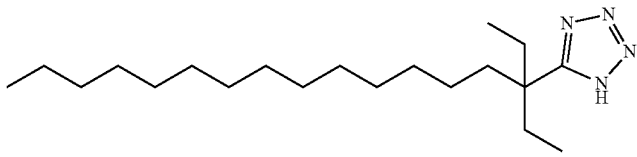 [SMILES: CCCCCCCCCCCCCCC(CC)(CC)c1nnn[nH]1]
5-(3-ethylheptadecan-3-yl)-1 H-tetrazole
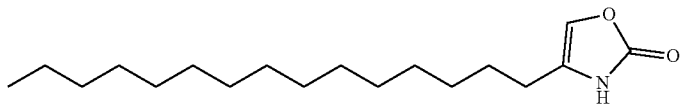
4-pentadecyloxazol-2(3 H)-one
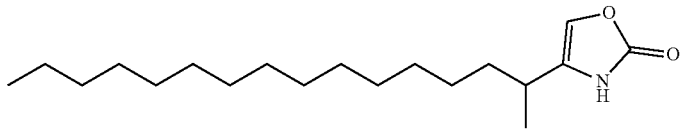 [SMILES: CCCCCCCCCCCCCCC(C)c1coc(=O)[nH]1]
4-(hexadecan-2-yl)oxazol-2(3 H)-one
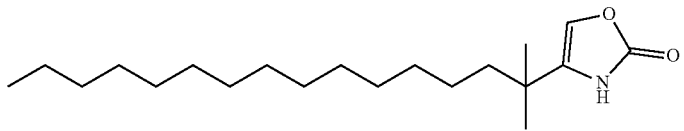 [SMILES: CCCCCCCCCCCCCCC(C)(C)c1coc(=O)[nH]1]
4-(2-methylhexadecan-2-yl)oxazol-2(3 H)-one
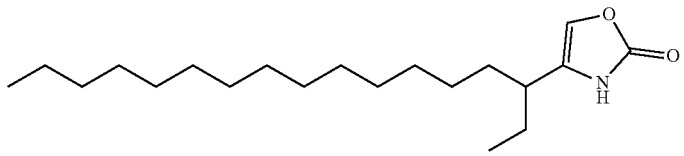 [SMILES: CCCCCCCCCCCCCCC(CC)c1coc(=O)[nH]1]
4-(heptadecan-3-yl)oxazol-2(3 H)-one
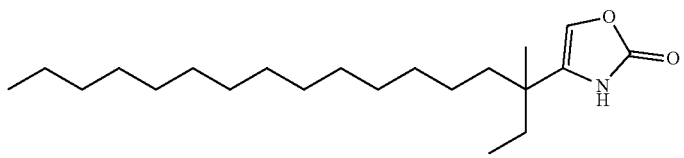 [SMILES: CCCCCCCCCCCCCCC(C)(CC)c1coc(=O)[nH]1]
4-(3-methylheptadecan-3-yl)oxazol-2(3 H)-one -continued
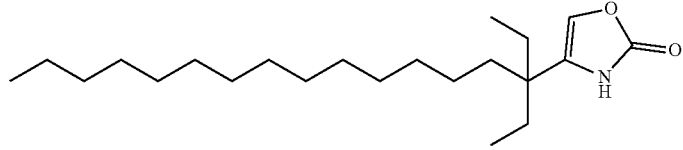 [SMILES: CCCCCCCCCCCCCCC(CC)(CC)c1coc(=O)[nH]1]
4-(3-ethylheptadecan-3-yl)oxazol-2(3H)-one
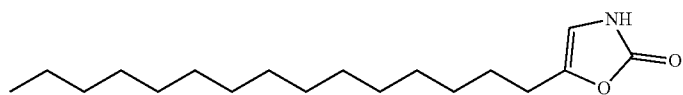 [SMILES: CCCCCCCCCCCCCCCc1c[nH]c(=O)o1]
5-pentadecyloxazol-2(3H)-one
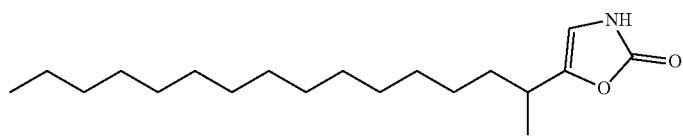 [SMILES: CCCCCCCCCCCCCCC(C)c1c[nH]c(=O)o1]
5-(hexadecan-2-yl)oxazol-2(3H)-one
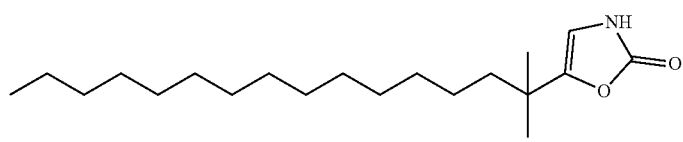 [SMILES: CCCCCCCCCCCCCCC(C)(C)c1c[nH]c(=O)o1]
5-(2-methylhexadecan-2-yl)oxazol-2(3H)-one
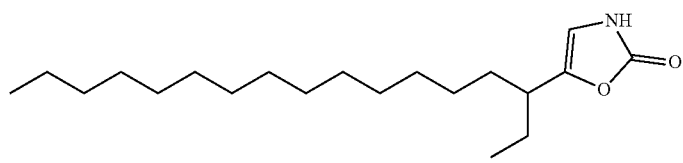 [SMILES: CCCCCCCCCCCCCCC(CC)c1c[nH]c(=O)o1]
5-(heptadecan-3-yl)oxazol-2(3H)-one
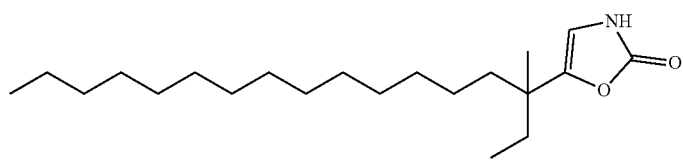 [SMILES: CCCCCCCCCCCCCCC(C)(CC)c1c[nH]c(=O)o1]
5-(3-methylheptadecan-3-yl)oxazol-2(3H)-one
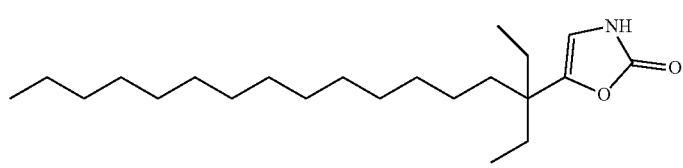 [SMILES: CCCCCCCCCCCCCCC(CC)(CC)c1c[nH]c(=O)o1]
5-(3-ethylheptadecan-3-yl)oxazol-2(3H)-one
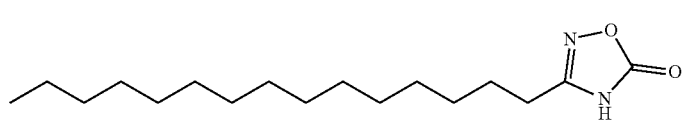 [SMILES: CCCCCCCCCCCCCCCc1noc(=O)[nH]1]
3-pentadecyl-1,2,4-oxadiazol-5(4H)-one

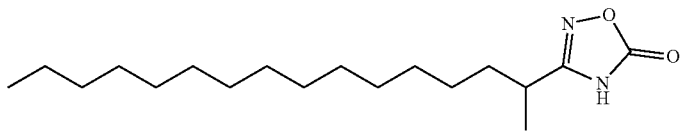 [SMILES: CCCCCCCCCCCCCCC(C)c1noc(=O)[nH]1]
3-(hexadecan-2-yl)-1,2,4-oxadiazol-5(4 H)-one
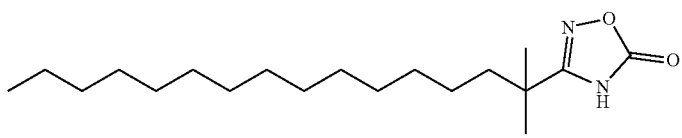 [SMILES: CCCCCCCCCCCCCCC(C)(C)c1noc(=O)[nH]1]
3-(2-methylhexadecan-2-yl)-1,2,4-oxadiazol-5(4 H)-one
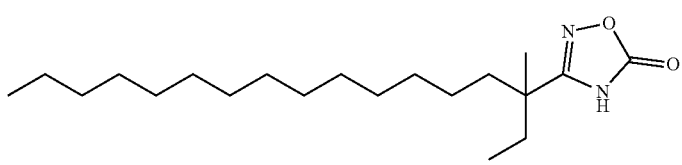 [SMILES: CCCCCCCCCCCCCCC(C)(CC)c1noc(=O)[nH]1]
3-(3-methylheptadecan-3-yl)-1,2,4-oxadiazol-5(4 H)-one
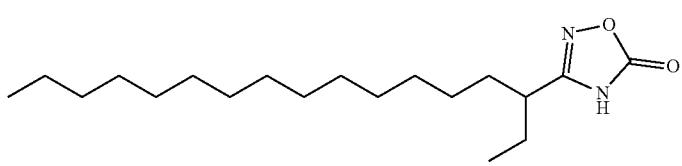 [SMILES: CCCCCCCCCCCCCCC(CC)c1noc(=O)[nH]1]
3-(heptadecan-3-yl)-1,2,4-oxadiazol-5(4 H)-one
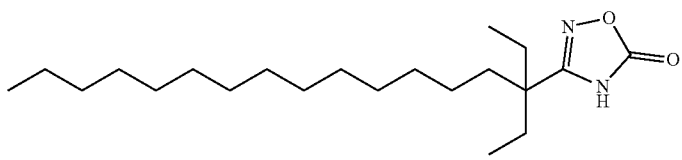 [SMILES: CCCCCCCCCCCCCCC(CC)(CC)c1noc(=O)[nH]1]
3-(3-ethylheptadecan-3-yl)-1,2,4-oxadiazol-5(4 H)-one
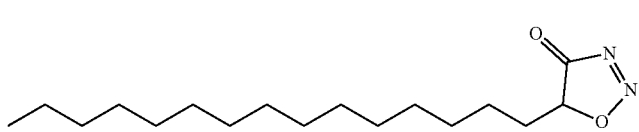 [SMILES: CCCCCCCCCCCCCCCC1ON=NC1=O]
5-pentadecyl-1,2,3-oxadiazol-4(5 H)-one
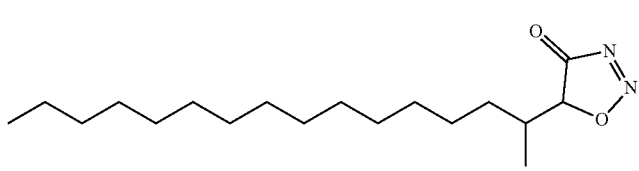 [SMILES: CCCCCCCCCCCCCCC(C)C1ON=NC1=O]
5-(hexadecan-2-yl)-1,2,3-oxadiazol-4(5 H)-one
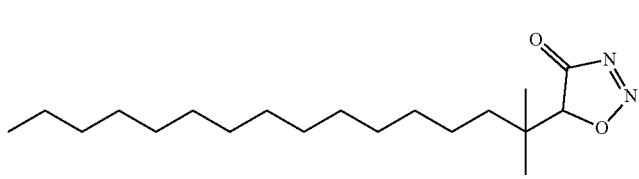 [SMILES: CCCCCCCCCCCCCCC(C)(C)C1ON=NC1=O]
5-(2-methylhexadecan-2-yl)-1,2,3-oxadiazol-4(5 H)-one

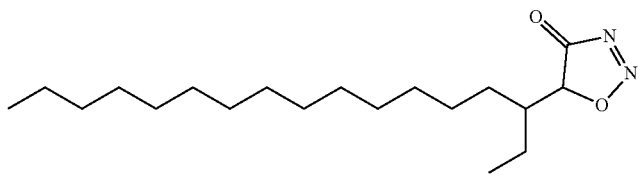 [SMILES: CCCCCCCCCCCCCCC(CC)C1ON=NC1=O]
5-(heptadecan-3-yl)-1,2,3-oxadiazol-4(5H)-one
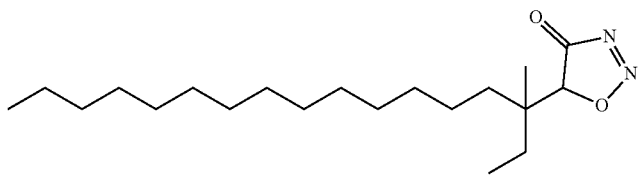 [SMILES: CCCCCCCCCCCCCCC(C)(CC)C1ON=NC1=O]
5-(3-methylheptadecan-3-yl)-1,2,3-oxadiazol-4(5H)-one
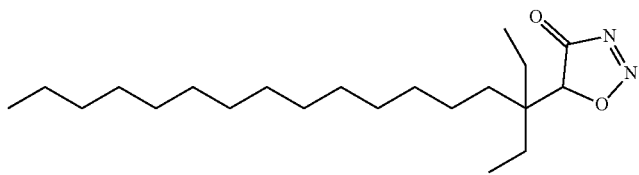 [SMILES: CCCCCCCCCCCCCCC(CC)(CC)C1ON=NC1=O]
5-(3-ethylheptadecan-3-yl)-1,2,3-oxadiazol-4(5H)-one
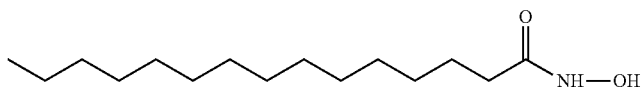 [SMILES: CCCCCCCCCCCCCCC(=O)NO]
N-hydroxypentadecanamide
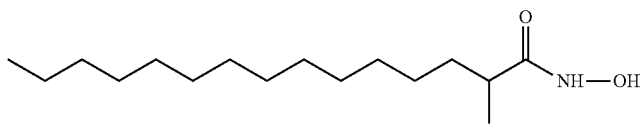 [SMILES: CCCCCCCCCCCCCC(C)C(=O)NO]
N-hydroxy-2-methylpentadecanamide
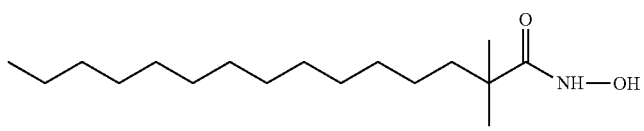 [SMILES: CCCCCCCCCCCCCC(C)(C)C(=O)NO]
N-hydroxy-2,2-dimethylpentadecanamide
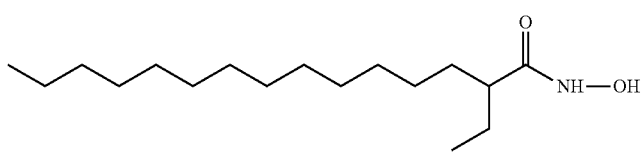 [SMILES: CCCCCCCCCCCCCC(CC)C(=O)NO]
2-ethyl-N-hydroxypentadecanamide
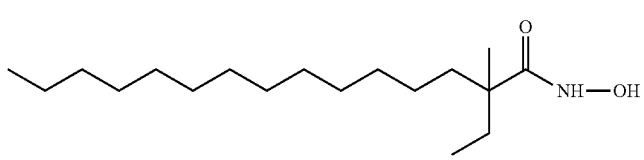 [SMILES: CCCCCCCCCCCCCC(C)(CC)C(=O)NO]
2-ethyl-N-hydroxy-2-methylpentadecanamide

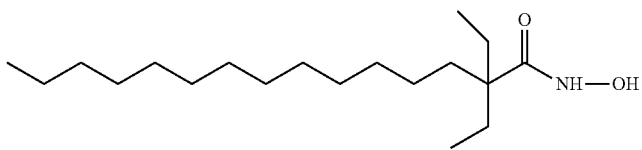 [SMILES: CCCCCCCCCCCCCC(CC)(CC)C(=O)NO]
2,2-diethyl-N-hydroxypentadecanamide
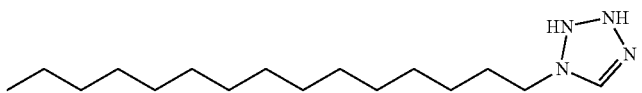 [SMILES: CCCCCCCCCCCCCCCN1C=NNN1]
1-pentadecyl-2,3-dihydro-1 H-tetrazole
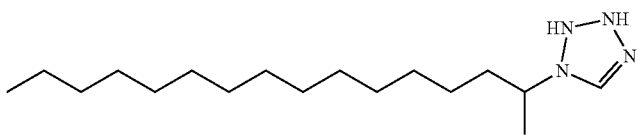 [SMILES: CCCCCCCCCCCCCCC(C)N1C=NNN1]
1-(hexadecan-2-yl)-2,3-dihydro-1 H-tetrazole
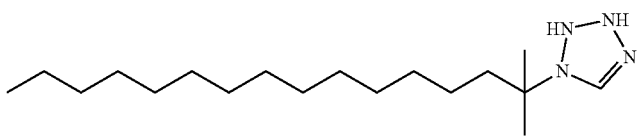 [SMILES: CCCCCCCCCCCCCCC(C)(C)N1C=NNN1]
1-(2-methylhexadecan-2-yl)-2,3-dihydro-1 H-tetrazole
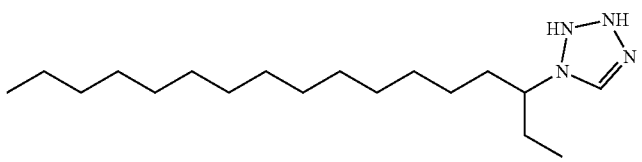 [SMILES: CCCCCCCCCCCCCCC(CC)N1C=NNN1]
1-(heptadecan-3-yl)-2,3-dihydro-1 H-tetrazole
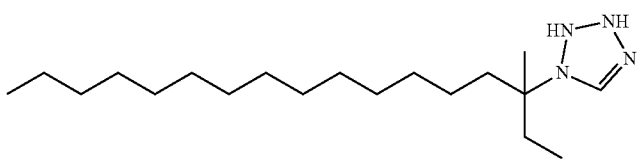 [SMILES: CCCCCCCCCCCCCCC(C)(CC)N1C=NNN1]
1-(3-methylheptadecan-3-yl)-2,3-dihydro-1 H-tetrazole
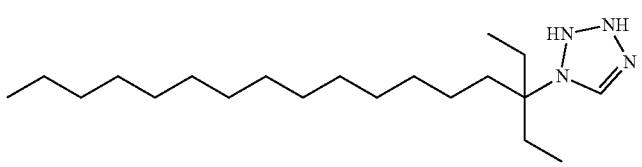 [SMILES: CCCCCCCCCCCCCCC(CC)(CC)N1C=NNN1]
1-(3-ethylheptadecan-3-yl)-2,3-dihydro-1 H-tetrazole
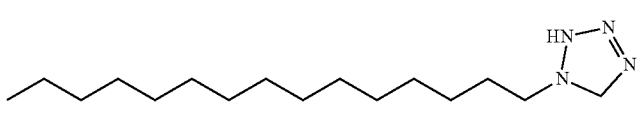 [SMILES: CCCCCCCCCCCCCCCN1CN=NN1]
1-pentadecyl-2,5-dihydro-1 H-tetrazole -continued
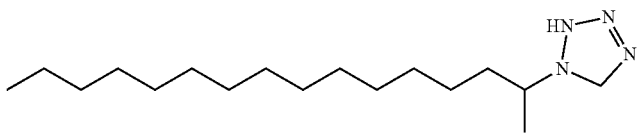 [SMILES: CCCCCCCCCCCCCCC(C)N1CN=NN1]
1-(hexadecan-2-yl)-2,5-dihydro-1 H-tetrazole
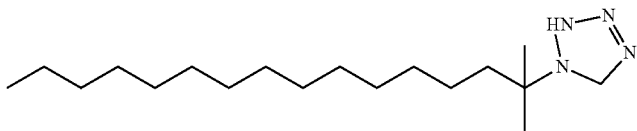 [SMILES: CCCCCCCCCCCCCCC(C)(C)N1CN=NN1]
1-(2-methylhexadecan-2-yl)-2,5-dihydro-1 H-tetrazole
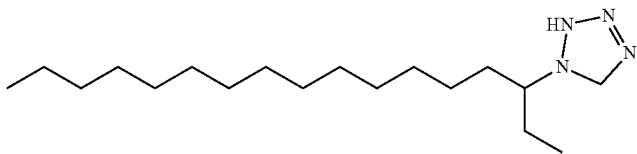 [SMILES: CCCCCCCCCCCCCCC(CC)N1CN=NN1]
1-(heptadecan-3-yl)-2,5-dihydro-1 H-tetrazole
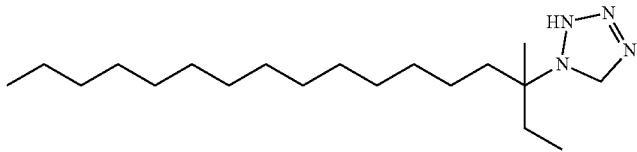 [SMILES: CCCCCCCCCCCCCCC(C)(CC)N1CN=NN1]
1-(3-methylheptadecan-3-yl)-2,5-dihydro-1 H-tetrazole
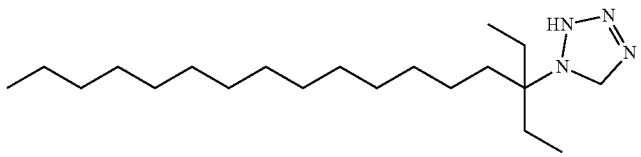 [SMILES: CCCCCCCCCCCCCCC(CC)(CC)N1CN=NN1]
1-(3-ethylheptadecan-3-yl)-2,5-dihydro-1 H-tetrazole
| Myristic Acid Analogs |
|---|
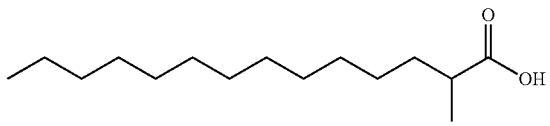 [SMILES: CCCCCCCCCCCCC(C)C(=O)O]
2-methyltetradecanoic acid
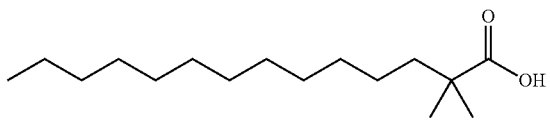 [SMILES: CCCCCCCCCCCCC(C)(C)C(=O)O]
2,2-dimethyltetradecanoic acid
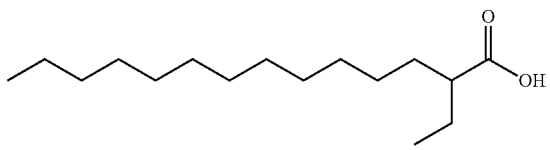 [SMILES: CCCCCCCCCCCCC(CC)C(=O)O]
2-ethyltetradecanoic acid -continued
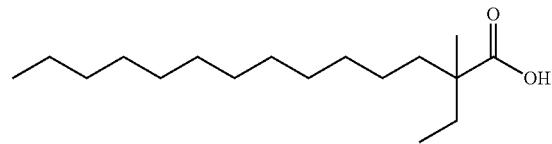 [SMILES: CCCCCCCCCCCCC(C)(CC)C(=O)O]
2-ethyl-2-methyltetradecanoic acid
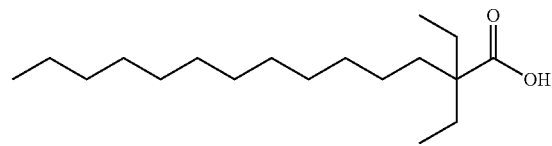 [SMILES: CCCCCCCCCCCCC(CC)(CC)C(=O)O]
2,2-diethyltetradecanoic acid
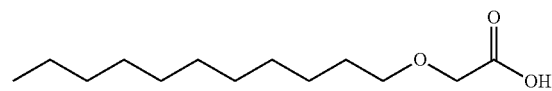 [SMILES: CCCCCCCCCCCOCC(=O)O]
2-(undecyloxy)acetic acid
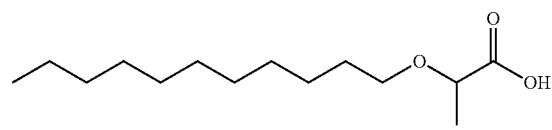 [SMILES: CCCCCCCCCCCOC(C)C(=O)O]
2-(undecyloxy)propanoic acid
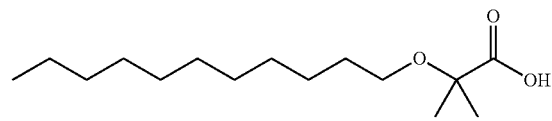 [SMILES: CCCCCCCCCCCOC(C)(C)C(=O)O]
2-methyl-2-(undecyloxy)propanoic acid
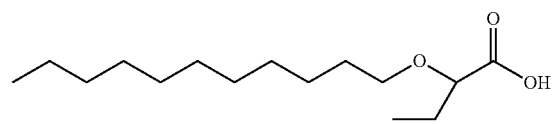 [SMILES: CCCCCCCCCCCOC(CC)C(=O)O]
2-(undecyloxy)butanoic acid
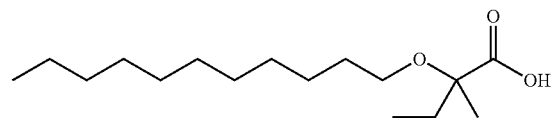 [SMILES: CCCCCCCCCCCOC(C)(CC)C(=O)O]
2-methyl-2-(undecyloxy)butanoic acid
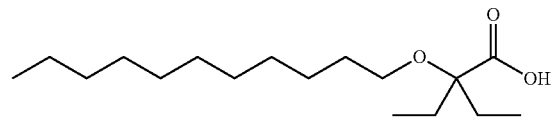 [SMILES: CCCCCCCCCCCOC(CC)(CC)C(=O)O]
2-ethyl-2-(undecyloxy)butanoic acid
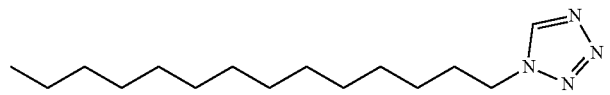 [SMILES: CCCCCCCCCCCCCCn1cnnn1]
1-tetradecyl-1 H-tetrazole

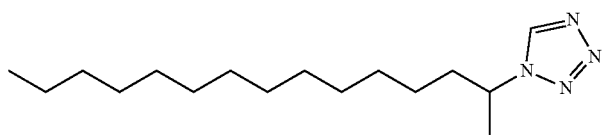 [SMILES: CCCCCCCCCCCCCC(C)n1cnnn1]
1-(pentadecan-2-yl)-1 H-tetrazole
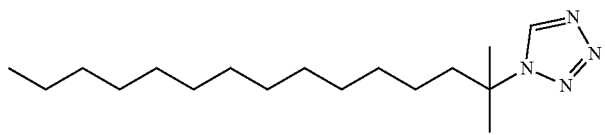 [SMILES: CCCCCCCCCCCCCC(C)(C)n1cnnn1]
1-(2-methylpentadecan-2-yl)-1 H-tetrazole
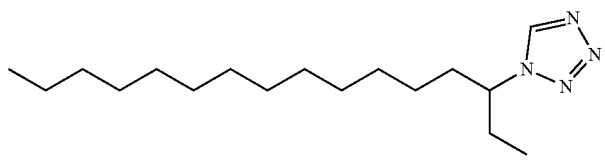 [SMILES: CCCCCCCCCCCCCC(CC)n1cnnn1]
1-(hexadecan-3-yl)-1 H-tetrazole
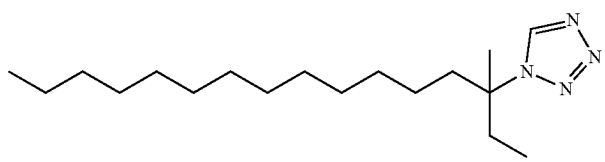 [SMILES: CCCCCCCCCCCCCC(C)(CC)n1cnnn1]
1-(3-methylhexadecan-3-yl)-1 H-tetrazole
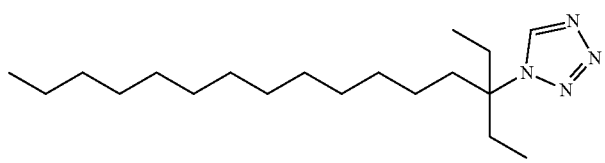 [SMILES: CCCCCCCCCCCCCC(CC)(CC)n1cnnn1]
1-(3-ethylhexadecan-3-yl)-1 H-tetrazole
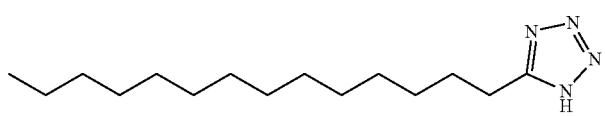 [SMILES: CCCCCCCCCCCCCCc1nnn[nH]1]
5-tetradecyl-1 H-tetrazole
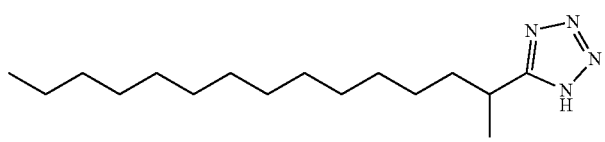 [SMILES: CCCCCCCCCCCCCC(C)c1nnn[nH]1]
5-(pentadecan-2-yl)-1 H-tetrazole
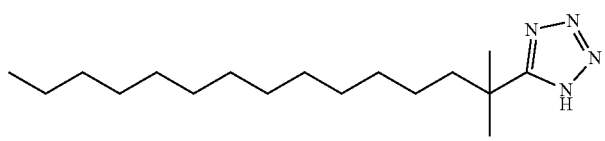 [SMILES: CCCCCCCCCCCCCC(C)(C)c1nnn[nH]1]
5-(2-methylpentadecan-2-yl)-1 H-tetrazole

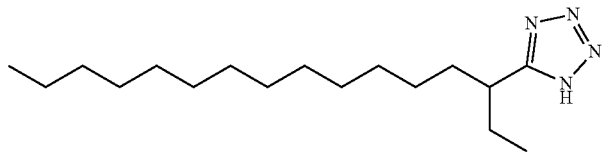 [SMILES: CCCCCCCCCCCCCC(CC)c1nnn[nH]1]
5-(hexadecan-3-yl)-1 H-tetrazole
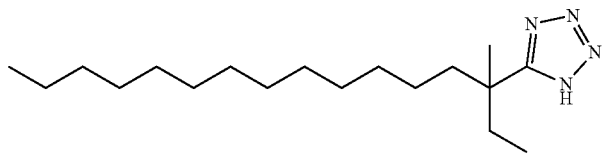 [SMILES: CCCCCCCCCCCCCC(C)(CC)c1nnn[nH]1]
5-(3-methylhexadecan-3-yl)-1 H-tetrazole
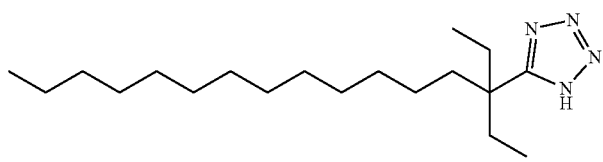 [SMILES: CCCCCCCCCCCCCC(CC)(CC)c1nnn[nH]1]
5-(3-ethylhexadecan-3-yl)-1 H-tetrazole
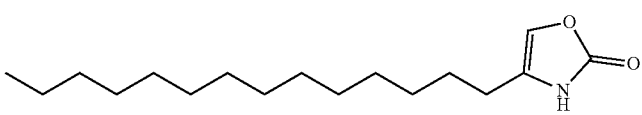 [SMILES: CCCCCCCCCCCCCCc1coc(=O)[nH]1]
4-tetradecyloxazol-2(3 H)-one
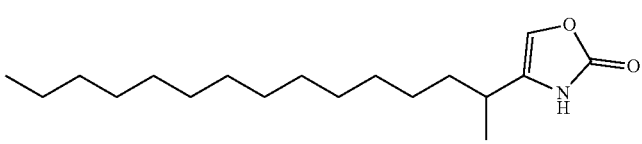 [SMILES: CCCCCCCCCCCCCC(C)c1coc(=O)[nH]1]
4-(pentadecan-2-yl)oxazol-2(3 H)-one
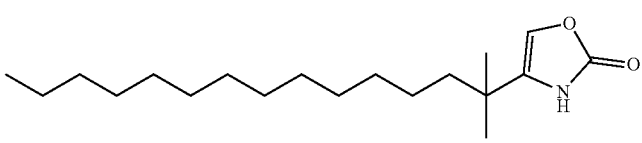 [SMILES: CCCCCCCCCCCCCC(C)(C)c1coc(=O)[nH]1]
4-(2-methylpentadecan-2-yl)oxazol-2(3 H)-one
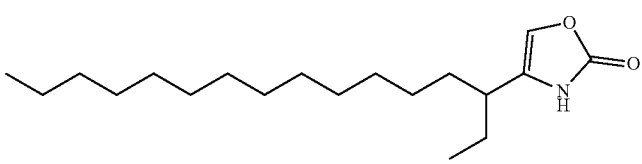 [SMILES: CCCCCCCCCCCCCC(CC)c1coc(=O)[nH]1]
4-(hexadecan-3-yl)oxazol-2(3 H)-one
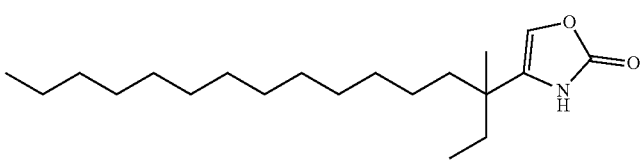 [SMILES: CCCCCCCCCCCCCC(C)(CC)c1coc(=O)[nH]1]
4-(3-methylhexadecan-3-yl)oxazol-2(3 H)-one -continued
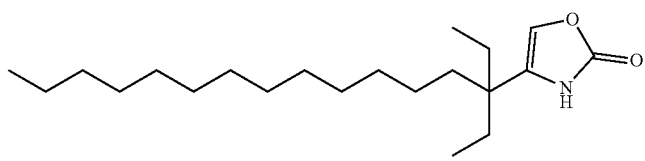 [SMILES: CCCCCCCCCCCCCC(CC)(CC)c1coc(=O)[nH]1]
4-(3-ethylhexadecan-3-yl)oxazol-2(3H)-one
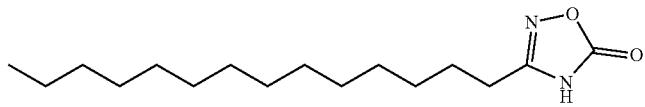 [SMILES: CCCCCCCCCCCCCCc1noc(=O)[nH]1]
3-tetradecyl-1,2,4-oxadiazol-5(4H)-one
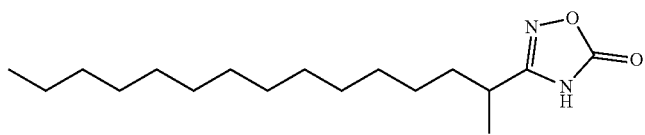 [SMILES: CCCCCCCCCCCCCC(C)c1noc(=O)[nH]1]
3-(pentadecan-2-yl)-1,2,4-oxadiazol-5(4H)-one
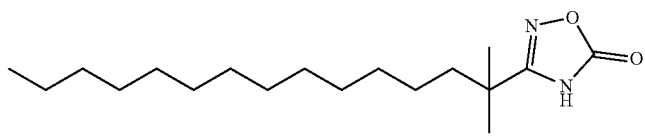 [SMILES: CCCCCCCCCCCCCC(C)(C)c1noc(=O)[nH]1]
3-(2-methylpentadecan-2-yl)-1,2,4-oxadiazol-5(4H)-one
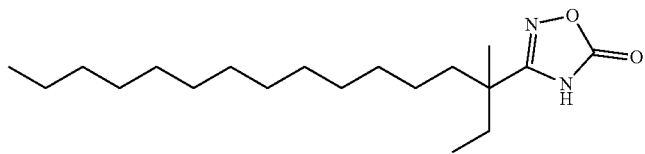 [SMILES: CCCCCCCCCCCCCC(C)(CC)c1noc(=O)[nH]1]
3-(3-methylhexadecan-3-yl)-1,2,4-oxadiazol-5(4H)-one
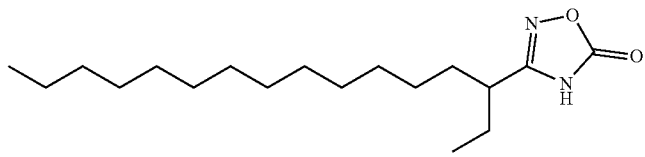 [SMILES: CCCCCCCCCCCCCC(CC)c1noc(=O)[nH]1]
3-(hexadecan-3-yl)-1,2,4-oxadiazol-5(4H)-one
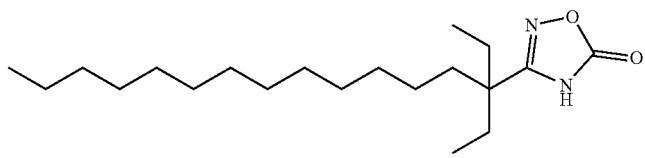 [SMILES: CCCCCCCCCCCCCC(CC)(CC)c1noc(=O)[nH]1]
3-(3-ethylhexadecan-3-yl)-1,2,4-oxadiazol-5(4H)-one
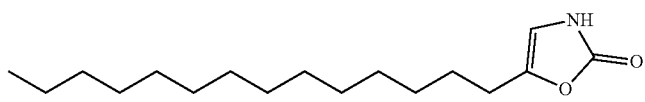 [SMILES: CCCCCCCCCCCCCCc1c[nH]c(=O)o1]
5-tetradecyloxazol-2(3H)-one

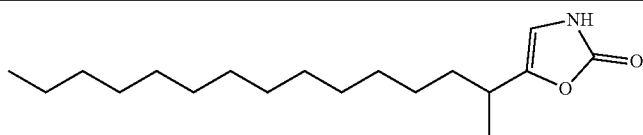
5-(pentadecan-2-yl)oxazol-2(3H)-one
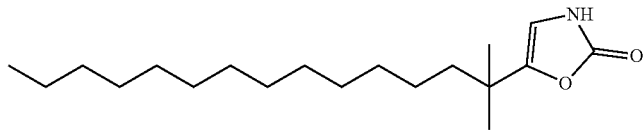 [SMILES: CCCCCCCCCCCCCC(C)(C)c1c[nH]c(=O)o1]
5-(2-methylpentadecan-2-yl)oxazol-2(3H)-one
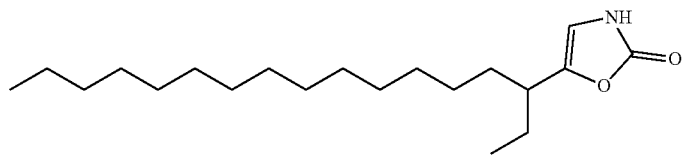 [SMILES: CCCCCCCCCCCCCCC(CC)c1c[nH]c(=O)o1]
5-(heptadecan-3-yl)oxazol-2(3H)-one
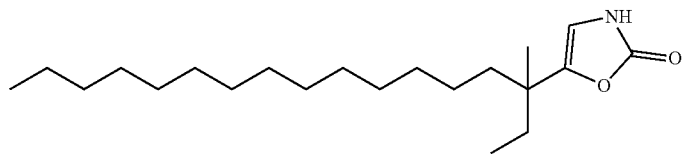 [SMILES: CCCCCCCCCCCCCCC(C)(CC)c1c[nH]c(=O)o1]
5-(3-methylheptadecan-3-yl)oxazol-2(3H)-one
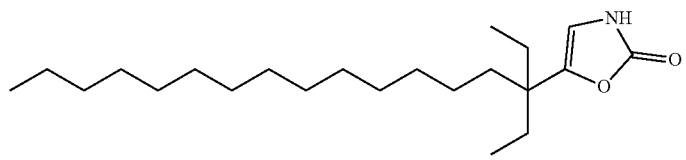 [SMILES: CCCCCCCCCCCCCCC(CC)(CC)c1c[nH]c(=O)o1]
5-(3-ethylheptadecan-3-yl)oxazol-2(3H)-one
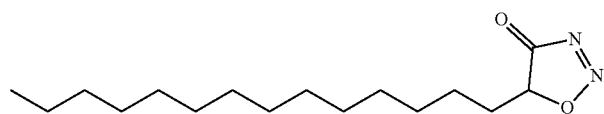 [SMILES: CCCCCCCCCCCCCCC1ON=NC1=O]
5-tetradecyl-1,2,3-oxadiazol-4(5H)-one
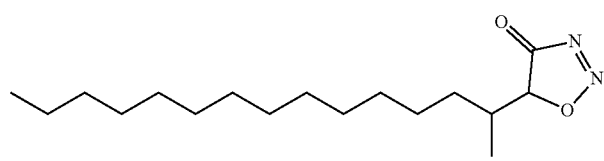 [SMILES: CCCCCCCCCCCCCC(C)C1ON=NC1=O]
5-(pentadecan-2-yl)-1,2,3-oxadiazol-4(5H)-one
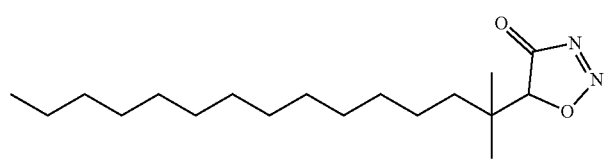 [SMILES: CCCCCCCCCCCCCC(C)(C)C1ON=NC1=O]
5-(2-methylpentadecan-2-yl)-1,2,3-oxadiazol-4(5H)-one

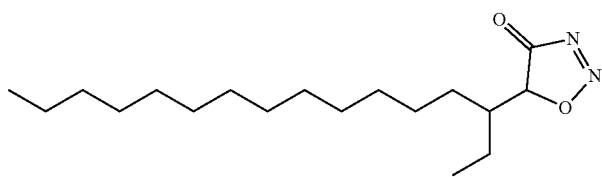 [SMILES: CCCCCCCCCCCCCC(CC)C1ON=NC1=O]
5-(hexadecan-3-yl)-1,2,3-oxadiazol-4(5H)-one
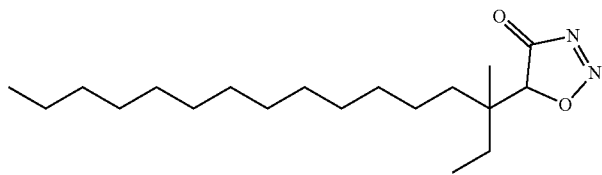 [SMILES: CCCCCCCCCCCCCC(C)(CC)C1ON=NC1=O]
5-(3-methylhexadecan-3-yl)-1,2,3-oxadiazol-4(5H)-one
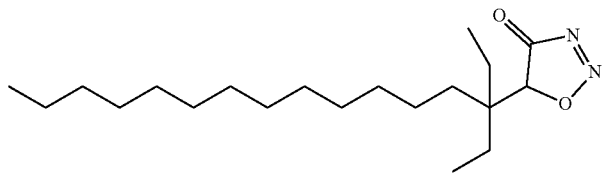 [SMILES: CCCCCCCCCCCCCC(CC)(CC)C1ON=NC1=O]
5-(3-ethylhexadecan-3-yl)-1,2,3-oxadiazol-4(5H)-one
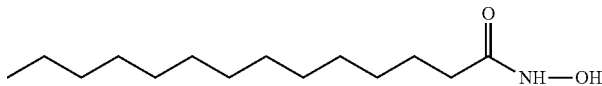 [SMILES: CCCCCCCCCCCCCC(=O)NO]
N-hydroxytetradecanamide
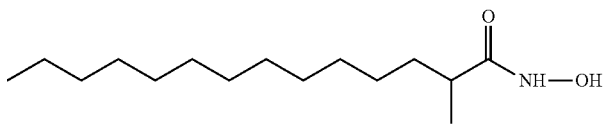 [SMILES: CCCCCCCCCCCCC(C)C(=O)NO]
N-hydroxy-2-methyltetradecanamide
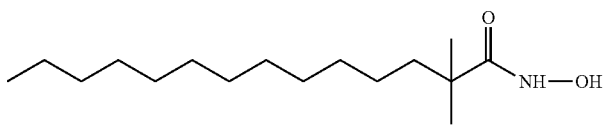 [SMILES: CCCCCCCCCCCCC(C)(C)C(=O)NO]
N-hydroxy-2,2-dimethyltetradecanamide
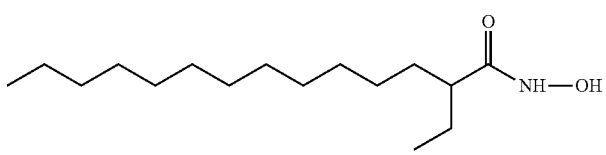 [SMILES: CCCCCCCCCCCCC(CC)C(=O)NO]
2-ethyl-N-hydroxytetradecanamide
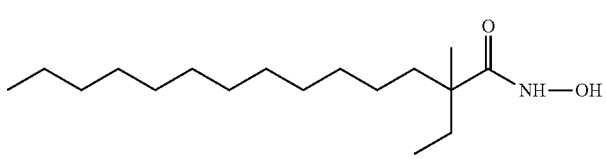 [SMILES: CCCCCCCCCCCCC(C)(CC)C(=O)NO]
2-ethyl-N-hydroxy-2-methyltetradecanamide

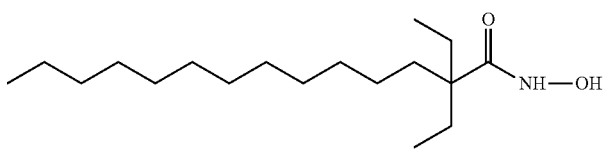 [SMILES: CCCCCCCCCCCCC(CC)(CC)C(=O)NO]
2,2-diethyl-N-hydroxytetradecanamide
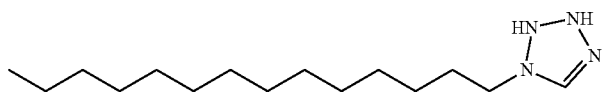 [SMILES: CCCCCCCCCCCCCCN1C=NNN1]
1-tetradecyl-2,3-dihydro-1 H-tetrazole
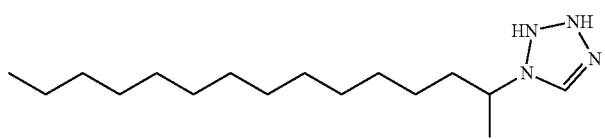 [SMILES: CCCCCCCCCCCCCC(C)N1C=NNN1]
1-(pentadecan-2-yl)-2,3-dihydro-1 H-tetrazole
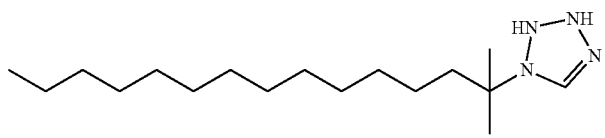 [SMILES: CCCCCCCCCCCCCC(C)(C)N1C=NNN1]
1-(2-methylpentadecan-2-yl)-2,3-dihydro-1 H-tetrazole
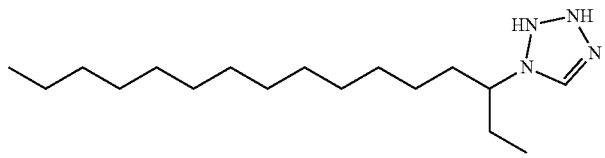 [SMILES: CCCCCCCCCCCCCC(CC)N1C=NNN1]
1-(hexadecan-3-yl)-2,3-dihydro-1 H-tetrazole
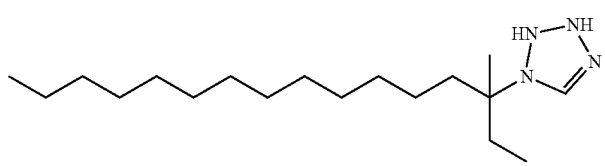 [SMILES: CCCCCCCCCCCCCC(C)(CC)N1C=NNN1]
1-(3-methylhexadecan-3-yl)-2,3-dihydro-1 H-tetrazole
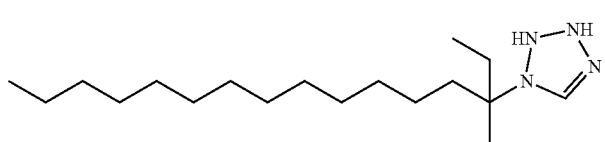
1-(3-ethylhexadecan-3-yl)-2,3-dihydro-1 H-tetrazole
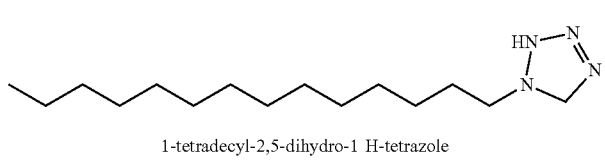
1-tetradecyl-2,5-dihydro-1 H-tetrazole

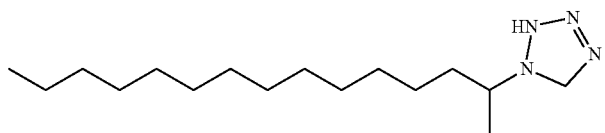 [SMILES: CCCCCCCCCCCCCC(C)N1CN=NN1]
1-(pentadecan-2-yl)-2,5-dihydro-1 H-tetrazole
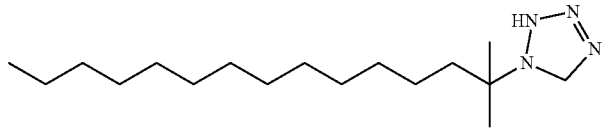 [SMILES: CCCCCCCCCCCCCC(C)(C)N1CN=NN1]
1-(2-methylpentadecan-2-yl)-2,5-dihydro-1 H-tetrazole
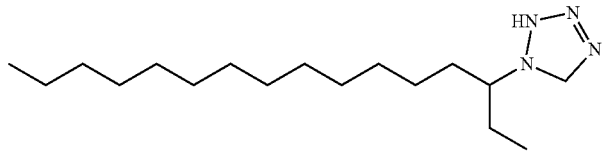 [SMILES: CCCCCCCCCCCCCC(CC)N1CN=NN1]
1-(hexadecan-3-yl)-2,5-dihydro-1 H-tetrazole
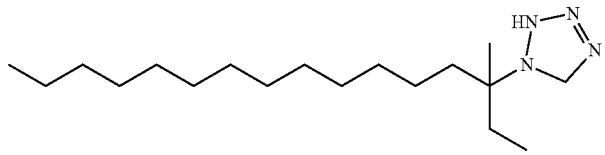 [SMILES: CCCCCCCCCCCCCC(C)(CC)N1CN=NN1]
1-(3-methylhexadecan-3-yl)-2,5-dihydro-1 H-tetrazole
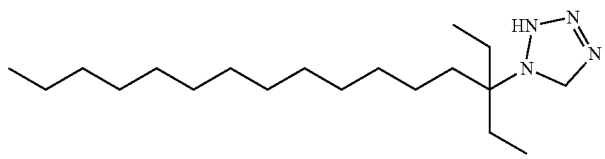 [SMILES: CCCCCCCCCCCCCC(CC)(CC)N1CN=NN1]
1-(3-ethylhexadecan-3-yl)-2,5-dihydro-1 H-tetrazole
| Tridecanoic Acid Analogs |
|---|
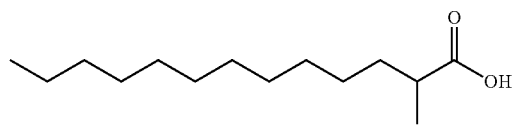
2-methyltridecanoic acid
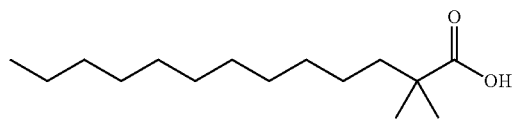 [SMILES: CCCCCCCCCCCC(C)(C)C(=O)O]
2,2-dimethyltridecanoic acid
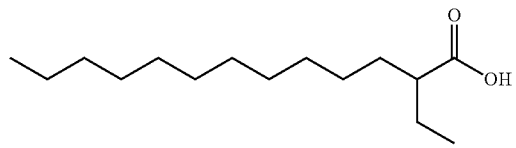 [SMILES: CCCCCCCCCCCC(CC)C(=O)O]
2-ethyltridecanoic acid

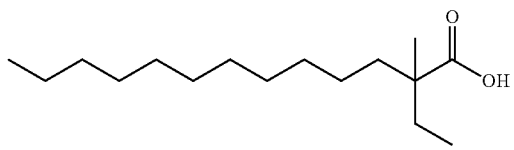 [SMILES: CCCCCCCCCCCC(C)(CC)C(=O)O]
2-ethyl-2-methyltridecanoic acid
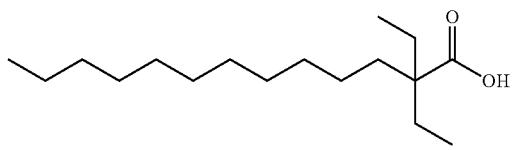 [SMILES: CCCCCCCCCCCC(CC)(CC)C(=O)O]
2,2-diethyltridecanoic acid
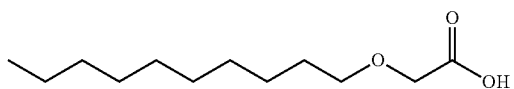
2-(decyloxy)acetic acid
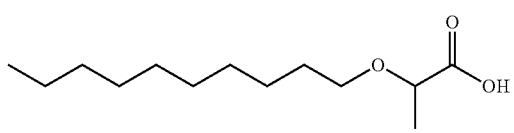 [SMILES: CCCCCCCCCCOC(C)C(=O)O]
2-(decyloxy)propanoic acid
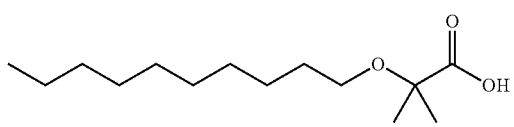 [SMILES: CCCCCCCCCCOC(C)(C)C(=O)O]
2-(decyloxy)-2-methylpropanoic acid
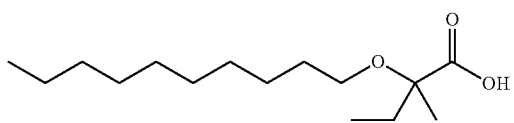 [SMILES: CCCCCCCCCCOC(C)(CC)C(=O)O]
2-(decyloxy)-2-methylbutanoic acid
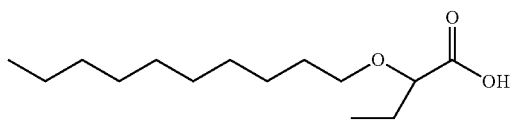 [SMILES: CCCCCCCCCCOC(CC)C(=O)O]
2-(decyloxy)butanoic acid
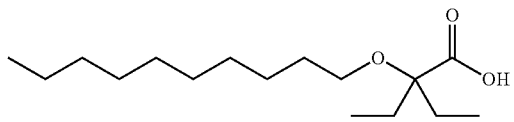 [SMILES: CCCCCCCCCCOC(CC)(CC)C(=O)O]
2-(decyloxy)-2-ethylbutanoic acid
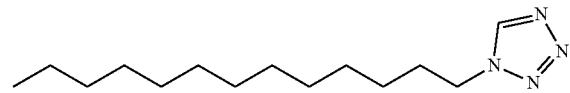 [SMILES: CCCCCCCCCCCCCn1cnnn1]
1-tridecyl-1 H-tetrazole

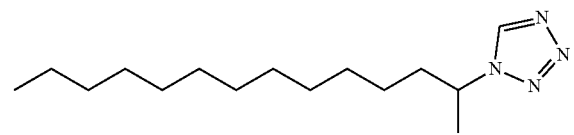 [SMILES: CCCCCCCCCCCCC(C)n1cnnn1]
1-(tetradecan-2-yl)-1 H-tetrazole
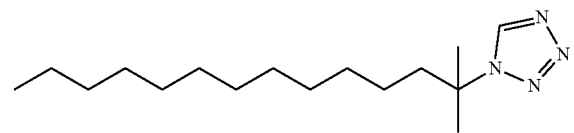 [SMILES: CCCCCCCCCCCCC(C)(C)n1cnnn1]
1-(2-methyltetradecan-2-yl)-1 H-tetrazole
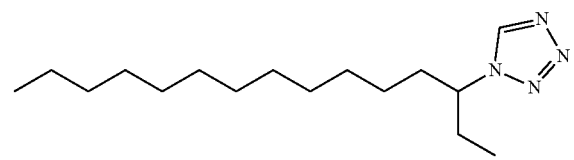 [SMILES: CCCCCCCCCCCCC(CC)n1cnnn1]
1-(pentadecan-3-yl)-1 H-tetrazole
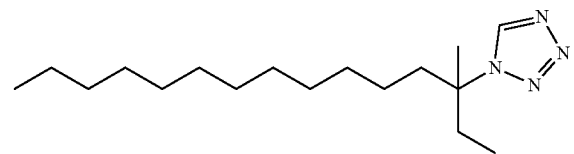 [SMILES: CCCCCCCCCCCCC(C)(CC)n1cnnn1]
1-(3-methylpentadecan-3-yl)-1 H-tetrazole
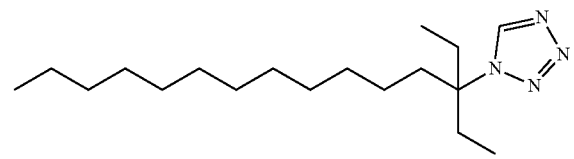 [SMILES: CCCCCCCCCCCCC(CC)(CC)n1cnnn1]
1-(3-ethylpentadecan-3-yl)-1 H-tetrazole
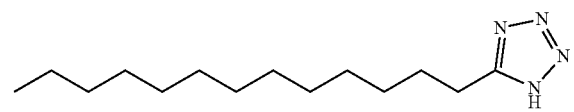 [SMILES: CCCCCCCCCCCCCc1nnn[nH]1]
5-tridecyl-1 H-tetrazole
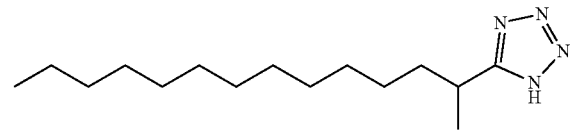 [SMILES: CCCCCCCCCCCCC(C)c1nnn[nH]1]
5-(tetradecan-2-yl)-1 H-tetrazole
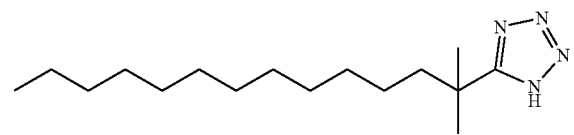 [SMILES: CCCCCCCCCCCCC(C)(C)c1nnn[nH]1]
5-(2-methyltetradecan-2-yl)-1 H-tetrazole

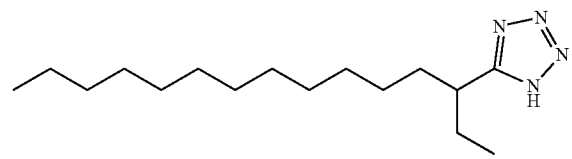 [SMILES: CCCCCCCCCCCCC(CC)c1nnn[nH]1]
5-(pentadecan-3-yl)-1H-tetrazole
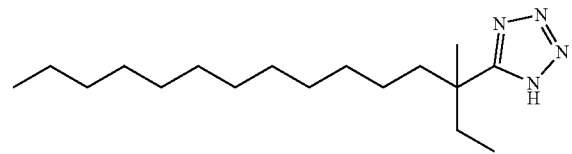 [SMILES: CCCCCCCCCCCCC(C)(CC)c1nnn[nH]1]
5-(3-methylpentadecan-3-yl)-1H-tetrazole
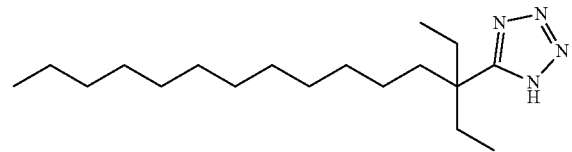 [SMILES: CCCCCCCCCCCCC(CC)(CC)c1nnn[nH]1]
5-(3-ethylpentadecan-3-yl)-1H-tetrazole
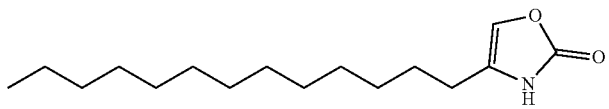 [SMILES: CCCCCCCCCCCCCc1coc(=O)[nH]1]
4-tridecyloxazol-2(3H)-one
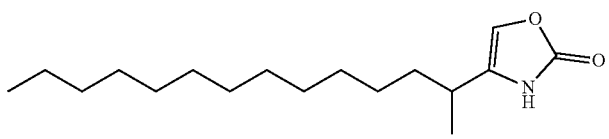
4-(tetradecan-2-yl)oxazol-2(3H)-one
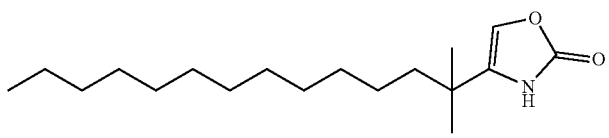 [SMILES: CCCCCCCCCCCCC(C)c1coc(=O)[nH]1]
4-(2-methyltetradecan-2-yl)oxazol-2(3H)-one
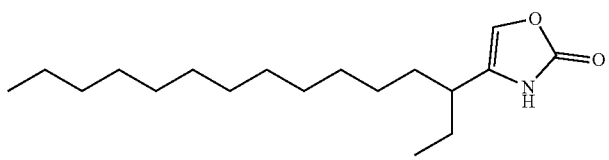 [SMILES: CCCCCCCCCCCCC(CC)c1coc(=O)[nH]1]
4-(pentadecan-3-yl)oxazol-2(3H)-one
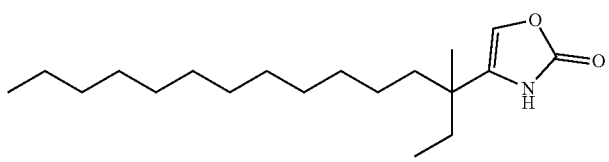 [SMILES: CCCCCCCCCCCCC(C)(CC)c1coc(=O)[nH]1]
4-(3-methylpentadecan-3-yl)oxazol-2(3H)-one

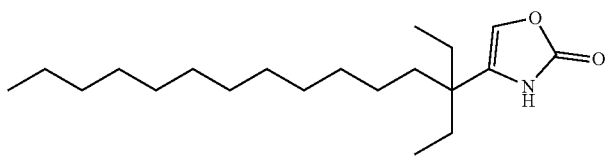 [SMILES: CCCCCCCCCCCCC(CC)(CC)c1coc(=O)[nH]1]
4-(3-ethylpentadecan-3-yl)oxazol-2(3 H)-one
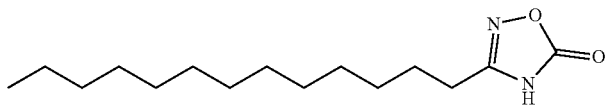 [SMILES: CCCCCCCCCCCCCc1noc(=O)[nH]1]
3-tridecyl-1,2,4-oxadiazol-5(4 H)-one
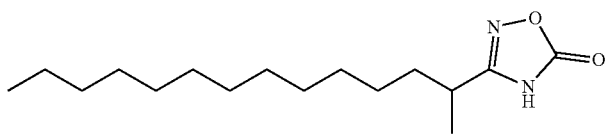 [SMILES: CCCCCCCCCCCCC(C)c1noc(=O)[nH]1]
3-(tetradecan-2-yl)-1,2,4-oxadiazol-5(4 H)-one
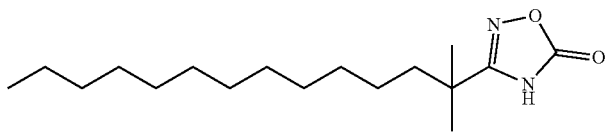 [SMILES: CCCCCCCCCCCCC(C)(C)c1noc(=O)[nH]1]
3-(2-methyltetradecan-2-yl)-1,2,4-oxadiazol-5(4 H)-one
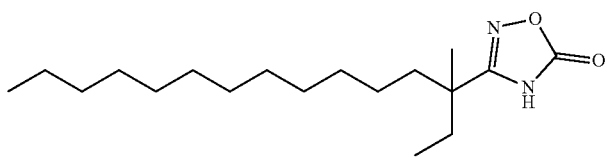 [SMILES: CCCCCCCCCCCCC(C)(CC)c1noc(=O)[nH]1]
3-(3-methylpentadecan-3-yl)-1,2,4-oxadiazol-5(4 H)-one
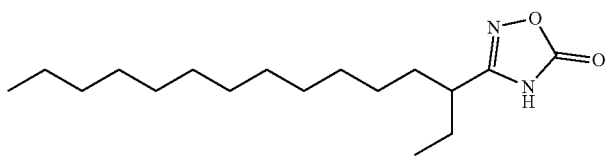 [SMILES: CCCCCCCCCCCCC(CC)c1noc(=O)[nH]1]
3-(pentadecan-3-yl)-1,2,4-oxadiazol-5(4 H)-one
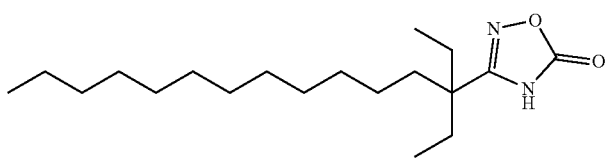 [SMILES: CCCCCCCCCCCCC(CC)(CC)c1noc(=O)[nH]1]
3-(3-ethylpentadecan-3-yl)-1,2,4-oxadiazol-5(4 H)-one
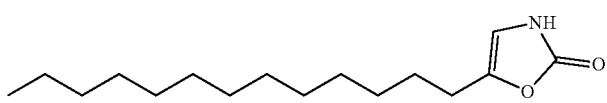 [SMILES: CCCCCCCCCCCCCc1c[nH]c(=O)o1]
5-tridecyloxazol-2(3 H)-one

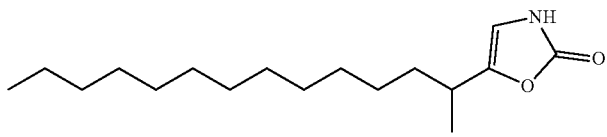 [SMILES: CCCCCCCCCCCCC(C)c1c[nH]c(=O)o1]
5-(tetradecan-2-yl)oxazol-2(3H)-one
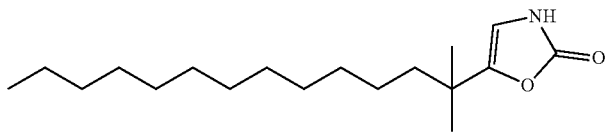 [SMILES: CCCCCCCCCCCCC(C)(C)c1c[nH]c(=O)o1]
5-(2-methyltetradecan-2-yl)oxazol-2(3H)-one
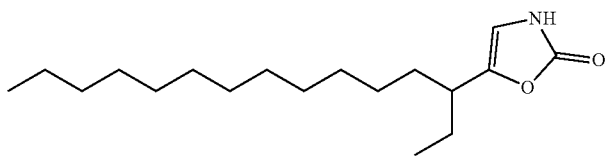 [SMILES: CCCCCCCCCCCCC(CC)c1c[nH]c(=O)o1]
5-(pentadecan-3-yl)oxazol-2(3H)-one
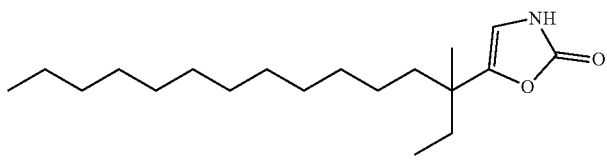 [SMILES: CCCCCCCCCCCCC(C)(CC)c1c[nH]c(=O)o1]
5-(3-methylpentadecan-3-yl)oxazol-2(3H)-one
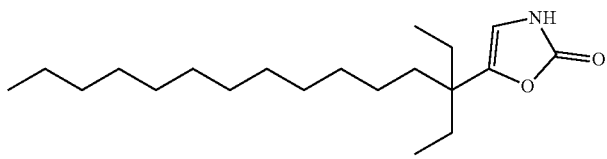 [SMILES: CCCCCCCCCCCCC(CC)(CC)c1c[nH]c(=O)o1]
5-(3-ethylpentadecan-3-yl)oxazol-2(3H)-one
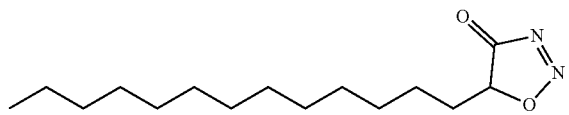 [SMILES: CCCCCCCCCCCCCC1ON=NC1=O]
5-tridecyl-1,2,3-oxadiazol-4(5H)-one
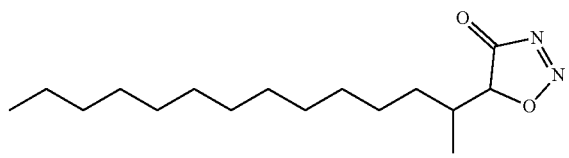 [SMILES: CCCCCCCCCCCCC(C)C1ON=NC1=O]
5-(tetradecan-2-yl)-1,2,3-oxadiazol-4(5H)-one
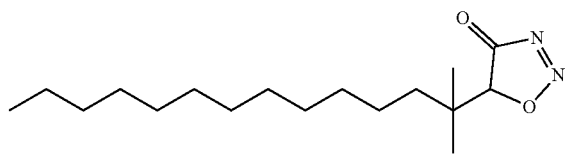 [SMILES: CCCCCCCCCCCCC(C)(C)C1ON=NC1=O]
5-(2-methyltetradecan-2-yl)-1,2,3-oxadiazol-4(5H)-one

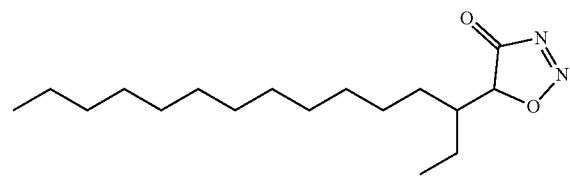 [SMILES: CCCCCCCCCCCCC(CC)C1ON=NC1=O]
5-(pentadecan-3-yl)-1,2,3-oxadiazol-4(5H)-one
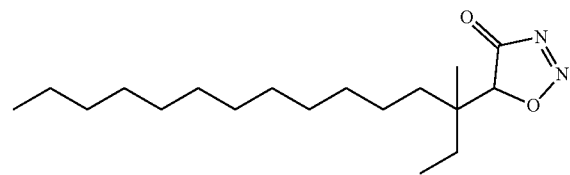 [SMILES: CCCCCCCCCCCCC(C)(CC)C1ON=NC1=O]
5-(3-methylpentadecan-3-yl)-1,2,3-oxadiazol-4(5H)-one
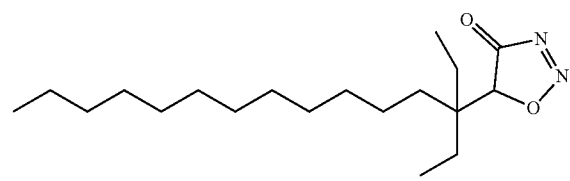 [SMILES: CCCCCCCCCCCCC(CC)(CC)C1ON=NC1=O]
5-(3-ethylpentadecan-3-yl)-1,2,3-oxadiazol-4(5H)-one
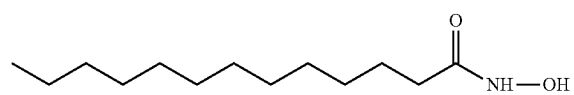 [SMILES: CCCCCCCCCCCCC(=O)NO]
N-hydroxytridecanamide
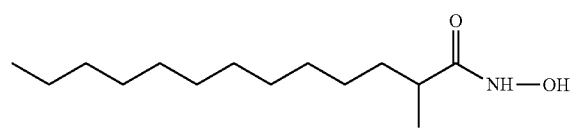 [SMILES: CCCCCCCCCCCC(C)C(=O)NO]
N-hydroxy-2-methyltridecanamide
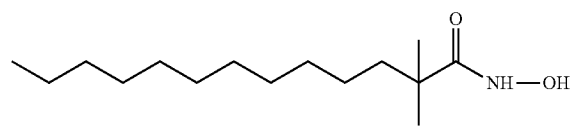 [SMILES: CCCCCCCCCCCC(C)(C)C(=O)NO]
N-hydroxy-2,2-dimethyltridecanamide
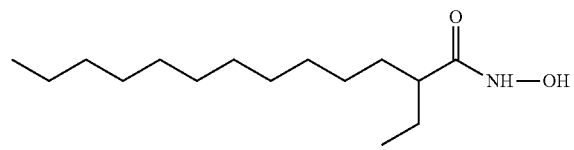 [SMILES: CCCCCCCCCCCC(CC)C(=O)NO]
2-ethyl-N-hydroxytridecanamide
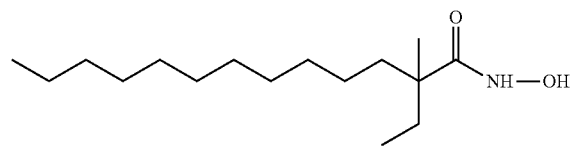 [SMILES: CCCCCCCCCCCC(C)(CC)C(=O)NO]
2-ethyl-N-hydroxy-2-methyltridecanamide

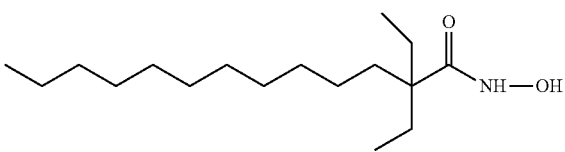 [SMILES: CCCCCCCCCCCC(CC)(CC)C(=O)NO]
2,2-diethyl-N-hydroxytridecanamide
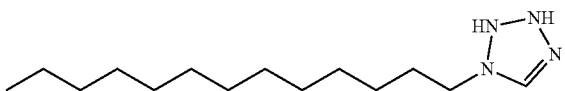 [SMILES: CCCCCCCCCCCCCN1C=NNN1]
1-tridecyl-2,3-dihydro-1 H-tetrazole
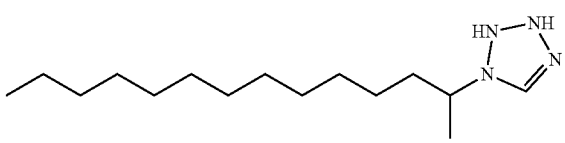 [SMILES: CCCCCCCCCCCCC(C)N1C=NNN1]
1-(tetradecan-2-yl)-2,3-dihydro-1 H-tetrazole
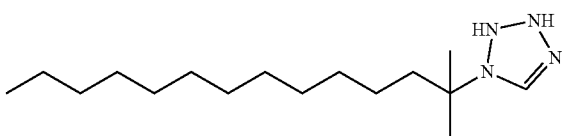 [SMILES: CCCCCCCCCCCCC(C)(C)N1C=NNN1]
1-(2-methyltetradecan-2-yl)-2,3-dihydro-1 H-tetrazole
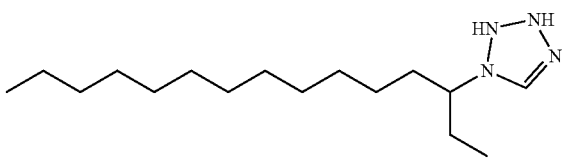 [SMILES: CCCCCCCCCCCCC(CC)N1C=NNN1]
1-(pentadecan-3-yl)-2,3-dihydro-1 H-tetrazole
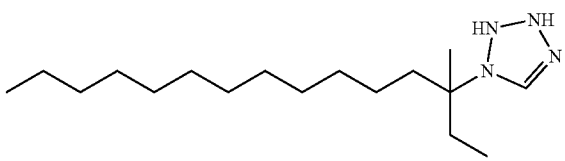 [SMILES: CCCCCCCCCCCCC(C)(CC)N1C=NNN1]
1-(3-methylpentadecan-3-yl)-2,3-dihydro-1 H-tetrazole
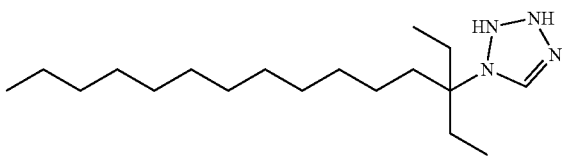 [SMILES: CCCCCCCCCCCCC(CC)(CC)N1C=NNN1]
1-(3-ethylpentadecan-3-yl)-2,3-dihydro-1 H-tetrazole
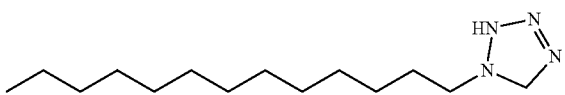 [SMILES: CCCCCCCCCCCCCN1CN=NN1]
1-tridecyl-2,5-dihydro-1 H-tetrazole -continued

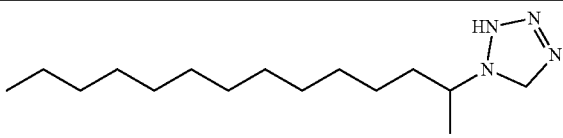

1-(tetradecan-2-yl)-2,5-dihydro-1 H-tetrazole

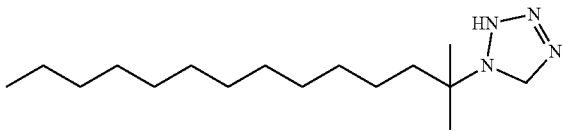 [SMILES: CCCCCCCCCCCCC(C)(C)N1CN=NN1]

1-(2-methyltetradecan-2-yl)-2,5-dihydro-1 H-tetrazole

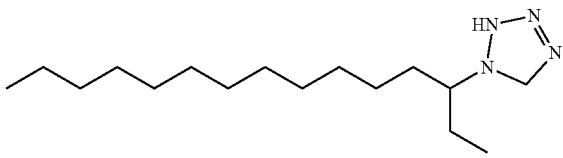 [SMILES: CCCCCCCCCCCCC(CC)N1CN=NN1]

1-(pentadecan-3-yl)-2,5-dihydro-1 H-tetrazole

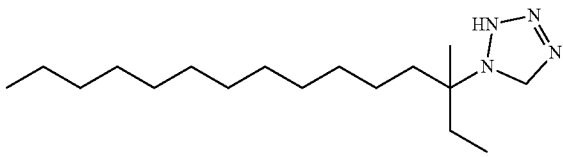 [SMILES: CCCCCCCCCCCCC(C)(CC)N1CN=NN1]

1-(3-methylpentadecan-3-yl)-2,5-dihydro-1 H-tetrazole

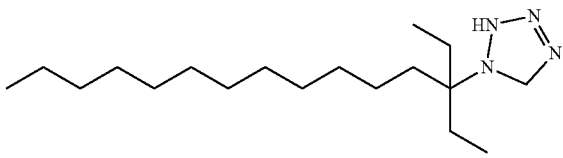 [SMILES: CCCCCCCCCCCCC(CC)(CC)N1CN=NN1]

1-(3-ethylpentadecan-3-yl)-2,5-dihydro-1 H-tetrazole

Accordingly, in a generally applicable third aspect (i.e., independently combinable with any of the aspects or embodiments identified herein), a pharmaceutical composition is provided, comprising: a compound of Formula (I), or a pharmaceutically acceptable salt thereof, and a pharmaceutically acceptable carrier. In various embodiments, the compound of Formula (I) may be a compound of Formula (Ia), Formula (Ib), Formula (Ic), Formula (Id), Formula (Ie), Formula (If), Formula (Ig), or Formula (Ih).

Any of the features of an embodiment of the first through third aspects is applicable to all aspects and embodiments identified herein. Moreover, any of the features of an embodiment of the first through third aspects is independently combinable, partly or wholly with other embodiments described herein in any way, e.g., one, two, or three or more embodiments may be combinable in whole or in part. Further, any of the features of an embodiment of the first through third aspects may be made optional to other aspects or embodiments. Any aspect or embodiment of a method can be performed by a system or apparatus of another aspect or embodiment, and any aspect or embodiment of a system can be configured to perform a method of another aspect or embodiment.

BRIEF DESCRIPTION OF THE DRAWINGS

FIG. 2A is a table providing comparisons of human primary cell-based activity (specifically, reductions of activated diseased states) among saturated free fatty acid forms and saturated fatty acids with substituents. The human cell systems included venular endothelial cells, bronchial epithelial cell, and other cells. An asterisk (*) identifies a value outside the 95% significance envelope generated from historical vehicle controls; boxes with darker borders indicate an effect size >20%.

FIG. 2B is a table providing comparisons of human primary cell-based activity (specifically, reductions of activated diseased states) among saturated free fatty acid forms and saturated fatty acids with substituents. The human cell systems included keratinocytes and other cells. An asterisk (*) identifies a value outside the 95% significance envelope generated from historical vehicle controls; boxes with darker borders indicate an effect size >20%.

DETAILED DESCRIPTION

Figure 1:
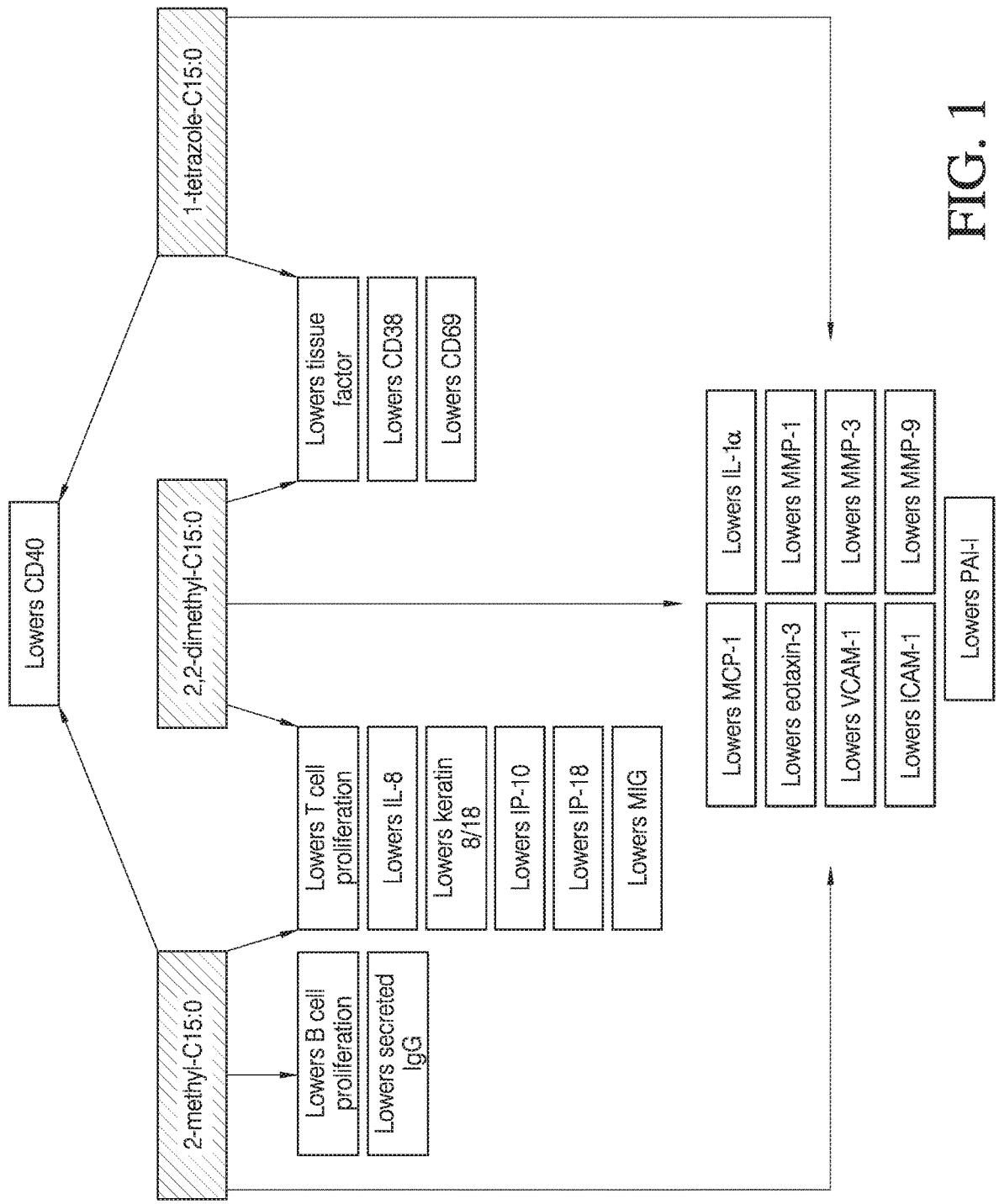
FIG. 1 provides a summary of protein-based biomarkers of various disease states that were significantly lower in human primary cell-based systems treated with saturated fatty acid substituents (2-methyl-C15:0, 2,2-dimethyl-C15:0, and 1-tetrazole-C15:0) compared to systems treated with saturated free fatty acids (C15:0) and non-treated controls.

Compositions including a compound, for example, a compound of Formula (I), or a pharmaceutically acceptable salt thereof, and associated methods for treatment of metabolic syndrome and related disorders are provided. In various embodiments, a compound provided herein can be a 2-alkyl or 2,2-di-alkyl substituted saturated fatty acid, or an acid isostere and/or pharmaceutically acceptable salt thereof.

Some embodiments relate to a pharmaceutical compositions, and methods of treatment using the pharmaceutical compositions, wherein the pharmaceutical composition comprises a compound of Formula (I), or a pharmaceutically acceptable salt thereof, having the structure:

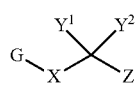

Formula (I)

wherein: G is selected from an unsubstituted or a substituted $C_{10}$-$C_{17}$ alkyl, an unsubstituted or a substituted $C_{10}$-$C_{17}$ alkenyl, or an unsubstituted or a substituted $C_{10}$-$C_{17}$ alkyl having one, two, or three oxa- and/or thia-substitutions, e.g., one or more oxygen and/or sulfur atoms replacing one or more of the carbon atoms of the alkyl or alkenyl chain; X is selected from O, and $CR^1R^2$, wherein $R^1$ and $R^2$ are each independently H or an unsubstituted or a substituted $C_1$-$C_6$ alkyl; $Y^1$ and $Y^2$ are each independently H, an unsubstituted or a substituted $C_1$-$C_6$ alkoxy, or an unsubstituted or a substituted $C_1$-$C_6$ alkyl, or $Y^1$ and $Y^2$ may be taken together to form an unsubstituted or a substituted cycloalkyl, cycloalkenyl, aryl, heteroaryl or heterocyclyl; and Z is selected from a carboxylic acid, a $C_1$-$C_6$ alkyl ester, an unsubstituted or a substituted amide, an unsubstituted or a substituted five- or six-membered heterocyclyl, and an unsubstituted or a substituted five- or six-membered heteroaryl. In Formula (I), if a group is indicated as being "substituted," that group is substituted with one or more substituents individually and independently selected from the group consisting of $C_1$-$C_6$ alkyl, $C_1$-$C_6$ alkenyl, $C_1$-$C_6$ alkynyl, $C_1$-$C_7$ cycloalkyl, $C_1$-$C_7$ cycloalkenyl, acyl($C_1$-$C_6$ alkyl), $C_1$-$C_6$ alkoxy($C_1$-$C_6$ alkyl), amino($C_1$-$C_6$ alkyl), amino acid, $C_6$-$C_{10}$ aryl, heteroaryl, heterocyclyl, $C_6$-$C_{10}$ aryl($C_1$-$C_6$ alkyl), heteroaryl($C_1$-$C_6$ alkyl), heterocyclyl($C_1$-$C_6$ alkyl), hydroxyl($C_1$-$C_6$ alkyl), acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, azido, nitro, silyl, sulfenyl, sulfinyl, sulfonyl, halo($C_1$-$C_6$ alkyl), $C_1$-$C_6$ haloalkoxy, trihalomethanesulfonyl, trihalomethanesulfonamido, and amino. The pharmaceutical composition may further comprise a pharmaceutically acceptable carrier.

In some embodiments, $Y^1$ and $Y^2$ are each independently H or $C_1$-$C_6$ alkyl substituted with one or more halogens. In further embodiments, $Y^1$ and $Y^2$ are each independently selected from H, unsubstituted methyl, methyl substituted with one to three halogens, unsubstituted ethyl, and ethyl substituted with one to five halogens. In still further embodiments, each halogen is independently selected from F, Cl, Br, and I. In some embodiments, each halogen is F. In some embodiments, $Y^1$ and $Y^2$ are each independently selected from H and unsubstituted methyl.

In some embodiments, Z is an unsubstituted or a substituted five-membered heteroaryl. In some embodiments, Z is an unsubstituted five-membered heteroaryl. In one embodiment the unsubstituted five-membered heteroaryl is an unsubstituted tetrazole or an unsubstituted 1,2,4-oxadiazol-5(4H)-one. In some embodiments, Z is a carboxylic acid or a $C_1$-$C_6$ alkyl ester. In some embodiments, Z is an unsubstituted or a substituted amide. In still further embodiments, Z is an amide substituted by one or two groups selected from $C_1$-$C_6$ alkyl, hydroxy, and $C_1$-$C_6$ hydroxyalkyl.

In some embodiments, $R^1$ and $R^2$ are each independently H or $C_1$-$C_6$ alkyl substituted with one or more halogens. In some embodiments, $R^1$ and $R^2$ are each independently H.

In some embodiments, G is a $C_{10}$-$C_{15}$ alkyl substituted by one or more halogens. In some embodiments, G is an unsubstituted $C_{12}$-$C_{14}$ alkyl.

In some embodiments, the compound of Formula (I) has the structure of Formula (Ia), Formula (Ib), Formula (Ic), Formula (Id), Formula (Ie), Formula (If), Formula (Ig), or Formula (Ih), wherein in each of Formula (Ia), Formula (Ib), Formula (Ic), Formula (Id), Formula (Ie), Formula (If), Formula (Ig), and Formula (Ih), all groups including G, X, $Y^1$, $Y^2$, and Z are as indicated with respect to Formula (I).

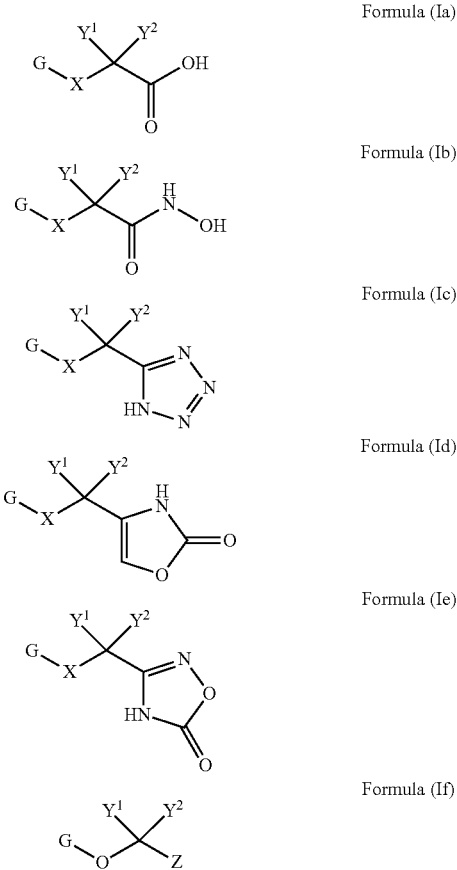

-continued

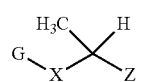
Formula (Ig)

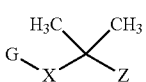
Formula (Ih)

In various embodiments, a compound of Formula (I) can be selected from the following, where in each instance G is an unsubstituted $C_{10}$-$C_{15}$ alkyl:

| X | $Y^1$, $Y^2$ | Z |
|---|---|---|
| $CH_2$ | H, H | -C(O)OH |
| O | H, H | -C(O)OH |
| O | $CH_3$, H | -C(O)OH |
| O | $CH_3$, $CH_3$ | -C(O)OH |
| $CH_2$ | H, H | -C(O)NHOH |
| $CH_2$ | H, H | tetrazole |
| $CH_2$ | H, H | oxadiazolone |
| $CH_2$ | H, H | oxazolone |

In some embodiments, the compound of Formula (I) can be selected from:

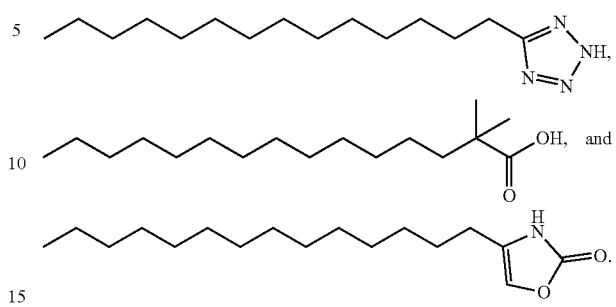

In further embodiments, the compound can be a 2-methyl, 2,2-dimethyl, 2-ethyl, 2,2-diethyl, 3-oxa, or 3-oxa-2,2-dimethyl substituted saturated fatty acid selected from tridecanoic acid (C13:0), myristic acid (C14:0), pentadecanoic acid (C15:0), palmitic acid (C16:0), heptadecanoic acid (C17:0), or stearic acid (C18:0), or a tetrazole acid isostere, an oxazolone acid isostere, an oxadiazolone acid isostere, an amide, an N-hydroxy amide, a (2-hydroxyethyl)amide or pharmaceutically acceptable salt thereof.

In some embodiments, the compound is 2,2-dimethyl pentadecanoic acid, 2-methyl palmitic acid, or 2,2-dimethyl palmitic acid.

In some embodiments, an oxadiazolone acid isostere is an unsubstituted 1,2,4-oxadiazol-5(4H)-one acid isostere. In further embodiments, an oxazolone acid isostere is an unsubstituted oxazol-2(3H)-one acid isostere.

Increased dietary intake of the odd chain saturated fatty acid, heptadecanoic acid, has been associated with improved metabolic syndrome bottlenose dolphins (see Venn-Watson et al. Increased dietary intake of saturated fatty acid heptadecanoic acid (C17:0) associated with decreasing ferritin and alleviated metabolic syndrome in dolphins, (2016) PLOS ONE 10(7):e0132117). Accordingly, oral administration of modified odd chain saturated fatty acids may be useful in the treatment of metabolic syndrome.

Certain lipid compounds have been proposed in WO 2017/093732 for the treatment of ophthalmic disorders such as retinal degenerative disorders and ocular inflammatory disease. However, these lipids are unsaturated fatty acid derivatives (e.g., alkyl groups containing 1 to 5 double bonds). Larson et al. in Lipids, Vol. 40, no. 1 (2005) demonstrates increased PPAR-alpha and PPAR-gamma activity with alpha-methylation of various fatty acids, including one saturated fatty acid (palmitic, or C16:0); however, the derivatives are described as poor, and nonsignificant, activators of PPARδ (delta). In contrast, it has been observed that C15:0 is a partial PPAR delta agonist and its derivatives often exhibit improved PPAR-delta EC50 and/or maximum concentrations.

Peroxisome proliferator-activated receptors (PPARs) are known orchestrators of mammalian metabolism and, as such, are targets for therapeutics across numerous diseases. There are three isotypes of PPARs: alpha, delta, and gamma. Molecules that differentially bind to and activate each of the three PPAR isotypes have been demonstrated to treat a variety of conditions related to metabolic syndrome, including inflammation, dyslipidemia, prediabetes and diabetes, fatty liver disease, nonalcoholic steatohepatitis and insulin resistance. In addition, PPAR agonists have been proposed as therapeutic targets for autoimmune diseases, asthma, anemia, cancer, cardiovascular disease, dermatitis, hypertension, pulmonary disease (including pulmonary fibrosis and systemic sclerosis), psoriasis, iron overload, and neurodegenerative diseases, including Alzheimer's disease and other forms of dementia. Saturated fatty acids are believed to be endogenous ligands for the PPAR isoforms PPAR-alpha and PPAR-delta, and it is hypothesized that structural features, such as carbon chain length, can influence PPAR agonist activity (see: Forman B M, Chen J, Evans R M (1997) Hypolipidemic drugs, polyunsaturated fatty acids, and eicosanoids are ligands for peroxisome proliferator-activated receptors α and δ. Proc Natl Acad Sci 94:4312-4317).

It can be hypothesized that the demonstrated efficacy of pentadecanoic acid (C15:0) and heptadecanoic acid (C17:0) in attenuating components of metabolic syndrome may be due, in part, to their roles as PPAR-alpha and PPAR-delta agonists. PPAR relationships to various indications are described in the following references: Aleshin S et al. (2013) Peroxisome proliferator-activated receptor (PPAR)β/δ, a possible nexus of PPARα- and PPARγ-dependent molecular pathways in neurodegenerative diseases: review and novel hypotheses. Neurochem Int 63:322-330; Barish G D et al. (2006) PPARδ: a dagger in the heart of metabolic syndrome. J Clin Invest 116:590-597; Bonomo L D F et al. (2012) Iron overload potentiates diet-induced hypercholesterolemia and reduces liver PPAR-α expression in hamsters. J Biochem Mol Toxicol 26:224-229; Chiba T et al. (2012) Topical application of PPARα (but not β/γ or γ) suppresses atopic dermatitis in NC/Nga mice. Allergy 67:936-942; Choi J M and Bothwell A L M (2012) The nuclear receptor PPARs as important regulators of T-cell functions and autoimmune diseases. Mol Cell 33:217-222; Hosokawa M et al. (2004) Fucoxanthin induces apoptosis and enhances the antiproliferative effect of the PPARγ ligand, troglitazone, on colon cancer cells. BBA Gen Subj 1675:113-119; Janani C and Kumari B D R (2015) PPAR gamma gene—a review. Diab Metab Synd Clin Res Rev 9:46-50; Leibovitz E et al. (2007) PPAR activation: a new target for the treatment of hypertension. J Cardio Pharmacol 50:120-125; Lee H Y et al. (2015) PPAR-α and glucocorticoid receptor synergize to promote erythroid progenitor self-renewal. Nature 522:474-477; Madrazo J A and Kelly D P (2008) The PPAR trio: Regulators of myocardial energy metabolism in health and disease. J Mol Cell Cariol 44:968-975; Milam J E et al. (2008) PPAR-γ agonists inhibit profibrotic phenotypes in human lung fibroblasts and bleomycin-induced pulmonary fibrosis. Am J Physiol Lung Cell Mol Physiol 294:L891-L901; Sertznig P et al. (2008) Peroxisome proliferator-activated receptors (PPARs) and the human skin. Am J Clin Dermatol 9:15-31; Sokolowska M et al. (2005) Peroxisome proliferator-activated receptor gamma (PPAR-gamma) and their role in immunoregulation and inflammation control. Postepy Higieny 59:472-484; Trifillieff A et al. (2009) PPAR-α and -γ but not -δ agonists inhibit airway inflammation in a murine model of asthma: in vitro evidence for an NF-kβ-independent effect. Br J Pharmacol 139:163-171; and Wei et al. (2010) Peroxisome proliferator-activated receptor γ: innate protection from excessive fibrinogenesis and potential therapeutic target in systemic sclerosis. Curr Opin Rhematol 22:671-676.

A modified saturated fatty acid may improve hydrophilic binding in the AF2 pocket of Arm-II. Thus, certain analogs of fatty acids might provide improved PPAR agonist activity compared to natural fatty acid forms. By improving PPAR agonist activity, it can be hypothesized that a saturated fatty acid analog such as a compound provided herein may be more effective at treating metabolic syndrome and components of metabolic syndrome compared to natural fatty acids.

Thus, the compound, for example, the compound of Formula (I), or pharmaceutically acceptable salt or metabolite thereof, may advantageously activate a PPAR.

It is an object of certain of the embodiments to provide a method for detecting protective and risk factors against and for metabolic syndrome and hyperferritinemia in mammal subjects such as dolphins and humans. An object of certain of the embodiments is to provide a method for treating metabolic syndrome and/or hyperferritinemia in mammal subjects, such as dolphins and humans. An object of certain of the embodiments is to provide a method for detecting metabolic syndrome and/or hyperferritinemia in mammal subjects, such as for dolphins and humans that increases the level of a compound of Formula (I), or corresponding fatty acid thereof, of the subject sera. An object of certain of the embodiments is to provide a method for detecting and treating hyperferritinemia without resorting to phlebotomy. An object of certain of the embodiments is to provide a supplement for detecting and treating metabolic syndrome and hyperferritinemia. An object of certain of the embodiments is to provide a method for detecting and treating metabolic syndrome and/or hyperferritinemia in mammal subjects, such as dolphins and humans that is easy to accomplish in a cost-effective manner. An object of certain of the embodiments is to provide a method for modulating markers of metabolic syndrome in a subject. An object of certain of the embodiments is to provide a method for detecting metabolic syndrome in a subject. An object of certain of the embodiments is to provide a method for treatment of metabolic syndrome in a subject. An object of certain of the embodiments is to provide a method for prophylaxis of metabolic syndrome in a subject. An object of certain of the embodiments is to provide a method for increasing a compound of Formula (I), or corresponding fatty acid thereof, in the sera of a subject. An object of certain of the embodiments is to provide a method for detecting or treating hyperferritinemia.

One or more than one of the aforementioned objects is provided by or achieved by the various compositions, methods, and uses as described herein.

Definitions

The term "alcohol" as used herein is a broad term, and is to be given its ordinary and customary meaning to a person of ordinary skill in the art (and is not to be limited to a special or customized meaning), and refers without limitation to any compound as described herein incorporating one or more hydroxy groups, or being substituted by or functionalized to include one or more hydroxy groups.

The term "derivative" as used herein is a broad term, and is to be given its ordinary and customary meaning to a person of ordinary skill in the art (and is not to be limited to a special or customized meaning), and refers without limitation to any compound as described herein incorporating one or more derivative groups, or being substituted by or functionalized to include one or more derivative groups. Derivatives include but are not limited to esters, amides, anhydrides, acid halides, thioesters, and phosphates.

The term "hydrocarbon" as used herein is a broad term, and is to be given its ordinary and customary meaning to a person of ordinary skill in the art (and is not to be limited to a special or customized meaning), and refers without limitation to any moiety comprising only carbon and hydrogen atoms. A functionalized or substituted hydrocarbon moiety has one or more substituents as described elsewhere herein.

The term "lipid" as used herein is a broad term, and is to be given its ordinary and customary meaning to a person of ordinary skill in the art (and is not to be limited to a special or customized meaning), and refers without limitation to saturated and unsaturated oils and waxes, derivatives, amides, glycerides, fatty acids, fatty alcohols, sterol and sterol derivatives, tocopherols, carotenoids, among others.

The terms "pharmaceutically acceptable" as used herein is a broad term, and is to be given its ordinary and customary meaning to a person of ordinary skill in the art (and is not to be limited to a special or customized meaning), and refers without limitation to those compounds, materials, compositions, and/or dosage forms which are, within the scope of sound medical judgment, suitable for contact with the tissues of and/or for consumption by human beings and animals without excessive toxicity, irritation, allergic response, or other problem complications commensurate with a reasonable risk/benefit ratio.

The terms "pharmaceutically acceptable salts" and "a pharmaceutically acceptable salt thereof" as used herein are broad terms, and are to be given their ordinary and customary meaning to a person of ordinary skill in the art (and is not to be limited to a special or customized meaning), and refer without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity. In addition to salts, pharmaceutically acceptable precursors and derivatives of the compounds can be employed. Pharmaceutically acceptable amides, lower alkyl derivatives, and protected derivatives can also be suitable for use in compositions and methods of preferred embodiments. While it may be possible to administer the compounds of the preferred embodiments in the form of pharmaceutically acceptable salts, it is generally preferred to administer the compounds in neutral form.

The term "pharmaceutical composition" as used herein is a broad term, and is to be given its ordinary and customary meaning to a person of ordinary skill in the art (and is not to be limited to a special or customized meaning), and refers without limitation to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids or bases. Pharmaceutical compositions will generally be tailored to the specific intended route of administration.

As used herein, a "carrier" as used herein is a broad term, and is to be given its ordinary and customary meaning to a person of ordinary skill in the art (and is not to be limited to a special or customized meaning), and refers without limitation to a compound that facilitates the incorporation of a compound into cells or tissues. For example, without limitation, dimethyl sulfoxide (DMSO) is a commonly utilized carrier that facilitates the uptake of many organic compounds into cells or tissues of a subject. Water, saline solution, ethanol, and mineral oil are also carriers employed in certain pharmaceutical compositions.

As used herein, a "diluent" as used herein is a broad term, and is to be given its ordinary and customary meaning to a person of ordinary skill in the art (and is not to be limited to a special or customized meaning), and refers without limitation to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" as used herein is a broad term, and is to be given its ordinary and customary meaning to a person of ordinary skill in the art (and is not to be limited to a special or customized meaning), and refers without limitation to a substance that is added to a pharmaceutical composition to provide, without limitation, bulk, consistency, stability, binding ability, lubrication, disintegrating ability etc., to the composition. A "diluent" is a type of excipient.

As used herein, a "subject" as used herein is a broad term, and is to be given its ordinary and customary meaning to a person of ordinary skill in the art (and is not to be limited to a special or customized meaning), and refers without limitation to an animal that is the object of treatment, observation or experiment. "Animal" includes cold- and warm-blooded vertebrates and invertebrates such as fish, shellfish, reptiles, and, in particular, mammals. "Mammal" includes, without limitation, dolphins, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" are broad terms, and are to be given their ordinary and customary meaning (and are not to be limited to a special or customized meaning) and, without limitation, do not necessarily mean total cure or abolition of the disease or condition. Any alleviation of any undesired markers, signs or symptoms of a disease or condition, to any extent, can be considered treatment and/or therapy. Furthermore, treatment may include acts that may worsen the patient's overall feeling of well-being or appearance.

The terms "therapeutically effective amount" and "effective amount" as used herein are broad terms, and are to be given its ordinary and customary meaning to a person of ordinary skill in the art (and are not to be limited to a special or customized meaning), and are used without limitation to indicate an amount of an active compound, or pharmaceutical agent, that elicits the biological or medicinal response indicated. For example, a therapeutically effective amount of compound can be the amount needed to prevent, alleviate or ameliorate markers or symptoms of a condition or prolong the survival of the subject being treated. This response may occur in a tissue, system, animal or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The term "solvents" as used herein is a broad term, and is to be given its ordinary and customary meaning to a person of ordinary skill in the art (and is not to be limited to a special or customized meaning), and refers without limitation to compounds with some characteristics of solvency for other compounds or means, that can be polar or nonpolar, linear or branched, cyclic or aliphatic, aromatic, naphthenic and that includes but is not limited to: alcohols, derivatives, diesters, ketones, acetates, terpenes, sulfoxides, glycols, paraffins, hydrocarbons, anhydrides, heterocyclics, among others.

The term "fatty acid" as used herein is a broad term, and is to be given its ordinary and customary meaning to a person of ordinary skill in the art (and is not to be limited to a special or customized meaning), and refers without limitation to non-natural fatty acids. Without limitation, the non-natural fatty acids may be derived from hydrolysis or metabolic cleavage of an acid isostere of a compound of Formula (I).

As used herein, any group(s) such as, without limitation, $R^1, R^2, Y^1$, and $Y^2$ represent substituents that can be attached to the indicated atom. If two groups are described as being "taken together" the groups and the atoms they are attached to can form a cycloalkyl, cycloalkenyl, aryl, heteroaryl or heterocycle. For example, without limitation, if $Y^1$ and $Y^2$ are indicated to be "taken together," it means that they are covalently bonded to one another through 0 to 5 intervening atoms to form a ring. In addition, if two groups are described as being "taken together" with the atom(s) to which they are attached to form a ring as an alternative, the groups are not limited to the variables or substituents defined previously.

As provided herein, an "oxa-" or "thia-" fatty acid is a fatty acid in which a methylene group in the indicated position is replaced (such that the number of chained atoms in the fatty acid chain is unchanged) by an oxygen or sulfur atom. As a non-limiting example, 3-oxapentadecanoic acid refers to 2-(dodecyloxy)acetic acid having the structure:

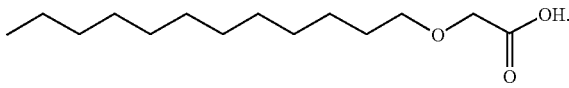 [SMILES: CCCCCCCCCCCCOCC(=O)O]

The sulfur atom may be oxidized, for example, as a sulfenyl, sulfinyl, or sulfonyl group. In some embodiments, the sulfur atom is part of a sulfenyl moiety.

The term "optionally substituted" as used herein indicates that the chemical group, for example, G, X, $Y^1$, $Y^2$, or Z, may be unsubstituted, or may be substituted with one or more of the indicated substituents. If no substituents are named, the indicated "optionally substituted" or "substituted" group may be substituted with one or more substituent(s) individually and independently selected from $C_1$-$C_6$ alkyl, $C_1$-$C_6$ alkenyl, $C_1$-$C_6$ alkynyl, $C_3$-$C_8$ cycloalkyl, $C_3$-$C_8$ cycloalkenyl, acyl($C_1$-$C_6$ alkyl), $C_1$-$C_6$ alkoxy($C_1$-$C_6$ alkyl), amino($C_1$-$C_6$ alkyl), amino acid, $C_6$-$C_{10}$ aryl, heteroaryl, heterocyclyl, $C_6$-$C_{10}$ aryl($C_1$-$C_6$ alkyl), heteroaryl ($C_1$-$C_6$ alkyl), heterocyclyl($C_1$-$C_6$ alkyl), hydroxyl($C_1$-$C_6$ alkyl), acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, azido, nitro, silyl, sulfenyl, sulfinyl, sulfonyl, halo($C_1$-$C_6$ alkyl), $C_1$-$C_6$ haloalkoxy, trihalomethanesulfonyl, trihalomethanesulfonamido, or amino.

As used herein, "$C_a$ to $C_b$" in which "a" and "b" are integers refer to the range of carbon atoms in an alkyl, alkenyl or alkynyl group, or the number of carbon atoms in the ring of a cycloalkyl, cycloalkenyl, aryl, heteroaryl or heterocyclyl group. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heteroalicyclyl group, the broadest range described in these definitions is to be assumed.

The term "alkyl" as used herein is a broad term, and is to be given its ordinary and customary meaning to a person of ordinary skill in the art (and is not to be limited to a special or customized meaning), and refers to a straight or branched hydrocarbon chain that comprises a fully saturated (no double or triple bonds) hydrocarbon group. The alkyl group may be a lower alkyl group having 1 to 6 carbon atoms. Typical alkyl groups include, but are in no way limited to, methyl, ethyl, propyl, isopropyl, butyl, isobutyl, tertiary butyl, pentyl and hexyl. The alkyl group may be a medium alkyl group having 7 to 14 carbon atoms. The alkyl group may be a higher alkyl group having 15 or more carbon atoms, e.g., 15-30 carbon atoms, or 15 to 25 carbon atoms. The alkyl group may be an odd chain alkyl group, e.g., having 1, 3, 5, 7, 9, 11, 13, 15, 17, 19, 21, 23, or 25 carbon atoms, e.g., 15 or 17 carbon atoms.

As used herein, "alkenyl" is a broad term, and is to be given its ordinary and customary meaning to a person of ordinary skill in the art (and is not to be limited to a special or customized meaning), and refers to a straight or branched, unsubstituted or substituted hydrocarbon chain that contains in the chain one or more carbon-carbon double bonds. Non-limiting examples of alkenyl groups include alkenyl, vinyl, and isoprenyl.

As used herein, "alkynyl" is a broad term, and is to be given its ordinary and customary meaning to a person of ordinary skill in the art (and is not to be limited to a special or customized meaning), and refers to a straight or branched, unsubstituted or substituted hydrocarbon chain that contains in the chain one or more carbon-carbon triple bonds. Non-limiting examples of alkynyls include ethynyl and propynyl.

As used herein, "heteroaryl" is a broad term, and is to be given its ordinary and customary meaning to a person of ordinary skill in the art (and is not to be limited to a special or customized meaning), and refers to a monocyclic or fused multicyclic ring system that includes an aromatic ring having one or more heteroatoms in the aromatic ring. The heteroatom can be, but is not limited to, nitrogen, oxygen or sulfur. An "n-membered heteroaryl" refers to a ring or ring system having n total atoms forming the ring(s) of the ring or ring system. Heteroaryls include oxo-substituted heterocyclic aromatic rings and ring systems, and hydroxy-tautomers thereof. Examples of heteroaryl rings include, but are not limited to, those described herein and the following: 1,2,4-oxadiazol-5(4H)-one, tetrazole, furan, furazan, thiophene, pyrrole, oxazole, 1,2,3-oxadiazole, 1,2,4-oxadiazole, thiazole, 1,2,3-thiadiazole, 1,2,4-thiadiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, quinoline, isoquinoline, quinazoline, quinoxaline, cinnoline, and triazine.

As used herein, "heterocyclyl" is a broad term, and is to be given its ordinary and customary meaning to a person of ordinary skill in the art (and is not to be limited to a special or customized meaning), and refers to a monocyclic, spirocyclic, and/or fused multicyclic ring system that does not include any aromatic rings, and has one or more heteroatoms in the ring or ring system. The heteroatom can be, but is not limited to, nitrogen, oxygen or sulfur. An "n-membered heterocyclyl" refers to a ring or ring system having n total atoms forming the ring(s) of the ring or ring system. Heterocyclyls include oxo-substituted heterocyclic rings and ring systems, and hydroxy-tautomers thereof. Examples of heteroaryl rings include, but are not limited to, those described herein and the following: groups include, but are not limited to, those described herein and the following: oxazolidinone, 1,3-dioxin, 1,4-dioxane, 1,2-dioxolane, 1,3-oxathiane, 1,3-oxathiolane, 1,3-dithiole, 1,3-dithiolane, 1,4-oxathiane, tetrahydro-1,4-thiazine, 1,3-thiazinane, 2H-1,2-oxazine, maleimide, succinimide, barbituric acid, thiobarbituric acid, dioxopiperazine, hydantoin, dihydrouracil, trioxane, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, and 3,4-methylenedioxyphenyl).

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group connected, as a substituent, via a lower alkylene group having 1 to 6 carbon atoms. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, imidazolylalkyl, and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and heterocyclyl of a heteroalicyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl), and 1,3-thiazinan-4-yl(methyl).

"Lower alkylene groups" are straight-chained —$CH_2$— tethering groups, forming bonds to connect molecular fragments via their terminal carbon atoms, and having 1 to 6 carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) is defined herein. A non-limiting list of alkoxys include methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "acylalkyl" refers to an acyl connected, as a substituent, via a lower alkylene group. Examples include aryl-C(=O)—$(CH_2)_n$— and heteroaryl-C(=O)—$(CH_2)_n$—, where n is an integer in the range of 1 to 6.

As used herein, "alkoxyalkyl" refers to an alkoxy group connected, as a substituent, via a lower alkylene group. Examples include $C_{1-4}$ alkyl-O—$(CH_2)_n$—, wherein n is an integer in the range of 1 to 6.

As used herein, "aminoalkyl" refers to an unsubstituted or a substituted amino group connected, as a substituent, via a lower alkylene group. Examples include $H_2N(CH_2)_n$—, wherein n is an integer in the range of 1 to 6.

As used herein, "amino" refers to an unsubstituted nitrogen or a nitrogen substituted by one or two optionally substituted $C_1$-$C_6$ alkyl groups. Examples of amino groups include, but are not limited to, —$NH_2$, —$NHCH_3$, —$N(CH_3)_2$, and —$N(CH_3)(CH_2CH_3)$.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, chlorofluoroalkyl, chloro-difluoroalkyl, and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, chloro-fluoroalkyl, chloro-difluoroalkoxy and 2-fluoroisobutoxy. A haloalkoxy may be substituted or unsubstituted.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl).

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "carbonyl" group refers to a C=O group.

An "S-sulfonamido" group refers to a "—SO$_2$N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carbamyl" group refers to a "—OC(=O)N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(=O)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(=S)—N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(=S)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

As used herein, "-------" indicates a single or double bond, unless stated otherwise.

Where the numbers of substituents is not specified (e.g. haloalkyl), there may be one or more substituents present. For example "haloalkyl" may include one or more of the same or different halogens. As another example, "C$_1$-C$_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

As used herein, the term "amino acid" refers to any amino acid (both natural and non-natural amino acids), including, but not limited to, α-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. As used herein, "amino acid" also includes amino acids wherein the main-chain carboxylic acid group has been converted to an ester group.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein).

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' preferred, 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and any intervening value between the upper and lower limit of the range is included.

Any percentages, ratios or other quantities referred to herein are on a weight basis, unless otherwise indicated.

Saturated Fatty Acids

Saturated and unsaturated fatty acids are known to be present in the body (see, e.g., Jenkins B, West J, Koulman A (2015), A review of odd-chain fatty acid metabolism and the role of pentadecanoic acid (C15:0) and heptadecanoic acid (C17:0) in health and disease, Molecules 20:2425-44). As provided herein, fatty acids are referred to and described using conventional nomenclature as is employed by one of skill in the art. A saturated fatty acid includes no carbon-carbon double bonds. An unsaturated fatty acid includes at least one carbon-carbon double bond. A monounsaturated fatty acid includes only one carbon-carbon double bond. A polyunsaturated fatty acid includes two or more carbon-carbon double bonds. Double bonds in fatty acids are generally cis; however, trans double bonds are also possible. The position of double bonds can be indicated by $\Delta n$, where n indicates the lower numbered carbon of each pair of double-bonded carbon atoms. A shorthand notation specifying total #carbons: #double bonds, $\Delta_{double\ bond\ positions}$ can be employed. For example, $20:4\Delta_{5,8,11,14}$ refers to a fatty acid having 20 carbon atoms and four double bonds, with the double bonds situated between the 5 and 6 carbon atom, the 8 and 9 carbon atom, the 11 and 12 carbon atom, and the 14 and 15 carbon atom, with carbon atom 1 being the carbon of the carboxylic acid group. Stearate (octadecanoate) is a saturated fatty acid. Oleate (cis-$\Delta$9-octadecenoate) is a monounsaturated fatty acid, linolenate (all-cis-$\Delta$9,12,15-octadecatrienoate) is a polyunsaturated fatty acid.

A saturated fatty acid may be referred to by various names, for example, heptadecanoic acid may be referred to as heptadecylic acid and n-heptadecylic acid, or C17:0. A saturated or unsaturated fatty acid may be referred to by lipid numbers, as known in the art. Examples of odd chain fatty acids are margaric acid (heptadecanoic acid, C17:0), pelargonate (nonanoic acid, $C_9$:0), undecanoic acid ($C_{11}$:0), nonadecanoic acid ($C_{19}$:0), arachidonate ((5Z,8Z,11Z,14Z)-icosa-5,8,11,14-tetraenoic acid), adrenate (all-cis-7,10,13,16-docosatetraenoic acid), and osbond acid (all-cis-4,7,10,13,16-docosapentaenoic acid). Generally, the one or more saturated fatty acids have from 9 carbon atoms to 31 carbon atoms in the longest alkyl chain (9, 11, 13, 15, 17, 19, 21, 23, 25, 27, 29, or 31 carbon atoms), for example, from 15 to 21 carbon atoms, for example 17 carbon atoms; however, in certain embodiments higher or lower odd numbers of carbon atoms can be acceptable. In some embodiments, the saturated fatty acids can be odd chain fatty acids or even chain fatty acids. In some embodiments, the saturated fatty acid can be an odd chain fatty acid. As described herein, an odd chain fatty acid is a fatty acid having an odd number of carbon atoms in the longest alkyl chain. As described herein, an even chain fatty acid is a fatty acid having an even number of carbon atoms in the longest alkyl chain.

A saturated fatty acid may be present as a salt, for example, at a carboxylic group. In some embodiments, one compound of Formula (I), or pharmaceutically acceptable salt thereof, may be present, for example, in a composition, two compounds of Formula (I) or pharmaceutically acceptable salts thereof may be present, three compounds of Formula (I), or pharmaceutically acceptable salts thereof, may be present, or more. In some embodiments, saturated fatty acids in a mixture including a plurality of compounds of Formula (I) fatty acids, or pharmaceutically acceptable salts thereof, may be distinguished by the amount of unsaturation, the length of the hydrocarbon chain, varying states of derivativeification, the number of alkyl substitutions, the identity of the acid isostere, the identity of the salt, or by other structural features. In further embodiments, a compound of Formula (I), or pharmaceutically acceptable salt thereof, may be present, for example, in a composition, with a naturally occurring fatty acid, or a naturally occurring unsaturated fatty acid.

Odd chain fatty acids are found in trace amounts in some dairy products, including butter, and is a component of some fish oils (see, e.g., Mansson H L (2008), Fatty acids in bovine milk fat, Food Nutr. Res. 52:4, Luzia L A, Sampaio G R, Castellucci C M N, Tones E A F S (2013) The influence of season on the lipid profiles of five commercially important species of Brazilian fish. Food Chem. 83:93-97). Studies have demonstrated that increasing daily dietary intake of foods with odd chain fatty acids successfully increases serum levels (see, e.g., Benatar J. R., Stewart R. A. H. (2014), The effects of changing dairy intake on trans and saturated fatty acid levels—results from a randomized controlled study. Nutr. J. 13:32).

The prevalence of various fatty acids in the diet has been correlated to the occurrence of metabolic syndrome in subjects (see, e.g., Forouhi N, Koulman A, Sharp S, Imamura F, Kröger J, Schulze M, et al. (2014), Differences in the prospective association between individual plasma phospholipid saturated fatty acids and incident type 2 diabetes: the EPIC-InterAct case-cohort study. Lancet Diabetes Endocrinol. 2:810-8). Indeed, whole-fat dairy consumption has been correlated with a decreased risk of metabolic syndrome markers (see, e.g., Kratz M, Marcovina S, Nelson J E, Yeh M M, Kowdley K V, Callahan H S, et al. (2014), Dairy fat intake is associated with glucose tolerance, hepatic and systemic insulin sensitivity, and liver fat but not beta-cell function in humans, Am. J. Clin. Nutr., 99:1385-96).

A pure or purified odd chain fatty acid may exist in various physical states. For example, heptadecanoic acid exists as an off-white powder that is stable at room temperature; this compound can be purchased in forms suitable for research purposes in small amounts from some commercial suppliers (for example, from Sigma-Aldrich corp., of St. Louis, MO). Other odd chain fatty acids, or salts or derivatives thereof, may exist as oils, solids, crystalline solids, or gases.

A compound of Formula (I), or pharmaceutically acceptable salt thereof, may be provided in a purity (e.g., a percentage of the compound of Formula (I), or pharmaceutically acceptable salt thereof, in a bulk form) of at least about 10%, at least about 20%, at least about 30%, at least about 40%, at least about 50%, at least about 60%, at least about 70%, at least about 80%, at least about 90%, at least about 95%, at least about 98%, at least about 99%, at least about 99.9%, at least about 99.99%, or substantially pure, wherein substantially pure may include, but not be limited to, a product with impurities at a level such that no physiological effect from the presence of the impurities is detectable. A mixture of compounds of Formula (I), or pharmaceutically acceptable salts thereof, may be present in a purity of at least about 10%, at least about 20%, at least about 30%, at least about 40%, at least about 50%, at least about 60%, at least about 70%, at least about 80%, at least about 90%, at least about 95%, at least about 98%, at least about 99%, at least about 99.9%, at least about 99.99%, or substantially pure. A compound of Formula (I), or pharmaceutically acceptable salt thereof, may be free from naturally occurring fatty acids or fatty acid derivatives, may be free from triglycerides, or may be free from phospholipids. Without limitation, a compound of Formula (I), or pharmaceutically acceptable salt thereof, may be substantially free from even chain fatty acids, singly or taken as a group; even chain fatty acids include, for example, myristic acid (C14:0), palmitic acid (C16:0), stearic acid (C18:0), or arachidic acid (C20:0). In further embodiments, and without limitation, a compound of Formula (I), or pharmaceutically acceptable salt thereof, may be substantially free from naturally occurring even chain fatty acids. In some embodiments, a compound of Formula (I), or pharmaceutically acceptable salt thereof, may be substantially free from short-chain fatty acids (SCFA), medium-chain fatty acids (MCFA), long-chain fatty acids (LCFA), or very long chain fatty acids (VLCFA). In some embodiments, "substantially free" can mean that the composition contains less than 5 wt. % of an impurity, e.g., naturally occurring even chain fatty acid(s), or less than 1 wt. % of an impurity, or has a level of impurity that is not detectable, e.g., using conventional GC/MS detection methods.

A compound of Formula (I), or pharmaceutically acceptable salt thereof, may be synthesized by any method including methods known to persons of skill in the art or those methods provided herein. In some embodiments, a compound of Formula (I), or pharmaceutically acceptable salt thereof, may be present in natural sources, may be isolated from natural sources, may be semi-synthetic, may be synthetic, or may be a mixture of one or more of these. A compound of Formula (I), or pharmaceutically acceptable salt thereof, may be produced in a laboratory, may be produced in nature, may be produced by enzymatic processes, may be produced by wild microbes, may be produced by genetically modified microbes, may be isolated from animal tissues, may be produced by chemical synthesis, or may be produced by a plurality of these processes.

A compound of Formula (I), or pharmaceutically acceptable salt thereof, may be derived from natural sources, e.g., fish oils, or can be synthesized by methods as are known in the art. In some embodiments, a compound of Formula (I), or pharmaceutically acceptable salt thereof, may be contaminated with even chain fatty acids, or other components present in unrefined or unpurified natural products. In such situations, it can be desirable to remove undesired components, or to increase the concentration of desired components using known separation or purification techniques.

In any compound described, all tautomeric forms are also intended to be included. Without limitation, all tautomers of carbon-carbon double bonds and carboxylic groups, and heterocycles, for example, tetrazoles, are intended to be included. An example tautomer provided herein is that of a tetrazole substituent:

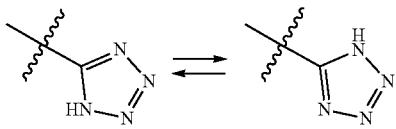 [SMILES: *Cc1nnn[nH]1 ; *Cc1nnn[nH]1]

In any compound described herein having one or more double bond(s) generating geometrical isomers that can be defined as E or Z, each double bond may independently be E or Z, or a mixture thereof.

Where compounds disclosed herein have unfilled valencies, then the valencies are to be filled with hydrogens or isotopes thereof, e.g., hydrogen-1 (protium) and hydrogen-2 (deuterium).

A compound of Formula (I), or a pharmaceutically acceptable salt thereof, includes crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

The compounds described herein can be labeled isotopically. In some circumstances, substitution with isotopes such as deuterium may afford certain therapeutic advantages resulting from greater metabolic stability, such as, for example, increased in vivo half-life or reduced dosage requirements. Isotopic substitution may be beneficial in monitoring subject response to administration of a compound, for example, by providing opportunity for monitoring of the fate of an atom in a compound. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Preparation of Compounds

Compounds of Formula (I) can be prepared by any suitable method known to those in the art. For representative methods, see, for example, Francis A. Carey et al., Advanced Organic Chemistry: Part B: Reaction and Synthesis (5$^{th}$ Ed. 2005).

Pharmaceutical Compositions Including a Compound of Formula (I)

Formulations including an odd chain fatty acid, or a salt or derivative thereof, and at least one excipient are provided. It is generally preferred to administer the compounds of the embodiments in oral formulations; however, other routes of administration are also contemplated.

The pharmaceutical compositions described herein can be administered by themselves to a subject, or in compositions where they are mixed with other active agents, as in combination therapy, or with carriers, diluents, excipients or combinations thereof. Formulation is dependent upon the route of administration chosen. Techniques for formulation and administration of the compounds described herein are known to those skilled in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

The pharmaceutical compositions disclosed herein may be manufactured by a process that is itself known, e.g., by means of conventional mixing, dissolving, granulating, dragee-making, levigating, emulsifying, encapsulating, entrapping, tableting, or extracting processes. Many of the compounds used in the pharmaceutical combinations disclosed herein may be provided as salts with pharmaceutically acceptable counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Contemplated herein is any combination of the forgoing, or other methods as would be known to one of ordinary skill in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

In practice, a compound of Formula (I), or a pharmaceutically acceptable salt thereof, may be combined as the active ingredient in intimate admixture with a pharmaceutical carrier according to conventional pharmaceutical compounding techniques. The carrier can take a wide variety of forms depending on the form of preparation desired for administration. Thus, the pharmaceutical compositions provided herein can be presented as discrete units suitable for oral administration such as capsules, cachets or tablets each containing a predetermined amount of the active ingredient. Further, the compositions can be presented as an oil, a powder, as granules, as a solution, as a suspension in an aqueous liquid, as a non-aqueous liquid, as an oil-in-water emulsion, or as a water-in-oil liquid emulsion. In addition to the common dosage forms set out above, the compounds provided herein, or pharmaceutically acceptable salts or derivatives thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

A formulation may also be administered in a local rather than systemic manner, for example, via injection of the compound directly into the infected area, often in a depot or sustained release formulation. Furthermore, a targeted drug delivery system might be used, for example, in a liposome coated with a tissue specific antibody.

The pharmaceutical compositions may contain a compound of Formula (I), or a pharmaceutically acceptable salt thereof, in an amount effective for the desired therapeutic effect. In some embodiments, the pharmaceutical compositions are in a unit dosage form and comprise from about 0.1 mg or less to about 5000 mg or more per unit dosage form. In further embodiments, the pharmaceutical compositions comprise from about 1 to about 500 mg per unit dosage form or from about 500 to 5000 mg per unit dosage form. Such dosage forms may be solid, semisolid, liquid, an emulsion, or adapted for delivery via aerosol or the like for inhalation administration.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, lower alcohols, and water. Examples of gaseous carriers include carbon dioxide and nitrogen.

Pharmaceutical compositions provided herein can be prepared as solutions or suspensions of the active compound(s) in water. A suitable surfactant can be included such as, for example, hydroxypropylcellulose. Dispersions can also be prepared in glycerol, liquid polyethylene glycols, and mixtures thereof in oils. Further, a preservative can be included to, for example, prevent the detrimental growth of microorganisms.

Pharmaceutical compositions provided herein suitable for injectable use include sterile aqueous solutions or dispersions. Furthermore, the compositions can be in the form of sterile powders for the extemporaneous preparation of such sterile injectable solutions or dispersions. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound provided herein, or pharmaceutically acceptable salt or derivative thereof, can also be prepared in powder or liquid concentrate form for dilution.

Contemplated herein are compositions including a compound of Formula (I), or a pharmaceutically acceptable salt thereof, in combination with at least one additional active agent. A compound of Formula (I), or a pharmaceutically acceptable salt thereof, and the at least one additional active agent(s) may be present in a single formulation or in multiple formulations provided together, or may be unformulated. In some embodiments, a compound of Formula (I), or a pharmaceutically acceptable salt thereof, can be administered with one or more additional agents together in a single composition. For example, a compound of Formula (I), or a pharmaceutically acceptable salt thereof, can be administered in one composition, and at least one of the additional agents can be administered in a second composition. In a further embodiment, a compound of Formula (I), or a pharmaceutically acceptable salt thereof, and the at least one additional active agent(s) are co-packaged in a kit. For example, a drug manufacturer, a drug reseller, a physician, a compounding shop, or a pharmacist can provide a kit comprising a disclosed compound or product and another component for delivery to a patient.

Some embodiments described herein relate to a pharmaceutical composition, which can include a therapeutically effective amount of one or more compounds described herein (e.g., a compound of Formula (I), or a pharmaceutically acceptable salt thereof,) and a pharmaceutically acceptable carrier, diluent, excipient or combination thereof. The pharmaceutical composition can include a compound of Formula (I), or a pharmaceutically acceptable salt thereof, in, for example, >1%, ≥2%, ≥3%, ≥4%, ≥5%, ≥6%, ≥7%, ≥8%, ≥9%, ≥10%, ≥20%, ≥30%, ≥40%, ≥50%, ≥60%, ≥70%, ≥80%, ≥90%, ≥95%, or ≥98% of the composition. In some embodiments, the pharmaceutical composition can include a plurality of compounds of Formula (I), or pharmaceutically acceptable salts thereof, in, for example, >1%, ≥2%, ≥3%, ≥4%, ≥5%, ≥6%, ≥7%, ≥8%, ≥9%, ≥10%, ≥20%, ≥30%, ≥40%, ≥50%, ≥60%, ≥70%, ≥80%, ≥90%, ≥95%, or ≥98% of the composition.

Foodstuffs

Foodstuffs and other comestibles including a compound of Formula (I), or a pharmaceutically acceptable salt thereof, are provided, wherein an amount of the compound of Formula (I), or pharmaceutically acceptable salt thereof, in the foodstuff has been fortified (e.g., enriched or concentrated). A compound of Formula (I), or a pharmaceutically acceptable salt thereof, provided herein may be added to foodstuffs for consumption by a subject. The compound of Formula (I), or pharmaceutically acceptable salt thereof, may be integrated into one or more ingredients of a foodstuff. The compound of Formula (I), or pharmaceutically acceptable salt thereof, may be prepared as an ingredient, or may be unprepared. The compound, or preparation including the compound, may be added prior to preparation, during preparation, or following preparation. Preparation may without limitation include cooking, mixing, flavoring, seasoning, blending, boiling, frying, baking, or other processes known in the art. Fortification is preferably at a level so as to provide a therapeutic daily dosage of the compound of Formula (I), or pharmaceutically acceptable salt thereof, as described elsewhere herein; however, beneficial effects may also be obtained at amounts below such dosages.

A compound of Formula (I), or a pharmaceutically acceptable salt thereof, may be present as a constituency in foodstuffs by operation of processes known in nature, for example, by altering the metabolic processes of a plant, animal, bacteria, or fungus. Genetic alteration of a plant, animal, bacteria, or fungus to increase the concentration of an odd chain fatty acid, or a salt or derivative thereof, is contemplated. By way of example, the compound of Formula (I), or pharmaceutically acceptable salt thereof, can be present in the foodstuff in a concentration of at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, or higher, for example, 1% to 2% or 3% or 4% or 5% or 6% or 7% or 8% or 9% or 10% or 20% or 30% or 40% or 50%.

Indications

Provided herein are compositions and methods for treating conditions including but not limited to metabolic syndrome, diabetes type I, diabetes type II, obesity, prediabetes, glucose intolerance, gestational diabetes mellitus (GDM), impaired fasting glycemia (IFG), hyperferritinemia, iron overload, postprandial hyperglycemia, dyslipidemia, post prandial dyslipidemia, hyperlipidemia, hypertriglyceridemia, post hypertriglyceridemia, insulin resistance, polycystic ovary syndrome (PCOS), non-alcoholic fatty liver disease (NAFL), non-alcoholic steatohepatitis (NASH), hypoinsulinemia, fatty liver disease, elevated glucose levels, elevated insulin levels, elevated LDL triglyceride levels. The compositions are also useful in the treatment or prophylaxis of autoimmune diseases, asthma, pulmonary disease (including but not limited to pulmonary fibrosis and systemic sclerosis), dermatitis, and psoriasis. The compositions are also useful in the treatment or prophylaxis of an anemic condition, wherein the anemic condition is selected from the group consisting of hemolytic anemia, thalassemia, hereditary spherocytosis, hereditary elliptocytosis, glucose-6-phosphate dehydrogenase deficiency, pyruvate kinase deficiency, immune hemolytic anemia, alloimmune hemolytic anemia, drug-induced hemolytic anemia, mechanical hemolytic anemia, paroxysmal nocturnal hemoglobinuria, anemia of chronic disease, anemia, aplastic anemia, congenital hypoplastic anemia, Diamond-Blackfan anemia, Fanconi anemia, iron deficiency anemia, anemia of abnormal RBC size, megaloblastic anemia, microcytic anemia, vitamin deficiency anemia, pernicious anemia, anemia of RBC mutation, sideroblastic anemia, and sickle cell anemia. The compositions are also useful in the treatment or prophylaxis of inflammation and conditions including cardiometabolic diseases, cancer, and conditions of aging, and conditions related to inflammation, including anemia of chronic disease, insulin resistance, metabolic syndrome, autoimmune disease, hypertension, diabetes, nonalcoholic fatty liver disease, cardiovascular disease, cancer, aging, neurodegenerative diseases, including Alzheimer's disease and other forms of dementia, and other related conditions.

In some embodiments, the compositions and methods provided herein are indicated for treatment, prophylaxis, prevention or maintenance of metabolic syndrome.

Metabolic syndrome as described herein generally relates to a cluster of risk factors that are associated with a number of conditions as described herein, including but not limited to diabetes (especially type 2 diabetes), hypertension, cardiovascular disease, and other conditions such as polycystic ovary syndrome, fatty liver, cholesterol gallstones, asthma, sleep disturbances, some forms of cancer, ischemia, oxidative stress, atherosclerosis, obesity, abnormal lipid metabolism, and stroke (see, e.g., Grundy S. M, et al, Definition of Metabolic Syndrome (2004), Circulation, 109: 433-438). Risk factors of metabolic syndrome include abdominal (central) obesity, elevated blood pressure, advanced age, and smoking. Indicators of metabolic syndrome, which may but need not present, include insulin resistance, elevated fasting plasma glucose, glucose intolerance, high serum triglycerides, abnormal serum lipids, decreased high-density lipoprotein (HDL) levels, body mass index (BMI), proinflammatory state, and prothrombotic state.

Metabolic syndrome is also correlated with hyperferritinemia (with or without iron overload). In some embodiments, metabolic syndrome is accompanied by iron overload.

While a cluster of signs and symptoms may coexist in an individual subject, in many cases only one or a few symptoms may dominate, due to individual differences in vulnerability of the many physiological systems affected.

Insulin resistance can be defined in many different ways, including impaired glucose metabolism (reduced clearance of glucose and/or the failure to suppress glucose production), the inability to suppress lipolysis in tissues, defective protein synthesis, altered cell differentiation, aberrant nitric oxide synthesis affecting regional blood flow, as well as abnormal cell cycle control and proliferation. Insulin resistance may also be indicated by serum protein concentrations of, for example, fibroblast growth factor 21 ("FGF21").

Disease symptoms secondary to hyperglycemia or other conditions may also occur in patients with metabolic syndrome. Because the compositions and methods provided herein help to reduce hyperglycemia in diabetes and other conditions related to metabolic syndrome, they are useful for prevention and amelioration of complications of these conditions. The compounds and methods provided herein are useful for prevention or amelioration of virtually any symptom that may be due to, or exacerbated by, metabolic syndrome and related conditions.

Metabolic syndrome may also be related to oxidative stress. See Roberts, C. K. et al., Oxidative stress and metabolic syndrome, Life Sciences, (2009) Vol. 84(21-22), pp. 705-712. Without wishing to be bound by theory, it is thought that chronic hyperglycemia causes oxidative stress in tissues prone to complications in patients with diabetes. Mahjoub, S., Role of oxidative stress in pathogenesis of metabolic syndrome, Caspian J. Intern. Med. (2012) Vol. 3(1) pp. 386-396.

Further provided herein are compositions and methods for treating conditions related to oxidative stress, which include those listed above and further include atherosclerosis, hypertension, kidney disease, adult respiratory distress syndrome, cancer, anemia, such as, for example, hemolytic anemia, neurodegenerative diseases such as, for example, Alzheimer's disease, inflammation including chronic inflammation, and aging.

Oxidative stress is a condition in which an imbalance results between the production and inactivation of reactive oxygen species. Reactive oxygen species play an essential role in multiple physiological systems. But under conditions of oxidative stress, reactive oxygen species contribute to cellular dysfunction. It is believed that oxidative stress plays a major role in the pathogenesis of a variety of human diseases, including those provided herein.

It is thought that oxidative stress occurs in a cellular system when the production of free radical moieties exceeds the antioxidant capacity of that system. If cellular antioxidants do not remove free radicals, radicals attack and damage proteins, lipids, and nucleic acids. The oxidized or nitrosylated products of free radical attack have decreased biological activity, leading to loss of energy metabolism, cell signaling, transport, and other major functions. These altered products are also targeted for proteosome degradation, further decreasing cellular function. Accumulation of such injury ultimately leads a cell to die through necrotic or apoptotic mechanisms. Persons of skill in the art will appreciate that pathological levels of such markers vary between patient populations, and between individual subjects, but that a given disease condition can be determined by reference to a cluster of risk factors, markers, and symptoms.

Subjects suffering from a neurodegenerative condition, such as, for example, Alzheimer's disease, may display increased levels of lipid peroxidation products, for example 4-HNE, in the cerebrospinal fluid. Amyloid beta, a peptide thought to be implicated in the development of neurodegenerative disease, may be correlated to lipid peroxidation and 4-HNE production, which may in turn lead to neuron damage. Reducing 4-HNE levels may also protect neurons against amyloid beta toxicity. See Mattson M. P., Roles of the lipid peroxidation product 4-hydroxynonenal in obesity, the metabolic syndrome, and associated vascular and neurodegenerative disorders, Exper. Geron. (2009) Vol. 44, pp. 625-633.

In some embodiments, the compositions and methods provided herein are indicated for treatment, prophylaxis, prevention or maintenance of a neurodegenerative disease. In variations of these embodiments, the disease is Alzheimer's disease. In further variations of these embodiments, the disease is Parkinson's disease. In still further variations of these embodiments, the disease is Huntington's disease or amyotrophic lateral sclerosis. In certain embodiments, a composition or method provided herein can reduce amyloid plaques.

Serum levels of certain fatty acids have been found to be correlated with improved indices for metabolic syndrome. However, the mechanism by which certain fatty acids act to inhibit or lessen metabolic syndrome or markers of metabolic syndrome is not presently well understood. The methods and markers provided herein are not to be construed as limited to any particular mechanism, mode of action, or theory. Accordingly, methods of treating, preventing or ameliorating metabolic syndrome are provided.

Provided herein are compositions and methods for preventing or treating diabetes in a wide range of subjects, including in particular a human patient that has, has had, is suspected of having, or who is pre-disposed to developing diabetes. Diabetes mellitus may be referred to as, for example, insulin-dependent diabetes mellitus (EDDM or type I diabetes) and non-insulin-dependent diabetes mellitus (NIDDM, or type II diabetes). Examples of disorders related to diabetes mellitus have been described and include, but are not limited to, impaired glucose tolerance (IGT), maturity-onset diabetes of youth (MODY), leprechaunism (insulin receptor mutation), tropical diabetes, diabetes secondary to a pancreatic disease or surgery, diabetes associated with a genetic syndrome (e.g., Prader-Willi syndrome), pancreatitis, diabetes secondary to endocrinopathies, adipositas, and metabolic syndrome.

Diabetic subjects appropriate for treating using the compositions and methods provided herein may be identified by the risk factors, indices and markers provided herein, and by other indications available to clinicians, and are characterized by, e.g., fasting hyperglycemia, impaired glucose tolerance, glycosylated hemoglobin, and, in some instances, ketoacidosis associated with trauma or illness. Hyperglycemia or high blood sugar is a condition in which an excessive amount of glucose circulates in the blood plasma. This is generally considered to be a blood glucose level of 10+ mmol/L, but symptoms and effects may not start to become noticeable until later numbers such as 15-20+ mmol/L. NIDDM patients have an abnormally high blood glucose concentration when fasting and delayed cellular uptake of glucose following meals or after a diagnostic test known as the glucose tolerance test. NIDDM is diagnosed based on recognized criteria (American Diabetes Association, Physician's Guide to Insulin-Dependent (Type I) Diabetes, 1988; American Diabetes Association, Physician's Guide to Non-Insulin-Dependent (Type II) Diabetes, 1988).

In some embodiments, the compositions and methods provided herein are indicated for treatment, prevention and or maintenance of conditions, disorders, diseases and defects associated with energy homeostasis. Energy homeostasis generally relates to the signal pathways, molecules and hormones associated with food intake and energy expenditure. Disorders, diseases and defects associated with energy homeostasis include but are not limited to diabetes type I, diabetes type II, prediabetes, impaired fasting glycemia (IFG), impaired postprandial glucose, and gestational diabetes. In some instances the compositions and methods provided herein are indicated for treatment, prevention and or maintenance of diabetes type I or type II.

In some embodiments, the compositions and methods provided herein are indicated for treatment, prevention and or maintenance of conditions, disorders, diseases and defects associated with fuel homeostasis. Disorders, diseases and defects associated with fuel homeostasis include but are not limited to non-alcoholic fatty liver disease (NAFL), non-alcoholic steatohepatitis (NASH), hyperlipidemia, post hypertriglyceridemia, hypertriglyceridemia, insulin resistance and polycystic ovary syndrome (PCOS).

In some embodiments, the compositions and methods provided herein are indicated for treatment, prevention, or maintenance of hyperferritinemia. High ferritin and iron overload have been associated with metabolic syndrome and diabetes in humans. It is unknown precisely why ferritin increases in some people and how high ferritin increases the risk of metabolic syndrome. While not wishing to be bound by theory, it is believed that direct injury to the liver and pancreas from excessive deposition, or indirect injury from increased oxidative radicals, may be causative factors. In some embodiments, the compounds and methods provided herein lead to reduced serum iron. In some embodiments, the compounds and methods provided herein lead to reduced serum ferritin. In some embodiments, the compounds and methods provided herein ameliorate hyperferritinemia without phlebotomy.

Elevated triglyceride (e.g., LDL) is an important risk factor for atherosclerosis and myocardial infarction. Provided herein are compositions and methods useful for reducing circulating triglycerides in hyperlipidemic patients. Cholesterol-lowering drugs such as HMG-CoA reductase inhibitors ("statins") can be administered to subjects in addition to compounds provided herein, optionally incorporated into the same pharmaceutical composition.

Autoimmune diseases, asthma, pulmonary disease (including pulmonary fibrosis and systemic sclerosis), dermatitis, and psoriasis are related to metabolic syndrome. See, e.g., Agrawal A et al. (2011) Emerging interface between metabolic syndrome and asthma. Am J Resp Cell Mol Biol 44; Gisondi P et al. (2007) Prevalence of metabolic syndrome in patients with psoriasis: a hospital-based case-control study. Brit J Dermatol 157:68-73; Naveed B. et al. (2012) Metabolic syndrome biomarkers predict lung function impairment: a nested case-control study. Am J Resp Crit Care Med 185:392-399; Pereira R M R et al. (2009) Metabolic syndrome in rheumatological diseases. Autoimmunity Rev 8:415-419; and Takahashi H and Iizuka H (2011) Psoriasis and metabolic syndrome. J Dermatol 39:211-289.

Protein-Based Contributors to Metabolic Syndrome and Associated Diseases

CD142/Tissue Factor

Tissue factor, or CD142, is a cell surface receptor for coagulation factor VII that promotes formation of thrombin and fibrin during the process of vascular thrombosis, including but not limited to the processes of Th1 vascular inflammation. Increased tissue factor in people with hyperglycemia, hyperinsulinemia and dyslipidemia, all components of metabolic syndrome, is believed to contribute to this population's increased susceptibility to chronic inflammation and cardiovascular diseases, including atherogenesis and thrombosis (Breitenstein A et al. (2010) Tissue factor and cardiovascular disease. Circulation J 74:3-12; Diamant M et al. (2002) Elevated numbers of tissue-factor exposing microparticles correlate with components of the metabolic syndrome in uncomplicated type 2 diabetes mellitus. Circulation 106:2442-2447; Vaidyula V R et al. (2006) Effects of hyperglycemia and hyperinsulinemia on circ). Tissue factor inhibitors, including PPARα activators, have been proposed as a means to treat diseases driven by tissue factor (Marx et al. (2018) PPARα activators inhibit tissue factor expression and activity in human monocytes. Circulation 103:213-21; Steffel J et al. (2006) Tissue factor in cardiovascular diseases: Molecular mechanisms and clinical implications. Circulation 113:722-731).

In addition to increased risk of thrombosis and atherosclerosis, tissue factor expression appears to be a driver for other diseases associated with metabolic syndrome, including cancer, Alzheimer's disease, and fibrotic diseases (e.g., steatohepatitis, nonalcoholic steatohepatitis, systemic sclerosis, pulmonary fibrosis, and ideopathic pulmonary fibrosis). Tissue factor in tumors is a key driver of poor differentiation and poor prognosis in cancer due to its role in metastasis, tumor growth, and tumor angiogenesis (Kasthuri R S et al. (2009) Role of tissue factor in cancer. J Clin Oncol. 27:4834-4838). Tissue factor has been proposed as the driving link between cardiovascular disease and cancer, and reduction of tissue factor may improve the prognosis of cancer (Tesselaar et al. (2007) Microparticle-associated tissue factor activity: a ling between cancer and thrombosis? J Thromb Haemostasis 5:520-527). Tissue factor levels are raised in senile plaques in brains of patients with Alzheimer's disease compared to control brains, suggesting tissue factor as a contributor to Alzheimer's disease (McComb R D (1991) Tissue factor antigen in senile plaques of Alzheimer's disease. Am J Pathol 139:491-494). Tissue factor has also been implicated as a contributor to the development of idiopathic pulmonary fibrosis and systemic sclerosis due to higher levels of tissue factor expression in case patients compared to normal lung (Imokawa S et al. (1997) Tissue factor expression and fibrin deposition in the lungs of patients with idiopathic pulmonary fibrosis and systemic sclerosis. Am J Resp Crit Care 156).

MCP-1

Monocyte chemoattractant protein-1 is a chemoattractant cytokine (chemokine) that regulates the recruitment of monocytes and T cells into sites of inflammation, including but not limited to the processes of Th2 vascular inflammation, Th2 airway inflammation, and Th1 cutaneous inflammation. Increased MCP-1 is a contributor to metabolic syndrome, allergic asthma, autoimmune diseases, chronic inflammation, cardiovascular disease, dermatitis, hypertension, insulin resistance, inflammatory bowel disease, iron overload, fatty liver disease, pulmonary fibrosis/systemic sclerosis, psoriasis, neurodegenerative diseases (including Alzheimer's disease), and type 2 diabetes (Conductier G et al. (2010) The role of monocyte chemoattractant protein MCP1/CCL2 in neuroinflammatory diseases. J Neuroimmunol 224:93-100; Deshmane S L et al. (2009) Monocyte chemoattractant protein-1 (MCP-1): An overview. J Interferon Cytokine Res 29:313-326; Dongiovanni P et. al. (2011) Iron in the fatty liver and in the metabolic syndrome: A promising therapeutic target. J Hepatol 55:920-932; Hasegawa M et al. (1999) Augmented production of chemokines (monocyte chemotactic protein-1 (MCP-1), macrophage inflammatory protein-1α (MIP-1α) and MIP-1β) in patients with systemic sclerosis: MCP-1 and MIP-1α may be involved in the development of pulmonary fibrosis. Clin Exp Immunol 117:159-165; Itoh T et al. (2006) Increased plasma monocyte chemoattractant protein-1 level in idiopathic pulmonary arterial hypertension. Respirol 11:158-163; Kamei N et al. (2006) Overexpression of MCP-1 in adipose tissues causes macrophage recruitment and insulin resistance. J Biol Chem 281:26602-26614; Kanda H et al. (2006) MCP-1 contributes to macrophage infiltration into adipose tissue, insulin resistance, and hepatic steatosis in obesity. J Clin Invest 116:1494-1505; Nedosytko et al (2014) Chemokines and cytokines network in the pathogenesis of the inflammatory skin diseases: atopic dermatitis, psoriasis and skin mastocytosis. Postepy Dermatol Alergol 31:84-91; Niu and Kolattukudy (2009) Role of MCP-1 in cardiovascular disease: molecular mechanisms and clinical implications. Clin Sci 117:95-109; Sartipy P and Loskutoff D J (2003) Monocyte chemoattractant protein 1 in obesity and insulin resistance. PNAS 100:7265-7270; Valenti L et al. (2010) Serum hepcidin and macrophage iron correlate with MCP-1 release and vascular damage in patients with metabolic syndrome alterations. Arterio Thromb Vasc Biol 31:683-690). Iron overload in macrophages, which occurs as a component of metabolic syndrome, is correlated with MCP-1 and vascular damage among patients with metabolic syndrome (Valenti L et al. (2010) Serum hepcidin and macrophage iron correlate with MCP-1 release and vascular damage in patients with metabolic syndrome alterations. Arterio Thromb Vasc Biol 31:683-690). Agents that lower or inhibit MCP-1 can or have been proposed to treat MCP-1 driven conditions, including nonalcoholic steatohepatitis (Baeck C et al. (2012) Pharmacological inhibition of the chemokine CCL2 (MCP-1) diminishes liver macrophage infiltration and steatohepatitis in chronic hepatic injury. Gut 61:416-426; Berres M L et al. (2010) Chemokines as immune mediators of liver diseases related to the metabolic syndrome. Dig Dis 28:192-196; Deshmane S L et al. (2009) Monocyte chemoattractant protein-1 (MCP-1): An overview. J Interferon Cytokine Res 29:313-326; Lee et al. (2001) Anti-atherogenic effect of citrus flavonoids, naringin and naringenin, associated with hepatic ACAT and aortic VCAM-1 and MCP-1 in high cholesterol-fed rabbits. Biochem Biophy Res Comm 284: 681-688).

Eotaxin-3

Eotaxin-3 is a chemokine that mediates recruitment of eosinophils and basophils into sites of tissue inflammation and is a contributor to numerous diseases, including but not limited to Th2 vascular inflammation, Th2 airway inflammation, allergic conditions, such as asthma and atopic dermatitis, autoimmune diseases, such as Churg-Strauss syndrome, cardiovascular disease other inflammatory disorders (Pozer K et al. (2008) Eotaxin-3 is involved in Churg-Strauss syndrome—a serum marker closely correlating with disease activity. Rheumatology 47:804-808; Rankin et al. (2000) Eotaxin and eosinophil recruitment: implications for human disease. Mol Med Today 6:20-27). Compared to control populations, obese people with metabolic syndrome are more likely to have eosinophilia and associated impaired lung function (Van Huisstede et al. (2012) Systemic inflammation and lung function impairment in morbidly obese subjects with the metabolic syndrome. J Obesity 2013: 131349). Obese people and obese mice have increased eotaxin levels, which is secreted from adipose tissue, providing an explanation for the link between obesity, eosinophilia, and asthma (Vasudevan A R et al. (2006) Eotaxin and obesity. J Clin Endocrinol Metab 91:256-261). Agents that reduce eotaxin have been proposed as promising therapeutics for a wide variety of diseases associated with increased eotaxin, including those associated with metabolic syndrome (Rankin et al. (2000) Eotaxin and eosinophil recruitment: implications for human disease. Mol Med Today 6:20-27).

CD40

CD40 is a cell surface adhesion receptor and costimulatory receptor for T cell activation that is expressed on antigen presenting cells, endothelial cells, smooth muscle cells, fibroblasts, and epithelial cells and is involved in processes including but not limited to monocyte-driven Th1 vascular inflammation and T cell-driven Th1 vascular inflammation. Compared to controls, people with metabolic syndrome have elevated circulating soluble CD40 ligand, which was independently associated with systemic inflammation and coronary disease (Lee W L et al. (2006) The presence of metabolic syndrome is independently associated with elevated serum CD40 ligand and disease severity in patients with symptomatic coronary artery disease. Metab 55:1029-1034). Elevated CD40 has been associated with Alzheimer's disease, hemolytic anemia, autoimmune diseases (including type 1 diabetes, autoimmune thyroiditis, inflammatory bowel disease, psoriasis, multiple sclerosis, rheumatoid arthritis, and systemic lupus erythematosus), fatty liver disease and nonalcoholic steatohepatitis, hypertension, and systemic sclerosis (Allanore Y et al. (2005) Increased plasma soluble CD40 ligand concentrations in systemic sclerosis and association with pulmonary arterial hypertension and digital ulcers. Ann Rheum Dis 64:481-483; Azzam et al. (2013) The expression and concentration of CD40 ligand in normal pregnancy, preeclampsia, and hemolytic anemia, elevated liver enzymes, and low platelet count (HELLP) syndrome. Blood Coag Fibrinol 24:71-75; Calingasan N Y et al. (2002) Identification of CD40 ligand in Alzheimer's disease and in animal models of Alzheimer's disease and brain injury. 23:31-39; Nanji S A et al. (2006) Costimulation blockade of both inducible costimulatory and CD40 ligand induces dominant tolerance to islet allografts and prevents spontaneous autoimmune diabetes in the NOD mouse. Diabetes 55:27-33; Peters A L et al. (2009) CD40 and autoimmunity: The dark side of a great activator. Sem Immunol 21:293-300; Sutti et al. (2014) Adaptive immune responses triggered by oxidative stress contribute to hepatic inflammation in NASH. Hepatol 59:886-897). Statins, PPAR agonists, and other cardiometabolic therapeutics reduce CD40 ligand levels in vivo and in vitro, and blocking CD40-TRAF6 signaling helps to treat insulin resistance (Chatzigeorgiou A et al. (2014) Blocking CD40-TRAF signaling is a therapeutic target in obesity-associated insulin resistance. PNAS 111:2686-2691; Vishnevestsky et al. (2004) CD40 ligand: a novel target in the fight against cardiovascular disease. Ann Pharmacol 38:1500-1508). Inhibition of CD40 by statins results in a greater anti-atherosclerotic effect, blockade of CD40 ligand prevents autoimmune diabetes in mice, and decreases in CD40 by a natural compound was associated with anti-asthmatic effects (Chen J et al. (2004) Inhibitory effect of candesartan and rosuvastatin on CD40 and MMPs expression in Apo-E knockout mice: novel insights into the role of RAS and dyslipidemia in atherogenesis. J Cardiovasc Pharmacol 44:446-452; Nanji S A et al. (2006) Costimulation blockade of both inducible costimulatory and CD40 ligand induces dominant tolerance to islet allografts and prevents spontaneous autoimmune diabetes in the NOD mouse. Diabetes 55:27-33; Zhang et al. (2015) Anti-asthmatic effects of oxymatrine in a mouse model of allergic asthma through regulating CD40 signaling. Chinese J Nat Med 13:368-374). As such, inhibitors or blockers of CD40 ligand have been identified as important therapeutics to treat CD40-associated diseases.

T and B Cell Proliferation

Proliferation of T cells is a critical event driving both adaptive immunity as well as many autoimmune diseases, including but not limited to rheumatoid arthritis, psoriasis, multiple sclerosis, inflammatory bowel disease. Proliferation of B cells is a critical event driving both adaptive immunity (antibody production) as well as many autoimmune diseases where B cells are key disease players, such as systemic lupus erythematous and rheumatoid arthritis. Inhibition of T or B cell proliferation is considered an immunosuppressive effect that may help treat autoimmune diseases.

VCAM-1 and ICAM-1

Vascular cell adhesion molecule 1 (VCAM-1) is a cell adhesion molecule that mediates adhesion of monocytes and T cells to endothelial cells. Intracellular cell adhesion molecule 1 (ICAM-1) is a cell adhesion molecule that mediates leukocyte-endothelial cell adhesion and leukocyte recruitment. These cell adhesion molecules are involved in processes including but not limited to Th2 airway inflammation and Th1 cutaneous inflammation. Elevated VCAM-1 and ICAM-1 are associated with Alzheimer's disease, cancer, chronic inflammatory diseases (including but not limited to rheumatoid arthritis, asthma, psoriasis, transplant-rejection, and allergies), allergies, asthma, diabetes, fatty liver disease, insulin resistance, metabolic syndrome (Banks R E et al. (1993) Circulating intercellular adhesion molecule-1 (ICAM-1), E-selectin and vascular cell adhesion molecule-1 (VCAM-1) in human malignancies. Br J Cancer 68:122-124; Bonora E et al. (2003) Metabolic syndrome: epidemiology and more extensive phenotypic description. Cross-sectional data from the Bruneck Study. Int J Obesity 27:1283-1289; Hwang S J et al. (2018) Circulating adhesion molecules VCAM-1, ICAM-1, and E-selectin in carotid atherosclerosis and incident coronary heart disease cases: The Atherosclerosis Risk in Communities (ARIC) Study. Circulation 96:4219-422; Leinonen E et al. (2003) Insulin resistance and adiposity correlate with acute-phase reaction and soluble cell adhesion molecules in type 2 diabetes. Atherosclerosis 166:387-394; Sookoian et al. (2010) Circulating levels and hepatic expression of molecular mediators of atherosclerosis in nonalcoholic fatty liver disease. Atherosclerosis 209:585-591). Elevated ICAM-1 predicts the risk of coronary heart disease (Hwang S J et al. (2018) Circulating adhesion molecules VCAM-1, ICAM-1, and E-selectin in carotid atherosclerosis and incident coronary heart disease cases: The Atherosclerosis Risk in Communities (ARIC) Study. Circulation 96:4219-422). Inhibition of ICAM-1 and VCAM-1 by small molecules has been proposed as a therapeutic approach to inflammation and autoimmune diseases (Yusuf-Makagiansar H et al. (2002) Inhibition of LFA-1/ICAM-1 and VLA-4/VCAM-1 as a therapeutic approach to inflammation and autoimmune diseases. Med Res Rev 22:146-167).

Interleukin-8 (IL-8)

IL-8 is a chemokine that mediates neutrophil recruitment into acute inflammatory sites during, but not limited to, Th2 airway inflammation. Elevated IL-8 is associated with multiple components of metabolic syndrome, including obesity, body mass index, and insulin resistance (Kim C S et al. (2006) Circulating levels of MCP-1 and IL-8 are elevated in human obese subjects and associated with obesity-related parameters. Int J Obesity 30:1347-1355). Elevated IL-8 has also been associated with or identified as contributors to Alzheimer's disease, anemia, autoimmune diseases (including but not limited to thyroid autoimmunity and multiple sclerosis), cardiovascular disease, dermatitis, hypercholesterolemia, lung diseases (including but not limited to asthma, chronic obstructive pulmonary disease, and idiopathic pulmonary fibrosis), and psoriasis (Akeno N et al. (2008) HCV E2 protein binds directly to thyroid cells and induces IL-8 production: a new mechanism for HCV induced thyroid autoimmunity. J Autoimm 31:339-344; Alsadany M A et al. (2013) Histone deacetylases enzyme, copper, and IL-8 levels in patients with Alzheimer's disease. Am J Alzheim Dis Demen 28:54-61; Arikan O et al. (2005) Serum levels of TNF-α, IFN-γ, IL-6, IL-8, IL-12, IL-17, and IL-18 in patients with active psoriasis and correlation with disease severity. Med Inflamm 2005:273-279; Boekholdt S M et al. (2004) IL-8 plasma concentrations and the risk of future coronary artery disease in apparently healthy men and women. 24:1503-1508; Carre P C et al. (1991) Increased expression of the interleukin-8 gene by alveolar macrophages in idiopathic pulmonary fibrosis. A potential mechanism for the recruitment and activation of neutrophils in lung fibrosis. J Clin Invest 88:1802-1810; Gu Y et al. (2008) Interleukin (IL)-17 promotes macrophages to produce IL-6, IL-6 and tumour necrosis factor-α in aplastic anemia. Br J Haematol 142:109-114; Hatano Y et al. (1999) Increased levels in vivo of mRNAs for IL-8 and macrophage protein-1α, but not RANTES mRNA in peripheral blood mononuclear cells of patients with atopic dermatitis. Clin Exp Immunol 117:237-243; Ishizu T et al. (2005) Intrathecal activation of the IL-17/IL-8 axis in opticospinal multiple sclerosis. Brain 128:988-1002; Keatings V M et al. (1996) Differences in interleukin-8 and tumor necrosis factor-alpha in induced sputum from patients with chronic obstructive pulmonary disease or asthma. Am J Resp Crit Care Med 153: https://doi.org/10.1164/ajrccm.153.2.8564092; Ordonez C L et al. (2000) Increased neutrophil numbers and IL-8 levels in airway secretions in acute severe asthma: Clinical and biological significance. Am J Resp Crit Care Med 161: https://doi.org/10.1164/ajrccm.161.4.9812061; Porreca E et al. (1999) Peripheral blood mononuclear cell production of interleukin-8 and IL-8 dependent neutrophil function in hypercholesterolemic patients. Atherosclerosis 146:345-350) Exercise reduces plasma levels of IL-8 in people with metabolic syndrome, supporting interventions that reduce IL-8 to help treat inflammation associated with metabolic syndrome (Trooseid M et al. (2004) Exercise reduces plasma levels of the chemokines MCP-1 and IL-8 in subjects with the metabolic syndrome. Eur Heart J 25:349-355). IL-8 appears to be a significant regulatory factor for cancer, and inhibiting IL-8 has been proposed as a therapeutic approach directly targeting the tumor environment (Waugh D J J and Wilson C (2008) The interleukin-8 pathway in cancer. Mol Path 14:6735-6741).

Interleukin 1α (IL-1α)

IL-1α is a secreted proinflammatory cytokine involved in endothelial cell activation and neutrophil recruitment including but not limited to during Th2 airway inflammation and systemic, chronic inflammation. During anemia of inflammation, activated T cells and monocytes induce production of cytokines, including IL-1α, which induce ferritin production and stimulate iron storage in macrophages (Weiss and Goodnough (2005) Anemia of chronic disease. New Engl J Med 352:1011-1023). This process decreases circulating iron, resulting in impaired erythrocytes. IL-1α also inhibits erythroid progenitor cells, creating a one-two hit on erythrocytes that results in anemia associated with chronic diseases, including metabolic syndrome. As such, agents that inhibit or reduce IL-1α may aid in the treatment of anemia of inflammation/chronic disease.

Keratin 8/18

Keratin 8 and keratin 18 are intermediate filament heterodimers of fibrous structural proteins involved in apoptosis, epithelial cell death, chronic obstructive pulmonary disease, and lung inflammation including, but not limited to Th2 airway inflammation. Keratin 8/18 levels rise when cell membranes have lost their integrity and are compromised (Schutte B et al. (2004) Keratin 8/18 breakdown and reorganization during apoptosis. Exp Cell Res 297:11-26). Elevated keratin 8/18 is associated with nonalcoholic steatohepatitis (NASH) among people with nonalcoholic fatty liver disease and metabolic syndrome (Anty R et al. (2010) A new composite model including metabolic syndrome, alanine aminotransferase and cytokeratin-18 for the diagnosis of non-alcoholic steatohepatitis in morbidly obese patients. Aliment Pharmacol Ther 32:1315-1322). Since keratin 8/18 is a biomarker of cell death and associated severity of diseases, agents that reduce keratin 8/18 are likely conferring a cell-protective effect.

MMP-1, MMP-3, and MMP-9

Matrix metalloproteinase 1 (MMP-1) is an interstitial collagenase that degrades collagens I, II and III and is involved in the process of tissue remodeling. Matrix metalloproteinase 3 (MMP-3) is an enzyme that can activate other MMPs (MMP-1, MMP-7, and MMP-9) and degrade collagens, proteoglycans, fibronectin, laminin and elastin. Matrix metalloproteinase 9 (MMP-9) is a gelatinase B that degrades collagen IV and gelatin and is involved in airway matrix remodeling. MMP-1 and MMP-3 are involved in processes including but not limited to Th2 airway inflammation. MMP-9 is involved in processes including but not limited to Th2 airway inflammation, Th1 lung inflammation, and Th1 cutaneous inflammation. Elevated MMP-9 is associated with Alzheimer's disease and other neuropathologies, inflammation, iron overload in tissues, pulmonary pathologies (including but not limited to asthma and chronic obstructive pulmonary disease), and Type 1 diabetes (Cataldo D et al. (2000) MMP-2- and MMP-9-linked gelatinolytic activity in the sputum from patients with asthma and chronic obstructive pulmonary disease. Int Arch Allergy Immunol 123:259-267; Chakrabarti S and Patel K D (2005) Matrix metalloproteinase-2 (MMP-2) and MMP-9 in pulmonary pathology. J Exper Lung Res 31: https://doi.org/10.1080/019021490944232; Halade G V et al. (2013) Matrix metalloproteinase (MMP)-9: A proximal biomarker for cardiac remodeling and a distal biomarker for inflammation. Pharmacol Therap 139:32-40; Mairuae N et al. (2011) Increased cellular iron levels affect matrix metalloproteinase expression and phagocytosis in activated microglia. Neurosci Lett 500:36-40; Maxwell P R et al. (2009) Peripheral blood level alterations of TIMP-1, MMP-2 and MMP-9 in patients with Type 1 diabetes. Diabet Med 18:777-780). Elevated MMP-1, MMP-3, and MMP-9 is associated with liver disease severity (Okamoto K et al. (2005) Association of functional gene polymorphisms of matrix metalloproteinase (MMP)-1, MMP-3 and MMP-9 with the progression of chronic liver disease. J Gastroenterol Hepatol 20:1102-1108). Elevated MMP-1 and MMP-9 are associated with the presence and severity of cardiovascular disease, including coronary artery disease and hypertension (Tanindi A et al. (2011) Relationship between MMP-1, MMP-9, TIMP-1, IL-6 and risk factors, clinical presentation, extent and severity of atherosclerotic coronary artery disease. Open Cardiovasc Med J 5:110-116; Yasmin et al. (2004) Matrix metalloproteinase-9 (MMP-9), MMP-2, and serum elastase activity are associated with systolic hypertension and arterial stiffness. Arterioscler Thromb Vasc Biol 25:372-378). Statins reduction of MMP-3 and MMP-9 have been proposed as a potential pharmacotherapy for abdominal aortic aneurysms, and MMP inhibitors may provide therapeutic benefits for other MMP-associated conditions, including autoimmune diseases (Goetzl E J et al. (1996) Matrix metalloproteinases in immunity. J Immunol 156:1-4; Wilson W R W et al. (2005) HMG-CoA reductase inhibitors (statins) decrease MMP-3 and MMP-9 concentrations in abdominal aortic aneurysms. Eur J Vasc Endovasc Surg 30:259-262).

Plasminogen Activator Inhibitor-1 (PAI-1)

PAI-1 is a serine proteinase inhibitor and inhibitor of tissue plasminogen activator and urokinase and is involved in tissue remodeling and fibrosis during processes including but not limited to Th2 airway inflammation, Th1 lung inflammation, and Th1 cutaneous inflammation. Elevated PAI-1 is considered a component of metabolic syndrome, and it is either associated with or a known contributor to asthma, cancer, cardiovascular disease, diabetes, hypertension, inflammation, insulin resistance, NASH, obesity, pulmonary fibrosis, and psoriasis (Adly A A M et al. (2014) Plasminogen activator inhibitor-1 (PAI-1) in children and adolescents with Type 1 diabetes mellitus: relation to diabetic microvascular complications and carotid intima media thickness. J Diab Complication 28:340-347; Alessi M C and Juhan-Vague I (2006) PAI-1 and the metabolic syndrome. Arterioscl Thromb Vasc Biol 26:2200-2207; Cho S H et al. (2004) Plasminogen activator inhibitor-1 in the pathogenesis of asthma. Experim Biol Med 229:138-146; Festa A et al. (2002) Elevated levels of acute-phase proteins and plasminogen activator inhibitor-1 predict the development of type 2 diabetes: The Insulin Resistance Atherosclerosis Study. Diabetes 51:1131-1137; Kubala M H et al. (2017) Abstract 3061: Tumor-derived PAI-1 promotes macrophage M2 polarization by stimulating an autocrine IL-6/STAT3 pathway. Proceedings: AACR Annual Meeting; Apr. 1-5, 2017, Washington, DC DOI: 10.1158/1538-7445.AM2017-3061; Landin K et al. (1990) Elevated fibrinogen and plasminogen activation inhibitor (PAI-1) in hypertension are related to metabolic risk factors for cardiovascular disease. J Int Med 227:273-278; Mertens I et al. (2006) Among inflammation and coagulation markers, PAI-1 is a true component of the metabolic syndrome. Int J Obesity 30:1308-1314; Nielsen H J et al. (2002) Elevated plasma levels of vascular endothelial growth facto and plasminogen activator inhibitor-1 decrease during improvement of psoriasis. Inflamm Res 51:563-567; Osterholzer J J et al. (2012) PAI-1 promotes the accumulation of exudate macrophages and worsens pulmonary fibrosis following type II alveolar epithelial cell injury. J Pathol 228:170-180; Sookoian et al. (2010) Circulating levels and hepatic expression of molecular mediators of atherosclerosis in nonalcoholic fatty liver disease. Atherosclerosis 209:585-591; Tofler et al. (2016) Plasminogen activator inhibitor and the risk of cardiovascular disease: The Framingham Heart Study. Thromb Res 140:30-35). Reduction of PAI-1 has been proposed as a promising means to attenuate liver injury, cardiovascular risks, and Alzheimer's disease (Jin R et al. (2017) Role of PAI-1 in pediatric obesity and nonalcoholic fatty liver disease. Curr Cardiovasc Risk Reports 11:11; Hasina A et al. (2018) A small molecule inhibitor of plasminogen activator inhibitor-1 reduces brain amyloid-β load and improves memory in an animal model of Alzheimer's disease. 64:447-457). Agents that lower PAI-1 may be promising therapeutics for PAI-1 associated diseases.

CXCL10/IP-10 and CXCL9/MIG

Interferon-gamma-inducible protein 10 (IP-10), or CXCL10, is a proinflammatory chemokine that mediates T cell, monocyte and dendritic cell chemotaxis. Monokine induced by gamma interferon (MIG), or CXCL9, is a chemokine that mediates T cell recruitment. Both chemokines are involved in, among other processes, in Th1 inflammation, and both activate the CXCR3 receptor. Elevated CXCL10 and/or CXCL9 are associated with asthma, autoimmune diseases (including but not limited to rheumatoid arthritis, systemic lupus erythematosus, Sjogen syndrome, systemic sclerosis, idiopathic inflammatory myopathy), cancer, chronic inflammation, graft-versus-host disease, hypertension, idiopathic pulmonary fibrosis, immune dysfunction, iron overload and accumulation, obesity, metabolic syndrome, neurodegenerative diseases (including but not limited to Alzheimer's disease and Parkinson's disease), nonalcoholic fatty liver disease, psoriasis, steatohepatitis, systemic sclerosis and type 2 diabetes (Antonelli A et al. (2012) High serum levels of CXC (CXCL10) and CC (CCL2) chemokines in untreated essential hypertension. Int J Immnopathol Pharmacol 25:387-395; Brightling C E et al. (2005) The CXCL10/CXCR3 axis mediates human lung mast cell migration to asthmatic airway smooth muscle. 171:1103-1108; Kitko et al. (2013) Plasma CXCL9 elevations correlate with chronic GVHD diagnosis. Blood 5:786-793; Lee E Y et al. (2009) CXCL and autoimmune diseases. Autoimmun Rev 8:379-383; Lee J et al. (2018) Brochoalveolar lavage (BAL) cells in idiopathic pulmonary fibrosis express a complex pro-inflammatory, pro-repair, angiongenic activation pattern, likely associated with macrophage iron accumulation. PLOS ONE 13:e0197794; Liu M et al. (2011) The emerging role of CXCL10 in cancer. Onc Letters 2:583-589; Van den Borne et al. (2014) The multifaceted functions of CXCL10 in cardiovascular disease. BioMed Res Int 2014:893106; Xie M et al. (2015) IL-27 and type 2 immunity in asthmatic patients: association with severity, CXCL9, and signal tranducer and activator of transcription signaling. J Allerg Clin Immunol 135:386-394; Zhang X et al. (2014) CXCL10 plays a key role as an inflammatory mediator and a non-invasive biomarker of non-alcoholic steatohepatitis. J Hepatol 61:1365-1375). CXCL10 and/or CXCL9 have been identified as a promising therapeutic targets for diseases including asthma, autoimmune diseases, cancer, psoriasis, and nonalcoholic steatohepatitis (Berres M L et al. (2010) Chemokines as immune mediators of liver diseases related to the metabolic syndrome. Dig Dis 28:192-196; Brightling C E et al. (2005) The CXCL10/CXCR3 axis mediates human lung mast cell migration to asthmatic airway smooth muscle. 171:1103-1108; Ferrari S M et al. (2015) CXCL10 in psoriasis. Adv Med Sci 60:349-354; Lee E Y et al. (2009) CXCL and autoimmune diseases. Autoimmun Rev 8:379-383; Liu M et. al. (2011) The emerging role of CXCL10 in cancer. Onc Letters 2:583-589).

In some embodiments provided herein, the subject to be treated may be an animal, for example, a dolphin, mouse, or a domestic animal such as a dog or cat; however, it is generally contemplated that the methods, uses, and compositions of the embodiments are applied to humans. Like human subjects, animal subjects including bottlenose dolphin (*Tursiops truncatus*) subjects can also be susceptible to metabolic syndrome, including high insulin, glucose, triglycerides, fatty liver disease, and iron overload. Iron overload in dolphins, involving excessive iron deposition primarily in the liver's Kupffer cells, can be progressive with age and can be associated with elevated insulin, lipids, and liver enzymes. This disease is associated with neither mutations in the HFE gene nor increases in studied acute phase proteins. Similar to humans, iron overload in dolphins is treated with phlebotomy, and repeated treatments are needed throughout life due to returning elevations of serum ferritin. The underlying causes of iron overload and hyperferritinemia in dolphins are unknown.

In some embodiments, the condition treated is metabolic syndrome.

In some embodiments, the condition treated is metabolic syndrome as indicated by the markers provided herein.

In some embodiments, the methods provided herein modulate markers of metabolic syndrome when the markers provide a clinical indication.

In some embodiments, the methods provided herein alleviate symptoms of metabolic syndrome.

In some embodiments, the methods provided herein reduce risk of metabolic syndrome.

In some embodiments, the condition treated is hyperferritinemia.

In some embodiments, the methods provided herein increase serum levels of certain fatty acids.

In some embodiments, the methods provided herein improve insulin sensitivity.

In some embodiments, the compositions and methods provided herein modulate a marker of metabolic syndrome. In certain embodiments, the marker is serum or red blood cell membrane odd chain fatty acid percentage, serum or red blood cell membrane percentage of a compound of Formula (I), or a salt or metabolite thereof, serum concentration of an odd chain fatty acid, serum concentration of a compound of Formula (I), or a salt or metabolite thereof, serum total odd chain fatty acid, serum ferritin, serum iron, transferritin saturation, serum glucose (for example fasting glucose), serum triglycerides, blood pressure, HDL cholesterol, microalbuminuria (i.e., elevated albumin excretion in the urine), CRP (C reactive protein), IL-6 and TNFα (and other cytokines associated with insulin resistance), c-Jun N-terminal kinase (JNK), ATM (Ataxia Telangiectasia Mutated) or monocyte-chemoattractant protein-1. In some embodiments, the odd chain fatty acid, or the compound of Formula (I), or salt or metabolite thereof, is measured as a constituent of glycolipids. In further embodiments, the odd chain fatty acid, or the compound of Formula (I), or salt or metabolite thereof, is measured as a constituent of phospholipids.

In some embodiments, the methods provided herein include the step of measuring the concentration of a marker of metabolic syndrome. One of skill in the art will be able to perform suitable methods for such measurements, including but not limited to those described herein.

Provided herein are methods for treating including the step of administering a dose of a compound of Formula (I), or pharmaceutically acceptable salt thereof, at a predetermined interval, or at an interval left to the discretion of the subject.

In some embodiments, oxidative stress can be measured as a concentration of TBARS. In further embodiments, oxidative stress can be measured as total antioxidant activity. In yet further embodiments, oxidative stress can be measured as a ratio of an oxidized species to an analogous unoxidized species, for example, by a ratio of uric acid to allantoin, ascorbic acid to dehydroascorbic acid, or glutathione (GSH) to GSSG. Other direct methods of measuring ROSs in a subject are known. See Fibach E, et al., The role of oxidative stress in hemolytic anemia. Curr. Mol. Med. (2008), Vol. 8, pp. 609-619. In some embodiments, a composition or method provided herein modulates a marker of oxidative stress, for example, a lipid peroxidation product such as, for example, 4-hydroxynonenal (4-HNE), 4-oxy-2-nonenal (ONE) or malondialdehyde (MDA), 8-iso-prostaglandin $F_2\alpha$ and 8-epi-prostaglandin $F_2\alpha$ (isoprostane), nitrotyrosine, oxLDL or a ratio of ox-LDL to LDL, MPO, erythrocyte GPX1, 8-oxodG, leukocyte peroxide, glycated hemoglobin (HbA1c), 11-dehydro-thromboxane (TXM), glutathione disulfide (GSSG), a thiobarbituric acid reactive substance (TBARS) such as MDA, or hematocrit. In variations of these embodiments, oxidative stress can be reduced by a substantial amount, where substantial indicates reduction of morbidity of a disease condition provided herein that is statistically significant in a population.

A compound of Formula (I), or pharmaceutically acceptable salt thereof, may be treated as, for example compared or measured, with respect to naturally occurring fatty acid in a tissue or tissues of the subject. A compound of Formula (I), or pharmaceutically acceptable salt thereof, may be incorporated into the body as if it were a naturally occurring dietary fatty acid. A compound of Formula (I), or pharmaceutically acceptable salt thereof, may undergo one or more metabolic processes in the body, and the concentration of the metabolite(s) may be indicative of the condition of the subject.

In some embodiments, the compounds and methods provided herein may provide a threshold serum or red blood cell membrane percentage of a compound of Formula (I), or a salt or metabolite thereof, relative to all serum or red blood cell membrane fatty acids, respectively. For example, the threshold value may be a value of about 0.05% or lower to 90% or higher, e.g., a value of at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.1%, at least about 1.2%, at least about 1.3%, at least about 1.4%, at least about 1.5%, at least about 1.6%, at least about 1.7%, at least about 1.8%, at least about 1.9%, at least about 2.1%, at least about 2.2%, at least about 2.3%, at least about 2.4%, at least about 2.5%, at least about 2.6%, at least about 2.7%, at least about 2.8%, at least about 2.9%, at least about 3.0%, at least about 3.5%, at least about 4.0%, at least about 4.5%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or more than 90%.

In some embodiments, the compounds and methods provided herein may provide an increase above a baseline value (e.g., pretreatment value in a patient being treated, or general value observed in a particular patient population) in a serum concentration of a compound of Formula (I), or a salt or metabolite thereof, or red blood cell membrane concentration of a compound of Formula (I), or a salt or metabolite thereof. For example, a serum compound of Formula (I), or salt or metabolite thereof, or red blood cell membrane concentration of a compound of Formula (I), or a salt or metabolite thereof, may be increased by at least about 1 μg/ml, at least about 2 μg/ml, at least about 3 μg/ml, at least about 4 μg/ml, at least about 5 μg/ml, at least about 6 μg/ml, at least about 7 μg/ml, at least about 8 μg/ml, at least about 9 μg/ml, at least about 10 μg/ml, at least about 15 μg/ml, at least about 20 μg/ml, at least about 25 μg/ml, at least about 30 μg/ml, at least about 35 μg/ml, at least about 40 μg/ml, at least about 45 μg/ml, at least about 50 μg/ml, or more than 50 μg/ml. In some embodiments, the serum concentration of a compound of Formula (I), or a salt or metabolite thereof, or red blood cell membrane concentration of a compound of Formula (I), or a salt or metabolite thereof, may increase above a baseline value (e.g., pretreatment value in a patient being treated, or general value observed in a particular patient population) by at least about $0.01 \times 10^{-4}$ M, at least about $0.05 \times 10^{-4}$ M, at least about $0.1 \times 10^{-4}$ M, at least about $0.2 \times 10^{-4}$ M, at least about $0.3 \times 10^{-4}$ M, at least about $0.4 \times 10^{-4}$ M, at least about $0.5 \times 10^{-4}$ M, at least about $0.6 \times 10^{-4}$ M, at least about $0.7 \times 10^{-4}$ M, at least about $0.8 \times 10^{-4}$ M, at least about $0.9 \times 10^{-4}$ M, at least about $1 \times 10^{-4}$ M, at least about $2 \times 10^{-4}$ M, or at least about $3 \times 10^{-4}$ M.

In some embodiments, the compounds and methods provided herein may provide an increase in serum total odd chain fatty acids, or red blood cell membrane total odd chain fatty acids. For example, serum total odd chain fatty acids, or red blood cell membrane total odd chain fatty acids, may be increased above a baseline value (e.g., pretreatment value in a patient being treated, or general value observed in a particular patient population) by at least about 5 μg/ml, at least about 6 μg/ml, at least about 7 μg/ml, at least about 8 μg/ml, at least about 9 μg/ml, at least about 10 μg/ml, at least about 15 μg/ml, at least about 20 μg/ml, at least about 25 μg/ml, at least about 30 μg/ml, at least about 35 μg/ml, at least about 40 μg/ml, at least about 45 μg/ml, at least about 50 μg/ml, at least about 60 μg/ml, at least about 70 μg/ml, at least about 80 μg/ml, at least about 90 μg/ml, at least about 100 μg/ml, at least about 150 μg/ml, at least about 200 μg/ml, at least about 250 μg/ml, at least about 300 μg/ml, at least about 350 μg/ml, at least about 400 μg/ml, at least about 450 μg/ml, at least about 500 μg/ml, or more than 500 μg/ml.

In some embodiments, the compounds and methods provided herein may provide an increase above a baseline value (e.g., pretreatment value in a patient being treated, or general value observed in a particular patient population) in a serum or red blood cell membrane odd chain fatty acids relative to all serum or red blood cell membrane fatty acids, respectively. For example, a serum or red blood cell membrane concentration of a compound of Formula (I), or a salt or metabolite thereof, may be increased above a baseline value (e.g., pretreatment value in a patient being treated, or general value observed in a particular patient population) by at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.1%, at least about 1.2%, at least about 1.3%, at least about 1.4%, at least about 1.5%, at least about 1.6%, at least about 1.7%, at least about 1.8%, at least about 1.9%, at least about 2%, at least about 2.1%, at least about 2.2%, at least about 2.3%, at least about 2.4%, at least about 2.5%, at least about 2.6%, at least about 2.7%, at least about 2.8%, at least about 2.9%, at least about 3%, at least about 3.5%, at least about 4%, at least about 4.5%, at least about 5%, or more than 5%.

In some embodiments, the compounds and methods provided herein may provide a reduction in serum insulin. For example, serum insulin may be reduced below a baseline value (e.g., pretreatment value in a patient being treated, or general value observed in a particular patient population) by at least about 0.1 μIU/ml, at least about 0.2 μIU/ml, at least about 0.3 μIU/ml, at least about 0.4 μIU/ml, at least about 0.5 μIU/ml, at least about 0.6 μIU/ml, at least about 0.7 μIU/ml, at least about 0.8 μIU/ml, at least about 0.9 μIU/ml, at least about 1.0 μIU/ml, at least about 1.1 μIU/ml, at least about 1.2 μIU/ml, at least about 1.3 μIU/ml, at least about 1.4 μIU/ml, at least about 1.5 μIU/ml, at least about 2 μIU/ml, at least about 2.5 μIU/ml, at least about 3.0 μIU/ml, at least about 3.5 μIU/ml, at least about 4 μIU/ml, at least about 5 μIU/ml, at least about 6 μIU/ml, at least about 7 μIU/ml, at least about 8 μIU/ml, at least about 9 μIU/ml, at least about 10 μIU/ml, at least about 11 μIU/ml, at least about 12 μIU/ml, at least about 13 μIU/ml, at least about 14 μIU/ml, at least about 15 μIU/ml, at least about 16 μIU/ml, at least about 17 μIU/ml, at least about 18 μIU/ml, at least about 19 μIU/ml, at least about 20 μIU/ml, at least about 25 μIU/ml, at least about 30 μIU/ml, or more than 30 μIU/ml.

In some embodiments, the compounds and methods provided herein may provide a reduction in serum triglycerides. For example, serum triglycerides may be reduced below a baseline value (e.g., pretreatment value in a patient being treated, or general value observed in a particular patient population) by at least about 1 mg/dl, at least about 3 mg/dl, at least about 4 mg/dl, at least about 5 mg/dl, at least about 10 mg/dl, at least about 15 mg/dl, at least about 20 mg/dl, at least about 25 mg/dl, at least about 30 mg/dl, at least about 35 mg/dl, at least about 40 mg/dl, at least about 45 mg/dl, at least about 50 mg/dl, at least about 60 mg/dl, at least about 70 mg/dl, at least about 80 mg/dl, at least about 90 mg/dl, at least about 100 mg/dl, at least about 110 mg/dl, at least about 120 mg/dl, at least about 130 mg/dl, at least about 140 mg/dl, at least about 150 mg/dl, at least about 200 mg/dl, at least about 250 mg/dl, at least about 300 mg/dl, or more than 300 mg/dl.

In some embodiments, the compounds and methods provided herein may provide a reduction in serum ferritin. For example, serum ferritin may be reduced below a baseline value (e.g., pretreatment value in a patient being treated, or general value observed in a particular patient population) by at least about 10 ng/ml, at least about 100 ng/ml, at least about 200 ng/ml, at least about 300 ng/ml, at least about 400 ng/ml, at least about 500 ng/ml, at least about 600 ng/ml, at least about 700 ng/ml, at least about 800 ng/ml, at least about 900 ng/ml, at least about 1000 ng/ml, at least about 1100 ng/ml, at least about 1200 ng/ml, at least about 1300 ng/ml, at least about 1400 ng/ml, at least about 1500 ng/ml, at least about 2000 ng/ml, at least about 2500 ng/ml, at least about 3000 ng/ml, at least about 3500 ng/ml, at least about 4000 ng/ml, at least about 4500 ng/ml, at least about 5000 ng/ml, at least about 6000 ng/ml, at least about 7000 ng/ml, at least about 8000 ng/ml, at least about 9000 ng/ml, at least about 10000 ng/ml, or more than 10000 ng/ml.

In some embodiments, the compounds and methods provided herein may provide a reduction in serum iron. For example, serum iron may be reduced below a baseline value (e.g., pretreatment value in a patient being treated, or general value observed in a particular patient population) by at least about 1 µg/dl, at least about 5 µg/dl, at least about 10 µg/dl, at least about 15 µg/dl, at least about 20 µg/dl, at least about 25 µg/dl, at least about 30 µg/dl, at least about 35 µg/dl, at least about 40 µg/dl, at least about 45 µg/dl, at least about 50 µg/dl, at least about 60 µg/dl, at least about 70 µg/dl, at least about 80 µg/dl, at least about 90 µg/dl, at least about 100 µg/dl, or more than 100 µg/dl.

In some embodiments, the compounds and methods provided herein may provide a reduction in transferritin saturation. For example, transferritin saturation may be reduced below a baseline value (e.g., pretreatment value in a patient being treated, or general value observed in a particular patient population) by at least about 5%, 10%, 15%, 20%, 25%, 30%, 35%, 40%, 50%, or more than 50%.

In some embodiments, the compounds and methods provided herein may provide a reduction in LDL-C. For example, LDL-C may be reduced below a baseline value (e.g., pretreatment value in a patient being treated, or general value observed in a particular patient population) by at least about 5 mg/dL, at least about 10 mg/dL, at least about 15 mg/dL, at least about 20 mg/dL, at least about 25 mg/dL, at least about 30 mg/dL, at least about 35 mg/dL, at least about 40 mg/dL, at least about 50 mg/dL, at least about 60 mg/dL, at least about 70 mg/dL, at least about 80 mg/dL, or more than 80 mg/dL.

In some embodiments, a composition or method provided herein may provide a reduction in 4-HNE levels. For example, a 4-HNE level may be reduced below a baseline value (e.g., pretreatment value in a patient being treated, or general value observed in a particular patient population) by at least about 0.1 µg/µl, at least about 0.5 µg/µl, at least about 1 µg/µl, at least about 2 µg/µl, at least about 3 µg/µl, at least about 4 µg/µl, at least about 5 µg/µl, at least about 6 µg/µl, at least about 7 µg/µl, at least about 8 µg/µl, at least about 9 µg/µl, at least about 10 µg/µl, at least about 11 µg/µl, at least about 12 µg/µl, at least about 14 µg/µl, at least about 16 µg/µl, at least about 18 µg/µl, at least about 20 µg/µl, or more than 20 µg/µl.

In some embodiments, a composition or method provided herein may provide an increase in hematocrit levels. For example, a hematocrit level may be increased above a baseline value (e.g., pretreatment value in a patient being treated, or general value observed in a particular patient population) by at least about 1%, at least about 2%, at least about 3%, at least about 5%, at least about 7%, at least about 10%, at least about 15%, at least about 20%, at least about 25%, or more than 25%.

In some embodiments, a compound of Formula (I), or a pharmaceutically acceptable salt thereof, is administered to maintain serum phospholipid percent of the compound of Formula (I), or salt or metabolite thereof, above a predetermined threshold value. In further variations, the compound of Formula (I), or pharmaceutically acceptable salt thereof, is administered to maintain serum phospholipid percent of the compound of Formula (I), or a salt or metabolite thereof, above about 0.1%, about 0.2%, about 0.3%, about 0.4%, about 0.5%, about 0.6%, about 0.7%, about 0.8%, about 0.9%, about 1%, about 1.2%, about 1.4%, about 1.6%, about 1.8%, about 2%, about 2.2%, about 2.4%, or about 2.6%.

Combination Therapies

In some embodiments, the compounds disclosed herein, such as a compound of Formula (I), or a pharmaceutically acceptable salt thereof, or a pharmaceutical composition that includes a compound described herein, or a salt thereof, may be used in combination with one or more additional active agents. Examples of additional active agents that can be used in combination with a compound of Formula (I), or a pharmaceutically acceptable salt thereof, or a composition that includes a compound of Formula (I), or a pharmaceutically acceptable salt thereof, include, but are not limited to, agents currently used for treating metabolic syndrome and related conditions, as described herein and as otherwise known to medical science.

In some embodiments, a compound of Formula (I), or a pharmaceutically acceptable salt thereof, or a composition that includes a compound of Formula (I), or a pharmaceutically acceptable salt thereof, can be used with one, two, three or more additional active agents described herein. Such agents include, but are not limited to, a second compound of Formula (I), or a pharmaceutically acceptable salt thereof, or a naturally occurring fatty acid, or a salt or derivative thereof.

In some embodiments, a compound of Formula (I), or a pharmaceutically acceptable salt thereof, or a composition that includes a compound of Formula (I), or a pharmaceutically acceptable salt thereof, can be used (for example, administered or ingested) in combination with another agent or agents for treatment, prevention, maintenance, or prophylaxis of metabolic syndrome, diabetes, and the like, or for modulation of markers of metabolic syndrome. For example, a compound of Formula (I), or a pharmaceutically acceptable salt thereof, can be used in combination with one or more agents selected from albiglutide, aleglitazar, balaglitazone, canagliflozin, CJ-30001 (CJ Cheiljedang Corporation), CJ-30002 (CJ Cheiljedang Corporation), Diamyd® (glutamic acid decarboxylase (rhGAD65)), dulaglutide, exendin 4, gemigliptin, lixisenatide, lobeglitazone, shengke I (Tibet Pharmaceuticals), SK-0403 (Sanwa Kagaku Kenkyusho), teneligliptin, teplizumab, tofogliflozin, acarbose, alogliptin benzoate, chlorpropamide, Diab II (Biotech Holdings), exenatide, glibenclamide, gliclazide, glimepiride, glipizide, gliquidone, glisentide, glisolamide, HL-002 (HanAII Biopharma), insulin (human), insulin, insulin analogue (Eli Lilly®), insulin aspart, insulin detemir, insulin glargine, insulin lispro, Janumet®, linagliptin, liraglutide, metformin, miglitol, mitiglinide, nateglinide, Novo Mix 30® (Novo Nordisk®) pioglitazone, pramlintide, repaglinide, rosiglitazone maleate, saxagliptin, sitagliptin, Tresiba, tolazamide, tolbutamide, vildagliptin, voglibose, bezafibrate, diflunisal, cinnamic acid, carbutamide, glyburide (glibenclamide), glibomuride, glyhexamide, phenbutamide, and tolcyclamide or with one or more agents selected from a class of agents, where the classes include sulfonylureas, non-sulfonylurea secretagogues, glucagon-like peptides, exendin-4 polypeptides, beta 3 adrenoceptor agonists, PPAR agonists, dipeptidyl peptidase IV inhibitors, biguanides, alpha-glucosidase inhibitors, immunomodulators, statins and statin-containing combinations, angiotensin converting enzyme inhibitors, adeno sine A1 receptor agonists, adenosine A2 receptor agonists, aldosterone antagonists, alpha 1 adrenoceptor antagonists, alpha 2 adrenoceptor agonists, alpha 2 adrenoceptor agonists, angiotensin receptor antagonists, antioxidants, ATPase inhibitors, atrial peptide agonists, beta adrenoceptor antagonists, calcium channel agonists, calcium channel antagonists, diguanides, diuretics, dopamine D1 receptor agonists, endopeptidase inhibitors, endothelin receptor antagonists, guanylate cyclase stimulants, phosphodiderivativease V inhibitors for example phosphodiesterase type 5 (PDE5) inhibitors, protein kinase inhibitors, Cdc2 kinase inhibitors, renin inhibitors, thromboxane synthase inhibitors, vasopeptidase inhibitors, vasopressin I antagonists, vasopressin 2 antagonists, angiogenesis inhibitors, advanced glycation end product inhibitors, bile acid binding agents, bile acid transport inhibitors, bone formation stimulants, apolipoprotein A1 agonists, DNA topoisomerase inhibitors, cholesterol absorption inhibitors, cholesterol antagonists, cholderivativeyl derivative transfer protein antagonists for example cholesteryl ester transfer protein (CETP) antagonists, cytokine synthesis inhibitors, DNA polymerase inhibitors, dopamine D2 receptor agonists, endothelin receptor antagonists, growth hormone antagonists, insulin sensitizers, lipase inhibitors, lipid peroxidation inhibitors, lipoprotein A antagonists, microsomal transport protein inhibitors, microsomal triglyceride transfer protein inhibitors, nitric oxide synthase inhibitors, oxidizing agents, phospholipase A2 inhibitors, radical formation agonists, platelet aggregation antagonists, prostaglandin synthase stimulants, reverse cholesterol transport activators, rho kinase inhibitors, selective estrogen receptor modulators, squalene epoxidase inhibitors, squalene synthase inhibitors, thromboxane A2 antagonists, amylin agonists, cannabinoid receptor antagonists, cholecystokinin A agonists, corticotropin-releasing factor agonists, dopamine uptake inhibitors, G protein-coupled receptor modulators, glutamate antagonists, glucagon-like peptide-1 agonists lipase inhibitors, melanin-concentrating hormone receptor antagonists, nerve growth factor agonists, neuropeptide Y agonists, neuropeptide Y antagonists, SNRIs, protein tyrosine phosphatase inhibitors, serotonin 2C receptor agonists, or with other agents such as central nervous system agents that affect neurotransmitters or neural ion channels, including antidepressants (bupropion), noradrenalin reuptake inhibitors (GW320659), selective serotonin 2c receptor agonists, selective 5HT 2c receptor agonists, antiseizure agents (topiramate, zonisamide), dopamine antagonists, cannabinoid-1 receptor antagonists (CB-1 receptor antagonists) (rimonabant); leptin/insulin/central nervous system pathway agents, including leptin analogues, leptin transport and/or leptin receptor promoters, ciliary neurotrophic factor (Axokine), neuropeptide Y and agouti-related peptide antagonists, pro-opiomelanocortin and cocaine and amphetamine regulated transcript promoters, α-melanocyte-stimulating hormone analogues, melanocoritin-4 receptor agonists, and agents that affect insulin metabolism/activity, which include protein-tyrosine phosphatase-IB inhibitors, peroxisome proliferator activated receptor-.gamma. receptor antagonists, short-acting bromocriptine (ergoset), somatostatin agonists (octreotide), and adiponectin/Acrp30 (Famoxin or Fatty Acid Metabolic Oxidation Inducer); gastrointestinal-neural pathway agents, including those that increase cholecystokinin activity (CCK), PYY activity, NPY activity, and PP activity, increase glucagon-like peptide-1 activity (exendin 4, dipeptidyl peptidase IV inhibitors), and those that decrease ghrelin activity, as well as amylin analogues (pramlintide); agents that may increase resting metabolic rate (selective β-3 stimulators/agonist, uncoupling protein homologues, and thyroid receptor agonists); other more diverse agents, including melanin concentrating hormone antagonists, phytostanol analogues, functional oils, P57, amylase inhibitors, growth hormone fragments, synthetic analogues of dehydroepiandrosterone sulfate, antagonists of adipocyte 11B-hydroxysteroid dehydrogenase type 1 activity, corticotropin-releasing hormone agonists, inhibitors of fatty acid synthesis (cerulenin and C75), carboxypeptidase inhibitors, indanone/indanols, aminosterols (trodusquemine/trodulamine), and other gastrointestinal lipase inhibitors (ATL962); amphetamines, such as dextroamphetamine; other sympathomimetic adrenergic agents, including phentermine, benzphetamine, phendimetrazine, mazindol, and diethylpropion; or with one or more agents selected from ecopipam; oxyntomodulin (OM); inhibitors of glucose-dependent insulinotropic polypeptide (GIP); gastrin-releasing peptide; neuromedin B; enterostatin; amfebutamone, SR-58611; CP-045598; AOD-0604; QC-BT16; rGLP-1; 1426 (HMR-1426); N-5984; ISIS-1 13715; solabegron; SR-147778; Org-34517; melanotan-II; cetilistat; c-2735; c-5093; c-2624; APD-356; radafaxine; fluasterone; GP-389255; 856464; S-2367; AVE-1625; T-71; oleoyl-estrone; peptide YY [3-36] intranasal; androgen receptor agonists; PYY 3-36; DOV-102677; tagatose; SLV-319; 1954 (Aventis Pharma AG); oxyntomodulin, Thiakis; bromocriptine, PLIVA; diabetes/hyperlipidemia therapy, Yissum; CKD-502; thyroid receptor beta agonists; beta-3 adrenoceptor agonist; CDK-A agonists; galanin antagonist; dopamine D1 D2 agonists; melanocortin modulators; verongamine; neuropeptide Y antagonists; melanin-concentrating hormone receptor antagonists; dual PPAR alpha/gamma agonists; CGEN-P-4; kinase inhibitors; human MCH receptor antagonists; GHS-R antagonists; ghrelin receptor agonists; DG70 inhibitors; cotinine; CRF-BP inhibitors; urocortin agonists; UCL-2000; impentamine; β-3 adrenergic receptor; pentapeptide MC4 agonists; trodusquemine; GT-2016; C-75; CPOP; MCH-1 receptor antagonists; RED-103004; aminosterols; orexin-1 antagonists; neuropeptide Y5 receptor antagonists; DRF-4158; PT-15; PTPase inhibitors; A37215; SA-0204; glycolipid metabolites; MC-4 agonist; produlestan; PTP-1B inhibitors; GT-2394; neuropeptide Y5 antagonists; melanocortin receptor modulators; MLN-4760; PPAR gamma/delta dual agonists; NPYSRA-972; 5-HT2C receptor agonist; neuropeptide Y5 receptor antagonists (phenyl urea analogs); AGRP/MC4 antagonists; neuropeptide Y5 antagonists (benzimidazole); glucocorticoid antagonists; MCHR1 antagonists; Acetyl-CoA carboxylase inhibitors; R-1496; HOB 1 modulators; NOX-B11; peptide YY 3-36 (eligen); 5-HT 1 modulators; pancreatic lipase inhibitors; GRC-1087; CB-1 antagonists; MCH-1 antagonists; LY-448100; bombesin BRS3 agonists; ghrelin antagonists; MC4 antagonists; stearoyl-CoA desaturase modulators; PPAR pan agonists; EP-01492; hormone-sensitive lipase inhibitors; fatty acid-binding protein 4 inhibitors; thiolactone derivatives; protein tyrosine phosphatase IB inhibitors; MCH-1 antagonist; P-64; PPAR gamma ligands; melanin concentrating hormone antagonists; thiazole gastroprokinetics; PA-452; T-226296; A-331440; immunodrug vaccines; diabetes/obesity therapeutics (Bioagency, Biofrontera Discovery GmbH); P-7 (Genfit); DT-011 M; PTP1B inhibitor; anti-diabetic peptide conjugates; KATP agonists; obesity therapeutics (Lexicon); 5-HT2 agonists; MCH-1 receptor antagonists; GMAD-1/GMAD-2; STG-a-MD; angiogenesis inhibitors; G protein-coupled receptor agonists; nicotinic therapeutics (ChemGenex); anti-obesity agents (Abbott); melanin concentrating hormone; GW-594884A; MC-4R agonist; histamine H3 antagonists; orphan GPCR modulators; MITO-3108; NLC-002; HE-2300; IGF/BBP-2-13; 5-HT2C agonists; ML-22952; neuropeptide Y receptor antagonists; AZ-40140; anti-obesity therapy (Nisshin Flour); GNTI; melanocortin receptor modulators; alpha-amylase inhibitors; beta-3 adrenoceptor agonists; ob gene products (Eli Lilly & Co.); SWR-0342-SA; SWR-0335; SP-18904; oral insulin mimetics; obesity therapeutics (7TM Pharma); beta-hydroxysteroid dehydrogenase (HSD) inhibitors; QRX-431; E-6776; RI-450; melanocortin-4 antagonists; melanocortin 4 receptor agonists; obesity therapeutics (CuraGen); leptin mimetics; A-74498; second-generation leptin; NBI-103; CL-314698; CP-114271; beta-3 adrenoceptor agonists; NMI-8739; UCL-1283; BMS-192548; CP-94253; PD-160170; nicotinic agonist; LG-100754; SB-226552; LY-355124; CKD-711; L-751250; PPAR inhibitors; G-protein therapeutics; obesity therapy (Amylin Pharmaceuticals Inc.); BW-1229; monoclonal antibody (ObeSys/CAT); L-742791; (S)-sibutramine; MBU-23; YM-268; BTS-78050; tubby-like protein genes; genomics (eating disorders; Allelix/Lilly); MS-706; GI-264879A; GW-409890; FR-79620 analogs; obesity therapy (Hybrigenics SA); ICI-198157; ESP-A; 5-HT2C agonists; PD-170292; AIT-202; LG-100641; GI-181771; anti-obesity therapeutics (Genzyme); leptin modulator; GHRH mimetics; obesity therapy (Yamanouchi Pharmaceutical Co. Ltd.); SB-251023; CP-331684; BIBO-3304; cholesten-3-ones; LY-362884; BRL-48962; PY-1 antagonists; A-71378; .RTM.-didesmethylsibutramine; obesity therapeutics (Bristol-Myers Squibb Co.); obesity therapeutics (Ligand Pharmaceuticals Inc.); LY-226936; NPY antagonists; CCK-A agonists; FPL-14294; PD-145942; ZA-7114; CL-316243; SR-58878; R-1065; BDBP-3226; HP-228; talibegron; FR-165914; AZM-008; AZM-016; AZM-120; AZM-090; AZM-131; AZM-132; AZM-134; AZM-127; AZM-083; AZM-1 15; AZM-140; vomeropherin; BMS-187257; D-3800; gene discovery (Axys/Glaxo); BRL-26830A; SX-013; ERR modulators; adipsin; AC-253; A-71623; A-68552; BMS-210285; TAK-677; MPV-1743; obesity therapeutics (Modex); GI-248573; exopipam; SSR-125180; obesity therapeutics (Melacure Therapeutics AB); BRL-35135; SR-146131; P-57; CGP-71583A; RF-1051; BMS-196085; manifaxine; DMNJ (Korea Research Institute of Bioscience and Biotechnology); BVT-5182; LY-255582; SNX-024; galanin antagonists; neurokinin-3 antagonists; dexfenfluramine; mazindol; diethylpropion; phendimetrazine; benzphetamine; amfebutmone; sertraline; AOD-9604; ATL-062; BVT-933; GT389-255; SLV319; HE-2500; PEG-axokine; L-796568; and ABT-239; rimonabant, sibutramine, orlistat, PYY or an analog thereof, CB-1 antagonist, leptin, phentermine, and exendin analogs; GPR1 19 agonists (e.g., anandamide; AR-231, 453; MBX-2982; Oleoylethanolamide; PSN-365,963; PSN-632,408; palmitoylethanolamide); GPR120 agonists; GPR 40 agonists; SGLT2 inhibitors.

Additionally, a compound of an odd chain fatty acid disclosed herein can be used in combination with one or more agents selected from Altoprev (lovastatin), Crestor (rosuvastatin), Lescol (fluvastatin), Lipitor (atorvastatin), Livalo (pitavastatin), Pravachol (pravastatin), Zocor (simvastatin), an anti-platelet medication, a beta blocker, an ACE inhibitor, a calcium channel blocker, a diuretic, anticoagulants, aspirin, bile acid sequestrants, Ezetimibe, Fibrates, Glycoprotein IIb/IIIa Receptor Inhibitors, Niacin (Nicotinic Acid), Nitrates, Platelet Inhibitors, Thrombolytics, lisinopril oral, atenolol oral, Bystolic oral, Diovan oral, hydrochlorothiazide oral, metoprolol succinate oral, amlodipine oral, Norvasc oral, Toprol XL oral, Benicar oral, metoprolol tartrate oral, losartan oral, lisinopril-hydrochlorothiazide oral, clonidine HCl oral, Diovan HCT oral, Cozaar oral, propranolol oral, spironolactone oral, Azor oral, carvedilol oral, Coreg oral, Benicar HCT oral, Exforge oral, Avapro oral, Lotrel oral, verapamil oral, furosemide oral, Lasix oral, Hyzaar oral, Tekturna oral, enalapril maleate oral, Micardis oral, losartan-hydrochlorothiazide oral, ramipril oral, Lopressor oral, Altace oral, Micardis HCT oral, Avalide oral, diltiazem oral, triamterene-hydrochlorothiazide oral, labetalol oral, terazosin oral, amlodipine-benazepril oral, hydralazine oral, Atacand oral, benazepril oral, Tribenzor oral, triamterene oral, doxazosin oral, nifedipine oral, Ziac oral, Aldactone oral, Maxzide oral, Cartia XT oral, prazosin oral, Cardizem CD oral, Zestril oral, Dyazide oral, bisoprolol fumarate oral, Tenex oral, Tenormin oral, Coreg CR oral, Prinivil oral, valsartan oral, atenolol-chlorthalidone oral, Edarbyclor oral, benazepril-hydrochlorothiazide oral, ferrous sulfate oral, Ferrlecit intravenous, Feraheme intravenous, Feosol oral, Infed injection, Integra oral, Ferrex 150 Forte oral, Tandem Dual Action oral, Ferrex 150 oral, ferrous gluconate oral, Corvite 150 oral, Integra F oral, NovaFerrum oral, Iron (ferrous sulfate) oral, Vitron-C oral, Folic acid, corticosteroids, rituximab, IVIG, prednisone, methylprednisolone oral, Kenalog injection, Medrol (Pak) oral, Medrol oral, dexamethasone oral, Depo-Medrol injection, prednisolone oral, DexPak 13 Day oral, Solu-Medrol intravenous, hydrocortisone oral, Cortef oral, Deltasone oral, triamcinolone acetonide injection, cortisone oral, cholinesterase inhibitors such as Donepezil (Aricept), Rivastigmine (Exelon), and Galantamine (Razadyne), Memantine, Aricept, Namenda, Namenda XR, Razadyne ER, Alpha E, vitamin E, Hydergine, Namzaric, Dopamine Agonists such as pramipexole (Mirapex), ropinirole (Requip), rotigotine (Neupro patch) and apomorphine (Apokyn), Anticholinergics such as benztropine (Cogentin) and trihexyphenidyl, MAO-B Inhibitors such as (Eldepryl, Zelapar) and rasagiline (Azilect), COMT Inhibitors such as Entacapone (Comtan), Carbidopa/Levodopa (Sinemet®), amantadine, Tetrabenazine (Xenazine), haloperidol (Haldol), chlorpromazine, risperidone (Risperdal), quetiapine (Seroquel), olanzapine (Zyprexa), indomethacin, sulindac, etodolac, mefenamic acid, meclofenamic acid, meclofenamate sodium, flufenamic acid, tolmetin, ketorolac, diclofenac, diclofenac sodium, ibuprofen, naproxen, naproxen sodium, fenoprofen, ketoprofen, flurbiprofen, oxaprozin piroxicam, meloxicam, ampiroxicam, droxicam, lornoxicam, cinnoxicam, sudoxicam, and tenoxicam.

Dosing

As will be readily apparent to one skilled in the art, the useful in vivo dosage to be administered and the particular mode of administration will vary depending upon the age, weight, the severity of the condition, and mammalian species treated, the particular forms of the compounds employed, and the specific use for which these compounds are employed. The determination of effective dosage levels, that is the dosage levels necessary to achieve the desired result, can be accomplished by one skilled in the art using routine methods, for example, in vivo studies. Reference may be made to, for example, "Estimating the Maximum Safe Starting Dose in Initial Clinical Trials for Therapeutics in Adult Healthy Volunteers," U.S. Food and Drug Administration, July 2005.

In some embodiments, a method provided herein may comprise administering a therapeutically effective amount of a composition provided herein. In some embodiments, a therapeutically effective amount may be determined by reference to the modulation of a marker of metabolic syndrome. In some embodiments, a therapeutically effective amount may be determined by reference to the modulation of a symptom of metabolic syndrome. In still other embodiments, reference may be made to established guidelines for the conditions described herein, including, but not limited to, guidelines for the treatment of diabetes.

The dosage may vary broadly, depending upon the desired effects and the therapeutic indication, such as marker values. Alternatively, dosages may be based and calculated upon the surface area or weight of the patient, as understood by those of skill in the art. The exact dosage will be determined on a case-by-case basis, or, in some cases, will be left to the informed discretion of the subject. The daily dosage regimen for an adult human patient may be, for example, an oral dose of a compound of Formula (I), or a pharmaceutically acceptable salt thereof, or a mixture of a plurality of compounds of Formula (I), or pharmaceutically acceptable salts thereof, or a mixture of a compound of Formula (I), or a pharmaceutically acceptable salt thereof, with a naturally occurring fatty acid, or a salt or derivative thereof, from about 0.01 mg to about 10000 mg, from about 1 mg to about 5000 mg, from about 5 mg to about 2000 mg, from about 10 mg to about 1000 mg, or from about 50 mg to about 500 mg. A single dose may include an odd chain fatty acid, or a salt or derivative thereof, in about 0.01 mg, about 0.1 mg, about 1 mg, about 5 mg, about 10 mg, about 20 mg, about 50 mg, about 100 mg, about 200 mg, about 300 mg, about 400 mg, about 500 mg, about 600 mg, about 800 mg, about 900 mg, about 1000 mg, about 2000 mg, about 5000 mg, or more. The dosage may be adjusted according to the body mass of the subject, for example, the dosage may be about 0.001 mg/kg, about 0.01 mg/kg, about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 15 mg/kg, about 20 mg/kg, about 25 mg/kg, about 30 mg/kg, or higher. The dosage may be a single one or a series of two or more given in the course of one or more days, as is appropriate for the individual subject. In some embodiments, the compounds will be administered for a period of continuous therapy, for example for about a week or more (e.g., one week, two weeks, three weeks, four weeks, five weeks, six weeks, seven weeks, eight weeks, or more), for several weeks, for about a month or more (e.g., one month, two months, three months, four months, five months, six months, seven months, eight months, nine months, ten months, eleven months, twelve months, or more), for about a year or more, or for a plurality of years. In some embodiments, a compound of Formula (I), or a pharmaceutically acceptable salt thereof, can be administered or ingested one time per day, two times per day, three times per day, or more.

As will be understood by those of skill in the art, in certain situations it may be necessary to administer the compounds disclosed herein in amounts that exceed the above-stated, preferred dosage range in order to effectively treat a subject.

Unit dosage forms can also be provided, e.g., individual packages with a premeasured amount of the composition, configured for administration on a predetermined schedule. Unit dosage forms configured for administration one to three times a day are preferred; however, in certain embodiments it may be desirable to configure the unit dosage form for administration more than three times a day, or less than one time per day.

Dosage amount and interval may be adjusted to the individual subject to provide plasma levels of the active moiety which are sufficient to maintain predetermined parameters, indicators, or marker values, or minimal effective concentration (MEC). Dosages necessary to achieve the desired result will depend on individual characteristics and route of administration. However, assays, for example, HPLC assays or bioassays, may be used to determine serum concentrations.

In some embodiments, the compounds and methods provided herein may be used in conjunction with devices and methods of using devices, for example, as provided in U.S. Pat. Nos. 7,651,845; 8,251,904; 8,251,904; 4,985,015; 8,827,957; 4,252,159; 5,318,521; 4,718,430; U.S. 2011/0190702; DE2615061; and in conjunction with diagnostic devices, for example, as provided in U.S. 2012/0072236, the contents of each of which are hereby incorporated by reference in their entireties.

Diagnosis and Monitoring

Provided herein are methods for the diagnosis and monitoring of metabolic syndrome and related conditions.

In some embodiments, the method of diagnosis or monitoring may comprise the step of measuring percentage of a compound of Formula (I), or a salt or metabolite thereof, or of a naturally occurring fatty acid. In some embodiments, the method of diagnosis or monitoring may comprise the step of measuring a marker of metabolic syndrome. In some embodiments, a correlation between one marker and another may prove instructive. In some embodiments, metabolic syndrome or a related condition may be diagnosed by reference to a threshold level of a marker of metabolic syndrome, for example, serum concentration of a compound of Formula (I), or salt or metabolite thereof, serum concentration of a naturally occurring fatty acid, such as, for example, odd chain fatty acid percentage, serum concentration of an odd chain fatty acid, or serum total odd chain fatty acid. For example, the threshold may be determined by reference to a symptom or marker of metabolic syndrome or a related condition, for example, diabetes.

The percentage of a compound of Formula (I), or a salt or metabolite thereof, or a marker of metabolic syndrome, in a subject may be monitored by any means. Samples for analysis may be derived any fluid or tissue of the subject. For example, from serum, plasma, erythrocyte membranes, urine, and feces.

EXAMPLES

Comparative Example 1

Forty C57BL/6J mice were fed a high fat diet (HFD) (D12492, 60% kcals fat) for 8 weeks. Study mice were then divided into the following four groups of ten: vehicle controls, low dose C17:0-treated (5 mg/kg body weight), high-dose C17:0-treated (50 mg/kg body weight), and low-dose C15:0-treated (5 mg/kg body weight). The test articles were in synthetic powder form stable at room temperature and purchased from Sigma-Aldrich (Products W433400 (≥99% C15:0) and H3500 SIGMA (≥98% C17:0). The test articles were provided daily via gastric gavage for 12 weeks (84 days) while continuing ad libitum access to the HFD.

Body weight and food intake were measured weekly. Serum insulin, glucose, cholesterol, and IL-6, TNF-α, and MCP-1 levels were measured at Day 84. Data from the treated groups were compared to the control group using Wilcoxon rank sum analyses. Significance was defined as a P value less than or equal to 0.05.

Mice in the treatment groups tolerated the test articles throughout the study. There were no early mortalities among mice in the treated groups; one mouse in the control group had an unscheduled death on Week 7. No changes were found in body weight, percent body weight change, or food intake when comparing the study groups (not shown).

When comparing the treatment groups with the vehicle control group, subjects treated with C15:0 (5 mg/kg) had attenuated metabolic syndrome, including lower glucose, insulin, cholesterol, and proinflammatory cytokines (IL-6, TNF-α, and MCP-1) compared to controls (Table 1). While subjects treated with C17:0 trended toward attenuated metabolic syndrome compared to controls (Table 1), only the high-dose C17:0 (50 mg/kg) had significantly lower proinflammatory cytokines and chemokines (TNF-α and MCP-1) compared to controls (Table 1).

Table 1 provides comparisons of cardiometabolic effects in diet-induced obese mice treated daily with oral pentadecanoic acid (5 mg/kg BW), heptadecanoic acid (5 and 50 mg/kg BW) for 12 weeks compared to vehicle controls. "Results" values are based on 6 h fasted samples.

nonalcoholic steatohepatitis, using an oral odd-chain saturated fatty acid. Sixteen New Zealand white rabbits were fed a high fat diet (HFD) (4% peanut oil and 0.5% cholesterol) for 2 weeks. Eight additional rabbits were maintained on a baseline diet. Study rabbits were then divided into the following three groups of eight: baseline diet controls, HFD controls, and C15:0-treated (35 mg/kg body weight) cases. The test article was a synthetic powder stable at room temperature and purchased from Sigma-Aldrich (Products W433400 (≥99% C15:0). The test article was provided daily in the diet for 11 weeks (76 days) while continuing ad libitum access to the HFD (HFD controls and treated groups) or baseline diet (baseline diet controls). Body weight and food intake were measured weekly. Plasma clinical chemistries and red blood cell indices, as well as iron deposition and fibrosis in the liver, were assessed at Day 76. Data from the treated group were compared to the control groups using Wilcoxon rank sum analyses. Significance was defined as a P value less than or equal to 0.05.

Rabbits in the treatment group tolerated the test article throughout the study. There were no early mortalities among rabbits in the study. At Day 76, subjects treated with C15:0 (35 mg/kg) had lower circulating cholesterol, triglycerides and globulins, as well as attenuated anemia, liver iron deposition, and liver fibrosis compared to the HFD controls (Table 2).

TABLE 1

| Variable | Vehicle control (n = 10) | Heptadecanoic acid 5 mg/kg dose (n = 10) | Heptadecanoic acid 50 mg/kg dose (n = 10) | Pentadecanoic acid 5 mg/kg dose (n = 10) |
| --- | --- | --- | --- | --- |
| Baseline (Day 1) | | | | |
| Glucose, 6 h fasted (mg/dl) | 211 ± 35 | 200 ± 23 | 196 ± 22 | 189 ± 46 |
| Insulin, non-fasting (ng/ml) | 9.0 ± 8.2 | 5.8 ± 3.1 | 6.1 ± 2.2 | 7.0 ± 4.1 |
| Cholesterol (mg/dl) | 147 ± 22 | 152 ± 23 | 144 ± 20 | 153 ± 20 |
| Results (Day 84) | | | | |
| Glucose (mg/dl) | 307 ± 54 | 296 ± 23 | 282 ± 31 | 245 ± 37* |
| Insulin (ng/ml) | 12.2 ± 10 | 7.4 ± 4.8 | 6.8 ± 3.5 | 4.9 ± 3.8* |
| Cholesterol (mg/dl) | 207 ± 20 | 197 ± 31 | 187 ± 44 | 183 ± 25* |
| LDL-C (mg/dl) | 11 ± 3 | 9 ± 3 | 8 ± 3 | 6 ± 4* |
| IL-6 (pg/ml) | 60 ± 68 | 42 ± 40 | 38 ± 32 | 19 ± 11* |
| MCP-1 (pg/ml) | 83 ± 31 | 86 ± 30 | 53 ± 32* | 52 ± 25* |
| TNF-α (pg/ml) | 3.3 ± 2.1 | 3.7 ± 1.9 | 1.5 ± 1.5* | 1.6 ± 1.0* |

*$P \leq 0.05$

Comparative Example 2

This study further assessed the efficacy of treating diseases associated with metabolic syndrome, including dyslipidemia, inflammation, anemia, liver iron overload and Table 2 provides comparisons of clinical effects from a diet-induced rabbit model for metabolic syndrome-associated dyslipidemia, inflammation, and hemolytic anemia, including a case group treated daily with oral pentadecanoic acid (C15:0) (35 mg/kg BW) for 11 weeks.

TABLE 2

| Plasma Lipids | High fat diet (HFD) (n = 8) | HFD C15:0 (35 mg/kg/day) (n = 8) | Baseline diet (n = 8) | Wilcoxon rank sum P values | | |
| --- | --- | --- | --- | --- | --- | --- |
| | | | | HFD vs Baseline | C15:0 vs Baseline | C15:0 vs HFD |
| Cholesterol (mg/dl) | 3576 ± 1018 | 2516 ± 746 | 23 ± 7 | 0.002 | 0.002 | 0.024 |
| Triglycerides (mg/dl) | 755 ± 555 | 235 ± 132 | 71 ± 38 | 0.002 | 0.003 | 0.008 |
| Lipemia (mg/dl) | 289 ± 202 | 341 ± 243 | 6 ± 1 | 0.002 | 0.002 | 0.398 |
| Globulins (G/dl) | 2.2 ± 0.3 | 1.3 ± 0.7 | 1.9 ± 0.6 | 0.047 | 0.088 | 0.004 |

TABLE 2-continued

| Plasma Lipids | High fat diet (HFD) (n = 8) | HFD C15:0 (35 mg/kg/day) (n = 8) | Baseline diet (n = 8) | Wilcoxon rank sum P values | | |
|---|---|---|---|---|---|---|
| | | | | HFD vs Baseline | C15:0 vs Baseline | C15:0 vs HFD |
| Nucleated red blood cells ($10^3$/ul) | 13 ± 9 | 8 ± 1 | 4 ± 1 | 0.002 | 0.002 | 0.036 |
| Hemoglobin (G/dl) | 9 ± 2 | 14 ± 1 | 15 ± 1 | 0.002 | 0.010 | 0.003 |
| Hematocrit (%) | 26 ± 5 | 38 ± 4 | 46 ± 2 | 0.002 | 0.003 | 0.003 |
| Red blood cells ($10^6$/ul) | 3.5 ± 1.2 | 6.0 ± 0.7 | 7.3 ± 0.3 | 0.002 | 0.005 | 0.002 |
| Mean cell volume (fl) | 79 ± 21 | 64 ± 2 | 63 ± 2 | 0.004 | 0.139 | 0.006 |
| Red blood cell distribution width (%) | 21 ± 3 | 15 ± 1 | 13 ± 1 | 0.002 | 0.011 | 0.002 |
| Reticulocytes ($10^3$/ul) | 885 ± 497 | 334 ± 71 | 181 ± 39 | 0.002 | 0.002 | 0.002 |
| Reticulocytes (%) | 30 ± 22 | 6 ± 2 | 2 ± 1 | 0.002 | 0.002 | 0.002 |
| Platelets ($10^3$/ul) | 639 ± 123 | 485 ± 87 | 335 ± 75 | 0.002 | 0.006 | 0.014 |
| Mean cell hemoglobin (PG) | 27 ± 5 | 23 ± 1 | 21 ± 1 | 0.002 | 0.004 | 0.004 |

Table 3 provides comparisons of effects on liver histology in a diet-induced rabbit model for metabolic syndrome-associated liver iron overload and nonalcoholic steatohepatitis, including a case group treated daily with oral pentadecanoic acid (C15:0) (35 mg/kg BW) for 11 weeks.

TABLE 3

| Liver Histology | High fat, high cholesterol diet (n = 8) | High fat, high cholesterol diet + ETI-101 (n = 8) | P value |
|---|---|---|---|
| Fibrosis stage (2 = portal/periportal, 3 = bridging fibrosis) | 2.9 ± 0.4 | 2.3 ± 0.5 | 0.016 |
| Fibrosis pixel (%) | 2.9 ± 0.8 | 2.1 ± 0.8 | 0.062 |
| Iron staining (mean score) | 1.1 | 0.4 | 0.010 |

Comparative Example 3

This study compared structure-activity relationships among saturated free fatty acids and substituents to optimize the observed health benefits of odd-chain saturated free fatty acids to treat metabolic syndrome and associated diseases. Since fatty acids are natural ligands for peroxisome proliferator-activated receptors (PPARs), lead optimization began with structure-activity relationships around cell-based PPAR agonist activity. Specifically, this study examined and compared PPAR agonist activity of three free fatty acid forms of saturated fatty acids (C14:0, C15:0 and C16:0) with a variety of saturated fatty acid substituents (2-methyl-, 2,2-dimethyl-, 1-tetrazole-, 3-oxy-, 2-methyl-1-tetrazole-, 2-ethyl-, 2,2-diethyl-, and 2-methyl-2-ethyl-). PPAR-α, PPAR-δ, and PPAR-γ agonist activities were measured using PathHunter Nuclear Hormone Receptor (NHR) Protein Interaction (Pro) assays (DiscoverX, Freemont, California). Briefly, Chinese hamster ovary (CHO) cell lines were used to monitor the activation of PPAR-α, PPAR-δ, and PPAR-γ in a homogenous, non-imaging assay format using Enzyme Fragment Complementation (EFC). The NHR Pro assay was based on detection of protein-protein interactions between activated, full length PPAR-α, PPAR-δ, and PPAR-γ proteins and a nuclear fusion protein containing Steroid Receptor Co-activator Peptide (SRCP) domains with one or more canonical LXXLL interaction motifs. PPAR-α, PPAR-δ, and PPAR-γ were tagged with the ProLink component of the EFC assay system, and the SRCP domain was fused to the enzyme acceptor component (EA) expressed in the nucleus. When bound by ligand, PPAR-α, PPAR-δ, or PPAR-γ migrated to the nucleus and recruited the SRCP domain, whereby complementation occurred, generating a unit of active β-Galactosidase (β-Gal) and production of chemiluminescent signal. Benefits associated with this approach included reduced compound incubation times, direct measurements of PPAR-α, PPAR-δ, and PPAR-γ targets, use of full length human PPAR-α, PPAR-δ, and PPAR-γ sequences, and the ability to select novel compound classes based on disruption of protein-protein interactions. PPAR-α, PPAR-δ, and PPAR-γ agonist dose curves were determined at 10 concentrations in duplicate for free fatty acid forms of C14:0, C15:0, C16:0; 2-methyl substituents of C14:0, C15:0, C16:0; 2,2-dimethyl substituents of C14:0, C15:0, C16:0; 1-tetrazole substituents of C14:0 and C15:0; and 3-oxy substituents of C15:0 and C16:0; and 2-methyl-1-tetrazole, 2-ethyl, 2,2-diethyl, and 2-methyl-2-ethyl substituents of C15:0, and positive controls for PPAR-α (GW7647), PPAR-δ (L-165,041), and PPAR-γ (Troglitazone). Data shown was normalized to the maximal and minimal response observed in the presence of control compound and vehicle respectively. Percentage activity was calculated using the following formula: % Activity=100%×(mean RLU of test sample−mean RLU of vehicle control)/(mean MAX control ligand−mean RLU of vehicle control).

Compared to saturated free fatty acid forms, saturated fatty acid substituents demonstrated improved, lower concentrations required to reach the half maximal effective concentrations for PPAR agonist activity (Table 4). Different substituents conferred improvements in different PPAR isotype (PPAR-α, -δ, and -γ) enabling selection among the tested group of constituents to target desired PPAR isotype agonist activity. 2-methyl-substituents for C14:0, C15:0, and C16:0 improved the PPAR-α agonist EC50 by 17%, 48% and 62% compared to their free fatty acid forms, respectively. 2,2-dimethyl-substituents for C14:0, C15:0, and C16:0 improved the PPAR-α agonist EC50 by 13%, 44% and 90% compared to their free fatty acid forms, respectively. 1-tetrazole-C15:0, 3-oxa-C15:0, and 2-methyl-1-tetrazole-C15:0 substituents improved the PPAR-α agonist EC50 by 77%, 54%, and 44%, respectively, compared to C15:0. 2-ethyl-C15:0 and 2,2-diethyl-C15:0 substituents improved the PPAR-α agonist EC50 by 90% and 85%, respectively, compared to C15:0.

1-tetrazole-substituents for C14:0 and C15:0 improved the PPAR-δ agonist EC50 by 63% and 81% compared to their free fatty acid forms, respectively. 3-oxa-substituents for C15:0 and C16:0 improved the PPAR-δ agonist EC50 by 85% and 70% compared to their free fatty acid forms, respectively. 2-methyl-1-tetrazole-C15:0 improved the PPAR-δ agonist EC50 by 59% compared to C15:0. 2-methyl-C16:0 and 2,2-dimethyl-C16:0 improved the PPAR-δ agonist EC50 by 11 and 50%, respectively, compared to C16:0. 2-ethyl-C15:0 improved the PPAR-δ agonist EC50 by 89% compared to C15:0. While none of the unsubstituted saturated free fatty acids had PPAR-γ activity, 2-methyl-C14:0, 2-methyl-C15:0, 2-methyl-C16:0, 2,2-dimethyl-C14:0, 2,2-dimethyl-C15:0, 2-ethyl-C15:0, 2,2-diethyl-C15:0 and 2-methyl-2-ethyl-C15:0 acquired PPAR-γ agonist activity. The strong activity of multiple analogs against cell systems mimicking systems including pulmonary systems, fibrotic systems, dermatitis systems, psoriasis systems, allergy systems, and autoimmune systems, which were completely untouched by the free fatty acid C15:0 form, was surprising. The analogs did not simply improve free fatty acid C15:0 activity, they exhibited changed targeted disease systems.

In summary, saturated fatty acid substituents successfully decreased the concentration of compound needed to demonstrate cell-based PPAR agonist activity compared to their free fatty acid forms. Further, different substituents improved different PPAR isotypes (PPAR-α, -δ, and -γ), enabling one to select specific substituents targeting diseases associated with specific PPARs.

Table 4 provides comparisons of PPAR agonist activity among selected saturated fatty acids using cell-based protein-protein interaction assays.

TABLE 4

| Saturated fatty acid (free fatty acid form) | PPAR isoform | EC50 (uM) | Maximum Response (%) |
|---|---|---|---|
| C14:0 | PPAR-alpha | 8.35 | 74.1 |
| C15:0 | PPAR-alpha | 11.45 | 65.8 |
| C16:0 | PPAR-alpha | 27.30 | 56.1 |
| C17:0 | PPAR-alpha | >100 | 16.7 |
| C14:0 | PPAR-delta | 3.19 | 81.2 |
| C15:0 | PPAR-delta | 2.70 | 52.8 |
| C16:0 | PPAR-delta | 4.66 | 55.6 |
| C17:0 | PPAR-delta | 17.37 | 39.8 |
| C14:0 | PPAR-gamma | >100 | 19.0 |
| C15:0 | PPAR-gamma | >100 | 7.0 |
| C16:0 | PPAR-gamma | >100 | 4.7 |
| C17:0 | PPAR-gamma | >100 | 1.0 |

Table 5 provides comparisons of PPAR-agonist activity among saturated free fatty acid (FFA) forms and saturated fatty acids with substituents, based on half-maximal effective concentrations (EC50).

TABLE 5

Cell-Based PPAR Agonist Activity
Half Maximal Effective Concentration (EC50)

| Saturated Fatty Acid | PPAR-α | | PPAR-δ | | PPAR-γ | |
|---|---|---|---|---|---|---|
| | μM | % improvement over FFA form | μM | % improvement over FFA form | μM | % improvement over FFA form |
| C14:0 | | | | | | |
| Free fatty acid | 8.4 | — | 3.2 | — | >100 | — |
| 2-methyl | 7.0 | 17% | 5.5 | — | 11.5 | >89% |
| 2,2-dimethyl | 7.3 | 13% | 6.0 | — | 10.4 | >90% |
| 1-tetrazole | 18.7 | — | 1.2 | 63% | — | — |
| C15:0 | | | | | | |
| Free fatty acid | 11.5 | — | 2.7 | — | >100 | — |
| 2-methyl | 6.0 | 48% | 2.7 | — | 11.5 | >89% |
| 2,2-dimethyl | 6.4 | 44% | 4.9 | — | >20 | 20% |
| 1-tetrazole | 2.6 | 77% | 0.5 | 81% | >100 | — |
| 3-oxa | 5.3 | 54% | 0.4 | 85% | >100 | — |
| 2-methyl-1-tetrazole | 6.4 | 44% | 1.1 | 59% | — | — |
| 2-ethyl | 1.2 | 90% | 0.3 | 89% | 51 | >49% |
| 2,2-diethyl | 1.7 | 85% | 5.1 | — | 47.6 | >52% |
| 2-methyl-2-ethyl | >100 | — | >100 | — | 19.6 | >80% |
| C16:0 | | | | | | |
| Free fatty acid | 27.3 | — | 4.6 | — | >100 | — |
| 2-methyl | 10.4 | 62% | 4.1 | 11% | 24.2 | >76% |
| 2,2-dimethyl | 2.6 | 90% | 2.3 | 50% | >100 | — |
| 3-oxa | >100 | — | 1.4 | 70% | >100 | — |

Example 4

This study examined and compared activities of a saturated free fatty acid (C15:0) and three substituents (2-methyl-, 2,2-dimethyl-, and 1-tetrazole-C15:0) across 12 human primary cell-based systems as part of DiscoverX's BioMAP Diversity Plus program. These systems are designed to model complex human tissue and disease biology of the vasculature, skin, lung, and inflammatory tissues. Quantitative measurements of biomarker activities across this broad panel, along with comparative analysis of biological activities of known bioactive agents were used to predict and compare the efficacy and function of the four compounds. Compounds were tested at four concentrations (740 nm and 2.2, 6.7 and 20 µM).

BioMAP panels consist of human primary cell-based systems designed to model different aspects of the human body in an in vitro format. The 12 systems in the Diversity PLUS panel allow test agent characterization in an unbiased way across a broad set of systems modeling various human disease states. BioMAP systems are constructed with one or more primary cell types from healthy human donors, with stimuli (such as cytokines or growth factors) added to capture relevant signaling networks that naturally occur in human tissue or pathological conditions. Vascular biology is modeled in both a Th1 (3C system) and a Th2 (4H system) inflammatory environment, as well as in a Th1 inflammatory state specific to arterial smooth muscle cells (CASM3C system). Additional systems recapitulate aspects of the systemic immune response including monocyte-driven Th1 inflammation (LPS system) or T cell stimulation (SAg system), chronic Th1 inflammation driven by macrophage activation (lMphg system) and the T cell-dependent activation of B cells that occurs in germinal centers (BT system). The BE3C system (Th1) and the BF4T system (Th2) represent airway inflammation of the lung, while the MyoF system models myofibroblast-lung tissue remodeling. Lastly, skin biology is addressed in the KF3CT system modeling Th1 cutaneous inflammation and the HDF3CGF system modeling wound healing.

Each test agent generates a signature BioMAP profile that is created from the changes in protein biomarker readouts within individual system environments. Biomarker readouts (7-17 per system) are selected for therapeutic and biological relevance, are predictive for disease outcomes or specific drug effects and are validated using agents with known mechanism of action (MoA). Each readout is measured quantitatively by immune-based methods that detect protein (e.g., ELISA) or functional assays that measure proliferation and viability. BioMAP readouts are diverse and include cell surface receptors, cytokines, chemokines, matrix molecules and enzymes. In total, the Diversity PLUS panel contains 148 biomarker readouts that capture biological changes that occur within the physiological context of the particular BioMAP system. Specific BioMAP activities have been correlated to in vivo biology, and multiparameter BioMAP profiles have been used to distinguish compounds based on MoA and target selectivity across diverse physiological systems.

Of 148 disease biomarkers measured across 12 cell systems, saturated fatty substituents (2-methyl-, 2,2-dimethyl-, and 1-tetrazole-C15:0) had improved anti-disease activities compared to C15:0-treated cell systems and non-treated controls for 21 biomarkers across 8 systems (FIG. 1, tables in FIGS. 2A and 2B). 2-methyl-C15:0, 2,2-dimethyl-C15:0, and 1-tetrazole-C15:0 all demonstrated lower MCP-1, PAI-1, eotaxin-3, VCAM-1, ICAM-1, IL-1α, MMP-1, MMP-3, and MMP-9 compared to C15:0-treated systems and non-treated controls. 2-methyl-C15:0 and 2,2-dimethyl-C15:0 demonstrated lower T cell proliferation, IL-8, keratin 8/18, IP-10, IP-18, and MIG compared to C15:0-treated systems and non-treated controls. 2,2-dimethyl-C15:0 and 1-tetrazole-C15:0 demonstrated lower tissue factor, CD38, and CD99 compared to C15:0-treated systems and non-treated controls. 2-methyl-C15:0 and 1-tetrazole-C15:0 demonstrated lower CD40 compared to C15:0-treated systems and non-treated controls. 2-methyl-C15:0 demonstrated lower B cell proliferation and lower secreted IgG compared to C15: 0-treated systems and non-treated controls. A summary of these biomarkers by saturated fatty acid substituent is provided in FIG. 1, which provides a summary of protein-based biomarkers of various disease states that were significantly lower in human primary cell-based systems treated with saturated fatty acid substituents (2-methyl-C15:0, 2,2-dimethyl-C15:0, and 1-tetrazole-C15:0) compared to systems treated with saturated free fatty acids (C15:0) and non-treated controls.

In summary, similar to the results from the PPAR-agonist study, multiple saturated fatty acid substituents successfully improved disease-specific biomarkers compared to the free fatty acid form. Further, different substituents improved different disease biomarkers in different cell-based disease systems, enabling one to select specific substituents targeting diseases associated with specific disease biomarkers.

FIGS. 2A and 2B provide comparisons of human primary cell-based activity (specifically, reductions of activated diseased states) among saturated free fatty acid forms and saturated fatty acids with substituents.

Example 5

This study compared 24-hour plasma bioavailability and pharmacokinetics of an orally administered saturated free fatty acid (C15:0) versus a saturated fatty acid substituent (2-methyl-C15:0). Briefly, 18 rats were randomly divided into the following three groups of six animals each: lower-dose 2-methyl-C15:0 (5 mg/kg body weight), higher-dose 2-methyl-C15:0 (35 mg/kg), and higher-dose C15:0 (35 mg/kg). Deuterated forms of 2-methyl-C15:0 and C15:0 were used to differentiate from natural fatty acids present in plasma. 2-methyl-C15:0 and C15:0 were analyzed by capillary gas chromatography/mass spectrometry of pentafluorobenzyl bromide fatty acid esters using a AT-Silar-100 column (Grace, Columbia, Maryland 21044). 2-methyl-C15:0 and C15:0, added to 0.5% methocellulose suspending vehicle and mixed well to form a dosable suspension, was administered via gastric gavage once. Plasma compound levels were monitored pre-dose (0 min) and post-dose (15 min, 30 min, and 1, 2, 4, 8, 12 and 24 hr).

Figure 3A:
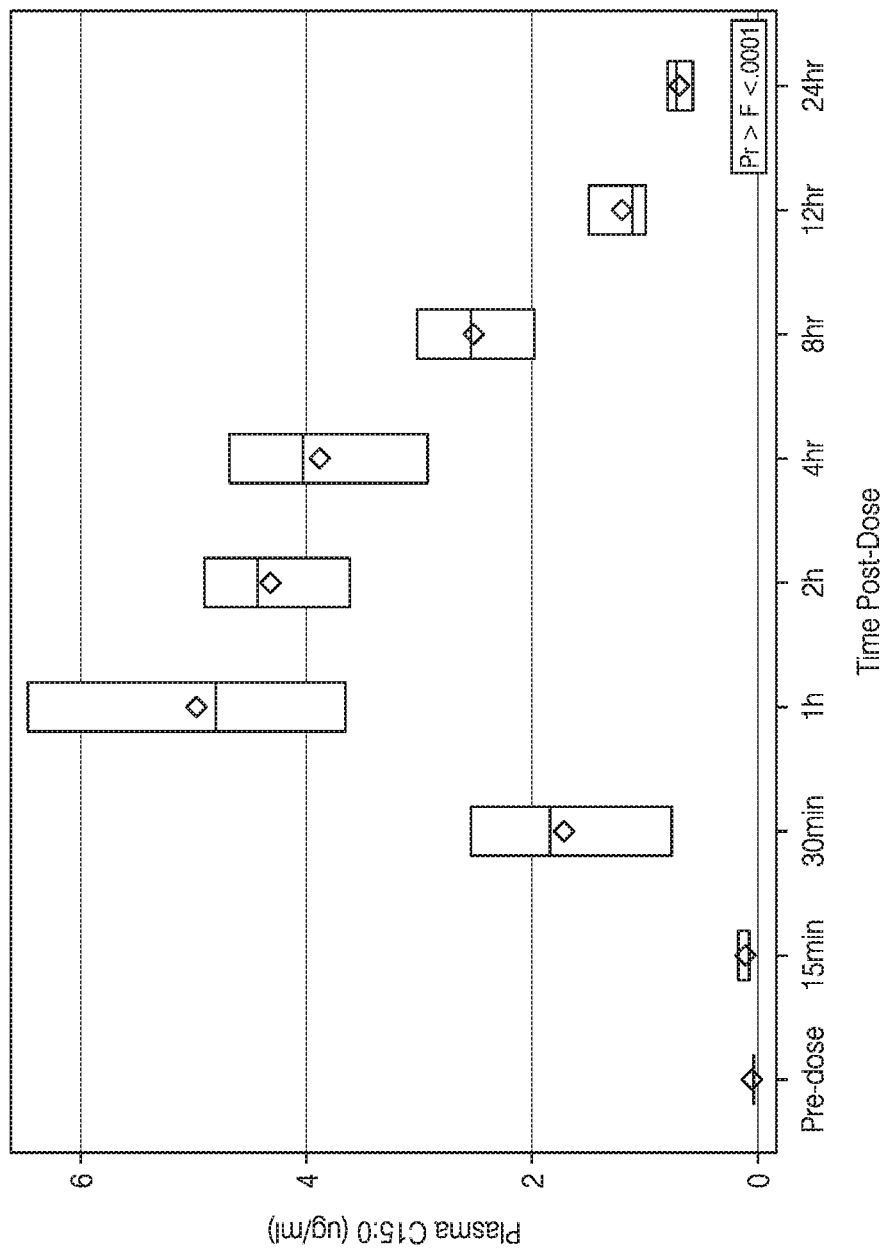
FIG. 3A depicts changes in plasma concentration of C15:0 over 24 h following a single oral 35 mg/kg body weight dose of deuterated C15:0 in rats.
Figure 3B:
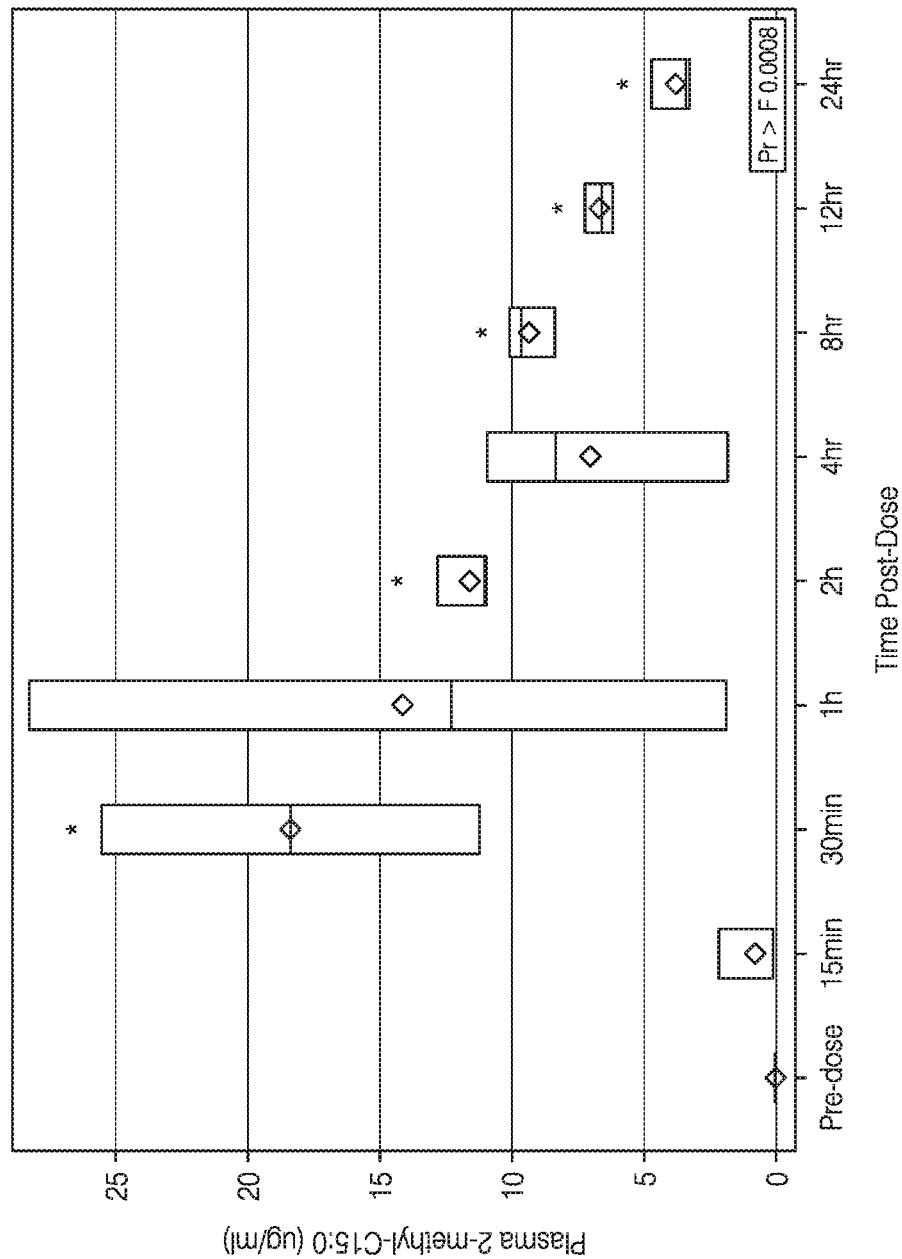
FIG. 3B depicts changes in plasma concentration of 2-methyl-C15:0 over 24 h following a single oral 35 mg/kg body weight dose of deuterated 2-methyl-C15:0 in rats.

Oral 2-methyl-C15:0 (35 mg/kg) dosing resulted in raised plasma 2-methyl-C15:0 levels at 30 min (FIG. 3B). 2-methyl-C15:0 (35 mg/kg) reached maximum plasma concentration of 20.29 µg/ml 1 hr post-dose. 2-methyl-C15:0 (35 mg/kg) plasma levels decreased over the 24 hr period but remained higher than pre-dose levels. 2-methyl-C15:0 (35 mg/kg) plasma levels at 30 min and 2, 8, 12, and 24 hours post-dose were approximately 4-fold higher than C15:0 (35 mg/kg) (FIG. 3A), supporting that 2-methyl-C15:0 has greater plasma bioavailability compared to C15:0. The estimated plasma % F (bioavailability) of 2-methyl-C15:0 was approximately 35%, compared to C15:0's plasma bioavailability of 9% (Table 6). Table 6 provides comparisons of 24-hour plasma pharmacokinetics of a saturated free fatty acid (C15:0, 35 mg/kg single oral dose) and a saturated fatty acid substituent (2-methyl-C15:0, 5 and 35 mg/kg single oral dose)

TABLE 6

| Pharmacokinetic metric | 2-methyl-C15:0 (5 mg/kg) | 2-methyl-C15:0 (35 mg/kg) | C15:0 (35 mg/kg) |
|---|---|---|---|
| $C_{max}$ (ug/ml) | 3.59 | 20.29 | 4.98 |
| $T_{max}$ (h) | 1 | 1 | 1 |
| $T_{last}$ (h) | 24 | 24 | 24 |

153

TABLE 6-continued

| Pharmacokinetic metric | 2-methyl-C15:0 (5 mg/kg) | 2-methyl-C15:0 (35 mg/kg) | C15:0 (35 mg/kg) |
|---|---|---|---|
| $C_{min}$ (ug/ml) | 0.66 | 3.79 | 0.70 |
| $AUC_{0\text{-}last}$ | 28.36 | 182.20 | 46.35 |
| % F* | 37.81 | 34.71 | 8.83 |

*This is an estimate using an AUC of 15 for a 1 mg/kg IV arm

In summary, this study supports that 2-methyl-C15:0, a saturated fatty acid substituent, has improved plasma bioavailability compared to C15:0, a saturated free fatty acid.

Example 6

PPARs are 'Y'-shaped with Arm-1 as the hydrophobic base, Arm-II with a hydrophilic AF-2 pocket, and a hydrophobic Arm-III. PPAR ligands typically enter the receptor up Arm-1 and rest across Arm-II and Arm-III. Most binding activity between a PPAR and a ligand occur between a ligand's hydrophilic head and the hydrophilic AF-2 pocket of Arm-II.

The same cell-based assay from EXAMPLE 2 was used to compare PPAR agonist activities among natural free fatty acid C16:0, a methyl C16:0, and a di-methyl C16:0.

Both methyl and di-methyl C16:0 had improved PPAR-alpha agonist activity, with maintained or improved PPAR-delta activity, compared to the natural, free fatty acid form of C16:0 (Table 3). 2-Methyl C16:0 also demonstrated PPAR-gamma agonist activity compared to the free fatty acid form of C16:0.

Table 7 provides comparisons of PPAR agonist activity among a natural saturated fatty acid, a 2-methyl saturated fatty acid, and a 2,2-di-methyl saturated fatty acid using cell-based protein-protein interaction assays.

TABLE 7

| Saturated fatty acid analog | PPAR isoform | EC50 (uM) | Maximum Response (%) |
|---|---|---|---|
| Free fatty acid C16:0 | PPAR-alpha | 27.3 | 56.1 |
| 2-Methyl C16:0 | PPAR-alpha | 10.4 | 110 |
| 2,2-Di-methyl C16:0 | PPAR-alpha | 2.6 | 88.8 |
| Free fatty acid C16:0 | PPAR-delta | 4.6 | 55.6 |
| 2-Methyl C16:0 | PPAR-delta | 4.1 | 64.9 |
| 2,2-Di-methyl C16:0 | PPAR-delta | 2.3 | 54.0 |
| Free fatty acid C16:0 | PPAR-gamma | >100 | 4.68 |
| 2-Methyl C16:0 | PPAR-gamma | 24.2 | 66.0 |
| 2,2-Di-methyl C16:0 | PPAR-gamma | >100 | 30.7 |

Exemplary Compositions, Methods and Uses

Method 1: A method of treatment or prophylaxis of metabolic syndrome, cardiovascular disease, diabetes, type 2 diabetes, anemia, cancer, cardiovascular disease, dyslipidemia, hypertension, inflammation, insulin resistance, prediabetes, fatty liver disease, steatohepatitis, iron overload, neurodegenerative diseases, or Alzheimer's disease, comprising administering a compound, or a pharmaceutically acceptable salt thereof, wherein the compound is a saturated fatty acid substituted with one or more substituents selected from the group consisting of a 2-methyl, 2,2-dimethyl, 2-ethyl, 2,2-diethyl, 3-oxa, or 3-oxa-2,2-dimethyl, 1-tetrazole, 1-oxazolone, 1-oxadiazolone, and N-hydroxyamide; wherein the fatty acid is selected from the group consisting of tridecanoic acid (C13:0), myristic acid (C14:0), pentadecanoic acid (C15:0), palmitic acid (C16:0), heptadecanoic acid (C17:0), and stearic acid (C18:0).

154

Pharmaceutical Composition 2: A pharmaceutical composition comprising: a compound of Formula (I), or a pharmaceutically acceptable salt thereof, wherein the compound of Formula (I) has the structure:

Formula (I)

wherein: G is selected from an unsubstituted or a substituted $C_{10}$-$C_{15}$ alkyl, an unsubstituted or a substituted $C_{10}$-$C_{15}$ alkenyl, or an unsubstituted $C_{10}$-$C_{15}$ alkyl or a substituted $C_{10}$-$C_{15}$ alkyl having one, two, or three oxa- or thia-substituents; X is selected from O and $CR^1R^2$, wherein $R^1$ and $R^2$ are each independently H, or an unsubstituted or a substituted $C_1$-$C_6$ alkyl; $Y^1$ and $Y^2$ are each independently H, an unsubstituted or a substituted $C_1$-$C_6$ alkoxy, or an unsubstituted or a substituted $C_1$-$C_6$ alkyl, or $Y^1$ and $Y^2$ may be taken together to form an unsubstituted or a substituted cycloalkyl, cycloalkenyl, aryl, heteroaryl or heterocyclyl; and Z is selected from the group consisting of a carboxylic acid, a $C_1$-$C_6$ alkyl ester, an unsubstituted or a substituted amide, an unsubstituted or a substituted five- or six-membered heterocyclyl, and an unsubstituted or a substituted five- or six-membered heteroaryl; wherein a substituted group is substituted with one or more substituents, wherein each substituent is independently selected from the group consisting of $C_1$-$C_6$ alkyl, $C_1$-$C_6$ alkenyl, $C_1$-$C_6$ alkynyl, $C_1$-$C_7$ cycloalkyl, $C_1$-$C_7$ cycloalkenyl, acyl($C_1$-$C_6$ alkyl), $C_1$-$C_6$ alkoxy($C_1$-$C_6$ alkyl), amino($C_1$-$C_6$ alkyl), amino acid, $C_6$-$C_{10}$ aryl, heteroaryl, heterocyclyl, $C_6$-$C_{10}$ aryl($C_1$-$C_6$ alkyl), heteroaryl($C_1$-$C_6$ alkyl), heterocyclyl($C_1$-$C_6$ alkyl), hydroxyl($C_1$-$C_6$ alkyl), acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, azido, nitro, silyl, sulfenyl, sulfinyl, sulfonyl, halo($C_1$-$C_6$ alkyl), $C_1$-$C_6$ haloalkoxy, trihalomethanesulfonyl, trihalomethanesulfonamido, and amino; and a pharmaceutically acceptable carrier.

Pharmaceutical Composition 3: Pharmaceutical Composition 2, wherein the composition is in a unit dosage form.

Pharmaceutical Composition 4: Pharmaceutical Composition 2 or 3, comprising from 0.01 mg to 10000 mg of the compound of Formula (I), or pharmaceutically acceptable salt thereof.

Use 5: Use of any of Pharmaceutical Compositions 2-4, in the treatment or prophylaxis of metabolic syndrome, cardiovascular disease, diabetes, type 2 diabetes, anemia, cancer, cardiovascular disease, dyslipidemia, hypertension, inflammation, insulin resistance, prediabetes, fatty liver disease, steatohepatitis, iron overload, neurodegenerative diseases, or Alzheimer's disease.

Use 6: Use 5, for treatment or prophylaxis of metabolic syndrome.

Use 7: Use 6, wherein the pharmaceutical composition is configured to modulate a marker of metabolic syndrome or a symptom of metabolic syndrome.

Use 8: Use 7, wherein the marker of metabolic syndrome is selected from the group consisting of odd chain fatty acid percentage, serum concentration of an odd chain fatty acid, red blood cell membrane concentration of an odd chain fatty acid, serum total odd chain fatty acids, red blood cell membrane total odd chain fatty acids, serum ferritin, serum iron, transferritin saturation, serum glucose, serum triglycerides, blood pressure, HDL cholesterol, urine microalbumin, CRP, IL-6, TNFα, c-Jun N-terminal kinase, ATM and monocyte-chemoattractant protein-1.

Method 9: A method of treatment or prophylaxis of metabolic syndrome, cardiovascular disease, diabetes, type 2 diabetes, anemia, cancer, cardiovascular disease, dyslipidemia, hypertension, inflammation, insulin resistance, pre-diabetes, fatty liver disease, steatohepatitis, iron overload, neurodegenerative diseases, or Alzheimer's disease, comprising: administering to a patient in need thereof, a pharmaceutical composition comprising an effective amount of a compound of Formula (I), or a pharmaceutically acceptable salt thereof.

Method 10: Method 9, wherein the compound of Formula (I) or pharmaceutically acceptable salt thereof is provided as a pharmaceutical composition in a unit dosage form comprising the compound of Formula (I) or pharmaceutically acceptable salt thereof and a pharmaceutically acceptable carrier.

Method 11: Method 9 or 10, wherein the unit dosage form comprises from 0.01 mg to 10000 mg of the compound of Formula (I) or pharmaceutically acceptable salt thereof.

Method 12: Any of Methods 9-11, wherein the compound of Formula (I), or pharmaceutically acceptable salt thereof, is administered to the patient once per day.

Composition 13: A composition substantially as provided herein.

Method 14: A method substantially as provided herein.

Pharmaceutical Composition 15: A pharmaceutical composition comprising: a compound of Formula (I), or a pharmaceutically acceptable salt thereof, wherein the compound of Formula (I) has a structure:

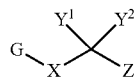

Formula (I)

wherein: G is selected from the group consisting of an unsubstituted or a substituted $C_{10}$-$C_{18}$ alkyl, an unsubstituted or a substituted $C_{10}$-$C_{18}$ alkenyl, an unsubstituted or substituted $C_{10}$-$C_{18}$ alkyl having one, two, or three oxa- or thia-substituents, and a substituted $C_{10}$-$C_{18}$ alkenyl having one, two, or three oxa- or thia-substituents; X is selected from the group consisting of O and $CR^1R^2$, wherein $R^1$ and $R^2$ are each independently selected from the group consisting of H and an unsubstituted or a substituted $C_1$-$C_6$ alkyl; $Y^1$ and $Y^2$ are each independently selected from the group consisting of H, an unsubstituted or a substituted $C_1$-$C_6$ alkoxy, and an unsubstituted or a substituted $C_1$-$C_6$ alkyl, or $Y^1$ and $Y^2$ may be taken together to form an unsubstituted or a substituted $C_3$-$C_8$ cycloalkyl, $C_3$-$C_8$ cycloalkenyl, $C_6$-$C_{10}$ aryl, $C_1$-$C_{10}$ heteroaryl, and $C_1$-$C_{10}$ heterocyclyl; and Z is selected from the group consisting of a carboxylic acid, —C(═O)—OH, a $C_1$-$C_6$ alkyl ester, an unsubstituted or a substituted amide, an unsubstituted or a substituted five- or six-membered heterocyclyl, and an unsubstituted or a substituted five- or six-membered heteroaryl; wherein a substituted group is substituted with one or more substituents, wherein each substituent is independently selected from the group consisting of $C_1$-$C_6$ alkyl, $C_1$-$C_6$ alkenyl, $C_1$-$C_6$ alkynyl, $C_1$-$C_7$ cycloalkyl, $C_1$-$C_7$ cycloalkenyl, acyl($C_1$-$C_6$ alkyl), $C_1$-$C_6$ alkoxy($C_1$-$C_6$ alkyl), amino($C_1$-$C_6$ alkyl), amino acid, $C_6$-$C_{10}$ aryl, $C_1$-$C_{10}$ heteroaryl, $C_1$-$C_{10}$ heterocyclyl, $C_6$-$C_{10}$ aryl($C_1$-$C_6$ alkyl), $C_1$-$C_{10}$ heteroaryl($C_1$-$C_6$ alkyl), $C_1$-$C_{10}$ heterocyclyl($C_1$-$C_6$ alkyl), hydroxyl($C_1$-$C_6$ alkyl), acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, azido, nitro, silyl, sulfenyl, sulfinyl, sulfonyl, halo($C_1$-$C_6$ alkyl), $C_1$-$C_6$ haloalkoxy, trihalomethanesulfonyl, trihalomethanesulfonamido, and amino; and a pharmaceutically acceptable carrier.

Pharmaceutical Composition 16: Pharmaceutical Composition 15, wherein G is an unsubstituted $C_{10}$-$C_{18}$ alkyl.

Pharmaceutical Composition 17: Pharmaceutical Composition 15 or 16, wherein X is $CR^1R^2$, and wherein $R^1$ and $R^2$ are each H.

Pharmaceutical Composition 18: Pharmaceutical Composition 15 or 16, wherein X is O.

Pharmaceutical Composition 19: Any of Pharmaceutical Compositions 15-18, wherein $Y^1$ is selected from the group consisting of H and an unsubstituted $C_1$-$C_6$ alkyl, and wherein $Y^2$ is an unsubstituted $C_1$-$C_6$ alkyl.

Pharmaceutical Composition 20: Any of Pharmaceutical Compositions 15-19, wherein Z is —C(═O)—OH.

Pharmaceutical Composition 21: Any of Pharmaceutical Compositions 15-19, wherein Z is

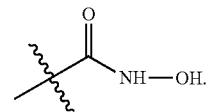

Pharmaceutical Composition 22: Any of Pharmaceutical Compositions 15-19, wherein Z is selected from the group consisting of:

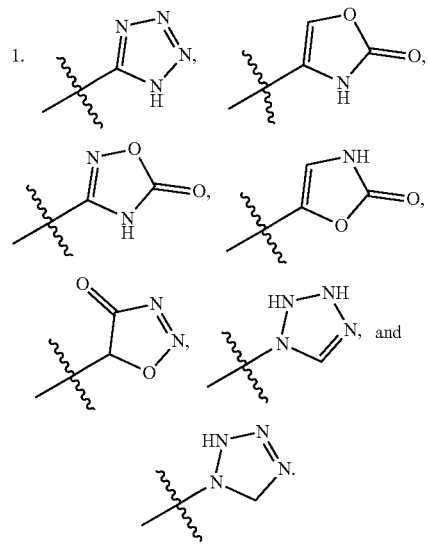

Pharmaceutical Composition 23: Pharmaceutical Composition 15, wherein the compound of Formula (I) is selected from the group consisting of:

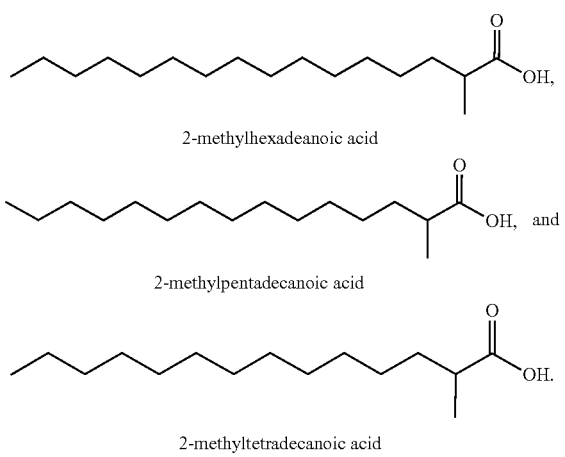

2-methylhexadeanoic acid 2-methylpentadecanoic acid 2-methyltetradecanoic acid

Pharmaceutical Composition 24: Pharmaceutical Composition 15, wherein the compound of Formula (I) is selected from the group consisting of:

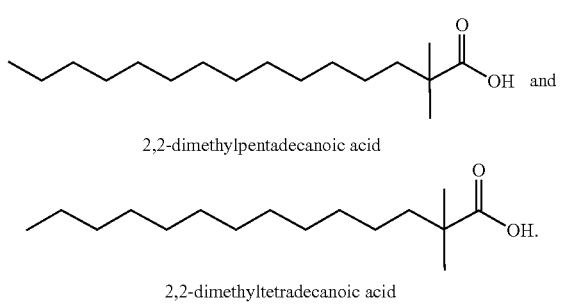

2,2-dimethylpentadecanoic acid 2,2-dimethyltetradecanoic acid

Pharmaceutical Composition 25: Pharmaceutical Composition 15, wherein the compound of Formula (I) is selected from the group consisting of:

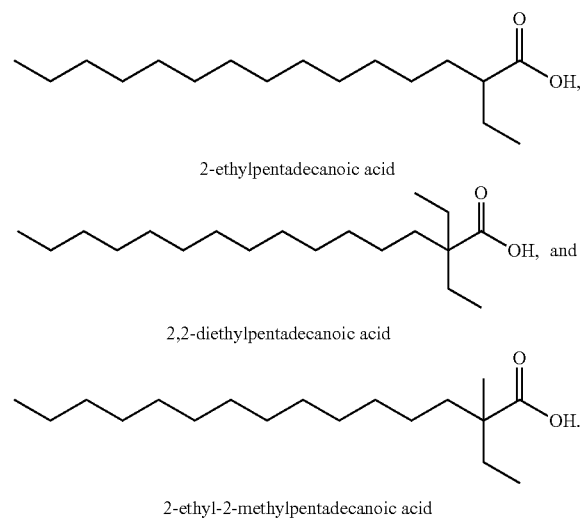

2-ethylpentadecanoic acid 2,2-diethylpentadecanoic acid 2-ethyl-2-methylpentadecanoic acid Pharmaceutical Composition 26: Any of Pharmaceutical Compositions 15-25, wherein the pharmaceutical composition is in a unit dosage form.

Pharmaceutical Composition 27: Any of Pharmaceutical Compositions 15-26, comprising from 0.01 mg to 10000 mg of the compound of Formula (I), or pharmaceutically acceptable salt thereof.

Use 28: Use of any of Pharmaceutical Compositions 15-26, for treatment or prophylaxis of a condition selected from the group consisting of metabolic syndrome, cardiovascular disease, diabetes, type 2 diabetes, anemia, cancer, cardiovascular disease, dyslipidemia, hypertension, inflammation, a chronic inflammatory disease, rheumatoid arthritis, insulin resistance, a fibrotic disease, prediabetes, fatty liver disease, steatohepatitis, iron overload, a neurodegenerative disease, Alzheimer's disease, nonalcoholic steatohepatitis, autoimmune diseases, asthma, anemia, dermatitis, pulmonary disease, pulmonary fibrosis, and systemic sclerosis, psoriasis, and dementia.

Use 29: Use 28, for the treatment or prophylaxis of a fibrotic disease, optionally selected from the group consisting of steatohepatitis, nonalcoholic steatohepatitis, systemic sclerosis, and idiopathic pulmonary fibrosis.

Use 30: Use 28, for treatment or prophylaxis of an autoimmune disease, optionally selected from the group consisting of psoriasis and rheumatoid arthritis.

Use 31: Use 28, for treatment or prophylaxis of chronic inflammatory disease, optionally an allergy or asthma.

Method 32: A method of treatment or prophylaxis of a condition selected from the group consisting of metabolic syndrome, cardiovascular disease, diabetes, type 2 diabetes, anemia, cancer, cardiovascular disease, dyslipidemia, hypertension, inflammation, a chronic inflammatory disease, rheumatoid arthritis, insulin resistance, a fibrotic disease, prediabetes, fatty liver disease, steatohepatitis, iron overload, a neurodegenerative disease, Alzheimer's disease, nonalcoholic steatohepatitis, autoimmune diseases, asthma, anemia, dermatitis, pulmonary disease, pulmonary fibrosis, and systemic sclerosis, psoriasis, and dementia, comprising: administering to a patient in need thereof, a pharmaceutical composition comprising an effective amount of a compound of Formula (I), or a pharmaceutically acceptable salt thereof, wherein the compound of Formula (I) has a structure:

Formula (I)

wherein: G is selected from the group consisting of an unsubstituted or a substituted $C_{10}$-$C_{18}$ alkyl, an unsubstituted or a substituted $C_{10}$-$C_{18}$ alkenyl, an unsubstituted or substituted $C_{10}$-$C_{18}$ alkyl having one, two, or three oxa- or thia-substituents, and a substituted $C_{10}$-$C_{18}$ alkenyl having one, two, or three oxa- or thia-substituents; X is selected from the group consisting of O and $CR^1R^2$, wherein $R^1$ and $R^2$ are each independently selected from the group consisting of H and an unsubstituted or a substituted $C_1$-$C_6$ alkyl; $Y^1$ and $Y^2$ are each independently selected from the group consisting of H, an unsubstituted or a substituted $C_1$-$C_6$ alkoxy, and an unsubstituted or a substituted $C_1$-$C_6$ alkyl, or $Y^1$ and $Y^2$ may be taken together to form an unsubstituted or a substituted $C_3$-$C_8$ cycloalkyl, $C_3$-$C_8$ cycloalkenyl, $C_6$-$C_{10}$ aryl, $C_1$-$C_{10}$ heteroaryl, and $C_1$-$C_{10}$ heterocyclyl; and Z is selected from the group consisting of a carboxylic acid, —C(=O)—OH, a $C_1$-$C_6$ alkyl ester, an unsubstituted or a substituted amide, an unsubstituted or a substituted five- or six-membered heterocyclyl, and an unsubstituted or a substituted five- or six-membered heteroaryl; wherein a substituted group is substituted with one or more substituents, wherein each substituent is independently selected from the group consisting of $C_1$-$C_6$ alkyl, $C_1$-$C_6$ alkenyl, $C_1$-$C_6$ alkynyl, $C_1$-$C_7$ cycloalkyl, $C_1$-$C_7$ cycloalkenyl, acyl($C_1$-$C_6$ alkyl), $C_1$-$C_6$ alkoxy($C_1$-$C_6$ alkyl), amino($C_1$-$C_6$ alkyl), amino acid, $C_6$-$C_{10}$ aryl, $C_1$-$C_{10}$ heteroaryl, $C_1$-$C_{10}$ heterocyclyl, $C_6$-$C_{10}$ aryl($C_1$-$C_6$ alkyl), $C_1$-$C_{10}$ heteroaryl($C_1$-$C_6$ alkyl), $C_1$-$C_{10}$ heterocyclyl($C_1$-$C_6$ alkyl), hydroxyl($C_1$-$C_6$ alkyl), acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, azido, nitro, silyl, sulfenyl, sulfinyl, sulfonyl, halo($C_1$-$C_6$ alkyl), $C_1$-$C_6$ haloalkoxy, trihalomethanesulfonyl, trihalomethanesulfonamido, and amino.

Method 33: Method 32, wherein G is an unsubstituted $C_{10}$-$C_{18}$ alkyl.

Method 34: Method 32 or 33, wherein X is $CR^1R^2$, and wherein $R^1$ and $R^2$ are each H.

Method 35: Any of Methods 32-34, wherein X is O.

Method 36: Any of Methods 32-35, wherein $Y^1$ is selected from the group consisting of H and an unsubstituted $C_1$-$C_6$ alkyl, and wherein $Y^2$ is an unsubstituted $C_1$-$C_6$ alkyl.

Method 37: Any of Methods 32-36, wherein Z is —C(=O)—OH.

Method 38: Any of Methods 32-36, wherein Z is

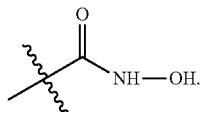 [SMILES: *C(=O)NO]

Method 39: Any of Methods 32-36, wherein Z is selected from the group consisting of:

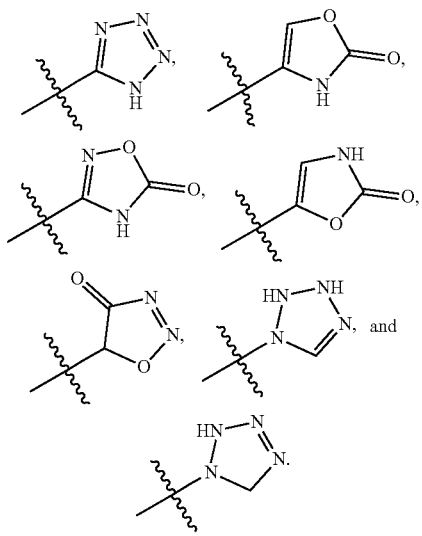

Method 40: Any of Methods 32-39, for the treatment or prophylaxis of a fibrotic disease, optionally selected from the group consisting of steatohepatitis, nonalcoholic steatohepatitis, systemic sclerosis, and idiopathic pulmonary fibrosis.

Method 41: Any of Methods 32-39, for treatment or prophylaxis of an autoimmune disease, optionally selected from the group consisting of psoriasis and rheumatoid arthritis.

Method 42: Any of Methods 32-39, for treatment or prophylaxis of chronic inflammatory disease, optionally an allergy or asthma.

Any of the features the above referenced pharmaceutical compositions, uses, and methods is applicable to any other pharmaceutical composition, use, or method identified herein. Moreover, any of the features of the above referenced pharmaceutical compositions, uses, and methods is independently combinable, partly or wholly, with other embodiments of the pharmaceutical compositions, uses, and methods described herein in any way, e.g., one, two, or three or more features may be combinable in whole or in part. Further, any of the features of the pharmaceutical compositions, uses, and methods described above may be made optional to other pharmaceutical compositions, uses, and methods described herein. Any aspect or embodiment of a method or use described herein can be performed using a composition, e.g., a pharmaceutical composition and/or a compound of Formula (I) as described herein or any compound having a structure described herein, and any aspect or embodiment of a composition, e.g., a pharmaceutical composition and/or a compound of Formula (I) or any compound having a structure described herein, can be used or adapted to perform a method or use as described herein.

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' preferred, 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of treatment of a condition selected from the group consisting of a pulmonary inflammatory disease and a pulmonary fibrotic disease, the method comprising:
   administering to a patient in need thereof a pharmaceutical composition comprising an effective amount of 2-ethylpentadecanoic acid, or a pharmaceutically acceptable salt thereof.

2. The method of claim 1, wherein the pharmaceutical composition is in a unit dosage form.

3. The method of claim 1, wherein the pharmaceutical composition comprises from 0.01 mg to 10000 mg of the 2-ethylpentadecanoic acid, or the pharmaceutically acceptable salt thereof.

4. The method of claim 1, wherein the condition is pulmonary fibrosis.

5. The method of claim 1, wherein the condition is chronic obstructive pulmonary disease (COPD).

6. The method of claim 1, wherein the condition is systemic sclerosis.

7. The method of claim 1, wherein the condition is lung inflammation.

\* \* \* \* \*

UNITED STATES PATENT AND TRADEMARK OFFICE
CERTIFICATE OF CORRECTION

PATENT NO. : 11,951,088 B2
APPLICATION NO. : 16/932508
DATED : April 9, 2024
INVENTOR(S) : Stephanie Venn-Watson It is certified that error appears in the above-identified patent and that said Letters Patent is hereby corrected as shown below:

On the Title Page

Column 2, under Item (56) Other Publications, Line 6, delete "orofile in health" and insert --profile in healthy--.

Column 2, under Item (56) Other Publications, Line 8, delete "Hemochronatosis" and insert --Hemochromatosis--.

On Page 3, Column 1, under Item (56) Other Publications, Line 44, delete "Neuroinflammunol." and insert --Neuroinflammation--.

On Page 3, Column 2, under Item (56) Other Publications, Line 15, delete "golyunsaturated" and insert --polyunsaturated--.

On Page 3, Column 2, under Item (56) Other Publications, Line 15, delete "Ligids" and insert --Lipids--.

On Page 3, Column 2, under Item (56) Other Publications, Line 56, delete "Sauid" and insert --Saudi--.

On Page 3, Column 2, under Item (56) Other Publications, Line 65, delete "obeity"," and insert --obesity",--.

On Page 4, Column 1, under Item (56) Other Publications, Line 5, delete "ofType" and insert --of Type--.

On Page 4, Column 1, under Item (56) Other Publications, Line 37, delete "B-" and insert --β- --.

On Page 4, Column 1, under Item (56) Other Publications, Line 53, delete "adposity" and insert --adiposity--.

Signed and Sealed this
Thirteenth Day of August, 2024

Katherine Kelly Vidal
*Director of the United States Patent and Trademark Office*

CERTIFICATE OF CORRECTION (continued)
U.S. Pat. No. 11,951,088 B2

On Page 4, Column 2, under Item (56) Other Publications, Line 5, delete "Cholesterolgallstones," and insert --Cholesterol Gallstones,--.

On Page 4, Column 2, under Item (56) Other Publications, Line 18, delete "Fuid." and insert --Fluid.--.

On Page 4, Column 2, under Item (56) Other Publications, Line 23, delete "<httgs:" and insert --<https:--.

On Page 4, Column 2, under Item (56) Other Publications, Line 26, delete "sgecies" and insert --species--.

On Page 5, Column 1, under Item (56) Other Publications, Line 18, delete "-6" and insert -- -δ--.

On Page 5, Column 1, under Item (56) Other Publications, Line 63, "Hapatitis" and insert --Hepatitis--.

On Page 5, Column 2, under Item (56) Other Publications, Line 72, delete "Aguatic" and insert --Aquatic--.

On Page 6, Column 2, under Item (56) Other Publications, Line 43, delete "Cariol." and insert --Cardiol.--.

On Page 7, Column 1, under Item (56) Other Publications, Line 21, delete "aI.," and insert --al.,--.

On Page 7, Column 1, under Item (56) Other Publications, Line 26, delete "phytohemagllutinin" and insert --phytohemagglutinin--.

On Page 7, Column 1, under Item (56) Other Publications, Line 31, delete "Cardiovsc" and insert --Cardiovasc--.

On Page 7, Column 2, under Item (56) Other Publications, Line 29, delete "2, 20127" and insert --27, 2012--.

On Page 8, Column 1, under Item (56) Other Publications, Line 49, delete "COX01" and insert --COX-1--.

On Page 8, Column 1, under Item (56) Other Publications, Line 57, delete "1, 19905" and insert --15, 1990--.

On Page 8, Column 1, under Item (56) Other Publications, Line 64, delete "parallelsbroad" and insert --parallels broad--.

On Page 8, Column 2, under Item (56) Other Publications, Line 4, delete "1, 20038" and insert --18, 2003--.

On Page 8, Column 2, under Item (56) Other Publications, Line 69, delete "retinalmicroangiopathy" and insert --retinal microangiopathy--.

On Page 9, Column 2, under Item (56) Other Publications, Line 58, delete "endocannabinoide" and insert --endocannabinoidome--.

On Page 10, Column 1, under Item (56) Other Publications, Line 22, delete "iintake," and insert --intake,--.

On Page 10, Column 1, under Item (56) Other Publications, Line 61, delete "comparedto" and insert --compared to--.

On Page 10, Column 1, under Item (56) Other Publications, Line 63, delete "2, 20226" and insert --26, 2022--.

On Page 10, Column 2, under Item (56) Other Publications, Line 2, delete "pleiotropic|activities" and insert --pleiotropic activities--.

On Page 10, Column 2, under Item (56) Other Publications, Line 12, delete "factorsand" and insert --factors and--.

On Page 10, Column 2, under Item (56) Other Publications, Line 16, delete "primaryimmunosuppression" and insert --primary immunosuppression--.

On Page 10, Column 2, under Item (56) Other Publications, Line 48, delete "oflipid," and insert --of lipid,--.

In the Specification

In Column 103, Line 42, delete "Cariol" and insert --Cardiol--.

In Column 103, Lines 57-58, delete "Rhematol" and insert --Rheumatol--.

In Column 108, Line 41, delete "alkenyl," and insert --allenyl,--.

In Column 113, Line 45, delete "preferred," and insert --'preferred,'--.

In Column 115, Line 40, delete "$C_9$:0)," and insert --C9:0),--.

In Column 115, Line 40, delete "($C_{11}$:0)," and insert --(C11:0),--.

In Column 115, Line 41, delete "($C_{19}$:0)," and insert --(C19:0),--.

In Column 116, Line 14, delete "Tones" and insert --Torres--.

In Column 121, Line 56, delete "(NAFL)," and insert --(NAFLD),--.

CERTIFICATE OF CORRECTION (continued)
U.S. Pat. No. 11,951,088 B2

In Column 123, Line 34, delete "proteosome" and insert --proteasome--.

In Column 124, Line 12, delete "(EDDM" and insert --(IDDM--.

In Column 124, Lines 44-45, delete "and or" and insert --and/or--.

In Column 124, Lines 54-55, delete "and or" and insert --and/or--.

In Column 124, Lines 57-58, delete "and or" and insert --and/or--.

In Column 124, Line 61, delete "(NAFL)," and insert --(NAFLD),--.

In Column 125, Line 67, delete "ideopathic" and insert --idiopathic--.

In Column 126, Line 37, delete "MCP1" and insert --MCP-1--.

In Column 126, Line 40, delete "et." and insert --et--.

In Column 132, Line 55, delete "Sjogen" and insert --Sjogren--.

In Column 132, Line 66, delete "Immnopathol" and insert --Immunopathol--.

In Column 133, Lines 5-6, delete "Brochoalveolar" and insert --Bronchoalveolar--.

In Column 133, Lines 7-8, delete "angiongenic" and insert --angiogenic--.

In Column 133, Line 15, delete "tranducer" and insert --transducer--.

In Column 133, Line 30, delete "et." and insert --et--.

In Column 134, Line 9, delete "transferritin" and insert --transferrin--.

In Column 134, Line 45, delete "4-oxy-2-" and insert --4-oxo-2- --.

In Column 137, Line 35, delete "transferritin" and insert --transferrin--.

In Column 137, Line 36, delete "transferritin" and insert --transferrin--.

In Column 138, Lines 61-62, delete "(HanAII" and insert --(HanALL--.

In Column 138, Line 65, delete "Novo Mix" and insert --Novomix--.

In Column 139, Lines 2-3, delete "glibomuride," and insert --glibornuride,--.

In Column 139, Line 54, delete "noradrenalin" and insert --noradrenaline--.

CERTIFICATE OF CORRECTION (continued)
U.S. Pat. No. 11,951,088 B2

In Column 139, Lines 64-65, delete "melanocoritin-4" and insert --melanocortin-4--.

In Column 140, Line 2, delete "(ergoset)," and insert --(ergot),--.

In Column 140, Line 16, delete "11B-hydroxysteroid" and insert --11β-hydroxysteroid--.

In Column 140, Line 53, delete "NPYSRA-" and insert --NPY5RA- --.

In Column 141, Line 49, delete "exopipam;" and insert --ecopipam;--.

In Column 141, Line 56, delete "amfebutmone;" and insert --amfebutamone;--.

In Columns 145-146 (TABLE 2), Line 3, "HFD" and insert --HFD+--.

In Column 147, Line 61, delete "Freemont," and insert --Fremont,--.

In Column 149, Line 7, delete "PPAR-6" and insert --PPAR-$\delta$--.

In Column 149, Line 9, delete "PPAR-6" and insert --PPAR-$\delta$--.

In Column 149, Line 12, delete "PPAR-6" and insert --PPAR-$\delta$--.

In Column 149, Line 14, delete "PPAR-6" and insert --PPAR-$\delta$--.

In Column 149, Line 15, delete "PPAR-6" and insert --PPAR-$\delta$--.

In Column 152, Line 35 (Approx.), delete "a" and insert --an--.

In Column 155, Line 1, delete "transferritin" and insert --transferrin--.

In Column 155, Line 48, delete "0" and insert --O--.

In Column 161, Line 16, delete "preferred," and insert --'preferred,'--.